US011542325B2

(12) United States Patent
Han et al.

(10) Patent No.: US 11,542,325 B2
(45) Date of Patent: *Jan. 3, 2023

(54) ANTI-ACTIVIN A ANTIBODIES AND USES THEREOF

(71) Applicant: Amgen Inc., Thousand Oaks, CA (US)

(72) Inventors: Huiquan Han, Thousand Oaks, CA (US); Qing Chen, Oxnard, CA (US); Keith Soo-Nyung Kwak, Thousand Oaks, CA (US); Xiaolan Zhou, Newbury Park, CA (US)

(73) Assignee: Amgen Inc., Thousand Oaks, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/128,831

(22) Filed: Sep. 12, 2018

(65) Prior Publication Data

US 2018/0371073 A1    Dec. 27, 2018

Related U.S. Application Data

(63) Continuation of application No. 15/346,617, filed on Nov. 8, 2016, now Pat. No. 10,100,109, which is a continuation of application No. 14/260,856, filed on Apr. 24, 2014, now abandoned, which is a continuation of application No. 13/550,447, filed on Jul. 16, 2012, now Pat. No. 8,753,627, which is a continuation of application No. 11/851,884, filed on Sep. 7, 2007, now Pat. No. 8,309,082.

(60) Provisional application No. 60/956,653, filed on Aug. 17, 2007, provisional application No. 60/843,430, filed on Sep. 8, 2006.

(51) Int. Cl.
*A61K 39/395* (2006.01)
*A61K 39/00* (2006.01)
*C07K 16/22* (2006.01)

(52) U.S. Cl.
CPC ........ *C07K 16/22* (2013.01); *A61K 2039/505* (2013.01); *C07K 2317/14* (2013.01); *C07K 2317/21* (2013.01); *C07K 2317/56* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,973,577 A | 11/1990 | Vale et al. | |
| 5,011,912 A | 4/1991 | Hopp et al. | |
| 5,545,616 A | 8/1996 | Woodruff | |
| 5,627,052 A | 5/1997 | Schrader | |
| 5,859,205 A | 1/1999 | Adair et al. | |
| 6,599,876 B2 | 7/2003 | Kojima | |
| 7,507,412 B2 | 3/2009 | Burger et al. | |
| 7,566,772 B2 | 7/2009 | Green et al. | |
| 7,585,500 B2 | 9/2009 | Foltz et al. | |
| 7,964,193 B2 | 6/2011 | Green et al. | |
| 7,994,302 B2 | 8/2011 | Foltz et al. | |
| 8,128,933 B2 | 3/2012 | Knopf et al. | |
| 8,309,082 B2* | 11/2012 | Han | A61P 1/00 424/130.1 |
| 8,410,043 B2 | 4/2013 | Sun et al. | |
| 8,753,627 B2* | 6/2014 | Han | C07K 16/22 424/130.1 |
| 9,273,114 B2 | 3/2016 | Sun et al. | |
| 2004/0209805 A1 | 10/2004 | Phillips | |
| 2007/0065444 A1 | 3/2007 | North et al. | |
| 2008/0248047 A1 | 10/2008 | Das et al. | |
| 2009/0118188 A1 | 5/2009 | Knopf et al. | |

(Continued)

FOREIGN PATENT DOCUMENTS

EP    2064239 A2    3/2008
EP    2559705 A2    2/2013

(Continued)

OTHER PUBLICATIONS

Abaza et al., "Effects of amino acid substitutions outside an antigenic site on protein binding to monoclonal antibodies of predetermined specificity obtained by peptide immunization: demonstration with region 94-100 (antigenic site 3) of myoglobin," *J. Protein Chem.* Oct. 1992; 11(5):433-444.

Anker et al., "Cardiac Cachexia: A Syndrome with Impaired Survival and Immune and Neuroendocrine Activation," *Chest*, 1999, vol. 115, pp. 836-847.

Anonymous, "Monoclonal Anti-human/mouse/rat Activin A Antibody," R&D Systems, Inc., Oct. 12, 2004, URL, http://www.rndsystems.com/pdflmab3381.pdf.

Babcock et al., "A Novel strategy for generating monoclonal antibodies from single, isolated C3 lymphocytes producing antibodies of defined specificities," *Proc. Natl. Acad. Sci., USA*, Jul. 1996, vol. 93, pp. 7843-7848.

(Continued)

*Primary Examiner* — Maher M Haddad
(74) *Attorney, Agent, or Firm* — Lisa E. Alexander

(57) ABSTRACT

The disclosure provides compositions and methods relating to or derived from anti-activin A binding proteins, including antibodies. In particular embodiments, the disclosure provides fully human, humanized, and chimeric anti-activin A antibodies that bind human activin A, activin A-binding fragments and derivatives of such antibodies, and activin A-binding polypeptides comprising such fragments. Other embodiments provide nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having activin A-related disorders or conditions including cachexia related to gonadal cancer, other cancers, rheumatoid arthritis, and other diseases.

4 Claims, 19 Drawing Sheets

Specification includes a Sequence Listing.

(56) References Cited

U.S. PATENT DOCUMENTS

| | | |
|---|---|---|
| 2010/0168020 A1 | 7/2010 | Sun et al. |
| 2011/0070233 A1 | 3/2011 | Seehra et al. |
| 2011/0243933 A1 | 10/2011 | Poradasu et al. |
| 2012/0121576 A1 | 5/2012 | Seehra et al. |
| 2012/0128668 A1 | 5/2012 | Knopf et al. |
| 2012/0295814 A1 | 11/2012 | Cramer et al. |
| 2013/0030159 A1 | 1/2013 | Han et al. |
| 2015/0037339 A1 | 2/2015 | Gromada et al. |

FOREIGN PATENT DOCUMENTS

| | | |
|---|---|---|
| JP | 1171495 A | 7/1989 |
| WO | 1992/02551 | 2/1992 |
| WO | 1996/033735 | 10/1996 |
| WO | 2005/051299 | 6/2005 |
| WO | 2005/116052 A2 | 12/2005 |
| WO | 2006/116269 A2 | 11/2006 |
| WO | 2008/031061 A2 | 3/2008 |
| WO | 2010/062383 A2 | 6/2010 |
| WO | 2013/106715 A1 | 7/2013 |

OTHER PUBLICATIONS

Beiboer et al., "Guided selection of a pan carcinoma specific antibody reveals similar binding characteristics yet structural divergence between the original murine antibody and its human equivalent," *J. Mol. Biol.* (2000) 296:833-849.

Birtalan et al., "The intrinsic contributions of tyrosine, serine, glycine and arginine to the affinity and specificity of antibodies," *J. Mol. Biology*, Apr. 2008, pp. 1518-1528, vol. 377.

Brown et al., "Tolerance of single, but not multiple, amino acid replacements in antibody VH CDR 2: a means of minimizing B cell wastage from somatic hypermutation?" *J. Immuno.* May 1996, 3285-91.

Casset et al. "A peptide mimetic of an anti-CD4 monoclonal antibody by rational design," *Biochem Biophys Res Commun.* Jul. 18, 2003, 307(1):198-205.

Chien et al., "Significant structural and functional change of an antigen-binding site by a distant amino acid substitution: proposal of a structural mechanism," *Proc. Natl. Acad. Sci. USA* Jul. 1989, 86(14):5532-6.

Choi et al., "Differential expression of activin/inhibin subunit and activin receptor mRNAs in normal neoplastic ovarian surface epithelium (OSE)," *Molecular and Cellular Endocrinology*, 2001, vol. 174, pp. 99-110.

Clackson et al., "Making antibody fragments using phage display libraries," *Nature* 352:624-628, 1991.

Cobellis et al., "High Concentrations of Activin A in the Peritoneal Fluid of Women with Epithelial Ovarian Cancer," *J. Soc. Gynecol. Investig.* 2004, vol. 11, pp. 203-206.

Coerver et al., "Activin Signaling through Activin Receptor Type II Causes the Cachexia-Like Symptoms in Inhibin-Deficient Mice," *Molecular Endocrinology* 10:534-543, 1996.

Colman, "Effects of amino acid sequence changes on antibody-antigen interactions," *Res. Immunol.* 145(1):33-36,1994.

Communication Pursuant to Article 94(3) EPC for European Patent Application No. 07842088.2, dated Feb. 18, 2013, 4 Pages.

Communication pursuant to Article 94(3) EPC for European Patent Application No. 07842088.2, dated Feb. 4, 2010, 3 Pages.

Communication pursuant to Article 94(3) EPC for European Patent Application No. 07842088.2, dated Jan. 24, 2012, 6 Pages.

Communication pursuant to Article 94(3) EPC for European Patent Application No. 07842088.2, dated Jul. 31, 2012, 4 Pages.

Communication pursuant to Article 94(3) EPC for European Patent Application No. 12154124.7, dated Feb. 17, 2014, 5 Pages.

Database WPI Week 198933 Derwent Publications Ltd., London, GB; AN 1989-237375 XP002471408 & JP 01 171495 A (Ajinomoto KK) Jul. 6, 1989 (Jul. 6, 1989).

Dot et al., "The role of activin A and Akt/GSK signaling in ovarian tumor biology", *Endocrinology*, Aug. 2008 US, Aug. 2008, pp. 3809-3816, vol. 149, No. 8.

Draper et al., "The Unterine Myometrium Is a Target for Increased Levels of Activin A During Pregnancy," *Endocrinology*, 1997, vol. 137, No. 7, pp. 3042-3046.

Eduardo, "Anatomy of the antibody molecule," *Mol. Immunol.* Feb. 1994; 31(3):169-217.

Extended European Search Report for European Patent Application No. 12154124.7, dated May 8, 2013, 12 pages.

Partial European Search Report for European Application No. 12154124, dated Jan. 21, 2013, 5 pages.

Supplementary European Search Report for European Application No. 14746114, dated Aug. 9, 2016, 19 Pages.

Extended European Search Report for European Patent Application No. 16178026.7, dated Jan. 23, 2017, 9 Pages.

Extended European Search Report for European Patent Application No. 16194631.4, dated Jan. 26, 2017, 7 Pages.

Fujii et al., "Regulation of prostate-specific antigen by activin A in prostate cancer LNCaP cells," *Am. J. Physiol. Endocrinol. Metab.*, 2004, vol. 286, pp. E927-E931.

Funaba et al., "Unique Recognition of Activin and Inhibin by Polyclonal Antibodies to Inhibin Subunits," *J. Biochem.* 119:953-960, 1996.

Funaba et al., "Requirement of Smad3 for mast cell growth," *Cellular Immunology* 240:47-52 (2006).

Gaedeke et al., "Glomerular activin A overexpression is linked to fibrosis in anti-Thy1glomerulonephritis," *Nephrol. Dial. Transplant*, 2005, vol. 20, pp. 319-328.

Groome et al., "Preparation of monoclonal Antibodies to the Beta A Subunit of Ovarian Inhibin Using a Synthetic Peptide Immunogen," *Hybridoma*, 1991, vol. 10, No. 2, pp. 309-316.

Harada et al., "Serum Immunoreactive Activin A Levels in Normal Subjects and Patients with Various Diseases," *Journal of Clinical Endocrinology and Metabolism*, 1996, vol. 81, pp. 2125-2130.

Hopp et al., "A Short Polypeptide Marker Sequence Useful for Recombinant Protein Identification and Purification," *Bio Technology*, 1998, vol. 6, pp. 1204-1210.

International Search Report and Written Opinion for PCT/US2007/077923, dated Jun. 9, 2008, 16 Pages.

International Search Report and Written Opinion for PCT/US2014/014490, dated Jun. 27, 2014, 20 Pages.

Jones "Activin A and Inhibin A Differentially Regulate Human Uterine Matrix Metalloproteinases: Potential Interactions during Decidualization and Trophoblast Invasion," *Endocrinology*, 2006, vol. 147, No. 2, pp. 724-732.

Klimka et al., "Human anti-CD30 recombinant antibodies by guided phage antibody selection using cell panning," *British Journal of Cancer* (2000) 83:252-260.

Lambert-Messerlian et al., "Secretion of Activin A in Recurrent Epithelial Ovarian Carcinoma," *Gynecologic Oncology*, 1999, vol. 74, pp. 93-97.

Lederman et al., "A single amino acid substitution in a common African allele of the CD4 molecule ablates binding of the monoclonal antibody," OKT4. *Mol. Immunol.* 28(11):1171-81, 1991.

Li et al., "Activin A Binds to Perlecan through Its Pro-region that has Heparin/Heparan Sulfate Binding Activity," (JBC, 285 (47) 36645-36655, 2010.

MacCallum et al., "Antibody-antigen interactions: contact analysis and binding site topography," *J Mol. Biol.* Oct. 11, 1996, 262(5):732-45.

Matzuk et al., "Development of cancer cachexia-like syndrome and adrenal tumors in inhibin-deficient mice," *Proc. Natl. Acad. Sci., Genetics*, Sep. 1994, pp. 8817-8821, vol. 91.

Menon et al., "Serum inhibin, activin and follistatin in postmenopausal women with epithelial ovarian carcinoma," *British Journal of Obstetrics and Gynecology*, 2000, vol. 107, pp. 1069-1074.

O'Connor et al., "Serum activin A and follistatin concentrations during human pregnancy: a cross-sectional and longitudinal study," *Human Reproduction*, 1999, vol. 14, No. 3, pp. 827-832.

Office Action for Australian Patent Application No. 2012265564, dated Jun. 19, 2015, 6 Pages.

(56) References Cited

OTHER PUBLICATIONS

Office Action for Australian Patent Application No. 2016219676, dated Feb. 23, 2017, 2 Pages.
Office Action for Canadian Patent Application No. 2,661,878, dated Jan. 10, 2014, 4 pages.
Office Action for Canadian Patent Application No. 2,661,878, dated Oct. 28, 2014, 4 pages.
Office Action for Canadian Patent Application No. 2,661,878, dated Nov. 10, 2015, 6 pages.
Office Action for Canadian Patent Application No. 2,661,878, dated Jan. 25, 2017, 6 Pages.
Office Action for Chilean Patent Application No. 2015-02166, dated Feb. 13, 2017, 13 Pages.
Office Action for Eurasian Patent Application No. 201491231, dated Nov. 25, 2016, 5 pages.
Office Action for European Application No. 12154124.7, dated Oct. 16, 2014, 4 pages.
Office Action for Israeli Patent Application No. 240139, dated Feb. 28, 2016, 3 pages (with concise explanation of relevance).
Office Action for Japanese Patent Application No. 2009-527594, dated Nov. 21, 2012, 16 pages.
Office Action for Japanese Patent Application No. 2009-527594, dated Sep. 12, 2013, 6 pages.
Office Action for Japanese Patent Application No. 2013-030740, dated Jul. 23, 2014, 12 Pages.
Office Action for Japanese Patent Application No. 2013-030740, dated Jun. 3, 2015, 8 pages.
Office Action for Japanese Patent Application No. 2013-030740, dated Jan. 6, 2016, 7 Pages.
Office Action for Japanese Patent Application No. 2016-092915, dated Mar. 29, 2017, 10 Pages.
Office Action for Thai Patent Application No. 1501004361, dated May 1, 2017, 2 Pages.
Office Action for Ukrainian Patent Application No. a 2012 14279, dated Jan. 20, 2017, 11 Pages.
Office Action for U.S. Appl. No. 11/851,884, dated Apr. 12, 2010, 20 pages.
Office Action for U.S. Appl. No. 11/851,884, dated Oct. 21, 2010, 12 pages.
Office Action for U.S. Appl. No. 11/851,884, dated Jul. 6, 2011, 16 pages.
Office Action for U.S. Appl. No. 11/851,884, dated Feb. 6, 2012, 15 pages.
Office Action for U.S. Appl. No. 14/171,670, dated Feb. 17, 2017, 19 Pages.
Office Action for U.S. Appl. No. 14/260,856, dated May 9, 2016, 17 pages.
Office Action for Vietnamese Patent Application No. 1-2015-03103, dated Feb. 26, 2016, 2 Pages.
Otani et al., "Production of Activin A and Hyperplasia and Adenocarcinoma of the Human Endometrium," *Gynecologic Oncology*, 2001, vol. 83, pp. 31-38.
Park et al., "Rationally designed anti-HER2/neu peptide mimetic disables P185HER2/neutyrosine kinases in vitro and in vivo," (2000) *Nature Biotech.* 18:194-198.
Paul, "Fundamental Immunology," 3rd Edition, 1993, pp. 292-295.
Petraglia et al., "Expression and Secretion of Inhibin and Activin in Normal and Neoplastic Uterine Tissues. High Levels of Serum Activin A in Women with Endometrial and Vercial Carcinoma," *Journal of Clinical Endocrinology and Metabolism*, 1998, vol. 83, pp. 1194-1200.
Portolano et al., "Lack of promiscuity in autoantigen-specific Hand L chain combinations as revealed by human H and L chain 'roulette'," *J. Immunology* 150(3):880-887, 1993.
R&D Systems, "Human/Mouse/Rat Activin A βA subunit Antibody," R&D Systems, Mar. 13, 2015, 2 pages, can be retrieved at <URL:http://www.rndsystems.com/pdf/mab3381.pdf>.
R&D Systems, Inc., "Monoclonal Anti-human/mouse/rat Activin A Antibody" Oct. 12, 2004, 1 page, can be retrieved at <URL:http://www.rndsystems.com/pdf/mab3381.pdf>.
Rabinovici et al., "Localization and regulation of the activin-A dimer in human placental cells," *Journal of Clinical Endocrinology and Metabolism*, vol. 75, No. 2, pp. 571-576, 1992.
Reis et al., "Serum and Tissue Expression of Activin A in Postmenopausal Women with Breast Cancer," Journal of Clinical Endocrinology and Metabolism, 2002, vol. 87, pp. 2277-2282.
Risbridger et al., "The contribution of inhibins and activins to malignant prostate disease," *Molecular and Cellular Endocrinology*, 2001, vol. 180, pp. 149-153.
Robertson et al., "Inhibin/activin and ovarian cancer," *Endocrine-Related Cancer*, 2004, pp. 35-49, vol. 11.
Rudikoff et al., "Single amino acid substitution altering antigen-binding specificity," *Proc. Natl. Acad. Sci.*, Mar. 1982, pp. 1979-1983, vol. 79, No. 6.
Schneyer et al., "Characterization of unique binding kinetics of follistatin and activin or inhibin in serum," *Endocrinology.* Aug. 1994, 135(2):667-74.
Steller et al., "Inhibin Resistance is Associated with Aggressive Tumorigenicity of Ovarian Cancer Cells," *Mol. Cancer Res.*, 2005, vol. 3, No. 1, pp. 50-61.
Summons to attend oral proceedings pursuant to Rule 115(1) EPC for European Patent Application No. EP 12154124.7, Jul. 27, 2015, 5 Pages.
Tanaka et al., "Expression and function of activin receptors in human endometrial adenocarcinoma cells," *International J. of Oncology*, 2003, vol. 23, pp. 657-663.
Thomas et al., "Expression and Localization of Activin Subunits and Follostatins in Tissues from Men with High Grade Prostate Cancer," *Journal of Clinical Endocrinology and Metabolism*, 1997, vol. 82, No. 11.
Thompson et al., "Structures of an ActRIIB:activin A complex reveal a novel binding mode for TGF-beta ligand:receptor interactions," *Embo J.* Apr. 1, 2003;22(7): 1555-66.
Tournier et al., "Germline Mutations of Inhibins in Early-Onset Ovarian Epithelial Tumors," Human Mutation, Dec. 2, 2013, pp. 294-297, vol. 35, No. 3.
Tsai et al., "Secreted Stress-Induced Phosphoprotein 1 Activates the ALK2-SMAD Signaling Pathways and Promotes Cell Proliferation of Ovarian Cancer Cells," *Cell Reports,* Aug. 2012, pp. 283-293, vol. 2, No. 2.
Vajdos et al., "Comprehensive functional maps of the antigen-binding site of an anti-ErbB2 antibody obtained with shotgun scanning mutagenesis," *J. Mol. Biol.* Jul. 5, 2002, 320(2):415-28 at 416.
Vale et al., "Chemical and Biological Characterization of the Inhibin Family of Protein Hormones," *Recent Progress in Hormone Research*, 1988, vol. 44, pp. 1-34.
Van Regenmortel, "Mapping Epitope Structure and Activity: From One-Dimensional Prediction to Four-Dimensional Description of Antigenic Specificity," *Methods* 9(3):465-472 (1996).
Welt et al., "Presence of Activin, Inhibin, and Follistatin in Epithelial Ovarian Carcinoma," *Journal of Clinical Endocrinology and Metabolism*, 1997, vol. 82, No. 11, pp. 3720-3727.
Wildi et al., "Overexpression of activin A in stage IV colorectal cancer," *Gut,* vol. 49, pp. 409-417, 2001.
Yamashita et al., "Activin A Is a Potent Activator of Renal Interstitial Fibroblast," *J. Am Soc Nephrol* 15:91-101, 2004.
Yndestad et al., "Elevated Levels of Activin A in Heart Failure Potential Role in Myocardial Remodeling," *Circulation,* 2004, vol. 109, pp. 1379-1385.
Zabetakis et al., "Contributions of the Complementarity Determining Regions to the Thermal Stability of a Single-Domain Antibody," *PLOS One,* Oct. 15, 2013, pp. 1-7, vol. 8, Article No. e77678.
Zhang et al., "Regulation of Growth and Prostatic Marker Expression by Activin A in an Androgen-Sensitive Prostate Cancer Cell Line LNCAP," *Biochemical and Biophysical Research Communications*, 1997, vol. 234, pp. 362-365.
Zheng et al., "Tumor Stroma as the main Source of Inhibin Production in Ovarian Epithelial Tumors," *AJRI,* 2000, vol. 44, pp. 104-113.
Harrison et al., "Antagonists of activin signaling: mechanisms and potential biological applications," *Trends in Endocrinology and Metabolism* 16(2): 73-78 (2005).

(56) References Cited

OTHER PUBLICATIONS

Communication of a Notice of Opposition, dated Apr. 18, 2017.
Communication re Notice of Appeal Filed, Mar. 25, 2019.
Communication of the Board of Appeals, dated May 18, 2022.
Curriculum vitae of Dr. Olav Olsen, cited in Opposition to EP Patent No. 2,559,705.
Declaration of Dr. Olav Olsen, Ph.D., May 3, 2019, cited in Opposition to EP Patent No. 2,559,705.
Decision Rejecting the Opposition, dated Jan. 10, 2019.
Enlarged versions of the figures from Declaration of Dr. Olav Olsen, Ph.D., May 3, 2019, cited in Opposition to EP Patent No. 2,559,705.
Enlarged and annotated version of Figure 14 from European Patent No. 2559705, cited in Opposition to EP Patent No. 2,559,705.
Additional email exchange with R&D Systems, May 1, 2019, cited in Opposition to EP Patent No. 2,559,705.
Email exchange with R&D Systems, Oct. 9, 2018, cited in Opposition to EP Patent No. 2,559,705.
First Examination Report for European Patent Application No. 12154124.7, dated Feb. 17, 2014, 5 pages, cited in Opposition to EP Patent No. 2,559,705.
Groome, "Ultrasensitive two-site assays for inhibin-A and activin-A using monoclonal antibodies raised to synthetic peptides," *Journal of Immunological Methods* 145: 65-69 (1991), cited in Opposition to EP Patent No. 2,559,705.
Kawase et al., "Anti-TGF-β antibody blocks enamel matrix derivative-induced upregulation of $p21^{WAF1/cip1}$ and prevents its inhibition of human oral epithelial cell proliferation," *J. Periodont Res* 37: 255-262 (2002), cited in Opposition to EP Patent No. 2,559,705.
Mason et al., "Functional Analysis of the Cysteine Residues of Activin A," *Molecular. Endocrinology* 8(3): 325-332 (1994), cited in Opposition to EP Patent No. 2,559,705.
Murata et al., "Anti-activin A Antibody (IgY) Specifically Neutralizes Various Activin A Activities," *Proc. Soc. Exp. Biol. Med.* 211: 100-107 (1996), cited in Opposition to EP Patent No. 2,559,705.
Non-Final Office Action for U.S. Appl. No. 14/260,856, dated Apr. 24, 2014, 16 pages, cited in Opposition to EP Patent No. 2,559,705.
Ogawa et al., "Activin A Stimulates Type IV Collagenase (Matrix Metalloproteinase-2) Production in Mouse Peritoneal Macrophages," *J. Immunol.* 165: 2997-3003 (2000), cited in Opposition to EP Patent No. 2,559,705.
Poulaki et al., "Activin A in the Regulation of Corneal Neovascularization and Vascular Endothelial Growth Factor Expression," *Am. J. Pathol.* 164(4): 1293-1302 (2004), cited in Opposition to EP Patent No. 2,559,705.
R&D Systems, Inc. datasheet, Oct. 12, 2004, retrieved from the internet at http://www.mdsystems.com/pdf/mab3381.pdf, cited in Opposition to EP Patent No. 2,559,705.
R&D Systems, Inc. datasheet retrieved from the internet at http://www.mdsystems.com/products/human-mouse-rat-activin-a-betaa-subunit-antibody af338, cited in Opposition to EP Patent No. 2,559,705.
Response to First Examination Report for European Patent Application No. 12154124.7, Aug. 26, 2014, 5 pages, cited in Opposition to EP Patent No. 2,559,705.
Response to Grounds of Appeal from Proprietor Amgen Inc., dated Sep. 23, 2019.
Response to Opposition from Proprietor Amgen Inc., dated Sep. 26, 2017.
Shikone et al., "Characterization of Gonadal Sex Cord-Stromal Tumor Cell Lines from Inhibin-α and p53-Deficient Mice: The Role of Activin as an Autocrine Growth Factor," *Molecular Endocrinology* 8(8): 983-995 (1994), cited in Opposition to EP Patent No. 2,559,705.
Statement of Grounds of Appeal Against the Decision from Opponent Regeneron Pharmaceuticals, Inc., dated May 20, 2019.
Statement of Opposition from Opponent Regeneron Pharmaceuticals, Inc., dated Apr. 7, 2017.
Vitt et al., "Evolution and Classification of Cystine Knot-Containing Hormones and Related Extracellular Signaling Molecules," *Molecular Endocrinology* 15(5): 681-694 (2001), cited in Opposition to EP Patent No. 2,559,705.
Written Submission from Proprietor Amgen Inc., dated Sep. 21, 2018.
Written Submission from Opponent Regeneron Pharmaceuticals, Inc., dated Sep. 21, 2018.
Written Submission from Opponent Regeneron Pharmaceuticals, Inc., dated Nov. 5, 2018.

* cited by examiner

Fig. 8C $^{1}$GLECDGK VNICCKKQFF VSFK DIGWNDW II$^{30}$ $^{31}$APSGY HANYCEGECPSHIAGTSGSSL SFHS$^{60}$ $^{61}$TVINHY RMRGHSPF ANLKSCCVPTKL MRPS$^{90}$ $^{91}$MLY YDDGQNIIK KDIQNMIVEECGCS$^{116}$ (SEQ ID NO:225)

Solid arrows – chymotrypsin cleavage
Broken arrows – LysC cleavage
M – putative CNBr cleavage Bold arrows and residues were not protected by antibody binding.

Activin A/B Chimeras

```
                      (1) 1        10        20        30        40           54
Activin A 13/39 B     (1) GLECDGKVNICCRQQFFIDFRLIGWNDWIIAPTGYYGNYCEGECPSHIAGTSGS
Activin A 82/107 B    (1) GLECDGKVNICCKKQFFVSFKDIGWNDWIIAPSGYHANYCEGECPSHIAGTSGS
Activin A             (1) GLECDGKVNICCKKQFFVSFKDIGWNDWIIAPSGYHANYCEGECPSHIAGTSGS
                                                                         Section 2
                     (55) 55   60        70        80        90             108
Activin A 13/39 B    (55) SLSFHSTVINHYRMRGHSPFANLKSCCVPTKLRPMSMLYYDDGQNIIKKDIQNM
Activin A 82/107 B   (55) SLSFHSTVINHYRMRGHSPFANLKSCCIPTKLSTMSMLYFDDEYNIVKRDVPNM
Activin A            (55) SLSFHSTVINHYRMRGHSPFANLKSCCVPTKLRPMSMLYYDDGQNIIKKDIQNM
                                                                         Section 3
                    (109) 109    116
Activin A 13/39 B   (109) IVEECGCS (SEQ ID NO:266)
Activin A 82/107 B  (109) IVEECGCS (SEQ ID NO:244)
Activin A           (109) IVEECGCS (SEQ ID NO:225)
```

ANTI-ACTIVIN A ANTIBODIES AND USES THEREOF

CROSS-REFERENCE TO RELATED APPLICATIONS

This application is a continuation of U.S. patent application Ser. No. 15/346,617, filed 8 Nov. 2016, which is a continuation of U.S. patent application Ser. No. 14/260,856, filed 24, April 2014, and entitled "ANTI-ACTIVIN A ANTIBODIES AND USES THEREOF"; which is a continuation of U.S. patent application Ser. No. 13/550,447 (now U.S. Pat. No. 8,753,627), filed 16, Jul. 2012, and entitled "ANTI-ACTIVIN A ANTIBODIES AND USES THEREOF"; which is a continuation of U.S. patent application Ser. No. 11/851,884 (non U.S. Pat. No. 8,309,082), filed 7 Sep. 2007, and entitled "ANTI-ACTIVIN A ANTIBODIES AND USES THEREOF"; which claims benefit of priority to U.S. Provisional Application Nos. 60/843,430 filed 8 Sep. 2006, and entitled "ANTI-ACTIVIN A ANTIBODIES AND USES THEREOF"; and 60/956,653 filed 17 Aug. 2007, and entitled "ANTI-ACTIVIN A ANTIBODIES AND USES THEREOF," all of which are incorporated by reference herein in their entireties.

TECHNICAL FIELD

The present invention relates generally to cysteine knot domains of activin A and antigen binding agents capable of binding to activin A or fragments thereof.

SEQUENCE LISTING

The instant application contains a Sequence Listing which has been submitted via EFS-Web and is hereby incorporated by reference in its entirely. Said ASCII copy, created on Sep. 11, 2018, is named A-1137-US-CNT4 Sequence Listing.txt, and is 125 kilobytes in size.

BACKGROUND OF THE INVENTION

Many serious disease states are accompanied by a condition known as cachexia, which refers to loss of body cell mass. Body cell mass (BCM) consists of muscle mass, visceral mass and immune cell mass. BCM is the most active body component of the human body, counting ninety-five percent of all metabolic activity. A five percent loss of BCM leads to changed morbidity, loss of muscle strength, altered metabolism and increased risk of infection. A forty percent loss can result in death.

Examples of conditions in which cachexia plays a role in determining the outcome of the underlying disease cover a range of the major health problems today. In rheumatoid cachexia, rheumatoid arthritis (RA) patients lose thirteen to fifteen percent of BCM. Two-thirds of RA patients have cachexia, and this results in a two- to five-fold higher mortality. Other related conditions include rheumatoid cachectic obesity and hypercytokinaemic cachexia. Cancer-related cachexia contributes significantly to the morbidity and mortality, also affecting a patient's ability to tolerate potentially life-saving therapies.

Because of the common role of activin A in a number of widespread diseases, all of which have high rates of mortality, there is a long-felt need in the art for compositions and methods to prevent or reverse the disease-related cachexia. Such compositions and methods are provided herein.

BRIEF SUMMARY OF THE INVENTION

In one aspect, the present invention provides an isolated antigen binding protein comprising either: a. a light chain CDR3 comprising a sequence selected from the group consisting of: i. a light chain CDR3 sequence that differs by no more than a total of two amino acid additions, substitutions, and/or deletions from a CDR3 sequence selected from the group consisting of the light chain CDR3 sequences of L1-L14; ii. $X_{73}$ Q $X_{74}$ $X_{75}$ $X_{76}$ $X_{77}$ $X_{78}$ $X_{79}$ $X_{80}$ (SEQ ID NO:132); iii. L Q H N $X_{81}$ Y $X_{82}$ $X_{83}$ T (SEQ ID NO:131); and iv. Q A W D $X_{84}$ S T $X_{85}$ $X_{86}$ (SEQ ID NO:248); b. a heavy chain CDR3 comprising a sequence selected from the group consisting of: i. a heavy chain CDR3 sequence that differs by no more than a total of three amino acid additions, substitutions, and/or deletions from a CDR3 sequence selected from the group consisting of the heavy chain CDR3 sequences of H1-H14; ii. $X_{87}$ $X_{88}$ $X_{89}$ $X_{90}$ $X_{91}$ $X_{92}$ $X_{93}$ $X_{94}$ F D Y (SEQ ID NO:187); iii. $X_{95}$ $X_{96}$ $X_{97}$ Y $X_{98}$ D $X_{99}$ $X_{100}$ G W $X_{101}$ $X_{102}$ $X_{103}$ (SEQ ID NO:188); iv. $X_{104}$ $X_{105}$ $X_{106}$ $X_{107}$ $X_{108}$ $X_{109}$ Y $X_{110}$ $X_{111}$ $X_{112}$ $X_{113}$ $X_{114}$ $X_{115}$ $X_{116}$ $X_{117}$ $X_{118}$ (SEQ ID NO:249); or c. the light chain CDR3 sequence of (a) and the heavy chain CDR3 sequence of (b); wherein $X_{73}$ is a methionine residue, a glutamine residue, or an arginine residue, $X_{74}$ is an alanine residue, a tyrosine residue, a glutamine residue, or a serine residue, $X_{75}$ is a leucine residue, a tyrosine residue, or an asparagine residue, $X_{76}$ is a glutamine residue, a serine residue, or a threonine residue, $X_{77}$ is a threonine residue, a tyrosine residue, or an isoleucine residue, $X_{78}$ is a proline residue or a serine residue, $X_{79}$ is a cysteine residue, a tryptophan residue, a leucine residue, or a proline residue, $X_{80}$ is a serine residue or a threonine residue, $X_{81}$ is a threonine residue or a serine residue, $X_{82}$ is a proline residue or a threonine residue, $X_{83}$ is a phenylalanine residue or a tryptophan residue, $X_{84}$ is an arginine residue or a serine residue, $X_{85}$ is a valine residue or an alanine residue, $X_{86}$ is a valine residue or no residue, $X_{87}$ is a valine residue or no residue, $X_{88}$ is a glutamine residue or no residue, $X_{89}$ is an aspartate residue, a tryptophan residue, or no residue, $X_{90}$ is a serine residue, a leucine residue, or no residue, $X_{91}$ is an isoleucine residue, a glutamate residue, or a glutamine residue, $X_{92}$ is an alanine residue, a leucine residue, or a glycine residue, $X_{93}$ is an alanine residue or a leucine residue, $X_{94}$ is a proline residue, a tyrosine residue, or a glycine residue, $X_{95}$ is an aspartate residue or no residue, $X_{96}$ is a glutamine residue or no residue, $X_{97}$ is an aspartate residue or an alanine residue, $X_{98}$ is a tyrosine residue or a glycine residue, $X_{99}$ is a serine residue or a tyrosine residue, $X_{100}$ is a serine residue or an arginine residue, $X_{101}$ is a phenylalanine residue or no residue, $X_{102}$ is a glycine residue or an aspartate residue, $X_{103}$ is a histidine residue or a proline residue, $X_{104}$ is a glycine residue or no residue, $X_{105}$ is a serine residue, a glutamate residue, or no residue, $X_{106}$ is an arginine residue, a serine residue, or no residue, $X_{107}$ is an aspartate residue, an asparagine residue, a serine residue, or a glutamine residue, $X_{108}$ is a serine residue, an arginine residue, or a tryptophan residue, $X_{109}$ is a glycine residue, an aspartate residue, an asparagine residue, a tyrosine residue, or a leucine residue, $X_{110}$ is a serine residue, a glycine residue, an aspartate residue, or no residue, $X_{111}$ is a serine residue, a valine residue, an asparagine residue, or a tyrosine residue, $X_{112}$ is a serine residue, an asparagine residue, a tyrosine residue, or a histidine residue, $X_{113}$ is a tryptophan residue, a tyrosine residue, or a glutamine residue, $X_{114}$ is a histidine residue, an aspartate residue, a tyrosine residue, or no residue, $X_{115}$ is a phenylalanine residue, an alanine residue, or a glycine residue, $X_{116}$ an aspartate residue, a phenylalanine residue, a leucine residue, or a methionine residue, $X_{117}$ a tyrosine residue, or an aspartate residue, $X_{118}$ is an isoleucine residue, a valine residue, or no residue, and the antigen binding protein binds specifically to human activin A.

In another aspect, the isolated antigen binding protein comprises an amino acid sequence selected from the group consisting of: a. a light chain CDR1 sequence that differs by no more than a total of six amino acid additions, substitutions, and/or deletions from a CDR1 sequence of L1-L14; b. a light chain CDR2 sequence that differs by no more than a total of two amino acid additions, substitutions, and/or deletions from a CDR2 sequence of L1-L14; c. a light chain CDR3 sequence that differs by no more than a total of three amino acid additions, substitutions, and/or deletions from a CDR3 sequence of L1-L14; d. a heavy chain CDR1 sequence that differs by no more than a total of two amino acid additions, substitutions, and/or deletions from a CDR1 sequence of H1-H14; e. a heavy chain CDR2 sequence that differs by no more than a total of five amino acid additions, substitutions, and/or deletions from a CDR2 sequence of H1-H14; and f. a heavy chain CDR3 sequence that differs by no more than a total of four amino acid additions, substitutions, and/or deletions from a CDR3 sequence of H1-H14.

In a further aspect, the isolated antigen binding protein comprises an amino acid sequence selected from the group consisting of: a. a light chain CDR1 sequence that differs by no more than a total of five amino acid additions, substitutions, and/or deletions from a CDR1 sequence of L1-L14; b. a light chain CDR2 sequence that differs by no more than a total of one amino acid addition, substitution, or deletion from a CDR2 sequence of L1-L14; c. a light chain CDR3 sequence that differs by no more than a total of two amino acid additions, substitutions, and/or deletions from a CDR3 sequence of L1-L14; d. a heavy chain CDR1 sequence that differs by no more than a total of one amino acid addition, substitution, or deletion from a CDR1 sequence of H1-H14; e. a heavy chain CDR2 sequence that differs by no more than a total of four amino acid additions, substitutions, and/or deletions from a CDR2 sequence of H1-H14; and f a heavy chain CDR3 sequence that differs by no more than a total of three amino acid additions, substitutions, and/or deletions from a CDR3 sequence of H1-H14.

In a further aspect, the isolated antigen binding protein comprises an amino acid sequence selected from the group consisting of: a. a light chain CDR1 sequence that differs by no more than a total of four amino acid additions, substitutions, and/or deletions from a CDR1 sequence of L1-L14; b. a light chain CDR2 sequence of L1-L14; c. a light chain CDR3 sequence that differs by no more than a total of one amino acid addition, substitution, or deletion from a CDR3 sequence of L1-L14; d. a heavy chain CDR1 sequence of H1-H14; e. a heavy chain CDR2 sequence that differs by no more than a total of three amino acid additions, substitutions, and/or deletions from a CDR2 sequence of H1-H14; and f a heavy chain CDR3 sequence that differs by no more than a total of two amino acid additions, substitutions, and/or deletions from a CDR3 sequence of H1-H14.

In yet a further aspect, the isolated antigen binding protein comprises an amino acid sequence selected from the group consisting of: a. a light chain CDR1 sequence that differs by no more than a total of three amino acid additions, substitutions, and/or deletions from a CDR1 sequence of L1-L14; b. a light chain CDR3 sequence of L1-L14; c. a heavy chain CDR2 sequence that differs by no more than a total of two amino acid additions, substitutions, and/or deletions from a CDR2 sequence of H1-H14; and d. a heavy chain CDR3 sequence that differs by no more than a total of one amino acid addition, substitution, or deletion from a CDR3 sequence of H1-H14.

In another aspect, the isolated antigen binding protein comprises an amino acid sequence selected from the group consisting of: a. a light chain CDR1 sequence that differs by no more than a total of two amino acid additions, substitutions, and/or deletions from a CDR1 sequence of L1-L14; b. a heavy chain CDR2 sequence that differs by no more than a total of one amino acid addition, substitution, or deletion from a CDR2 sequence of H1-H14; and c. a heavy chain CDR3 sequence of H1-H14.

In a still further aspect, the isolated antigen binding protein comprises an amino acid sequence selected from the group consisting of: a. a light chain CDR1 sequence that differs by no more than a total of one amino acid addition, substitution, or deletion from a CDR1 sequence of L1-L14; and b. a heavy chain CDR2 sequence of H1-H14.

In a yet further aspect, the isolated antigen binding protein comprises a CDR1 sequence of L1-L14.

The isolated antigen binding protein may comprise a sequence selected from the group consisting of: a. a light chain CDR1 sequence selected from the group consisting of: i. (R/K)SSQS(L/I)L(H/Y)S(T/S)(GN)(Y/N)(N/K)(-/K)YL(D/V) (SEQ ID NO:115); ii. RA(S/G)QGI(S/R)N(D/N)L-(V/G) (SEQ ID NO:250); iii. RASQSISNYLNT (SEQ ID NO:251); and iv. SG(D/E)K(L/W)G(D/E)K(F/Y)(A/V)(F/C) (SEQ ID NO:123); b. a light chain CDR2 sequence selected from the group consisting of: i. (H/Q/L)D(T/N/S)KRPS (SEQ ID NO:128); and ii. $X_{40}$ $X_{41}$ S $X_{42}$ $X_{43}$ $X_{44}$ S (SEQ ID NO:124), wherein $X_{40}$ is an alanine residue, a tryptophan residue, or a leucine residue, $X_{41}$ is a threonine residue, an alanine residue, or a glycine residue, $X_{42}$ is a serine residue, a methionine residue, or a phenylalanine residue, $X_{43}$ is a leucine residue or an arginine residue, $X_{44}$ is a glutamine residue, a glutamate residue, or an alanine residue, c. a heavy chain CDR1 sequence selected from the group consisting of: i. GGS(I/F)(N/S)(S/A)(-/G)(-/G)(F/Y)YWS (SEQ ID NO:252); ii. G $X_{27}$ $X_{28}$ F $X_{29}$ $X_{30}$ Y $X_{31}$ $X_{32}$ $X_{33}$ (SEQ ID NO:139), wherein $X_{27}$ is a tyrosine residue or a phenylalanine residue, $X_{28}$ is a threonine residue or a serine residue, $X_{29}$ is a threonine residue, a serine residue, or an isoleucine residue, $X_{30}$ is a glycine residue or a serine residue, $X_{31}$ is a tyrosine residue, a glycine residue, or a tryptophan residue, $X_{32}$ is an isoleucine residue or a methionine residue, $X_{33}$ is a histidine residue or a glycine residue; and iii. G(Y/F)TF(T/S)-(S/A)Y(G/W)(L/M/I)(S/H) (SEQ ID NO:140); d. a heavy chain CDR2 sequence selected from the group consisting of: i. (Y/E)I(S/Y/N)(Y/H)SG(S/G)T(Y/N)YNPSLK(S/R) (SEQ ID NO:142); ii. (V/N)I(K/W)(Y/Q)DGS(N/E/T)(K/E)Y(H/Y)(A/V)DSVKG (SEQ ID NO:179); and iii. $X_{60}$ I $X_{61}$ $X_{62}$ $X_{63}$ $X_{64}$ $X_{65}$ $X_{66}$ T $X_{67}$ $X_{68}$ $X_{69}$ $X_{70}$ $X_{71}$ $X_{72}$ Q G (SEQ ID NO:180), wherein $X_{60}$ is a tryptophan residue or an isoleucine residue, $X_{61}$ is an asparagine residue, an isoleucine residue, a serine residue, or a tyrosine residue, $X_{62}$ is a proline residue or an alanine residue, $X_{63}$ is an asparagine residue, a tyrosine residue, or a glycine residue, $X_{64}$ is a serine residue, an asparagine residue, or an aspartate residue, $X_{65}$ is a glycine residue or a serine residue, $X_{66}$ is a glycine residue, an asparagine residue, or an aspartate residue, $X_{67}$ is an asparagine residue or an arginine residue, $X_{68}$ is a tyrosine residue or a serine residue, $X_{69}$ is an alanine residue or a serine residue, $X_{70}$ is a glutamine residue or a proline residue, $X_{71}$ is a lysine residue or a serine residue, and $X_{72}$ is a phenylalanine residue or a leucine residue, wherein amino acid residue symbols enclosed in parentheses identify alternative residues for the same position in a sequence.

In certain aspects, the isolated antigen binding protein comprises a heavy chain CDR3 sequence that differs by no more than a total of two amino acid additions, substitutions, and/or deletions from a CDR3 sequence of H1-H14.

In further aspects, the isolated antigen binding protein comprises a heavy chain CDR3 sequence that differs by no more than a total of one amino acid addition, substitution, or deletion from a CDR3 sequence of H1-H14.

In yet further aspects, the isolated antigen binding protein comprises a heavy chain CDR3 sequence of H1-H14.

In another aspect, the isolated antigen binding protein comprises two amino acid sequences selected from the group consisting of: a. a light chain CDR1 sequence that differs by no more than a total of six amino acid additions, substitutions, and/or deletions from a CDR1 sequence of L1-L14; b. a light chain CDR2 sequence that differs by no more than a total of two amino acid additions, substitutions, and/or deletions from a CDR2 sequence of L1-L14; c. a light chain CDR3 sequence that differs by no more than a total of three amino acid additions, substitutions, and/or deletions from a CDR3 sequence of L1-L14; d. a heavy chain CDR1 sequence that differs by no more than a total of two amino acid additions, substitutions, and/or deletions from a CDR1 sequence of H1-H14; e. a heavy chain CDR2 sequence that differs by no more than a total of five amino acid additions, substitutions, and/or deletions from a CDR2 sequence of H1-H14; and f a heavy chain CDR3 sequence that differs by no more than a total of four amino acid additions, substitutions, and/or deletions from a CDR3 sequence of H1-H14.

In a further aspect, the isolated antigen binding protein comprises three amino acid sequences selected from the group consisting of: a. a light chain CDR1 sequence that differs by no more than a total of six amino acid additions, substitutions, and/or deletions from a CDR1 sequence of L1-L14; b. a light chain CDR2 sequence that differs by no more than a total of two amino acid additions, substitutions, and/or deletions from a CDR2 sequence of L1-L14; c. a light chain CDR3 sequence that differs by no more than a total of three amino acid additions, substitutions, and/or deletions from a CDR3 sequence of L1-L14; d. a heavy chain CDR1 sequence that differs by no more than a total of two amino acid additions, substitutions, and/or deletions from a CDR1 sequence of H1-H14; e. a heavy chain CDR2 sequence that differs by no more than a total of five amino acid additions, substitutions, and/or deletions from a CDR2 sequence of H1-H14; and f a heavy chain CDR3 sequence that differs by no more than a total of four amino acid additions, substitutions, and/or deletions from a CDR3 sequence of H1-H14.

In another aspect, the isolated antigen binding protein comprises four amino acid sequences selected from the group consisting of: a. a light chain CDR1 sequence that differs by no more than a total of six amino acid additions, substitutions, and/or deletions from a CDR1 sequence of L1-L14; b. a light chain CDR2 sequence that differs by no more than a total of two amino acid additions, substitutions, and/or deletions from a CDR2 sequence of L1-L14; c. a light chain CDR3 sequence that differs by no more than a total of three amino acid additions, substitutions, and/or deletions from a CDR3 sequence of L1-L14; d. a heavy chain CDR1 sequence that differs by no more than a total of two amino acid additions, substitutions, and/or deletions from a CDR1 sequence of H1-H14; e. a heavy chain CDR2 sequence that differs by no more than a total of five amino acid additions, substitutions, and/or deletions from a CDR2 sequence of H1-H14; and f a heavy chain CDR3 sequence that differs by no more than a total of four amino acid additions, substitutions, and/or deletions from a CDR3 sequence of H1-H14.

In another aspect, the isolated antigen binding protein comprises five amino acid sequences selected from the group consisting of: a. a light chain CDR1 sequence that differs by no more than a total of six amino acid additions, substitutions, and/or deletions from a CDR1 sequence of L1-L14; b. a light chain CDR2 sequence that differs by no more than a total of two amino acid additions, substitutions, and/or deletions from a CDR2 sequence of L1-L14; c. a light chain CDR3 sequence that differs by no more than a total of three amino acid additions, substitutions, and/or deletions from a CDR3 sequence of L1-L14; d. a heavy chain CDR1 sequence that differs by no more than a total of two amino acid additions, substitutions, and/or deletions from a CDR1 sequence of H1-H14; e. a heavy chain CDR2 sequence that differs by no more than a total of five amino acid additions, substitutions, and/or deletions from a CDR2 sequence of H1-H14; and f a heavy chain CDR3 sequence that differs by no more than a total of four amino acid additions, substitutions, and/or deletions from a CDR3 sequence of H1-H14.

In a still further aspect, the isolated antigen binding protein comprises: a. a light chain CDR1 sequence that differs by no more than a total of six amino acid additions, substitutions, and/or deletions from a CDR1 sequence of L1-L14; b. a light chain CDR2 sequence that differs by no more than a total of two amino acid additions, substitutions, and/or deletions from a CDR2 sequence of L1-L14; c. a light chain CDR3 sequence that differs by no more than a total of three amino acid additions, substitutions, and/or deletions from a CDR3 sequence of L1-L14; d. a heavy chain CDR1 sequence that differs by no more than a total of two amino acid additions, substitutions, and/or deletions from a CDR1 sequence of H1-H14; e. a heavy chain CDR2 sequence that differs by no more than a total of five amino acid additions, substitutions, and/or deletions from a CDR2 sequence of H1-H14; and f a heavy chain CDR3 sequence that differs by no more than a total of four amino acid additions, substitutions, and/or deletions from a CDR3 sequence of H1-H14.

In another aspect, the isolated antigen binding protein comprises either: a. a light chain variable domain comprising: i. a light chain CDR1 sequence; ii. a light chain CDR2 sequence; and iii. a light chain CDR3 sequence; b. a heavy chain variable domain comprising: i. a heavy chain CDR1 sequence; ii. a heavy chain CDR2 sequence; and iii. a heavy chain CDR3 sequence; or c. the light chain variable domain of (a) and the heavy chain variable domain of (b).

In one embodiment, the isolated antigen binding protein comprises a combination of a light chain variable domain and a heavy chain variable domain selected from the group of combinations consisting of: L1H1, L2H2, L3H3, L4H4, L5H5, L6H6, L7H7, L8H8, L9H9, L10H10, L11H11, L12H12, L13H13, and L14H14.

In one embodiment, the isolated antigen binding protein further comprises: the kappa light chain constant sequence of SEQ ID NO:84, 100 or 108, and/or the heavy chain constant sequence of SEQ ID NO:214, 215 or 221.

In one embodiment, the isolated antigen binding protein, when bound to activin A: a. inhibits activin A; b. cross-competes with a reference antibody for binding to activin A; c. binds to the same epitope of activin A as said reference antibody; d. binds to activin A with substantially the same Kd as said reference antibody; or e. binds to activin A with substantially the same off rate as said reference antibody; wherein the reference antibody comprises a combination of light chain and heavy chain variable domain sequences selected from the group of combinations consisting of L1H1, L2H2, L3H3, L4H4, L5H5, L6H6, L7H7, L8H8, L9H9, L10H10, L11H11, L12H12, L13H13, and L14H14.

In one embodiment, the isolated antigen binding protein, when bound to a human activin A, inhibits binding of activin A to human activin A receptor; attenuates cachexia in colon tumor-bearing mice; ameliorates the loss of body weight in colon tumor-bearing mice; ameliorates the loss of body weight in a collagen-induced animal model of rheumatoid arthritis; ameliorates the loss of muscle mass in a collagen-induced animal model of rheumatoid arthritis; ameliorates the loss of fat mass in a collagen-induced animal model of rheumatoid arthritis; and/or ameliorates the loss of body weight in a AAV-activin A transfected animal model.

In one aspect, the isolated antigen binding protein comprises: a. a human antibody; b. a humanized antibody; c. a chimeric antibody; d. a monoclonal antibody; e. a polyclonal antibody; f a recombinant antibody; g. an antigen-binding antibody fragment; h. a single chain antibody; i. a diabody; j. a triabody; k. a tetrabody; l. a Fab fragment; m. a F(ab')$_2$ fragment; n. a domain antibody; o. an IgD antibody; p. an IgE antibody; q. an IgM antibody; r. an IgG1 antibody; s. an IgG2 antibody; t. an IgG3 antibody; u. an IgG4 antibody; or v. an IgG4 antibody having at least one mutation in a hinge region that alleviates a tendency to form intra-H chain disulfide bond.

Also provided is a human antigen binding protein specific for activin A, wherein the antigen binding protein possesses at least one in vivo biological activity of a human anti-activin A antibody; such as the attenuation of cachexia.

Further provided is a human antigen binding protein that ameliorates the loss of body weight in colon tumor-bearing mice, or that ameliorates the loss of body weight in a collagen-induced animal model of rheumatoid arthritis.

Also provided is a human antigen binding protein that ameliorates the loss of muscle mass in a collagen-induced animal model of rheumatoid arthritis, that ameliorates the loss of fat mass in a collagen-induced animal model of rheumatoid arthritis or that ameliorates the loss of body weight in a AAV-activin A transfected animal model.

Further provided is a human antigen binding protein specific for activin A, wherein the antigen binding protein inhibits the binding of activin A to activin A receptor in vitro.

Also provided is a human antigen binding protein specific for activin A, wherein the antigen binding protein inhibits the binding of activin A to activin A receptor in vivo.

In another aspect, provided is an isolated polynucleotide comprising a sequence that encodes the light chain, the heavy chain, or both of an antigen binding protein of the invention; the polynucleotide may comprise a light chain variable domain nucleic acid sequence of SEQ ID NO:1, 17, 33, 49, 65, 81, 97, 113, 129, 145, 161, 177, 193 or 209 and/or a heavy chain variable domain nucleic acid sequence of SEQ ID NO:2, 18, 34, 50, 66, 82, 98, 114, 130, 146, 162, 178, 194 or 210.

Also provided is a plasmid comprising the isolated polynucleotide; the plasmid may be an expression vector; and an isolated cell is provided that comprises the polynucleotide; the isolated cell may be a hybridoma, and the cell may be a CHO cell.

Further provided is a method of making an antigen binding protein that binds human activin A, comprising incubating the isolated cell under conditions that allow it to express said antigen binding protein.

Also provided is a pharmaceutical composition comprising the antigen binding protein of the invention, a method of treating a condition in a subject comprising administering to the subject the pharmaceutical composition, wherein the condition is treatable by reducing the activity of activin A in said subject; the subject may be a human being, and the condition may be cachexia associated with a tumor, wherein the tumor is a gonadal tumor, such as ovarian cancer, benign prostatic hyperplasia, prostate intraepithelial neoplasia, or prostate cancer, or wherein the tumor is bladder cancer, Wilm's tumor, pancreatic cancer, breast cancer, bone cancer, lung cancer, colorectal cancer, cervical cancer, synovial sarcoma, vasoactive intestinal peptide secreting tumors, glioblastoma, medulloblastoma, head and neck squamous cell cancer, oral cancer, oral leukoplakia, anal cancer, esophageal cancer, gastric cancer, bone cancer, or metastatic cancer; the condition may be cachexia associated with a rheumatoid arthritis; or the condition may be the need for decreasing activin A activity in a subject.

In another aspect, the present invention provides a method of maintaining muscle mass of a subject comprising administering to said subject said pharmaceutical composition.

In another aspect, the present invention provides a method of decreasing activin A activity in a subject in need thereof comprising administering to said subject said pharmaceutical composition.

In another aspect, the present invention provides antibodies that are able to specifically bind amino acids K13-Y39 of activin A in vitro or in vivo. In another aspect, the present invention provides antibodies that are able to specifically bind amino acids V82-N107 in vitro or in vivo.

BRIEF DESCRIPTION OF THE DRAWINGS

FIG. 9 shows epitope regions that were not protected from degradation by binding of antibodies A1, A2 or A3.

FIG. 13 shows the amino acid sequences of activin A/activin B chimeras utilized in the antibody testing described in FIG. 11.

DETAILED DESCRIPTION

Figure 1:
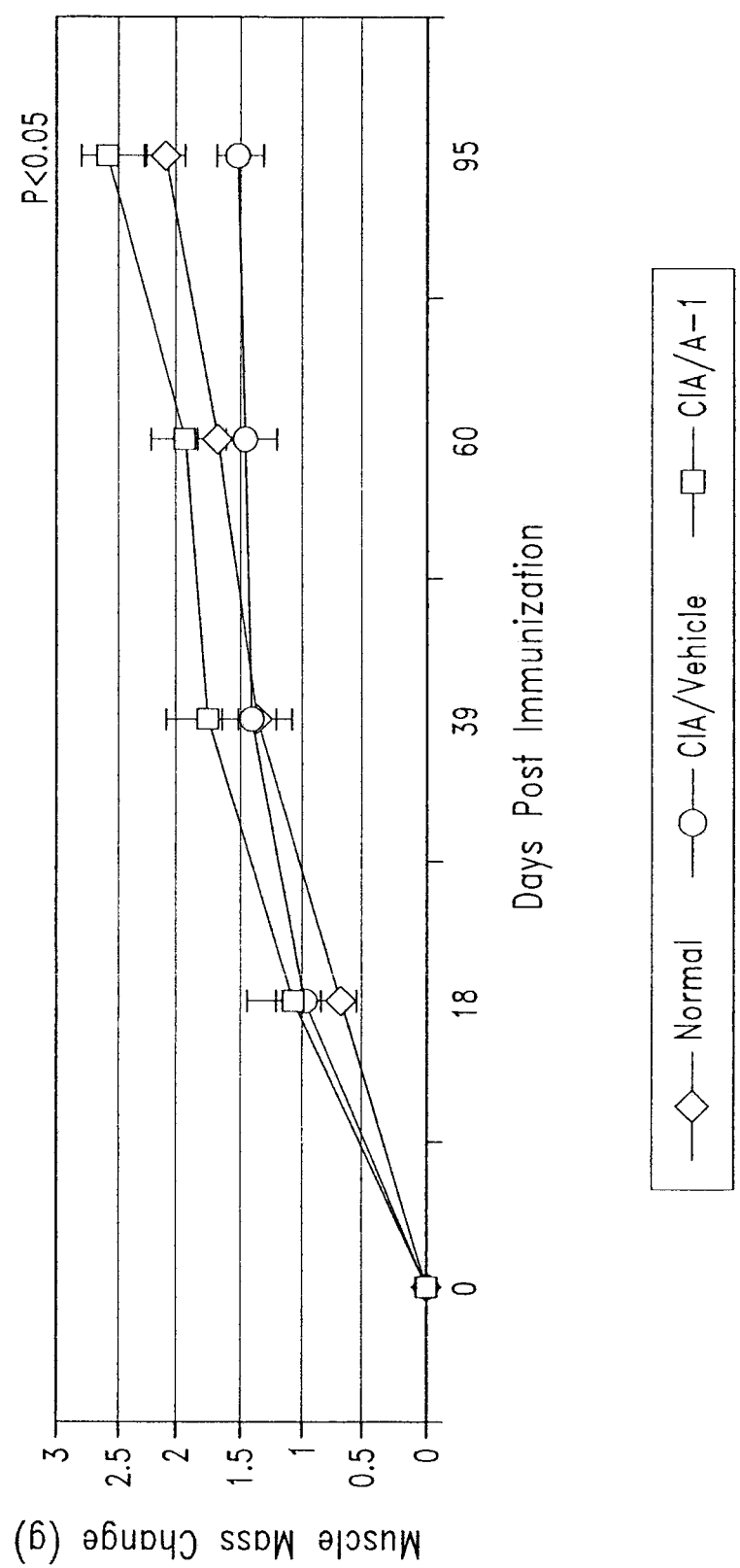
FIG. 1 provides the muscle mass change for collagen induced arthritis mice treated with anti-activin A antibody A1.

The present invention relates to regions of the human activin A that contain cysteine knot domains recognized by antibodies that also bind to full-length activin A, and/or a region of activin A that overlaps or encompasses a cysteine knot region of activin A, and methods of making and using these cysteine knot domains. The invention also provides antigen binding agents, including antibodies, that specifically bind to activin A or portions of activin A, and methods for using such binding agents. The binding agents are useful to block or impair binding of human activin A to one or more ligand.

Mortality from congestive heart failure (CHF) is related to cachexia. In one study (Anker, S. D. and Coats, A. J., Chest 115:836-847, 1999), sixteen percent of an unselected CHF outpatient population was cachectic. This state was predictive of impaired prognosis independent of age, functional disease classification, left ventricular ejection fraction, and peak oxygen consumption. The mortality in the cachectic cohort was fifty percent at eighteen months.

One pathway common to the disease progression in cancer, rheumatoid arthritis, chronic renal failure, congestive heart failure, and other conditions in which cachexia is a factor is the activin A pathway. Muscle wasting and weakness are common in many disease states and conditions including aging, cancer cachexia, sepsis, denervation, disuse, inactivity, burns, HIV-acquired immunodeficiency syndrome (AIDS), chronic kidney or heart failure, unloading/microgravity, and muscular dystrophies. Activins and inhibins are members of the TGF-beta superfamily. Activins and inhibins function as stimulators and inhibitors, respectively, of pituitary follicle-stimulating hormone (FSH) secretion and biosynthesis. Activin A is the predominant form of activin. In reproductive biology, activins and inhibins are important regulators of the ovarian cycle and the ovulation process, and may play a role in embryo implantation, and/or maintenance of pregnancy. (O'Connor et al., *Human Reproduction*, V. 14, No. 3, 827-832, March 1999; Draper et al., *Endocrin.*, V. 138, No. 7: 3042-3046; Jones, et al., *Endocrin.* V. 147, No. 2: 724-732, February 2006). The identification of inhibins and activins in a wide variety of tissues suggests that these factors play much greater roles than the control of FSH secretion.

Activins interact with two structurally related classes of serine/threonine kinase receptors (type I and type II). Inhibin antagonizes activin by binding to the proteoglycan, betaglycan, and forming a stable complex with and thereby sequestering type II activin receptors while excluding type I receptors. Two major forms of activin exist: activin A is a homodimer of $\beta_A$-subunits and activin B is a homodimer of $\beta_B$-subunits. (Vale, et al., *Recent Prog Horm Res V.* 44: 1-34, 1988). Heterodimers of an α-subunit that is dissimilar to either β-subunit results in the functional antagonist inhibin.

The literature has shown that activin A is overexpressed and/or localized in cancer tissues. For example, high levels of serum activin A were found in women with endometrial and cervical carcinoma (Petraglia, F. et al., *Jour. Clin. Endocrin. Metab.* 83:1194-1200, 1998). Activin A was overexpressed in stage IV colorectal cancer (Wildi, S. et al., Gut 49:409-417, 2001). A role of activin A in ovarian cancer was reported (Steller, M. D. et al., *Mol. Cancer Res.* 3:50-61, 2005).

The literature has also implicated activin A in renal disease. (Yamashita, S. et al. *J. Am. Soc. Nephrol.* 15:91-101, 2004.) Serum immunoreactive activin A levels in normal subjects and patients with disease were reported by Harada, K. et al. in *J. Clin. Endocrin. and Metab.* 81:2125-2130, 1996. Activin A is a potent activator of renal interstitial fibroblasts (Harada, K. et al., *J. Am. Soc. Nephrol.* 15:91-101, 2004). Glomerular activin A overexpression is linked to fibrosis in anti-Thy 1 glomerulonephritis (Gaedeke, J. et al., *Neph. Dial. Transpl.* 20:319-328, 2005).

Serum activin A levels in heart failure patients increased according to disease severity (Yndestal et al., *Circulation* 109:1379-1385, 2004). In a rat model of heart failure, serum activin A elevated immediately after myocardial infarct and persisted for six months, and activin A immunostaining was localized solely to cardiomyocytes (Yndestad et al., 2004). Elevated levels of activin A were reported in heart failure (Yndestad, A. et al., *Circulation* 109:1379-1385, 2004).

The present invention provides compositions, kits, and methods relating to molecules that bind to the activin A, including molecules that agonize or antagonize activin A, such as anti-activin A antibodies, antibody fragments, and antibody derivatives, e.g., antagonistic anti-activin A antibodies, antibody fragments, or antibody derivatives. Also provided are compositions, kits, and methods relating to molecules that specifically bind to a portion of activin A, such as amino acids R13-Y39, or amino acids V82-N107 of activin A. Such molecules may include antibodies, antibody fragments, and antibody derivatives. Also provided are nucleic acids, and derivatives and fragments thereof, comprising a sequence of nucleotides that encodes all or a portion of a polypeptide that binds to activin A, e.g., a nucleic acid encoding all or part of an anti-activin A antibody, antibody fragment, antibody variant, or antibody derivative, plasmids and vectors comprising such nucleic acids, and cells or cell lines comprising such nucleic acids and/or vectors and plasmids. The provided methods include, for example, methods of making, identifying, or isolating molecules that bind to activin A, such as anti-activin A antibodies, methods of determining whether a molecule binds to activin A, methods of making compositions, such as pharmaceutical compositions, comprising a molecule that binds to activin A, and methods for administering a molecule that binds activin A to a subject, for example, methods for treating a condition mediated by activin A, and for modulating a biological activity of activin A in vivo or in vitro.

Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular polypeptide or polynucleotide sequence also can be described by explaining how it differs from a reference sequence. Unless otherwise indicated, it is understood that polynucleotide and polypeptide sequences include each nucleic acid or amino acid listed, respectively, as well as the intervening nucleic acids or amino acids. For example, the polypeptide sequence R13-Y39 sets forth a polypeptide sequence that includes the amino acids R13, and Y39, as well as the amino acids found between R13 and Y39 in the polypeptide sequence. Correspondingly, the polynucleotide sequence C1-T5 sets forth a polynucleotide sequence that includes nucleic acids C1, and T5, as well as nucleic acids at positions 2, 3, and 4 of the sequence. Accordingly, designations of SEQ ID NO: 1-5 likewise designates the inclusive group of SEQ ID NO: 1, SEQ ID NO: 2, SEQ ID NO: 3, SEQ ID NO: 4, and SEQ ID NO: 5. Finally, amino acid groupings are also intended to be inclusive, unless otherwise designated. For example, the phrase "amino acids 1-5 of SEQ ID NO: 28" includes amino acids at positions 1, 2, 3, 4, and 5 of SEQ ID NO: 28.

Polynucleotide and polypeptide sequences of particular light and heavy chain variable domains are shown below. Antibodies comprising a light chain and heavy chain are designated by combining the name of the light chain and the name of the heavy chain variable domains. For example, "L4H7," indicates an antibody comprising the light chain variable domain of L4 and the heavy chain variable domain of H7.

Kappa light chain constant sequences are shown in SEQ ID NO:84, 100 and 108, and heavy chain constant sequence are shown in SEQ ID NO:214, 215 and 221. Polynucleotides encoding these sequences are shown in, for the light chains, respectively, SEQ ID NO:222, 223 and 239, and for the heavy chains, respectively, SEQ ID NO:240, 241, and 242. Thus, in addition to the variable sequences as disclosed herein, an antibody can comprise one or both of SEQ ID NO:84 and 214; or SEQ ID NO:215 and 223; or SEQ ID NO:108 and 221.

In other embodiments, an antibody may comprise a specific heavy or light chain, while the complementary light or heavy chain variable domain remains unspecified. In particular, certain embodiments herein include antibodies that bind a specific antigen (such as activin A) by way of a specific light or heavy chain, such that the complementary heavy or light chain may be promiscuous, or even irrelevant, but may be determined by, for example, screening combinatorial libraries. Portolano et al., *J. Immunol.* V. 150 (3), pp. 880-887 (1993); Clackson et al., *Nature* v. 352 pp. 624-628 (1991).

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings:

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or synthesized in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The terms "activin A inhibitor" and "activin A antagonist" are used interchangeably. Each is a molecule that detectably inhibits at least one function of activin A. Conversely, an "activin A agonist" is a molecule that detectably increases at least one function of activin A. The inhibition caused by an activin A inhibitor need not be complete so long as it is detectable using an assay. Any assay of a function of activin A can be used, examples of which are provided herein. Examples of functions of activin A that can be inhibited by an activin A inhibitor, or increased by an activin A agonist, include binding to activin A. Examples of types of activin A inhibitors and activin A agonists include, but are not limited to, activin A binding polypeptides such as antigen binding proteins (e.g., activin A inhibiting antigen binding proteins), antibodies, antibody fragments, and antibody derivatives.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

A "variant" of a polypeptide (e.g., an antibody) comprises an amino acid sequence wherein one or more amino acid residues are inserted into, deleted from and/or substituted into the amino acid sequence relative to the native polypeptide sequence, and retains essentially the same biological activity as the native polypeptide. The biological activity of the polypeptide can be measured using standard techniques in the art (for example, if the variant is an antibody, its activity may be tested by binding assays, as described herein). Variants of the invention include fragments, analogs, recombinant polypeptides, synthetic polypeptides, and/or fusion proteins. A "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in *Sequences of Proteins of Immunological Interest*, 5$^{th}$ Ed., US Dept. of Health and Human Services, PHS, NIH, NIH Publication no. 91-3242, 1991.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_H1$ domains; a F(ab')$_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, US App. Pub. No. 05/0202512, 04/0202995, 04/0038291, 04/0009507, 03/0039958, Ward et al., Nature 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, *Science* 242:423-26 and Huston et al., 1988, *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody," also referred to as "fully human antibody," includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-activin A antibody. In another embodiment, all of the CDRs are derived from a human anti-activin A antibody. In another embodiment, the CDRs from more than one human anti-activin A antibodies are mixed and matched in a chimeric antibody. For instance, a chimeric antibody may comprise a CDR1 from the light chain of a first human anti-activin A antibody, a CDR2 and a CDR3 from the light chain of a second human anti-activin A antibody, and the CDRs from the heavy chain from a third anti-activin A antibody. Further, the framework regions may be derived from one of the same anti-activin A antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind activin A).

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., 1991, *Science* 253:164.

Additionally, antigen specific (i.e., activin A specific) antibodies can be produced by methods known in the art by using a specific VL or VH domain to screen a library of the complementary variable domain. Such methods of producing antibodies are known in the art. For example, antibody fragments fused to another protein, such as a minor coat protein, can be used to enrich phage with antigen. Then, using a random combinatorial library of rearranged heavy (VH) and light (VL) chains from mice immune to the antigen (e.g., activin A), diverse libraries of antibody fragments are displayed on the surface of the phage. These libraries can be screened for complementary variable domains, and the domains purified by, for example, affinity column. See Clackson et al., *Nature*, V. 352 pp. 624-628 (1991).

In another example, individual VL or VH chains from an antibody (i.e., activin A antibody) can be used to search for other VH or VL chains that could form antigen-binding fragments (or Fab), with the same specificity. Thus, random combinations of VH and VL chain Ig genes can be expresses as antigen-binding fragments in a bacteriophage library (such as fd or lambda phage). For instance, a combinatorial library may be generated by utilizing the parent VL or VH chain library combined with antigen-binding specific VL or VH chain libraries, respectively. The combinatorial libraries may then be screened by conventional techniques, for example by using radioactively labeled probe (such as radioactively labeled activin A). See, for example, Portolano et al., *J. Immunol*. V. 150 (3) pp. 880-887 (1993).

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein), and includes the end sequence amino acids listed. For example the polypeptide sequence R13-Y39 includes amino acids R13, and Y39, as well as the amino acids found between R13 and Y39 in the sequence. In embodiments in which the epitope comprises non-contiguous portions of a molecule, the sequences will be noted accordingly.

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, *Nucleic Acids Res*. 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Example 3 herein described the use of CS-9 cells. Examples of other host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31), HeLa cells, BHK (ATCC CRL 10) cell lines, the CV1/EBNA cell line derived from the African green monkey kidney cell line CV1 (ATCC CCL 70) (see McMahan et al., 1991, *EMBO J*. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

In one aspect, the present invention provides antigen binding proteins (e.g., antibodies, antibody fragments, antibody derivatives, antibody muteins, and antibody variants), that bind to activin A, e.g., human activin A.

Antigen binding proteins in accordance with the present invention include antigen binding proteins that inhibit a biological activity of activin A. For example, antigen binding proteins may attenuate cachexia, and this activity can be present when the antigen binding protein is fully human, such as a fully human antibody.

Different antigen binding proteins may bind to different domains or cysteine knot domains of activin A or act by different mechanisms of action. Examples include but are not limited to antigen binding proteins that specifically bind one or more particular cysteine knot domains, or regions interspersed between disulfide bonds, including regions spanning from about amino acids 4-12, amino acids 11-81, amino acids 11-33, amino acids 13-39, amino acids 40-113, amino acids 44-115, amino acids 81-111, and/or amino acids 82-107 of SEQ ID NO:1. As indicated herein inter alia, the domain region are designated such as to be inclusive of the group, unless otherwise indicated. For example, amino acids 4-12 refers to nine amino acids: amino acids at positions 4, and 12, as well as the seven intervening amino acids in the sequence. Other examples include antigen binding proteins that inhibit binding of activin A to its receptor. An antigen binding protein need not completely inhibit an activin A-induced activity to find use in the present invention; rather, antigen binding proteins that reduce a particular activity of activin A are contemplated for use as well. (Discussions herein of particular mechanisms of action for activin A-binding antigen binding proteins in treating particular diseases are illustrative only, and the methods presented herein are not bound thereby.)

In another aspect, the present invention provides antigen binding proteins that comprise a light chain variable region selected from the group consisting of A1-A14 or a heavy chain variable region selected from the group consisting of A1-A14, and fragments, derivatives, muteins, and variants thereof. Such an antigen binding protein can be denoted using the nomenclature "LxHy", wherein "x" corresponds to the number of the light chain variable region and "y" corresponds to the number of the heavy chain variable region as they are labeled in the sequences below. That is to say, for example, that "A1HC" denotes the heavy chain variable region of antibody A1; "A1LC" denotes the light chain variable region of antibody A1, and so forth. More generally speaking, "L2H1" refers to an antigen binding protein with a light chain variable region comprising the amino acid sequence of L2 and a heavy chain variable region comprising the amino acid sequence of H1. For clarity, all ranges denoted by at least two members of a group include all members of the group between and including the end range members. Thus, the group range A1-A14, includes all members between A1 and A14, as well as members A1 and A14 themselves. The group range A4-A6 includes members A4, A5, and A6, etc.

Also shown below are the locations of the CDRs, or Complementarity Determining Regions (shaded and underlined) that create part of the antigen-binding site, while the Framework Regions (FRs) are the intervening segments of these variable domain sequences. In both light chain variable regions and heavy chain variable regions there are three CDRs (CDR 1-3) and four FRs (FR 1-4). The CDR regions of each light and heavy chain also are grouped by antibody type (A1, A2, A3, etc.). Antigen binding proteins of the invention include, for example, antigen binding proteins having a combination of light chain and heavy chain variable domains selected from the group of combinations consisting of L1H1 (antibody A1), L2H2 (antibody A2), L3H3 (antibody A3), L4H4 (antibody A4), L5H5 (antibody A5), L6H6 (antibody A6), L7H7 (antibody A7), L8H8 (antibody A8), L9H9 (antibody A9), L10H10 (antibody A10), L11H11 (antibody A11), L12H12 (antibody A12), L13H13 (antibody A13), and L14H14 (antibody A14).

Antibodies A1-A14 Heavy and Light Chain Variable Region Polynucleotides (Also Referred to Herein as H1-H14 and L1-L14).

A1 HC (SEQ ID NO: 2)

CAGGTTCAGCTGGTGCAGTCTGGAGCTGAGGTGAAGAAGCCTGGGGCCTCAGTGAA

GGTCTCCTGCAAGGCTTCTGGTTACACCTTTACCAGTTATGGTCTCAGCTGGGTGCG

ACAGGCCCCTGGACAAGGGCTTGAGTGGATGGGATGGATCATCCCTTACAATGGTA

ACACAAACTCTGCACAGAAACTCCAGGGCAGAGTCACCATGACCACAGACACATCC

ACGAGCACAGCCTACATGGAGCTGAGGAGCCTGAGATCTGACGACACGGCCGTGTA

TTTCTGTGCGAGAGACAGGGACTACGGTGTCAATTATGATGCTTTTGATATCTGGGG

CCAAGGGACAATGGTCACCGTCTCTTCA

-continued

A1 LC (SEQ ID NO: 1)
TCCTATGAGGTGACTCAGGCACCCTCAGTGTCCGTGTCCCCAGGACAGACAGCCAGC

ATCACCTGCTCTGGAGATAAATTGGGGGATAAATATGCTTGTTGGTATCAGCAGAAG

CCAGGCCAGTCCCCTGTGCTGGTCATCTATCAAGATAGCAAGCGGCCCTCAGGGATC

CCTGAGCGATTCTCTGGCTCCAACTCTGGAAACACAGCCACTCTGACCATCAGCGGG

ACCCAGGCTATGGATGAGGCTGACTATTACTGTCAGGCGTGGGACAGCAGCACTGC

GGTATTCGGCGGAGGGACCAAGCTGACCGTCCTA

A2 HC (SEQ ID NO: 18)
CAGGTGCAGCTGGTGGAGTCTGGGGGAGGCGTGGTCCAGCCTGGGAGGTCCCTGAG

ACTCTCCTGTGCAGCGTCTGGATTCACCTTCAGTAGTTACGGCATGCACTGGGTCCG

CCAGGCTCCAGGCAAGGGGCTGGAGTGGGTGGCAGTTATATGGTATGATGGAAGTA

ATAAATACCATGCAGACTCCGTGAAGGGCCGATTCACCATCTCCAGAGACAATTCC

AAGAACACGCTGTATCTGCAAGTGAACAGCCTGAGAGCCGAGGACACGGCTGTGTA

TTACTGTGTGAGAAGTCGGAACTGGAACTACGACAACTACTACTACGGTCTGGACGT

CTGGGGCCAAGGGACCACGGTCACCGTCTCCTCAG

A2 LC (SEQ ID NO: 17)
GACATCCAGATGACCCAGTCTCCATCCTCCCTGTCTGCATCTGTAGGAGACAGAGTC

ACCATCACTTGCCGGGCAAGTCAGGGCATTAGAAATAATTTAGGCTGGTATCAGCA

GAAACCAGGGAAAGCCCCTAAGCGCCTGATTTATGCTGCATCCAGTTTGCAAAGTG

GGGTCCCATCAAGGTTCAGCGGCAGTGGATCTGGGACAGAATTCACTCTCACAATCA

GCAGTCTGCAGCCTGAAGATTTTACAACTTATTACTGTCTACAGCATAATAGTTACC

CGTGGACGTTCGGCCAAGGGACCAAGGTGGAAATCAAA

A3 HC (SEQ ID NO: 34)
GAGGTGCAGTTGGTGGAGTCTGGGGGAGGCTTGGTCCAGCCTGGGGGGTCCCTGAG

ACTCTCCTGTGCAGCCTCTGGATTCACCTTTAGTAGTTATTGGATGAGCTGGGTCCGC

CAGGCTCCAGGGAAGGGGCTGGAGTGCGTGGCCAACATAAAGCAAGATGGAAGTG

AGGAATACTATGTGGACTCTGTGAAGGGCCGATTCACCATCTCCAGAGACAACGCC

AAGAATTCACTGTATCTGCAAATGAACAGCCTGAGAGCCGAGGACACGGCTGTGTA

TTACTGTGCGAGAGGTAGCAGCAGCTGGTACTACTACAACTACGGTATGGACGTCTG

GGGCCAAGGGACCACGGTCACCGTCTCCTCA

A3 LC (SEQ ID NO: 33)
GACATCCAGATGACCCAGTCTCCATCCTCCCTGTCTGCATCTGTAGGAGACAGAGTC

ACCATCACTTGCCGGGCAAGTCAGGGCATTAGAAATGATTTAGGCTGGTATCAGCA

GAAACCAGGGAAAGCCCCTAAGCGCCTGATCTATGCTGCATCCAGTTTGCAAAGTG

GGGTCCCATCAAGGTTCAGCGGCAGTGGATCTGGGACAGAATTCACTCTCACAATCA

GCAGCCTGCAGCCTGAAGATTTTGCAACTTATTACTGTCGACAGCAAAATACTTACC

CGCTCACTTTCGGCGGAGGGACCAAGGTGGAGATCAAA

A4 HC (SEQ ID NO: 50)
CAGGTGCAGCTGGTGCAGTCTGGGGCTGAGGTGAAGAAGCCTGGGGCCTCAGTGAA

GGTCTCCTGCAAGGCTTCTGGATACACCTTCACCGGCTACTATATCCACTGGGTGCG

-continued

ACAGGCCCCTGGACAAGGGCTTGAGTGGATGGG<u>ATGGATCAACCCTAACAGTGGTG</u>
<u>GCACAAACTATGCACAGAAGTTTCAGGGC</u>AGGGTCACCATGACCAGGGACACGTCC
ATCAGCACAGCCTACATGGAGCTGAGCAGGCTGAGATCTGACGACACGGCCGTGTA
TTTCTGTGCGAGA<u>GATTCGGGGTATAGCAGCAGCTGGCACTTTGACTAC</u>TGGGGCCA
GGGAACCCTGGTCACCGTCTCCTCA

A4 LC
(SEQ ID NO: 49)
GATATTGTGATGACTCAGTCTCCACTCTCCCTGCCCGTCACCCCTGGAGAGCCGGCC
TCCATCTCCTGC<u>AGGTCTAGTCAGAGCCTCCTGCATAGTACTGGATACAACTATTTG</u>
<u>GA</u>TTGGTACCTGCAGAAGCCAGGGCAGTCTCCACAGCTCCTGATCTAT<u>TTGGGTTCT</u>
<u>TTTCGGGCCTCC</u>GGGGTCCCTGACAGGTTCAGTGGCAGTGGGTCAGGCACAGATTTT
ACACTGAAAATCAGCAGAGTGGAGGCTGAGGATGTTGGGGTTTATTACTGC<u>ATGCA</u>
<u>AGCTCTCCAAACTCCGTGCAG</u>TTTTGGCCAGGGGACCAAGCTGGAGATCAAG

A5 HC
(SEQ ID NO: 66)
CAGGTGCAGCTGCAGGAGTCGGGCCCAGGACTGGTGAAGCCTTCGGAGACCCTGTC
CCTCACCTGCACTGTCTCT<u>GGTGGCTCCATCAATAGTTTCTACTGGAGC</u>TGGATCCGG
CAGCCCCCAGGGAAGGGACTGGAGTGGATTGGG<u>TATATCTATTACAGTGGGAGCAC</u>
<u>CAACTACAATCCCTCCCTCAAGAGT</u>CGAGTCACCATATCAGTAGACACGTCCAAGAC
CCAGTTCTCCCTGAAGCTGAGCTCTGTGACCGCTGCGGACACGGCCGTGTATTACTG
TGCGAGA<u>GACAGTATAGCAGCCCCCTTTGACTAC</u>TGGGGCCAGGGAACCCTGGTCA
CCGTCTCCTCAGCTTCCACCAAGGGCCCATCCGTCTTCCCCCTGGCGCCCTGCTCCAG
GAGCACCTCCGAGAGCACAGCCGCCCTGGGCTGCCTGGTCAAGGACTACTTCCCCG
AACCGGTGACGGTGTCGTGGAACTCATGCGCCCT

A5 LC
(SEQ ID NO: 65)
GACATCGTGATGACCCAGTCTCCAGACTCCCTGGCTGTGTCTCTGGGCGAGAGGGCC
ACCATCACCTGC<u>AAGTCCAGCCAGAGTATTTTATACAGTTCCAACAATAAGAAGTAT</u>
<u>CTAGTTT</u>GGTACCAGCAGAAACCAGGACAGCCTCCTAAGCTGATCATTTAC<u>TGGACA</u>
<u>TCTATGCGGGAATCC</u>GGGGTCCCTGACCGATTCAGTGGCAGCGGGTCTGGGACAGA
TTTCACTCTCACCATCAACAGCCTGCAGGCTGAAGATGTGGCAGTTTATTACTGT<u>CA</u>
<u>GCAATATTATAGTACTCCGTGGACG</u>TTCGGCCAAGGGACCAAGGTGGAAATCAAA

A6 HC
(SEQ ID NO: 82)
CAGGTGCAGCTACAGCAGTGGGGCGCAGGACTGTTGAAGCCTTCGGAGACCCTGTC
CCTCACCTGCGCTGTCTAT<u>GGTGGGTCCTTCAGTGCTTACTACTGGAGC</u>TGGATCCGC
CAGCCCCCAGGGAAGGGACTGGAGTGGATTGGG<u>GAAATCAATCATAGTGGAGGCAC</u>
<u>CAACTACAACCCGTCCCTCAAGAGT</u>CGAGTCACCATATCAGTAGACACGTCCAAGA
ACCAGTTCTCCCTGAAGCTGAGCTCTGTGACCGCCGCGGACACGGCTGTGTATTACT
GTGCGAGA<u>GTACAGTGGCTCGAACTGGCCTACTTTGACTAC</u>TGGGGCCAGGGAACC
CTGGTCACCGTCTCCTCA

A6 LC
(SEQ ID NO: 81)
GACATCCAGATGACCCAGTCTCCATCCTCCCTGTCTGCATCTGTAGGAGACAGAGTC
ACCATCACTTGC<u>CGGGCAAGTCAGAGCATTAGCAACTATTTAAATT</u>GGTATCAGCAG
AGACCAGGGAAAGCCCCTAAGCTCCTGATCTAT<u>GCTACATCCAGTTTGCAAAGTGGG</u>

-continued

GTCCCATCAAGGTTCAGTGGCAGTGGATCTGGGACAGATTTCACTCTCACCATCAGC

AGTCTGCAACCTGAAGATTTTGTAAGTTACTACTGT<u>CAACAGAGTTACAGTATTTCG</u>

<u>CCCACT</u>TTCGGCGGCGGGACCAAGGTGGAGAACAAA

A7 HC
(SEQ ID NO: 98)
CAGGTGCAGCTGGTGGACTCTGGGGGAGGCGTGGTCCAGCCTGGGAGGTCCCTGAG

ACTCTCCTGTGCAGCGTCT<u>GGATTCACCTTCATTAGCTATGGCATGCAC</u>TGGGTCCGC

CAGGCTCCAGGCAAGGGGCTGGAGTGGGTGGCA<u>GTTATCTGGTATGATGGAAGTAC</u>

<u>TGAATACTATGCAGACTCCGTGAAGGGC</u>CGATTCACCATCTCCAGAGACAATTCCAA

GAACACGCTGTATCTGCAAATGAACAGCCTGAGAGCCGAGGACACGGCTGTGTATT

ACTGTGCGAGA<u>GAGAGGCAGTGGCTCTACCACTACGGTATGGACGTC</u>TGGGGCCAA

GGGACCACGGTCACCGTCTCCTCA

A7 LC
(SEQ ID NO: 97)
GACATCCAGATGACCCAGTCTCCATCCTCCCTGTCTGCATCTGTAGGAGACAGAGTC

ACCATCACTTGC<u>CGGGCAGGTCAGGGCATTAGAAATGATTTAGT</u>CTGGTATCAGCAG

AAACCAGGGAAAGCCCCTAAGCGCCTGATCTAT<u>GCTGCATCCAGTTTGCAAAGT</u>GG

GGTCCCATCAAGGTTCAGCGGCAGTGGATCTGGGACAGAATTCACTCTCACAATCAG

CAGCCTGCAGCCTGAAGATTTTGCAACTTATTACTGT<u>CTACAACATAATACTTACCC</u>

<u>ATTCACT</u>TTCGGCCCTGGGACCAAAGTGGATATCAAA

A8 HC
(SEQ ID NO: 114)
CAGGTGCAGCTGCAGGAGTCGGGCCCAGGACTGGTGAAGCCCTCGGAGACCCTGTC

CCTCACCTGCACTGTCTCT<u>GGTGGCTCCATCAATAGTTTCTACTGGAGC</u>TGGATCCGG

CAGCCCCCAGGGAAGGGACTGGAGTGGATTGGG<u>TATATCTATTACAGTGGGAGCAC</u>

<u>CAACTACAATCCCTCCCTCAAGAGG</u>CGAGTCACCATATCAGTAGACACGTCCAAGA

CCCAGTTCTCCCTGAAGCTGAGCTCTGTGACCGCTGCGGACACGGCCGTGTATTACT

GTGCGAGA<u>GACAGTATAGCAGCCCCCTTTGACTAC</u>TGGGGCCAGGGAACCCTGGTC

ACCGTCTCCTCA

A8 LC
(SEQ ID NO: 113)
GACATCGTGATGACCCAGTCTCCAGACTCCCTGGCTGTGTCTCTGGGCGAGAGGGCC

ACCATCACCTGC<u>AAGTCCAGCCAGAGTATTTTATACAGCTCCAACAATAAGAAGTAT</u>

<u>CTAGTTT</u>GGTACCAGCAGAAACCAGGACAGCCTCCTAAGTTGATCATTTAC<u>TGGACA</u>

<u>TCTATGCGGGAATCC</u>GGGGTCCCTGACCGATTCAGTGGCAGCGGGTCTGGGACAGA

TTTCACTCTCACCATCAGCAGCCTGCAGGCTGAAGATGTGGCAGTTTATTACTGT<u>CA</u>

<u>GCAATATTATAGTACTCCGTGGACG</u>TTCGGCCAAGGGACCAAGGTGGAAATCAAA

A9 HC
(SEQ ID NO: 130)
CAGGTGCAGCTGGTGGAGTCTGGGGGAGGCGTGGTCCAGCCTGGGAGGTCCCTGAG

ACTCTCCTGTGCAGCGTCT<u>GGATTCACCTTCAGTAGTTACGGCATGCAC</u>TGGGTCCG

CCAGGCTCCAGGCAAGGGGCTGGAGTGGGTGGCA<u>GTTATATGGTATGATGGAAGTA</u>

<u>ATAAATACCATGCAGACTCCGTGAAGGGC</u>CGATTCACCATCTCCAGAGACAATTCC

AAGAACACGCTGTATCTGCAAGTGAACAGCCTGAGAGCCGAGGACACGGCTGTGTA

```
TTACTGTGTGAGAAGTCGGAACTGGAACTACGACAACTACTACTACGGTCTGGACGT

CTGGGGCCAAGGGACCACGGTCACCGTCTCCTCA

A9 LC
                                                   (SEQ ID NO: 129)
GACATCCAGATGACCCAGTCTCCATCCTCCCTGTCTGCATCTGTAGGAGACAGAGTC

ACCATCACTTGCCGGGCAAGTCAGGGCATTAGAAATAATTTAGGCTGGTATCAGCA

GAAACCAGGGAAAGCCCCTAAGCGCCTGATTTATGCTGCATCCAGTTTGCAAAGTG

GGGTCCCATCAAGGTTCAGCGGCAGTGGATCTGGGACAGAATTCACTCTCACAATCA

GCAGCCTGCAGCCTGAAGATTTTACAACTTATTACTGTCTACAGCATAATAGTTACC

CGTGGACGTTCGGCCAAGGGACCAAGGTGGAAATCAAA

A10 HC
                                                   (SEQ ID NO: 146)
GAGGTGCAGCTGGTGCAGTCTGGAGCAGAGGTGAAAAAGCCCGGGGAGTCTCTGAA

GATCTCCTGTCAGGGTTCTGGATACAGCTTTACCAGCTACTGGATCGGCTGGGTGCG

CCAGATGCCCGGGAAAGGCCTGGAGTGGATGGGGATCATCTATCCTGGTGACTCTG

ATACCAGATACAGCCCGTCCTTCCAAGGCCAGGTCACCATCTCAGCCGACAAGTCCA

TCAGCACCGCCTACCTGCAGTGGAGCAGCCTGAAGGCCTCGGACACCGCCATGTATT

ACTGTGCGAGACAAGGACTGGGGTTTGACTACTGGGGCCAGGGAACCCTGGTCACC

GTCTCCTCA

A10 LC
                                                   (SEQ ID NO: 145)
TCCTATGAGCTGACTCAGCCACCCTCAGTGTCCGTGTCCCCAGGACAGACAGCCAGC

ATCACCTGCTCTGGAGAAAAATGGGGAGAGAAATATGCTTGTTGGTATCAGCAGAA

GCCAGGCCAGTCCCCTGTGCTGGTCATCTATCAAGATACCAAGCGGCCCTCCGGGAT

CCCTGAGCGATTCTCTGGCTCCATTTCTGGGAACACAGCCACTCTGACCATCAGCGG

GACCCAGGCTATGGATGAGGCTGACTATTATTGTCAGGCGTGGGACAGGAGCACTG

TATTCGGCGGAGGGACCAAGCTGACCGTCCTA

A11 HC
                                                   (SEQ ID NO: 162)
CAGGTGCAGCTGCAGGAGTCGGGCCCAGGACTGGTGAAGCCTTCACAGACCCTGTC

CCTCACCTGCACTGTCTCTGGTGGCTCCATCAGCAGTGGTGGTTACTACTGGAGCTG

GATCCGCCAGCACCCAGGGAAGGGCCTGGAGTGGATTGGGTACATCTCTTACAGTG

GGAGCACCTACTACAACCCGTCCCTCAAGAGTCGAGTTACCATATCAGTTGACACGT

CTAAGAACCAGTTCTCCCTGAAGCTGAACTCTGTGACTGCCGCGGACACGGCCGTGT

ATTACTGTGCGCGCGCTTACGGTGACTATCGCGGCTGGTTCGACCCCTGGGGCCAGG

GAACCCTGGTCACCGTCTCCTCA

A11 LC
                                                   (SEQ ID NO: 161)
TCCTATGAGCTGACTCAGCCACCCTCAGTGTCCGTGTCCCCAGGACAGACAGCCAGC

ATCACCTGCTCTGGAGATAAATTGGGGGATAAATTTGCTTTCTGGTATCAGCTGAAG

CCAGGCCAGTCCCCTGTGCTGGTCATCTATCAAGATAACAAGCGGCCCTCAGGGATC

CCTGAGCGATTCTCTGGCTCCAACTCTGGGAACACAGCCACTCTGACCATCAGCGGG

ACCCAGGCTATGGATGCGGCTGACTTTTACTGTCAGGCGTGGGACAGCAGCACTGTG

GTATTCGGCGGAGGGACCAAGCTGACCGTCCTA
```

A12 HL (SEQ ID NO: 178)

CAGGTGCAGCTGGTGGAGTCTGGGGGAGGCGTGGTCCAGCCTGGGAGGTCCCTGAG

ACTCTCCTGTGTAGCGTCT<u>GGATTCACCTTCAGTGCCTATGGCATGCAC</u>TGGGTCCGC

CAGGCTCCAGGCAAGGGGCTGGAGTGGGTGGCA<u>GTTATATGGTATGATGGAAGTAA</u>

<u>TAAATACTATGCAGACTCCGTGAAGGGC</u>CGATTCATCATCTCCAGAGACAATTCCAA

GAACACGCTGTATCTGCAAATGAACAGCCTGAGAGCCGAGGACACGGCTGTGTATT

ACTGTGCGAGA<u>AGTCGGAACTGGAACTACGACTCCTACCAATACGGTTTGGACGTCT</u>

GGGGCCAAGGGACCACGGTCACCGTCTCCTCA

A12 LC (SEQ ID NO:177)

GACATCCAGATGACCCAGTCTCCATCCTCCCTGTCTGCATCTGTAGGAGACAGAGTC

ACCATCACTTGC<u>CGGGCAAGTCAGGGCATTAGAAATGATTTAGGC</u>TGGTATCAGCA

GAAACCAGGGAAAGCCCCTAAGCGCCTGATCTAT<u>GCTGCATCCAGTTTGCAAAGT</u>G

GGGTCCCATCAAGGTTCAGCGGCAGTGGATCTGGGACAGAATTCACTCTCACAATCA

GCAGCCTGCAGCCTGAAGATTGTGCAACTTATTATTGT<u>CTACAGCATAATAGTTATA</u>

<u>CGTGGAC</u>GTTCGGCCAAGGGACCAAGGTGGAAATCAAA

A13 HC (SEQ ID NO: 194)

CAGGTTCAGCTGGTGCAGTCTGGAGCTGAGGTGAAGAAGCCTGGGGCCTCAGTGAA

GGTCTCCTGCAAGGCTTCT<u>GGTTACACCTTTACCAGCTATGGTATCAGC</u>TGGGTGCG

ACAGGCCCCTGGACAAGGGCTTGAGAGGATGGGA<u>TGGATCAGCGCTTACAATGGTA</u>

<u>ACACAAACTATGCACAGAAGTTCCAGGGC</u>AGAGTCACCATGACCACAGACACATCA

ACGACCACAGCCTACATGGAGCTGAGGAGCCTGAGATCTGACGACACGGCCGTGTA

TTACTGTGCGAGA<u>GATCAAGATTACTATGATAGTAGTGGTTGGGGCCAC</u>TGGGGCCA

GGGAACCCTGGTCACCGTCTCCTCA

A13 LC (SEQ ID NO: 193)

TCCTATGAGCTGACTCAGCCACCCTCAGTGTCCGTGTCCCCAGGACAGACAGCCAGC

ATCACCTGC<u>TCTGGAGATAAATTGGGGGATAAATATGTTTGTT</u>GGTATCAGCAGAAG

CCAGGCCAGTCCCCTGAACTGGTCATCTAT<u>CTAGATAACAAGCGGCCCTCA</u>GGGATC

CCTGAGCGATTCTCTGGCTCCAACTCTGGGAACACAGCCACTCTGACCATCAGCGGG

ACCCAGGCTATGGATGAGGCTGACTATTACTGT<u>CAGGCGTGGGACAGCAGCACGGT</u>

ATTCGGCGGAGGGACCAAACTGACCGTCCTG

A14 HC (SEQ ID NO: 210)

CAGGTTCAGCTGGTGCAATCTGGAGCTGAGGTGAAGAAGCCTGGGGCCTCAGTGAA

GGTCTCCTGCAAGACTTCT<u>GGTTACACCTTTACCAGCTATGGTATCAGC</u>TGGGTGCG

ACAGGCCCCTGGACAAGGGCTTGAGTGGATGGGA<u>TGGATCAGCCCTTACAATGGTA</u>

<u>ACACAAACTATGCACAGAAGTTCCAGGGC</u>AGAGTCACCATGACCACAGACAAATCC

ACGAGCACAGCCTACATGGAGCTGAGGAGCCTGCGATCTGACGACACGGCCGTGTA

TTACTGTGCGAGA<u>GATCAAGATTACTATGATAGTAGTGGTTGGGACCCC</u>TGGGGCCA

GGGAACCCTGGTCACCGTCTCCTCG

-continued

A14 LC
(SEQ ID NO: 209)
TCCTATGAGCTGACTCAGCCACCCTCAGTGTCCGTGTCCCCAGGACAGACAGCCTCC

ATCACCTGCTCTGGAGATAAATTGGGGGATAAATATGCTTTCTGGTATCAGCAGAAG

CCAGGCCAGTCCCCTGTGCTGGTCTTCTATCATGATACCAAGCGGCCCTCAGGGATC

CCTGAGCGATTCTCTGGCTCCAACTCTGGGAACACAGCCACTCTGACCATCAGCGGG

ACCCAGGCTATGGATGAGGCTGACTATCACTGTCAGGCGTGGGACAGCAGCACGGT

CTTCGGCGGAGGGACCAAGCTGACCGTCCTAC

Antibodies A1-A14 Amino Acid Sequences, Light Chain Variable Regions. CDR Regions are Shaded and Underlined; the Intervening Segments or Regions are Referred to as Framework (FR) Herein.

A1
(SEQ ID NO: 9)
SYEVTQAPSVSVSPGQTASITCSGDKLGDKYACWYQQKPGQSPVLVIYQD
SKRPSGIPERFSGSNSGNTATLTISGTQAMDEADYYCQAWDSSTAVFGGG
TKLTVL

A2
(SEQ ID NO: 25)
DIQMTQSPSSLSASVGDRVTITCRASQGIRNNLGWYQQKPGKAPKRLIYA
ASSLQSGVPSRFSGSGSGTEFTLTISSLQPEDFTTYYCLQHNSYPWTFGQ
GTKVEIK

A3
(SEQ ID NO: 41)
DIQMTQSPSSLSASVGDRVTITCRASQGIRNDLGWYQQKPGKAPKRLIYA
ASSLQSGVPSRFSGSGSGTEFTLTISSLQPEDFATYYCRQQNTYPLTFGG
GTKVEIK

A4
(SEQ ID NO: 57)
DIVMTQSPLSLPVTPGEPASISCRSSQSLLHSTGYNYLDWYLQKPGQSPQ
LLIYLGSFRASGVPDRFSGSGSGTDFTLKISRVEAEDVGVYYCMQALQTP
CSFGQGTKLEIK

A5
(SEQ ID NO: 73)
DIVMTQSPDSLAVSLGERATITCKSSQSILYSSNNKKYLVWYQQKPGQPP
KLIIYWTSMRESGVPDRFSGSGSGTDFTLTINSLQAEDVAVYYCQQYYST
PWTFGQGTKVEIK

A6
(SEQ ID NO: 89)
DIQMTQSPSSLSASVGDRVTITCRASQSISNYLNWYQQRPGKAPKLLIYA
TSSLQSGVPSRFSGSGSGTDFTLTISSLQPEDFVSYYCQQSYSISPTFGG
GTKVENK

A7
(SEQ ID NO: 105)
DIQMTQSPSSLSASVGDRVTITCRAGQGIRNDLVWYQQKPGKAPKRLIYA
ASSLQSGVPSRFSGSGSGTEFTLTISSLQPEDFATYYCLQHNTYPFTFGP
GTKVDIK

A8
(SEQ ID NO: 121)
DIVMTQSPDSLAVSLGERATITCKSSQSILYSSNNKKYLVWYQQKPGQPP
KLIIYWTSMRESGVPDRFSGSGSGTDFTLTISSLQAEDVAVYYCQQYYST
PWTFGQGTKVEIK

A9
(SEQ ID NO: 137)
DIQMTQSPSSLSASVGDRVTITCRASQGIRNNLGWYQQKPGKAPKRLIYA
ASSLQSGVPSRFSGSGSGTEFTLTISSLQPEDFTTYYCLQHNSYPWTFGQ
GTKVEIK

-continued

A10
(SEQ ID NO: 153)
SYELTQPPSVSVSPGQTASITCSGEKWGEKYACWYQQKPGQSPVLVIYQD
TKRPSGIPERFSGSISGNTATLTISGTQAMDEADYYCQAWDRSTVFGGGT
KLTVL

A11
(SEQ ID NO: 169)
SYELTQPPSVSVSPGQTASITCSGDKLGDKFAFWYQLKPGQSPVLVIYQD
NKRPSGIPERFSGSNSGNTATLTISGTQAMDAADFYCQAWDSSTVVFGGG
TKLTVL

A12
(SEQ ID NO: 185)
DIQMTQSPSSLSASVGDRVTITCRASQGIRNDLGWYQQKPGKAPKRLIYA
ASSLQSGVPSRFSGSGSGTEFTLTISSLQPEDCATYYCLQHNSYTWTFGQ
GTKVEIK

A13
(SEQ ID NO: 201)
SYELTQPPSVSVSPGQTASITCSGDKLGDKYVCWYQQKPGQSPELVIYLD
NKRPSGIPERFSGSNSGNTATLTISGTQAMDEADYYCQAWDSSTVFGGGT
KLTVL

A14
(SEQ ID NO: 217)
SYELTQPPSVSVSPGQTASITCSGDKLGDKYAFWYQQKPGQSPVLVFYHD
TKRPSGIPERFSGSNSGNTATLTISGTQAMDEADYHCQAWDSSTVFGGGT
KLTVL

Antibodies A1-A14, Amino Acid Sequences of Heavy Chain Variable Regions. CDR Regions are Shaded and Underlined, the Other Regions are Referred to as Framework (FR) Herein.

A1
(SEQ ID NO: 10)
QVQLVQSGAEVKKPGASVKVSCKASGYTFTSYGLSWVRQAPGQGLEWMGW
IIPYNGNTNSAQKLQGRVTMTTDTSTSTAYMELRSLRSDDTAVYFCARDR
DYGVNYDAFDIWGQGTMVTVSS

A2
(SEQ ID NO: 26)
QVQLVESGGGVVQPGRSLRLSCAASGFTFSSYGMHWVRQAPGKGLEWVAV
IWYDGSNKYHADSVKGRFTISRDNSKNTLYLQVNSLRAEDTAVYYCVRSR
NWNYDNYYYGLDVWGQGTTVTVSS

A3
(SEQ ID NO: 42)
EVQLVESGGGLVQPGGSLRLSCAASGFTFSSYWMSWVRQAPGKGLECVAN
IKQDGSEEYYVDSVKGRFTISRDNAKNSLYLQMNSLRAEDTAVYYCARGS
SSWYYYNYGMDVWGQGTTVTVSS

A4
(SEQ ID NO: 58)
QVQLVQSGAEVKKPGASVKVSCKASGYTFTGYYIHWVRQAPGQGLEWMGW
INPNSGGTNYAQKFQGRVTMTRDTSISTAYMELSRLRSDDTAVYFCARDS
GYSSSWHFDYWGQGTLVTVSS

-continued

A5
(SEQ ID NO: 74)
QVQLQESGPGLVKPSETLSLTCTVSGGSINSFYWSWIRQPPGKGLEWIGY
IYYSGSTNYNPSLKSRVTISVDTSKTQFSLKLSSVTAADTAVYYCARDSI
AAPFDYWGQGTLVTVSS

A6
(SEQ ID NO: 90)
QVQLQQWGAGLLKPSETLSLTCAVYGGSFSAYYWSWIRQPPGKGLEWIGE
INHSGGTNYNPSLKSRVTISVDTSKNQFSLKLSSVTAADTAVYYCARVQW
LELAYFDYWGQGTLVTVSS

A7
(SEQ ID NO: 106)
QVQLVDSGGGVVQPGRSLRLSCAASGFTFISYGMHWVRQAPGKGLEWVAV
IWYDGSTEYYADSVKGRFTISRDNSKNTLYLQMNSLRAEDTAVYYCARER
QWLYHYGMDVWGQGTTVTVSS

A8
(SEQ ID NO: 122)
QVQLQESGPGLVKPSETLSLTCTVSGGSINSFYWSWIRQPPGKGLEWIGY
IYYSGSTNYNPSLKRRVTISVDTSKTQFSLKLSSVTAADTAVYYCARDSI
AAPFDYWGQGTLVTVSS

A9
(SEQ ID NO: 138)
QVQLVESGGGVVQPGRSLRLSCAASGFTFSSYGMHWVRQAPGKGLEWVAV
IWYDGSNKYHADSVKGRFTISRDNSKNTLYLQVNSLRAEDTAVYYCVRSR
NWNYDNYYYGLDVWGQGTTVTVSS

A10
(SEQ ID NO: 154)
EVQLVQSGAEVKKPGESLKISCQGSGYSFTSYWIGWVRQMPGKGLEWMGI
IYPGDSDTRYSPSFQGQVTISADKSISTAYLQWSSLKASDTAMYYCARQG
LGFDYWGQGTLVTVSS

A11
(SEQ ID NO: 170)
QVQLQESGPGLVKPSQTLSLTCTVSGGSISSGGYYWSWIRQHPGKGLEWI
GYISYSGSTYYNPSLKRVTISVDTSKNQFSLKLNSVTAADTAVYYCARA
YGDYRGWFDPWGQGTLVTVSS

A12
(SEQ ID NO: 186)
QVQLVESGGGVVQPGRSLRLSCVASGFTFSAYGMHWVRQAPGKGLEWVAV
IWYDGSNKYYADSVKGRFIISRDNSKNTLYLQMNSLRAEDTAVYYCARSR
NWNYDSYQYGLDVWGQGTTVTVSS

A13
(SEQ ID NO: 202)
QVQLVQSGAEVKKPGASVKVSCKASGYTFTSYGISWVRQAPGQGLERMGW
ISAYNGNTNYAQKFQGRVTMTTDTSTTTAYMELRSLRSDDTAVYYCARDQ
DYYDSSGWGHWGQGTLVTVSS

A14
(SEQ ID NO: 218)
QVQLVQSGAEVKKPGASVKVSCKTSGYTFTSYGISWVRQAPGQGLEWMGW
ISPYNGNTNYAQKFQGRVTMTTDKSTSTAYMELRSLRSDDTAVYYCARDQ
DYYDSSGWDPWGQGTLVTVSS

CDR consensus sequences for Antibodies A1-A14.

| Light Chain | CDR1 Sequence |
| --- | --- |
| L4 | RSSQSLLHSTGYN-YLD (SEQ ID NO: 253) |
| L5, L8 | KSSQSILYSSNNKKYLV (SEQ ID NO: 75) |
| CONSENSUS: | $X_1SSQSX_2LX_3SX_4X_5X_6X_7X_8YLX_9$ (SEQ ID NO: 115) |

$X_1$ is an arginine residue or a lysine residue,
$X_2$ is a leucine residue or a isoleucine residue,
$X_3$ is a histidine residue or a tyrosine residue,
$X_4$ is a threonine residue or a serine residue,
$X_5$ is a glycine residue or an asparagine residue,
$X_6$ is a tyrosine residue or an asparagine residue,
$X_7$ is an asparagine residue or a lysine residue,
$X_8$ is a lysine residue or no residue,
$X_9$ is an aspartate residue or a valine residue

| | |
| --- | --- |
| L2, L9 | RASQGIRNNLG (SEQ ID NO: 27) |
| L3, L12 | RASQGIRNDLG (SEQ ID NO: 43) |
| L6 | RASQSISNYLN (SEQ ID NO: 91) |
| L7 | RAGQGIRNDLV (SEQ ID NO: 107) |
| CONSENSUS: | $RAX_{10}QX_{11}IX_{12}NX_{13}LX_{14}$ (SEQ ID NO: 116) |

$X_{10}$ is a serine residue or a glycine residue,
$X_{11}$ is a serine residue or a glycine residue,
$X_{12}$ is a serine residue or an arginine residue,
$X_{13}$ is a tyrosine residue, an aspartate residue, or an asparagine residue
$X_{14}$ is an aspartate residue, a valine residue, or a glycine residue

| | |
| --- | --- |
| L1 | SGDKLGDKYAC (SEQ ID NO: 11) |
| L10 | SGEKWGEKYAC (SEQ ID NO: 155) |
| L11 | SGDKLGDKFAF (SEQ ID NO: 171) |
| L13 | SGDKLGDKYVC (SEQ ID NO: 203) |
| L14 | SGDKLGDKYAF (SEQ ID NO: 219) |
| CONSENSUS: | $SGX_{15}KX_{16}GX_{17}KX_{18}X_{19}X_{20}$ (SEQ ID NO: 123) |

$X_{15}$ is a glutamate residue or an aspartate residue,
$X_{16}$ is a tryptophan residue or a leucine residue,
$X_{17}$ is a glutamate residue or an aspartate residue,
$X_{18}$ is a tyrosine residue or a phenylalanine residue,
$X_{19}$ is an alanine residue or a valine residue,
$X_{20}$ is a cysteine residue or a phenylalanine residue

| Light Chain | CDR2 Sequence |
| --- | --- |
| L2 | ATSSLQS (SEQ ID NO: 92) |
| L3, L6, L7, L9, L12 | AASSLQS (SEQ ID NO: 44) |
| L5, L8 | WTSMRES (SEQ ID NO: 76) |
| L4 | LGSFRAS (SEQ ID NO: 254) |
| CONSENSUS: | $X_{40}X_{41}SX_{42}X_{43}X_{44}S$ (SEQ ID NO: 124) |

$X_{40}$ is an alanine residue, a tryptophan residue, or a leucine residue,
$X_{41}$ is a threonine residue, an alanine residue, or a glycine residue,
$X_{42}$ is a serine residue, a methionine residue, or a phenylalanine residue,
$X_{43}$ is a leucine residue or an arginine residue,
$X_{44}$ is a glutamine residue, a glutamate residue, or an alanine residue

| | |
| --- | --- |
| L10 | QDTKRPS (SEQ ID NO: 156) |
| L11 | QDNKRPS (SEQ ID NO: 172) |

| | |
|---|---|
| L1 | QDSKRPS (SEQ ID NO: 12) |
| L13 | LDNKRPS (SEQ ID NO: 204) |
| L14 | HDTKRPS (SEQ ID NO: 220) |
| CONSENSUS: | $X_{45}DX_{46}KRPS$ (SEQ ID NO: 128) |

$X_{45}$ is a glutamine residue, a leucine residue, or a histidine residue,
$X_{46}$ is a threonine residue, an asparagine residue, or a serine residue

| Light Chain | CDR3 Sequence |
|---|---|
| L1 | QAWDSSTAV (SEQ ID NO: 13) |
| L10 | QAWDRST-V (SEQ ID NO: 157) |
| L11 | QAWDSSTVV (SEQ ID NO: 173) |
| L13, L14 | QAWDSSTV- (SEQ ID NO: 205) |
| L2 | LQHNSYPWT (SEQ ID NO: 29) |
| L7 | LQHNTYPFT (SEQ ID NO: 109) |
| L9 | LQHNSYPWT (SEQ ID NO: 141) |
| L12 | LQHNSYTWT (SEQ ID NO: 189) |
| CONSENSUS: | $LQHNX_{81}YX_{82}X_{83}T$ (SEQ ID NO: 131) |

$X_{81}$ is a threonine residue or a serine residue,
$X_{82}$ is a proline residue or a threonine residue,
$X_{83}$ is a phenylalanine residue or a tryptophan residue

| | |
|---|---|
| L3 | RQQNTYPLT (SEQ ID NO: 45) |
| L4 | MQALQTPCS (SEQ ID NO: 255) |
| L5 | QQYYSTPWT (SEQ ID NO: 77) |
| L6 | QQSYSISPT (SEQ ID NO: 93) |
| L8 | QQYYSTPWT (SEQ ID NO: 125) |
| CONSENSUS: | $X_{73}QX_{74}X_{75}X_{76}X_{77}X_{78}X_{79}X_{80}$ (SEQ ID NO: 132) |

$X_{73}$ is a methionine residue, a glutamine residue, or an arginine residue,
$X_{74}$ is an alanine residue, a tyrosine residue, a glutamine residue, or a serine residue,
$X_{75}$ is a leucine residue, a tyrosine residue, or an asparagine residue,
$X_{76}$ is a glutamine residue, a serine residue, or a threonine residue,
$X_{77}$ is a threonine residue, a tyrosine residue, or an isoleucine residue,
$X_{78}$ is a proline residue or a serine residue,
$X_{79}$ is a cysteine residue, a tryptophan residue, a leucine residue, or a proline residue,
$X_{80}$ is a serine residue or a threonine residue

| Heavy Chain | CDR1 Sequence |
|---|---|
| H5 | GGSINS--FYWS (SEQ ID NO: 78) |
| H6 | GGSFSA--YYWS (SEQ ID NO: 94) |
| H8 | GGSINS--FYWS (SEQ ID NO: 126) |
| H11 | GGSISSGGYYWS (SEQ ID NO: 174) |
| CONSENSUS: | $GGSX_{21}X_{22}X_{23}X_{24}X_{25}X_{26}YWS$ (SEQ ID NO: 252) |

$X_{21}$ is an isoleucine residue or a phenylalanine residue
$X_{22}$ is an asparagine residue or a serine residue
$X_{23}$ is a serine residue or an alanine residue
$X_{24}$ is a glycine residue or no residue
$X_{25}$ is a glycine residue or no residue
$X_{26}$ is a phenylalanine residue or a tyrosine residue

| | |
|---|---|
| H7 | GFTFISYGMH (SEQ ID NO: 110) |
| H4 | GYTFTGYYIH (SEQ ID NO: 256) |
| H2, H9 | GFTFSSYGMH (SEQ ID NO: 30) |
| H10 | GYSFTSYWIG (SEQ ID NO: 158) |
| CONSENSUS: | $GX_{27}X_{28}FX_{29}X_{30}YX_{31}X_{32}X_{33}$ (SEQ ID NO: 257) |

$X_{27}$ is a tyrosine residue or a phenylalanine residue,
$X_{28}$ is a threonine residue or a serine residue,
$X_{29}$ is a threonine residue, a serine residue, or an isoleucine residue,
$X_{30}$ is a glycine residue or a serine residue,
$X_{31}$ is a tyrosine residue, a glycine residue, or a tryptophan residue,
$X_{32}$ is an isoleucine residue or a methionine residue,
$X_{33}$ is a histidine residue or a glycine residue

| | |
|---|---|
| H13 | GYTFTSYGLS (SEQ ID NO: 62) |
| H12 | GFTFSAYGMH (SEQ ID NO: 190) |
| H3 | GFTFSSYWMS (SEQ ID NO: 46) |
| H1, H14 | GYTFTSYGIS (SEQ ID NO: 206) |
| CONSENSUS: | $GX_{34}TFX_{35}X_{36}YX_{37}X_{38}X_{39}$ (SEQ ID NO: 140) |

$X_{34}$ is a tyrosine residue or a phenylalanine residue,
$X_{35}$ is a threonine residue or a serine residue,
$X_{36}$ is a serine residue or an alanine residue,
$X_{37}$ is a glycine residue or a tryptophan residue,
$X_{38}$ is a leucine residue, a methionine residue, or an isoleucine residue,
$X_{39}$ is a serine residue or a histidine residue

| Heavy Chain | CDR2 Sequence |
|---|---|
| H11 | YISYSGSTYYNPSLKS (SEQ ID NO: 175) |
| H5 | YIYYSGSTNYNPSLKS (SEQ ID NO: 79) |
| H6 | EINHSGGTNYNPSLKS (SEQ ID NO: 95) |

| Heavy Chain | CDR2 Sequence |
|---|---|
| H8 | YIYYSGSTNYNPSLKR (SEQ ID NO: 127) |
| CONSENSUS: | $X_{47}IX_{48}X_{49}SGX_{50}TX_{51}YNPSLKX_{52}$ (SEQ ID NO: 142) |

$X_{47}$ is a tyrosine residue or a glutamate residue,
$X_{48}$ is a serine residue, a tyrosine residue, or an asparagine residue,
$X_{49}$ is a tyrosine residue or a histidine residue
$X_{50}$ is a serine residue or a glycine residue,
$X_{51}$ is a tyrosine residue or an asparagine residue,
$X_{52}$ is a serine residue or an arginine residue

| H2, H9 | VIWYDGSNKYHADSVKG (SEQ ID NO: 31) |
|---|---|
| H12 | VIWYDGSNKYYADSVKG (SEQ ID NO: 191) |
| H3 | NIKQDGSEEYYVDSVKG (SEQ ID NO: 47) |
| H7 | VIWYDGSTEYYADSVKG (SEQ ID NO: 111) |
| CONSENSUS: | $X_{53}IX_{54}X_{55}DGSX_{56}X_{57}YX_{58}X_{59}DSVKG$ (SEQ ID NO: 179) |

$X_{53}$ is an asparagine residue or a valine residue,
$X_{54}$ is a tryptophan residue or a lysine residue,
$X_{55}$ is a tyrosine residue or a glutamine residue,
$X_{56}$ is an asparagine residue, a glutamate residue, or a serine residue,
$X_{57}$ is a lysine residue or a glutamate residue,
$X_{58}$ is a histidine residue or a tyrosine residue,
$X_{59}$ is an alanine residue or a valine residue

| H4 | WINPNSGGTNYAQKFQG (SEQ ID NO: 258) |
|---|---|
| H1 | WITPYNGNTNSAQKLQG (SEQ ID NO: 63) |
| H13 | WISAYNGNTNYAQKFQG (SEQ ID NO: 207) |
| H14 | WISPYNGNTNYAQKFQG (SEQ ID NO: 259) |
| H10 | IIYPGDSDTRYSPSFQG (SEQ ID NO: 159) |
| CONSENSUS: | $X_{60}IX_{61}X_{62}X_{63}X_{64}X_{65}X_{66}TX_{67}X_{68}X_{69}X_{70}X_{71}X_{72}QG$ (SEQ ID NO:180) |

$X_{60}$ is a tryptophan residue or an isoleucine residue,
$X_{61}$ is an asparagine residue, an isoleucine residue, a serine residue, or a tyrosine residue,
$X_{62}$ is a proline residue or an alanine residue,
$X_{63}$ is an asparagine residue, a tyrosine residue, or a glycine residue,
$X_{64}$ is a serine residue, an asparagine residue, or an aspartate residue,
$X_{65}$ is a glycine residue or a serine residue,
$X_{66}$ is a glycine residue, an asparagine residue, or an aspartate residue,
$X_{67}$ is an asparagine residue or an arginine residue,
$X_{68}$ is a tyrosine residue or a serine residue,
$X_{69}$ is an alanine residue or a serine residue
$X_{70}$ is a glutamine residue or a proline residue,
$X_{71}$ is a lysine residue or a serine residue,
$X_{72}$ is a phenylalanine residue or a leucine residue

| Heavy Chain | CDR3 Sequence |
|---|---|
| H5, H8 | --DSIAAPFDY (SEQ ID NO: 80) |
| H6 | VQWLELAYFDY (SEQ ID NO: 96) |
| H10 | ----QGLGFDY (SEQ ID NO: 160) |
| CONSENSUS: | $X_{87}X_{88}X_{89}X_{90}X_{91}X_{92}X_{93}X_{94}FDY$ (SEQ ID NO: 187) |

$X_{87}$ is a valine residue or no residue,
$X_{88}$ is a glutamine residue or no residue,
$X_{89}$ is an aspartate residue, a tryptophan residue, or no residue,
$X_{90}$ is a serine residue, a leucine residue, or no residue,
$X_{91}$ is an isoleucine residue, a glutamate residue, or a glutamine residue,
$X_{92}$ is an alanine residue, a leucine residue, or a glycine residue,
$X_{93}$ is an alanine residue or a leucine residue,
$X_{94}$ is a proline residue, a tyrosine residue, or a glycine residue

| H13 | DQDYYDSSGW-GH (SEQ ID NO: 208) |
|---|---|
| H14 | DQDYYDSSGW-DP (SEQ ID NO: 224) |
| H11 | --AYGDYRGWFDP (SEQ ID NO: 176) |
| CONSENSUS: | $X_{95}X_{96}X_{97}YX_{98}DX_{99}X_{100}GWX_{101}X_{102}X_{103}$ (SEQ ID NO: 188) |

$X_{95}$ is an aspartate residue or no residue,
$X_{96}$ is a glutamine residue or no residue,
$X_{97}$ is an aspartate residue or an alanine residue,
$X_{98}$ is a tyrosine residue or a glycine residue,
$X_{99}$ is a serine residue or a tyrosine residue,
$X_{100}$ is a serine residue or an arginine residue,
$X_{101}$ is a phenylalanine residue or no residue,
$X_{102}$ is a glycine residue or an aspartate residue,
$X_{103}$ is a histidine residue or a proline residue

| H4 | ---DSGYSSSWHFDY- (SEQ ID NO: 260) |
|---|---|
| H1 | ---DRDYGVNYDAFDI (SEQ ID NO: 64) |
| H2 | -SRNWNYDNYYYGLDV (SEQ ID NO: 32) |
| H12 | -SRNWNYDSYQYGLDV (SEQ ID NO: 192) |
| H9 | -SRNWNYDNYYYGLDV (SEQ ID NO: 144) |
| H3 | GSSSWYY-YNGMDV- (SEQ ID NO: 261) |
| H7 | -ERQWLY--HYGMDV (SEQ ID NO: 112) |
| CONSENSUS: | $X_{104}X_{105}X_{106}X_{107}X_{108}X_{109}YX_{110}X_{111}X_{112}X_{113}X_{114}X_{115}X_{116}X_{117}X_{118}$ (SEQ ID NO: 249)) |

$X_{104}$ is a glycine residue or no residue
$X_{105}$ is a serine residue, a glutamate residue, or no residue
$X_{106}$ is an arginine residue, a serine residue, or no residue,
$X_{107}$ is an aspartate residue, an asparagine residue, a serine residue, or a glutamine residue
$X_{108}$ is a serine residue, an arginine residue, or a tryptophan residue,
$X_{109}$ is a glycine residue, an aspartate residue, an asparagine residue, a tyrosine residue, or a leucine residue, $X_{110}$ is a serine residue, a glycine residue, an aspartate residue, or no residue, $X_{111}$ is a serine residue, a valine residue, an asparagine residue, or a tyrosine residue, $X_{112}$ is a serine residue, an asparagine residue, a tyrosine residue, or a histidine residue $X_{113}$ is a tryptophan residue, a tyrosine residue, or a glutamine residue, $X_{114}$ is a histidine residue, an aspartate residue, a tyrosine residue, or no residue, $X_{115}$ is a phenylalanine residue, an alanine residue, or a glycine residue, $X_{116}$ an aspartate residue, a phenylalanine residue, a leucine residue, or a methionine residue $X_{117}$ a tyrosine residue, or an aspartate residue, $X_{118}$ is an isoleucine residue, a valine residue, or no residue In one embodiment, the present invention provides an antigen binding protein comprising a light chain variable domain comprising a sequence of amino acids that differs from the sequence of a light chain variable domain selected from the group consisting of L1 through L14 only at 15, 14, 13, 12, 11, 10, 9, 8, 7, 6, 5, 4, 3, 2, or 1 residues, wherein each such sequence difference is independently either a deletion, insertion, or substitution of one amino acid residue. In another embodiment, the light-chain variable domain comprises a sequence of amino acids that is at least 70%, 75%, 80%, 85%, 90%, 95%, 97%, or 99% identical to the sequence of a light chain variable domain selected from the group consisting of L1-L14. In another embodiment, the light chain variable domain comprises a sequence of amino acids that is encoded by a nucleotide sequence that is at least 70%, 75%, 80%, 85%, 90%, 95%, 97%, or 99% identical to a nucleotide sequence that encodes a light chain variable domain selected from the group consisting of L1-L14 (which includes L1, L2, L3, L4, L5, L6, L7, L8, L9, L10, L11, L12, L13, and L14). In another embodiment, the light chain variable domain comprises a sequence of amino acids that is encoded by a polynucleotide that hybridizes under moderately stringent conditions to the complement of a polynucleotide that encodes a light chain variable domain selected from the group consisting of L1-L14. In another embodiment, the light chain variable domain comprises a sequence of amino acids that is encoded by a polynucleotide that hybridizes under moderately stringent conditions to the complement of a polynucleotide that encodes a light chain variable domain selected from the group consisting of L1-L14. In another embodiment, the light chain variable domain comprises a sequence of amino acids that is encoded by a polynucleotide that hybridizes under moderately stringent conditions to a complement of a light chain polynucleotide of L1-L14.

In another embodiment, the present invention provides an antigen binding protein comprising a heavy chain variable domain comprising a sequence of amino acids that differs from the sequence of a heavy chain variable domain selected from the group consisting of H1-H14 only at 15, 14, 13, 12, 11, 10, 9, 8, 7, 6, 5, 4, 3, 2, or 1 residue(s), wherein each such sequence difference is independently either a deletion, insertion, or substitution of one amino acid residue. In another embodiment, the heavy chain variable domain comprises a sequence of amino acids that is at least 70%, 75%, 80%, 85%, 90%, 95%, 97%, or 99% identical to the sequence of a heavy chain variable domain selected from the group consisting of H1-H14. In another embodiment, the heavy chain variable domain comprises a sequence of amino acids that is encoded by a nucleotide sequence that is at least 70%, 75%, 80%, 85%, 90%, 95%, 97%, or 99% identical to a nucleotide sequence that encodes a heavy chain variable domain selected from the group consisting of H1-H14. In another embodiment, the heavy chain variable domain comprises a sequence of amino acids that is encoded by a polynucleotide that hybridizes under moderately stringent conditions to the complement of a polynucleotide that encodes a heavy chain variable domain selected from the group consisting of H1-H14. In another embodiment, the heavy chain variable domain comprises a sequence of amino acids that is encoded by a polynucleotide that hybridizes under moderately stringent conditions to the complement of a polynucleotide that encodes a heavy chain variable domain selected from the group consisting of H1-H14. In another embodiment, the heavy chain variable domain comprises a sequence of amino acids that is encoded by a polynucleotide that hybridizes under moderately stringent conditions to a complement of a heavy chain polynucleotide selected from SEQ ID NO:10, 26, 42, 58, 74, 90, 106, 122, 136, 154, 170, 186, 202, and 218.

Particular embodiments of antigen binding proteins of the present invention comprise one or more amino acid sequences that are identical to the amino acid sequences of one or more of the CDRs and/or FRs referenced herein for example, one or more CDR or FR from one or more of SEQ ID Nos: 9-16, 22, 25-32, 36, 41-48-57-62, 64, 73-80, 89-91, 93-96, 105-107, 109-112, 115, 116, 121-128, 131, 132, 134, 137-142, 144, 153-160, 169-176, 179, 180, 185-192, 201-208, 217-220, and 223. In one embodiment, the antigen binding protein comprises a light chain CDR1 sequence illustrated above. In another embodiment, the antigen binding protein comprises a light chain CDR2 sequence illustrated above. In another embodiment, the antigen binding protein comprises a light chain CDR3 sequence illustrated above. In another embodiment, the antigen binding protein comprises a heavy chain CDR1 sequence illustrated above. In another embodiment, the antigen binding protein comprises a heavy chain CDR2 sequence illustrated above. In another embodiment, the antigen binding protein comprises a heavy chain CDR3 sequence illustrated above. In another embodiment, the antigen binding protein comprises a light chain FR1 sequence illustrated above. In another embodiment, the antigen binding protein comprises a light chain FR2 sequence illustrated above. In another embodiment, the antigen binding protein comprises a light chain FR3 sequence illustrated above. In another embodiment, the antigen binding protein comprises a light chain FR4 sequence illustrated above. In another embodiment, the antigen binding protein comprises a heavy chain FR1 sequence illustrated above. In another embodiment, the antigen binding protein comprises a heavy chain FR2 sequence illustrated above. In another embodiment, the antigen binding protein comprises a heavy chain FR3 sequence illustrated above. In another embodiment, the antigen binding protein comprises a heavy chain FR4 sequence illustrated above.

In one embodiment, the present invention provides an antigen binding protein that comprises one or more CDR sequences that differ from a CDR sequence shown above by no more than 5, 4, 3, 2, or 1 amino acid residues.

In another embodiment, at least one of the antigen binding protein's CDR3 sequences is a CDR3 sequence from A1-A14, as shown in Table 1 or Table 2. In another embodiment, the antigen binding protein's light chain CDR3 sequence is a light chain CDR3 sequence from A1-A14 as shown Table 1 and the antigen binding protein's heavy chain CDR3 sequence is a heavy chain sequence from A1-A14 as shown in Table 2. In another embodiment, the antigen binding protein comprises 1, 2, 3, 4, or 5 CDR sequence(s) that each independently differs by 6, 5, 4, 3, 2, 1, or 0 single amino acid additions, substitutions, and/or deletions from a CDR sequence of A1-A14, and the antigen binding protein further comprises 1, 2, 3, 4, or 5 CDR sequence(s) that each independently differs by 6, 5, 4, 3, 2, 1, or 0 single amino acid additions, substitutions, and/or deletions from a CDR sequence.

The light chain CDR's of antibodies A1-A14 are shown below in Table 1, and the heavy chain CDR's of antibodies A1-A14 are shown below in Table 2.

TABLE 1

Light Chain

| Antibody | CDR1 | CDR2 | CDR3 |
|---|---|---|---|
| A1 | SGDKLGDKYAC (SEQ ID NO: 11) | QDSKRPS (SEQ ID NO: 12) | QAWDSSTAV (SEQ ID NO: 13) |
| A2 | RASQGIRNNLG (SEQ ID NO: 27) | AASSLQS (SEQ ID NO: 28) | LQHNSYPWT (SEQ ID NO: 29) |
| A3 | RASQGIRNDLG (SEQ ID NO: 43) | AASSLQS (SEQ ID NO: 44) | RQQNTYPLT (SEQ ID NO: 45) |
| A4 | RSSQSLLHSTGYNYLD (SEQ ID NO: 253) | LGSFRAS (SEQ ID NO: 254) | MQALQTPCS (SEQ ID NO: 255) |
| A5 | KSSQSILYSSNNKKYLV (SEQ ID NO: 75) | WTSMRES (SEQ ID NO: 76) | QQYYSTPWT (SEQ ID NO: 77) |
| A6 | RASQSISNYLN (SEQ ID NO: 91) | ATSSLQS (SEQ ID NO: 92) | QQSYSISPT (SEQ ID NO: 93) |
| A7 | RAGQGIRNDLV (SEQ ID NO: 107) | AASSLQS (SEQ ID NO: 44) | LQHNTYPFT (SEQ ID NO: 109) |
| A8 | KSSQSILYSSNNKKYLV (SEQ ID NO: 75) | WTSMRES (SEQ ID NO: 76) | QQYYSTPWT (SEQ ID NO: 125) |
| A9 | RASQGIRNNLG (SEQ ID NO: 27) | AASSLQS (SEQ ID NO: 44) | LQHNSYPWT (SEQ ID NO: 141) |
| A10 | SGEKWGEKYAC (SEQ ID NO: 155) | QDTKRPS (SEQ ID NO: 156) | QAWDRSTV (SEQ ID NO: 157) |
| A11 | SGDKLGDKFAF (SEQ ID NO: 171) | QDNKRPS (SEQ ID NO: 172) | QAWDSSTVV (SEQ ID NO: 173) |
| A12 | RASQGIRNDLG (SEQ ID NO: 43) | AASSLQS (SEQ ID NO: 44) | LQHNSYTWT (SEQ ID NO: 189) |
| A13 | SGDKLGDKYVC (SEQ ID NO: 203) | LDNKRPS (SEQ ID NO: 204) | QAWDSSTV (SEQ ID NO: 205) |
| A14 | SGDKLGDKYAF (SEQ ID NO: 219) | HDTKRPS (SEQ ID NO: 220) | QAWDSSTV (SEQ ID NO: 205) |

TABLE 2

Heavy Chain

| Antibody | CDR1 | CDR2 | CDR3 |
|---|---|---|---|
| A1 | GYTFTSYGLS (SEQ ID NO: 62) | WIIPYNGNTNSAQKLQG (SEQ ID NO: 63) | DRDYGVNYDAFDI (SEQ ID NO: 64) |
| A2 | GFTFSSYGMH (SEQ ID NO: 30) | VIWYDGSNKYHADSVKG (SEQ ID NO: 31) | SRNWNYDNYYYGLDV (SEQ ID NO: 32) |
| A3 | GFTFSSYWMS (SEQ ID NO: 46) | NIKQDGSEEYYVDSVKG (SEQ ID NO: 47) | GSSSWYYYNYGMDV (SEQ ID NO: 48) |
| A4 | GYTFTGYYIH (SEQ ID NO: 256) | WINPNSGGTNYAQKFQG (SEQ ID NO: 258) | DSGYSSSWHFDY (SEQ ID NO: 260) |
| A5 | GGSINSFYWS (SEQ ID NO: 78) | YIYYSGSTNYNPSLKS (SEQ ID NO: 79) | DSIAAPFDY (SEQ ID NO: 80) |

TABLE 2-continued

Heavy Chain

| Antibody | CDR1 | CDR2 | CDR3 |
|---|---|---|---|
| A6 | GGSFSAYYWS (SEQ ID NO: 94) | EINHSGGTNYNPSLKS (SEQ ID NO: 95) | VQWLELAYFDY (SEQ ID NO: 96) |
| A7 | GFTFISYGMH (SEQ ID NO: 110) | VIWYDGSTEYYADSV KG (SEQ ID NO: 111) | ERQWLYHYGMDV (SEQ ID NO: 112) |
| A8 | GGSINSFYWS (SEQ ID NO: 126) | YIYYSGSTNYNPSLKR (SEQ ID NO: 127) | DSIAAPFDY (SEQ ID NO: 80) |
| A9 | GFTFSSYGMH (SEQ ID NO: 30) | VIWYDGSNKYHADSV KG (SEQ ID NO: 31) | SRNWNYDNYYYGL DV (SEQ ID NO: 144) |
| A10 | GYSFTSYWIG (SEQ ID NO: 158) | IIYPGDSDTRYSPSFQG (SEQ ID NO: 159) | QGLGFDY (SEQ ID NO: 160) |
| A11 | GGSISSGGYYWS (SEQ ID NO: 174) | YISYSGSTYYNPSLKS (SEQ ID NO: 175) | AYGDYRGWFDP (SEQ ID NO: 176) |
| A12 | GFTFSAYGMH (SEQ ID NO: 190) | VIWYDGSNKYYADSV KG (SEQ ID NO: 191) | SRNWNYDSYQYGL DV (SEQ ID NO: 192) |
| A13 | GYTFTSYGIS (SEQ ID NO: 206) | WISAYNGNTNYAQKF QG (SEQ ID NO: 207) | DQDYYDSSGWGH (SEQ ID NO: 208) |
| A14 | GYTFTSYGIS (SEQ ID NO: 206) | WISPYNGNTNYAQKF QG (SEQ ID NO: 259) | DQDYYDSSGWDP (SEQ ID NO: 224) |

The nucleotide sequences of A1-A14, or the amino acid sequences of A1-A14, can be altered, for example, by random mutagenesis or by site-directed mutagenesis (e.g., oligonucleotide-directed site-specific mutagenesis) to create an altered polynucleotide comprising one or more particular nucleotide substitutions, deletions, or insertions as compared to the non-mutated polynucleotide. Examples of techniques for making such alterations are described in Walder et al., 1986, Gene 42:133; Bauer et al. 1985, Gene 37:73; Craik, BioTechniques, January 1985, 12-19; Smith et al., 1981, *Genetic Engineering: Principles and Methods*, Plenum Press; and U.S. Pat. Nos. 4,518,584 and 4,737,462. These and other methods can be used to make, for example, derivatives of anti-activin A antibodies that have a desired property, for example, increased affinity, avidity, or specificity for activin A, increased activity or stability in vivo or in vitro, or reduced in vivo side-effects as compared to the underivatized antibody.

Other derivatives of anti-activin A antibodies within the scope of this invention include covalent or aggregative conjugates of anti-activin A antibodies, or fragments thereof, with other proteins or polypeptides, such as by expression of recombinant fusion proteins comprising heterologous polypeptides fused to the N-terminus or C-terminus of an anti-activin A antibody polypeptide. For example, the conjugated peptide may be a heterologous signal (or leader) polypeptide, e.g., the yeast alpha-factor leader, or a peptide such as an epitope tag. Antigen binding protein-containing fusion proteins can comprise peptides added to facilitate purification or identification of antigen binding protein (e.g., poly-His). An antigen binding protein also can be linked to the FLAG peptide Asp-Tyr-Lys-Asp-Asp-Asp-Asp-Lys (DYKDDDDK) (SEQ ID NO:226) as described in Hopp et al., *Bio/Technology* 6:1204, 1988, and U.S. Pat. No. 5,011, 912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more antigen binding proteins may be employed as activin A antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have activin A binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 *Curr. Prot.s in Immunol.*, Suppl. 4, pages 10.19.1-10.19.11.

One embodiment of the present invention is directed to a dimer comprising two fusion proteins created by fusing an activin A binding fragment of an anti-activin A antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of an anti-activin A antibody may be substituted for the variable portion of an antibody heavy and/or light chain.

Alternatively, the oligomer is a fusion protein comprising multiple antigen binding proteins, with or without peptide linkers (spacer peptides). Among the suitable peptide linkers are those described in U.S. Pat. Nos. 4,751,180 and 4,935,233.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an anti-activin A antibody fragment or derivative fused to a leucine zipper peptide are expressed in suitable host cells, and the soluble oligomeric anti-activin A antibody fragments or derivatives that form are recovered from the culture supernatant.

In one aspect, the present invention provides antigen binding proteins that interfere with the binding of activin A to an activin A receptor. Such antigen binding proteins can be made against activin A, or a fragment, variant or derivative thereof, and screened in conventional assays for the ability to interfere with binding of activin A to activin A receptor. Examples of suitable assays are assays that test the antigen binding proteins for the ability to inhibit binding of activin A to cells expressing activin A receptor, or that test antigen binding proteins for the ability to reduce a biological or cellular response that results from the binding of activin A to cell surface activin A receptors. For example, as set forth in FIG. 10, as well as the Examples below, antibodies can be screened according to their ability to bind to immobilized antibody surfaces (activin A and/or activin B).

Antigen-binding fragments of antigen binding proteins of the invention may be produced by conventional techniques. Examples of such fragments include, but are not limited to, Fab and F(ab')$_2$ fragments. Antibody fragments and derivatives produced by genetic engineering techniques also are contemplated.

Additional embodiments include chimeric antibodies, e.g., humanized versions of non-human (e.g., murine) monoclonal antibodies. Such humanized antibodies may be prepared by known techniques, and offer the advantage of reduced immunogenicity when the antibodies are administered to humans. In one embodiment, a humanized monoclonal antibody comprises the variable domain of a murine antibody (or all or part of the antigen binding site thereof) and a constant domain derived from a human antibody. Alternatively, a humanized antibody fragment may comprise the antigen binding site of a murine monoclonal antibody and a variable domain fragment (lacking the antigen-binding site) derived from a human antibody. Procedures for the production of chimeric and further engineered monoclonal antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139. In one embodiment, the chimeric antibody is a CDR grafted antibody. Techniques for humanizing antibodies are discussed in, e.g., U.S. Pat. Nos. 5,869,619, 5,225,539, 5,821,337, 5,859,205, 6,881,557, Padlan et al., 1995, FASEB J. 9:133-39, and Tamura et al., 2000, J. Immunol. 164:1432-41.

Procedures have been developed for generating human or partially human antibodies in non-human animals. For example, mice in which one or more endogenous immunoglobulin genes have been inactivated by various means have been prepared. Human immunoglobulin genes have been introduced into the mice to replace the inactivated mouse genes. Antibodies produced in the animal incorporate human immunoglobulin polypeptide chains encoded by the human genetic material introduced into the animal. In one embodiment, a non-human animal, such as a transgenic mouse, is immunized with an activin A polypeptide, such that antibodies directed against the activin A polypeptide are generated in the animal.

One example of a suitable immunogen is a soluble human activin A, such as a polypeptide comprising the extracellular domain of the protein of SEQ ID NO:225, or other immunogenic fragment of the protein of SEQ ID NO:225. Examples of techniques for production and use of transgenic animals for the production of human or partially human antibodies are described in U.S. Pat. Nos. 5,814,318, 5,569,825, and 5,545,806, Davis et al., 2003, Production of human antibodies from transgenic mice in Lo, ed. Antibody Engineering: Methods and Protocols, Humana Press, NJ:191-200, Kellermann et al., 2002, *Curr Opin Biotechnol.* 13:593-97, Russel et al., 2000, *Infect Immun.* 68:1820-26, Gallo et al., 2000, *Eur J Immun.* 30:534-40, Davis et al., 1999, *Cancer Metastasis Rev.* 18:421-25, Green, 1999, *J Immunol Methods.* 231:11-23, Jakobovits, 1998, *Advanced Drug Delivery Reviews* 31:33-42, Green et al., 1998, *J Exp Med.* 188:483-95, Jakobovits A, 1998, *Exp. Opin. Invest. Drugs.*

7:607-14, Tsuda et al., 1997, *Genomics*. 42:413-21, Mendez et al., 1997, *Nat Genet*. 15:146-56, Jakobovits, 1994, *Curr Biol*. 4:761-63, Arbones et al., 1994, *Immunity*. 1:247-60, Green et al., 1994, *Nat Genet*. 7:13-21, Jakobovits et al., 1993, Nature. 362:255-58, Jakobovits et al., 1993, *Proc Natl Acad Sci USA*. 90:2551-55. Chen, J., M. Trounstine, F. W. Alt, F. Young, C. Kurahara, J. Loring, D. Huszar. *Inter'l Immunol.* 5 (1993): 647-656, Choi et al., 1993, *Nature Genetics* 4: 117-23, Fishwild et al., 1996, *Nature Biotech.* 14: 845-51, Harding et al., 1995, Annals of the New York Academy of Sciences, Lonberg et al., 1994, Nature 368: 856-59, Lonberg, 1994, Transgenic Approaches to Human Monoclonal Antibodies in Handbook of Experimental Pharmacology 113: 49-101, Lonberg et al., 1995, Internal Review of Immunology 13: 65-93, Neuberger, 1996, *Nature Biotechnology* 14: 826, Taylor et al., 1992, *Nucleic Acids Res.* 20: 6287-95, Taylor et al., 1994, *Inter'l Immunol.* 6: 579-91, Tomizuka et al., 1997, *Nature Genetics* 16: 133-43, Tomizuka et al., 2000, *Pro. Nat'l Acad. Sci. USA* 97: 722-27, Tuaillon et al., 1993, *Pro. Nat'l Acad. Sci. USA* 90: 3720-24, and Tuaillon et al., 1994, *J. Immunol.* 152: 2912-20.

In another aspect, the present invention provides monoclonal antibodies that bind to activin A. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In one embodiment, a hybridoma cell line is produced by immunizing an animal (e.g., a transgenic animal having human immunoglobulin sequences) with an activin A immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds an activin A polypeptide. Such hybridoma cell lines, and anti-activin A monoclonal antibodies produced by them, are encompassed by the present invention.

Monoclonal antibodies secreted by a hybridoma cell line can be purified using any technique known in the art. Hybridomas or mAbs may be further screened to identify mAbs with particular properties, such as the ability to block an activin A-induced activity. Examples of such screens are provided in the examples below.

Molecular evolution of the complementarity determining regions (CDRs) in the center of the antibody binding site also has been used to isolate antibodies with increased affinity, for example, antibodies having increased affinity for c-erbB-2, as described by Schier et al., 1996, *J. Mol. Biol.* 263:551. Accordingly, such techniques are useful in preparing antibodies to activin A.

Antigen binding proteins directed against an activin A can be used, for example, in assays to detect the presence of activin A polypeptides, either in vitro or in vivo. The antigen binding proteins also may be employed in purifying activin A proteins by immunoaffinity chromatography. Those antigen binding proteins that additionally can block binding of activin A may be used to inhibit a biological activity that results from such binding. Blocking antigen binding proteins can be used in the methods of the present invention. Such antigen binding proteins that function as activin A antagonists may be employed in treating any activin A-related condition, including but not limited to cachexia. In one embodiment, a human anti-activin A monoclonal antibody generated by procedures involving immunization of transgenic mice is employed in treating such conditions.

Although human, partially human, or humanized antibodies will be suitable for many applications, particularly those involving administration of the antibody to a human subject, other types of antigen binding proteins will be suitable for certain applications. The non-human antibodies of the invention can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired. In one embodiment, a non-human antibody of the invention is administered to a non-human subject. In another embodiment, the non-human antibody does not elicit an immune response in the non-human subject. In another embodiment, the non-human antibody is from the same species as the non-human subject, e.g., a mouse antibody of the invention is administered to a mouse. An antibody from a particular species can be made by, for example, immunizing an animal of that species with the desired immunogen (e.g., a soluble activin A polypeptide) or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or Bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (*Cloning Vectors: A Laboratory Manual*, Elsevier, New York, 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of activin A bound thereto. Polypeptides contemplated for use herein include substantially homogeneous recombinant mammalian anti-activin A antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-activin A antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

In one aspect, the present invention provides antigen-binding fragments of an anti-activin A antibody of the invention. Such fragments can consist entirely of antibody-derived sequences or can comprise additional sequences. Examples of antigen-binding fragments include Fab, F(ab')2, single chain antibodies, diabodies, triabodies, tetrabodies, and domain antibodies. Other examples are provided in Lunde et al., 2002, Biochem. Soc. Trans. 30:500-06.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol Biol.* 178:379-87. Single chain antibodies derived from antibodies provided herein include, but are not limited to, scFvs comprising the variable domain combinations L1H1, L2H2, L3H3, L4H4, L5H5, L6H6, L7H7, L8H8, L9H9, L10H10, L11H11, L12H12, L13H13, and L14H14 are encompassed by the present invention.

Antigen binding proteins (e.g., antibodies, antibody fragments, and antibody derivatives) of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al., 2002, *Methods Mol. Biol.* 178:303-16.

In one embodiment, an antigen binding protein of the invention comprises the IgG1 heavy chain domain of any of A1-A14 (H1-H14) or a fragment of the IgG1 heavy chain domain of any of A1-A14 (H1-H14). In another embodiment, an antigen binding protein of the invention comprises the kappa light chain constant chain region of A1-A14 (L1-L14), or a fragment of the kappa light chain constant region of A1-A14 (L1-L14). In another embodiment, an antigen binding protein of the invention comprises both the IgG1 heavy chain domain, or a fragment thereof, of A1-A14 (L1-L14) and the kappa light chain domain, or a fragment thereof, of A1-A14 (L1-L14).

Accordingly, the antigen binding proteins of the present invention include those comprising, for example, the variable domain combinations L1H1, L2H2, L3H3, L4H4, L5H5, L6H6, L7H7, L8H8, L9H9, L10H10, L11H11, L12H12, L13H13, and L14H14, having a desired isotype (for example, IgA, IgG1, IgG2, IgG3, IgG4, IgM, IgE, and IgD) as well as Fab or F(ab')2 fragments thereof. Moreover, if an IgG4 is desired, it may also be desired to introduce a point mutation (CPSCP→CPPCP) in the hinge region as described in Bloom et al., 1997, *Protein Science* 6:407, incorporated by reference herein) to alleviate a tendency to form intra-H chain disulfide bonds that can lead to heterogeneity in the IgG4 antibodies.

In one embodiment, the antigen binding protein has a $K_{off}$ of $1\times10^{-4}$ $s^{-1}$ or lower. In another embodiment, the $K_{off}$ is $5\times10^{-5}$ $s^{-1}$ or lower. In another embodiment, the $K_{off}$ is substantially the same as an antibody having a combination of light chain and heavy chain variable domain sequences selected from the group of combinations consisting of L1H1, L2H2, L3H3, L4H4, L5H5, L6H6, L7H7, L8H8, L9H9, L10H10, L11H11, L12H12, L13H13, and L14H14. In another embodiment, the antigen binding protein binds to activin A with substantially the same $K_{off}$ as an antibody that comprises one or more CDRs from an antibody having a combination of light chain and heavy chain variable domain sequences selected from the group of combinations consisting of L1H1, L2H2, L3H3, L4H4, L5H5, L6H6, L7H7, L8H8, L9H9, L10H10, L11H11, L12H12, L13H13, and L14H14. In another embodiment, the antigen binding protein binds to activin A with substantially the same $K_{off}$ as an antibody that comprises one of the amino acid sequences illustrated above. In another embodiment, the antigen binding protein binds to activin A with substantially the same $K_{off}$ as an antibody that comprises one or more CDRs from an antibody that comprises one of the amino acid sequences illustrated above.

As used herein, the term human activin A is intended to include the protein of SEQ ID NO:1 and allelic variants thereof. Activin A can be purified from host cells that have been transfected by a gene encoding activin A by elution of filtered supernatant of host cell culture fluid using a Heparin HP column, using a salt gradient.

The term "antibody" refers to an intact antibody, or a binding fragment thereof. An antibody may comprise a complete antibody molecule (including polyclonal, monoclonal, chimeric, humanized, or human versions having full length heavy and/or light chains), or comprise an antigen binding fragment thereof. Antibody fragments include F(ab')$_2$, Fab, Fab', Fv, Fc, and Fd fragments, and can be incorporated into single domain antibodies, single-chain antibodies, maxibodies, minibodies, intrabodies, diabodies, triabodies, tetrabodies, v-NAR and bis-scFv (See e.g., Hollinger and Hudson, 2005, *Nature Biotech.*, 23, 9, 1126-1136). Antibody polypeptides are also disclosed in U.S. Pat. No. 6,703,199, including fibronectin polypeptide monobodies. Other antibody polypeptides are disclosed in U.S. Patent Publication 2005/0238646, which are single-chain polypeptides.

Antigen binding fragments derived from an antibody can be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 5S fragment termed F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., *Arch. Biochem. Biophys.* 89:230, 1960; Porter, *Biochem. J.* 73:119, 1959; Edelman et al., in *Methods in Enzymology* 1:422 (Academic Press 1967); and by Andrews, S. M. and Titus, J. A. in *Current Protocols in Immunology* (Coligan J. E., et al., eds), John Wiley & Sons, New York (2003), pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

An antibody fragment may also be any synthetic or genetically engineered protein. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker (scFv proteins).

Another form of an antibody fragment is a peptide comprising one or more complementarity determining regions (CDRs) of an antibody. CDRs (also termed "minimal recognition units", or "hypervariable region") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)).

Thus, in one embodiment, the binding agent comprises at least one CDR as described herein. The binding agent may comprise at least two, three, four, five or six CDR's as described herein. The binding agent further may comprise at least one variable region domain of an antibody described herein. The variable region domain may be of any size or amino acid composition and will generally comprise at least one CDR sequence responsible for binding to human activin A, for example CDR-H1, CDR-H2, CDR-H3 and/or the light chain CDRs specifically described herein and which is adjacent to or in frame with one or more framework sequences. In general terms, the variable (V) region domain may be any suitable arrangement of immunoglobulin heavy ($V_H$) and/or light ($V_L$) chain variable domains. Thus, for example, the V region domain may be monomeric and be a $V_H$ or $V_L$ domain, which is capable of independently binding human activin A with an affinity at least equal to $1\times10^{-7}$M or less as described below. Alternatively, the V region domain may be dimeric and contain $V_H$-$V_H$, $V_H$-$V_L$, or $V_L$-$V_L$, dimers. The V region dimer comprises at least one $V_H$ and at least one $V_L$ chain that may be non-covalently associated (hereinafter referred to as $F_V$). If desired, the chains may be covalently coupled either directly, for example via a disulfide bond between the two variable domains, or through a linker, for example a peptide linker, to form a single chain Fv (scF$_V$).

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly a $V_L$ domain may be linked to a $C_K$ domain or a fragment thereof. In this way, for example, the antibody may be a Fab fragment wherein the antigen binding domain contains associated $V_H$ and $V_L$ domains covalently linked at their C-termini to a CH1 and $C_K$ domain, respectively. The CH1 domain may be extended with further amino acids, for example to provide a hinge region or a portion of a hinge region domain as found in a Fab' fragment, or to provide further domains, such as antibody CH2 and CH3 domains.

As described herein, antibodies comprise at least one of these CDRs. For example, one or more CDR may be incorporated into known antibody framework regions (IgG1, IgG2, etc.), or conjugated to a suitable vehicle to enhance the half-life thereof. Suitable vehicles include, but are not limited to Fc, polyethylene glycol (PEG), albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent.

In certain preferred embodiments, an antibody comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative binding agent comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

It will be appreciated that an antibody of the present invention may have at least one amino acid substitution, providing that the antibody retains binding specificity. Therefore, modifications to the antibody structures are encompassed within the scope of the invention. These may include amino acid substitutions, which may be conservative or non-conservative, that do not destroy the activin A binding capability of an antibody. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position.

Non-conservative substitutions may involve the exchange of a member of one class of amino acids or amino acid mimetics for a member from another class with different physical properties (e.g., size, polarity, hydrophobicity, charge). Such substituted residues may be introduced into regions of the human antibody that are homologous with non-human antibodies, or into the non-homologous regions of the molecule.

Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules.

A number of scientific publications have been devoted to the prediction of secondary structure. See Moult J., *Curr. Op. in Biotech.*, 7(4):422-427 (1996), Chou et al., *Biochem.*, 13(2):222-245 (1974); Chou et al., *Biochem.*, 113(2):211-222 (1974); Chou et al., *Adv. Enzymol. Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., *Nucl. Acid. Res.*, 27(1):244-247 (1999). It has been suggested (Brenner et al., *Curr. Op. Struct. Biol.*, 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., *Curr. Opin. Struct. Biol.*, 7(3):377-87 (1997); Sippl et al., *Structure*, 4(1):15-19 (1996)), "profile analysis" (Bowie et al., *Science*, 253:164-170 (1991); Gribskov et al., *Meth. Enzym.*, 183:146-159 (1990); Gribskov et al., *Proc. Nat. Acad. Sci.*, 84(13):4355-4358 (1987)), and "evolutionary linkage" (See Holm, supra (1999), and Brenner, supra (1997)).

In certain embodiments, variants of antibodies include glycosylation variants wherein the number and/or type of glycosylation site has been altered compared to the amino acid sequences of a parent polypeptide. In certain embodiments, variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to activin A, or to increase or decrease the affinity of the antibodies to activin A described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. *Nature* 354:105 (1991), which are each incorporated herein by reference.

In certain embodiments, antibodies of the invention may be chemically bonded with polymers, lipids, or other moieties.

The binding agents may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendamistat domains may be used (See e.g., Nygren and Uhlen, 1997, *Curr. Opin. in Struct. Biol.*, 7, 463-469).

It will be appreciated that the antibodies of the invention include the humanized antibodies described herein. Humanized antibodies such as those described herein can be produced using techniques known to those skilled in the art (Zhang, W., et al., *Molecular Immunology.* 42(12):1445-1451, 2005; Hwang W. et al., *Methods.* 36(1):35-42, 2005; Dall'Acqua W F, et al., *Methods* 36(1):43-60, 2005; and Clark, M., *Immunology Today.* 21(8):397-402, 2000).

Additionally, one skilled in the art will recognize that suitable binding agents include portions of these antibodies, such as one or more of CDR-H1, CDR-H2, CDR-H3, CDR-L1, CDR-L2 and CDR-L3 as specifically disclosed herein. At least one of the regions of CDR-H1, CDR-H2, CDR-H3, CDR-L1, CDR-L2 and CDR-L3 may have at least one amino acid substitution, provided that the antibody retains the binding specificity of the non-substituted CDR. The non-CDR portion of the antibody may be a non-protein molecule, wherein the binding agent cross-blocks the binding of an antibody disclosed herein to activin A and/or neutralizes activin A. The non-CDR portion of the antibody may be a non-protein molecule in which the antibody exhibits a similar binding pattern to human activin A peptides in a competition binding assay as that exhibited by at least one of antibodies A1-A14, and/or neutralizes activin A. The non-CDR portion of the antibody may be composed of amino acids, wherein the antibody is a recombinant binding protein or a synthetic peptide, and the recombinant binding protein cross-blocks the binding of an antibody disclosed herein to activin A and/or neutralizes activin A. The non-CDR portion of the antibody may be composed of amino acids, wherein the antibody is a recombinant antibody, and the recombinant antibody exhibits a similar binding pattern to human activin A peptides in the human activin A peptide epitope competition binding assay (described hereinbelow) as that exhibited by at least one of the antibodies A1-A14, and/or neutralizes activin A.

Where an antibody comprises one or more of CDR-H1, CDR-H2, CDR-H3, CDR-L1, CDR-L2 and CDR-L3 as described above, it may be obtained by expression from a host cell containing DNA coding for these sequences. A DNA coding for each CDR sequence may be determined on the basis of the amino acid sequence of the CDR and synthesized together with any desired antibody variable region framework and constant region DNA sequences using oligonucleotide synthesis techniques, site-directed mutagenesis and polymerase chain reaction (PCR) techniques as appropriate. DNA coding for variable region frameworks and constant regions is widely available to those skilled in the art from genetic sequences databases such as GenBank®.

Once synthesized, the DNA encoding an antibody of the invention or fragment thereof may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as *Escherichia coli* (see, e.g., Pluckthun et al., 1989 *Methods Enzymol.* 178:497-515). In certain other embodiments, expression of the antibody or a fragment thereof may be preferred in a eukaryotic host cell, including yeast (e.g., *Saccharomyces cerevisiae, Schizosaccharomyces pombe,* and *Pichia pastoris*), animal cells (including mammalian cells) or plant cells. Examples of suitable animal cells include, but are not limited to, myeloma (such as a mouse NSO line), COS, CHO, or hybridoma cells. Examples of plant cells include tobacco, corn, soybean, and rice cells.

One or more replicable expression vectors containing DNA encoding an antibody variable and/or constant region may be prepared and used to transform an appropriate cell line, for example, a non-producing myeloma cell line, such as a mouse NSO line or a bacteria, such as *E. coli*, in which production of the antibody will occur. In order to obtain efficient transcription and translation, the DNA sequence in each vector should include appropriate regulatory sequences, particularly a promoter and leader sequence operatively linked to the variable domain sequence. Particular methods for producing antibodies in this way are generally well-known and routinely used. For example, basic molecular biology procedures are described by Maniatis et al. (*Molecular Cloning, A Laboratory Manual,* 2nd ed., Cold Spring Harbor Laboratory, New York, 1989; see also Maniatis et al, 3rd ed., Cold Spring Harbor Laboratory, New York, (2001)). DNA sequencing can be performed as described in Sanger et al. (PNAS 74:5463, (1977)) and the Amersham International plc sequencing handbook, and site directed mutagenesis can be carried out according to methods known in the art (Kramer et al., *Nucleic Acids Res.* 12:9441, (1984); Kunkel *Proc. Natl. Acad. Sci. USA* 82:488-92 (1985); Kunkel et al., *Methods in Enzymol.* 154:367-82 (1987); the Anglian Biotechnology Ltd. handbook). Additionally, numerous publications describe techniques suitable for the preparation of antibodies by manipulation of DNA, creation of expression vectors, and transformation and culture of appropriate cells (Mountain A and Adair, J R in *Biotechnology and Genetic Engineering Reviews* (ed. Tombs, M P, 10, Chapter 1, 1992, Intercept, Andover, UK); "Current Protocols in Molecular Biology", 1999, F. M. Ausubel (ed.), Wiley Interscience, New York).

Where it is desired to improve the affinity of antibodies according to the invention containing one or more of the above-mentioned CDRs can be obtained by a number of affinity maturation protocols including maintaining the CDRs (Yang et al., *J. Mol. Biol.,* 254, 392-403, 1995), chain shuffling (Marks et al., *Bio/Technology,* 10, 779-783, 1992), use of mutation strains of *E. coli*. (Low et al., *J. Mol. Biol.,* 250, 350-368, 1996), DNA shuffling (Patten et al., *Curr. Opin. Biotechnol.,* 8, 724-733, 1997), phage display (Thompson et al., *J. Mol. Biol.,* 256, 7-88, 1996) and sexual PCR (Crameri, et al., *Nature,* 391, 288-291, 1998). All of these methods of affinity maturation are discussed by Vaughan et al. (*Nature Biotech.,* 16, 535-539, 1998).

Other antibodies according to the invention may be obtained by conventional immunization and cell fusion procedures as described herein and known in the art. Monoclonal antibodies of the invention may be generated using a variety of known techniques. In general, monoclonal antibodies that bind to specific antigens may be obtained by methods known to those skilled in the art (see, for example, Kohler et al., *Nature* 256:495, 1975; Coligan et al. (eds.), *Current Protocols in Immunology,* 1:2.5.12.6.7 (John Wiley & Sons 1991); U.S. Pat. Nos. RE 32,011, 4,902,614, 4,543, 439, and 4,411,993; *Monoclonal Antibodies, Hybridomas: A New Dimension in Biological Analyses,* Plenum Press, Kennett, McKearn, and Bechtol (eds.) (1980); and *Antibodies: A Laboratory Manual,* Harlow and Lane (eds.), Cold Spring Harbor Laboratory Press (1988); Picksley et al., "Production of monoclonal antibodies against proteins expressed in *E. coli*," in *DNA Cloning* 2: *Expression Systems, 2nd Edition,* Glover et al. (eds.), page 93 (Oxford University Press 1995)). Antibody fragments may be derived therefrom using any suitable standard technique such as proteolytic digestion, or optionally, by proteolytic digestion (for example, using papain or pepsin) followed by mild reduction of disulfide bonds and alkylation. Alternatively, such fragments may also be generated by recombinant genetic engineering techniques as described herein.

Monoclonal antibodies can be obtained by injecting an animal, for example, a rat, hamster, a rabbit, or preferably a mouse, including for example a transgenic or a knock-out, as known in the art, with an immunogen comprising human activin A of (SEQ ID NO:225), or a fragment thereof, according to methods known in the art and described herein. The presence of specific antibody production may be monitored after the initial injection and/or after a booster injection by obtaining a serum sample and detecting the presence of an antibody that binds to human activin A or peptide using any one of several immunodetection methods known in the art and described herein. From animals producing the desired antibodies, lymphoid cells, most commonly cells from the spleen or lymph node, are removed to obtain B-lymphocytes. The B lymphocytes are then fused with a drug-sensitized myeloma cell fusion partner, preferably one that is syngeneic with the immunized animal and that optionally has other desirable properties (e.g., inability to express endogenous Ig gene products, e.g., P3X63-Ag 8.653 (ATCC No. CRL 1580); NSO, SP20) to produce hybridomas, which are immortal eukaryotic cell lines.

The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. A preferred selection media is HAT (hypoxanthine, aminopterin, thymidine). After a sufficient time, usually about one to two weeks, colonies of cells are observed. Single colonies are isolated, and antibodies produced by the cells may be tested for binding activity to human activin A, using any one of a variety of immunoassays known in the art and described herein. The hybridomas are cloned (e.g., by limited dilution cloning or by soft agar plaque isolation) and positive clones that produce an antibody specific to activin A are selected and cultured. The monoclonal antibodies from the hybridoma cultures may be isolated from the supernatants of hybridoma cultures.

An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol. 10, pages 79-104 (The Humana Press, Inc. 1992)). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anticonstant region (light chain or heavy chain) antibody, an anti-idiotype antibody, and a TGF-beta binding protein, or fragment or variant thereof.

An antibody of the present invention may also be a fully human monoclonal antibody. An isolated fully human antibody is provided that specifically binds to the cysteine knot region (amino acids C11-S33 and/or amino acids C81-E111) of activin A, wherein the antigen binding protein possesses at least one in vivo biological activity of a human anti-activin A antibody. The biological activity may be attenuation of cachexia, for example cachexia in colon cancer, such as in a mouse model of colon cancer described herein. The cachexia amenable to such treatment is associated with loss of body weight, loss of muscle mass, and/or loss of fat mass. The cachexia may be associated with rheumatoid arthritis, such as in a collagen-induced animal model of rheumatoid arthritis. Treatment with a fully human antibody described herein ameliorates the loss of body weight, the loss of muscle mass, and/or the loss of fat mass in vivo in a collagen-induced animal model of rheumatoid arthritis. A fully human antibody described herein ameliorates the loss of body weight in a AAV-activin A transfected animal model. A fully human antibody described herein, that specifically binds to the cysteine knot region (amino acids C11-S33 and/or amino acids C81-E111) of activin A, inhibits the binding of activin A to activin A receptor in vitro. A fully human isolated antibody that specifically binds to the cysteine knot region (amino acids C11-S33 and/or amino acids C81-E111) of activin A, inhibits the binding of activin A to activin A receptor in vivo.

Fully human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein. For example, fully human monoclonal antibodies may be obtained from transgenic mice that have been engineered to produce specific human antibodies in response to antigenic challenge. Methods for obtaining fully human antibodies from transgenic mice are described, for example, by Green et al., *Nature Genet.* 7:13, 1994; Lonberg et al., *Nature* 368:856, 1994; Taylor et al., *Int. Immun.* 6:579, 1994; U.S. Pat. No. 5,877,397; Bruggemann et al., 1997 *Curr. Opin. Biotechnol.* 8:455-58; Jakobovits et al., 1995 *Ann. N.Y. Acad. Sci.* 764:525-35. In this technique, elements of the human heavy and light chain locus are introduced into strains of mice derived from embryonic stem cell lines that contain targeted disruptions of the endogenous heavy chain and light chain loci (see also Bruggemann et al., *Curr. Opin. Biotechnol.* 8:455-58 (1997)). For example, human immunoglobulin transgenes may be mini-gene constructs, or transloci on yeast artificial chromosomes, which undergo B-cell-specific DNA rearrangement and hypermutation in the mouse lymphoid tissue. Fully human monoclonal antibodies may be obtained by immunizing the transgenic mice, which may then produce human antibodies specific for activin A. Lymphoid cells of the immunized transgenic mice can be used to produce human antibody-secreting hybridomas according to the methods described herein. Polyclonal sera containing fully human antibodies may also be obtained from the blood of the immunized animals.

Another method for generating human antibodies of the invention includes immortalizing human peripheral blood cells by EBV transformation. See, e.g., U.S. Pat. No. 4,464,456. Such an immortalized B-cell line (or lymphoblastoid cell line) producing a monoclonal antibody that specifically binds to activin A can be identified by immunodetection methods as provided herein, for example, an ELISA, and then isolated by standard cloning techniques. The stability of the lymphoblastoid cell line producing an anti-activin A antibody may be improved by fusing the transformed cell line with a murine myeloma to produce a mouse-human hybrid cell line according to methods known in the art (see, e.g., Glasky et al., *Hybridoma* 8:377-89 (1989)). Still another method to generate human monoclonal antibodies is in vitro immunization, which includes priming human splenic B-cells with human activin A, followed by fusion of primed B-cells with a heterohybrid fusion partner. See, e.g., Boerner et al., 1991 *J. Immunol.* 147:86-95.

In certain embodiments, a B-cell that is producing an anti-human activin A antibody is selected and the light chain and heavy chain variable regions are cloned from the B-cell according to molecular biology techniques known in the art (WO 92/02551; U.S. Pat. No. 5,627,052; Babcook et al., *Proc. Natl. Acad. Sci. USA* 93:7843-48 (1996)) and described herein. B-cells from an immunized animal may be isolated from the spleen, lymph node, or peripheral blood sample by selecting a cell that is producing an antibody that specifically binds to activin A. B-cells may also be isolated from humans, for example, from a peripheral blood sample. Methods for detecting single B-cells that are producing an antibody with the desired specificity are well known in the art, for example, by plaque formation, fluorescence-activated cell sorting, in vitro stimulation followed by detection of specific antibody, and the like. Methods for selection of specific antibody-producing B-cells include, for example, preparing a single cell suspension of B-cells in soft agar that contains human activin A. Binding of the specific antibody produced by the B-cell to the antigen results in the formation of a complex, which may be visible as an immunoprecipitate. After the B-cells producing the desired antibody are selected, the specific antibody genes may be cloned by isolating and amplifying DNA or mRNA according to methods known in the art and described herein.

An additional method for obtaining antibodies of the invention is by phage display. See, e.g., Winter et al., 1994 *Annu. Rev. Immunol.* 12:433-55; Burton et al., 1994 *Adv. Immunol.* 57:191-280. Human or murine immunoglobulin variable region gene combinatorial libraries may be created in phage vectors that can be screened to select Ig fragments (Fab, Fv, sFv, or multimers thereof) that bind specifically to TGF-beta binding protein or variant or fragment thereof. See, e.g., U.S. Pat. No. 5,223,409; Huse et al., 1989 *Science* 246:1275-81; Sastry et al., *Proc. Natl. Acad. Sci. USA* 86:5728-32 (1989); Alting-Mees et al., *Strategies in Molecular Biology* 3:1-9 (1990); Kang et al., 1991 *Proc. Natl. Acad. Sci. USA* 88:4363-66; Hoogenboom et al., 1992 *J. Molec. Biol.* 227:381-388; Schlebusch et al., 1997 *Hybridoma* 16:47-52 and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using λImmunoZap™ (H) and λImmunoZap™ (L) vectors (Stratagene, La Jolla, Calif.). Briefly, mRNA is isolated from a B-cell population, and used to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid that allows high level expression of monoclonal antibody fragments from *E. coli*.

In one embodiment, in a hybridoma the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, Calif.), which sells primers for mouse and human variable regions including, among others, primers for $V_{Ha}$, $V_{Hb}$, $V_{Hc}$, $V_{Hd}$, $C_{H1}$, $V_L$ and $C_L$ regions.) These primers may be used to amplify heavy or light chain variable regions, which may then be inserted into vectors such as ImmunoZAP™ H or ImmunoZAP™ L (Stratagene), respectively. These vectors may then be introduced into *E. coli*, yeast, or mammalian-based systems for expression. Large amounts of a single-chain protein containing a fusion of the $V_H$ and $V_L$ domains may be produced using these methods (see Bird et al., *Science* 242:423-426, 1988).

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

Activin A binding agents of the present invention preferably modulate activin A function in the cell-based assay described herein and/or the in vivo assay described herein and/or bind to one or more of the cysteine knot domains described herein and/or cross-block the binding of one of the antibodies described in this application and/or are cross-blocked from binding activin A by one of the antibodies described in this application. Accordingly such binding agents can be identified using the assays described herein.

In certain embodiments, antibodies are generated by first identifying antibodies that bind to one more of the cysteine knot domains provided herein and/or neutralize in the cell-based and/or in vivo assays described herein and/or cross-block the antibodies described in this application and/or are cross-blocked from binding activin A by one of the antibodies described in this application. The CDR regions from these antibodies are then used to insert into appropriate biocompatible frameworks to generate activin A binding agents. The non-CDR portion of the binding agent may be composed of amino acids, or may be a non-protein molecule. The assays described herein allow the characterization of binding agents. Preferably the binding agents of the present invention are antibodies as defined herein.

It will be understood by one skilled in the art that some proteins, such as antibodies, may undergo a variety of posttranslational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R. J. *Journal of Chromatography* 705:129-134, 1995).

Nucleic Acids

In one aspect, the present invention provides isolated nucleic acid molecules. The nucleic acids comprise, for example, polynucleotides that encode all or part of an antigen binding protein, for example, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) may be isolated from B-cells of mice that have been immunized with activin A. The nucleic acid may be isolated by conventional procedures such as polymerase chain reaction (PCR).

Nucleic acid sequences encoding the variable regions of the heavy and light chain variable regions are shown above. The skilled artisan will appreciate that, due to the degeneracy of the genetic code, each of the polypeptide sequences disclosed herein is encoded by a large number of other nucleic acid sequences. The present invention provides each degenerate nucleotide sequence encoding each antigen binding protein of the invention.

The invention further provides nucleic acids that hybridize to other nucleic acids (e.g., nucleic acids comprising a nucleotide sequence of any of A1-A14) under particular hybridization conditions. Methods for hybridizing nucleic acids are well-known in the art. See, e.g., *Curr. Prot. in Mol. Biol.*, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Curr. Prot. in Mol. Biol. 1995, Ausubel et al., eds., John Wiley & Sons, Inc., sections 2.10 and 6.3-6.4), and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an antigen binding protein) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property (e.g., binding to activin A).

Mutations can be introduced into a nucleic acid without significantly altering the biological activity of a polypeptide that it encodes. For example, one can make nucleotide substitutions leading to amino acid substitutions at nonessential amino acid residues. In one embodiment, a nucleotide sequence provided herein for A1-A14, or a desired fragment, variant, or derivative thereof, is mutated such that it encodes an amino acid sequence comprising one or more deletions or substitutions of amino acid residues that are shown herein for A1-A14 to be residues where two or more sequences differ. As described herein inter alia, A1-A14 refers to 14 sequences, A1, and A14, as well as the 12 intervening amino acid residues. In another embodiment, the mutagenesis inserts an amino acid adjacent to one or more amino acid residues shown herein for A1-A14 to be residues where two or more sequences differ. Alternatively, one or more mutations can be introduced into a nucleic acid that selectively change the biological activity (e.g., binding of activin A) of a polypeptide that it encodes. For example, the mutation can quantitatively or qualitatively change the biological activity. Examples of quantitative changes include increasing, reducing or eliminating the activity. Examples of qualitative changes include changing the antigen specificity of an antigen binding protein.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., an activin A binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, *Trends Biochem. Sci.* 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell (for example, *E. coli*) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Indications

In one aspect, the present invention provides methods of treating a subject. The method can, for example, have a generally beneficial effect on the subject's health, e.g., it can increase the subject's expected longevity. Alternatively, the method can, for example, treat, prevent, cure, relieve, or ameliorate ("treat") a disease, disorder, condition, or illness ("a condition"). Among the conditions to be treated in accordance with the present invention are conditions characterized by inappropriate expression or activity of activin A. In some such conditions, the expression or activity level is too high, and the treatment comprises administering an activin A antagonist as described herein.

One example of a type of condition that can be treated using the methods and compositions of the present invention is a condition that involves cell growth, for example, a cancerous condition which is accompanied by cachexia. Thus, in one embodiment, the present invention provides compositions and methods for treating a cancerous condition. In particular, the cancerous condition is a gonadal cancer, including tumors of the ovary and testis. (Fujii, Y. et al., *Am. J. Phys. Endocrin. Metab.*, 286:E927-E931, 2004; Reis, F. M. et al., *J. Clin. Endocrin.* 87:2277-2282, 2005.) Activin A is known for its action in stimulating FSH biosynthesis and secretion in the pituitary gland, and has a physiological role in the regulation of gonadal function. Activin A has been associated with many types of human cancers and in particular with tumors of the reproductive system. Specifically, overexpression or deregulation of activin A has been implicated in ovarian cancer, (Menon U, et al., *BJOG: An International Journal of Obstetrics & Gynaecology;* 107(9):1069-74, 2000. Choi K C, et al., *Molecular & Cellular Endocrinology.* 174(1-2):99-110, 2001; Zheng W, et al., *American Journal of Reproductive Immunology.* 44(2):104-13, 2000; Lambert-Messerlian G M, et al., *Gynecologic Oncology.* 74(1):93-7, 1999; Steller M D, et al., *Molecular Cancer Research: MCR.* 3(1):50-61, 2005; Corbellis L., et al., *Journal of the Society for Gynecologic Investigation.* 11(4):203-6, 2004; Welt C K, et al., *Journal of Clinical Endocrinology & Metabolism.* 82(11):3720-7, 1997; and Harada K., et al., *Journal of Clinical Endocrinology & Metabolism.* 81(6):2125-30, 1996, endometrial adenocarcinoma Otani, T, et a., *Gynecologic Oncology.* 83(1):31-8, 2001; Tanaka T, et al., *International Journal of Oncology.* 23(3):657-63, 2003 and prostate cancer (Thomas T Z, et al., *Journal of Clinical Endocrinology & Metabolism.* 82(11):3851-8, 1997; Zhang, Z, et al., *Biochemical & Biophysical Research Communications.* 234(2):362-5, 1997; and Risbridger G P, et al., *Molecular & Cellular Endocrinology.* 180(1-2):149-53, 2001

The cancerous condition can be any cancerous condition that can be treated using the compositions comprised herein, for example, activin A antigen binding proteins such as anti-activin A antibodies, antibody fragments, or antibody derivatives. Examples of cancerous conditions include, for example, acute lymphoblastic leukemia, adrenocortical carcinoma, AIDS-related cancers, AIDS-related lymphoma, anal cancer, childhood cerebellar astrocytoma, childhood cerebral astrocytoma, basal cell carcinoma, extrahepatic bile duct cancer, bladder cancer, osteosarcoma/malignant fibrous histiocytoma bone cancer, brain tumors (e.g., brain stem glioma, cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, Burkitt's Lymphoma, carcinoid tumor, gastrointestinal carcinoid tumor, carcinoma of unknown primary, primary central nervous system, cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, colorectal cancer, cutaneous t-cell lymphoma, endometrial cancer, ependymoma, esophageal cancer, ewing's family of tumors, extracranial germ cell tumor, extragonadal germ cell tumor, extrahepatic bile duct cancer, intraocular melanoma eye cancer, retinoblastoma eye cancer, gallbladder cancer, gastric (stomach) cancer, gastrointestinal carcinoid tumor, germ cell tumors (e.g., extracranial, extragonadal, and ovarian), gestational trophoblastic tumor, glioma (e.g., adult, childhood brain stem, childhood cerebral astrocytoma, childhood visual pathway and hypothalamic), hairy cell leukemia, head and neck cancer, hepatocellular (liver) cancer, Hodgkin's lymphoma, hypopharyngeal cancer, hypothalamic and visual pathway glioma, intraocular melanoma, islet cell carcinoma (endocrine pancreas), Kaposi's Sarcoma, kidney (renal cell) cancer, laryngeal cancer, leukemia (e.g., acute lymphoblastic, acute myeloid, chronic lymphocytic, chronic myelogenous, and hairy cell), lip and oral cavity cancer, liver cancer, non-small cell lung cancer, small cell lung cancer, lymphoma (e.g., AIDS-related, Burkitt's, cutaneous t-cell, Hodgkin's, non-Hodgkin's, and primary central nervous system), Waldenström's Macroglobulinemia, malignant fibrous histiocytoma of bone/osteosarcoma, medulloblastoma, melanoma, intraocular (eye) melanoma, Merkel cell carcinoma, mesothelioma, metastatic squamous neck cancer with occult primary, multiple endocrine neoplasia syndrome, multiple myeloma/plasma cell neoplasm, mycosis fungoides, myelodysplastic syndromes, myelodysplastic/myeloproliferative diseases, myelogenous leukemia, chronic myeloid leukemia, multiple myeloma, chronic myeloproliferative disorders, nasal cavity and paranasal sinus cancer, nasopharyngeal cancer, neuroblastoma, oral cancer, oropharyngeal cancer, osteosarcoma/malignant fibrous histiocytoma of bone, ovarian cancer, ovarian epithelial cancer, ovarian germ cell tumor, ovarian low malignant potential tumor, pancreatic cancer, islet cell pancreatic cancer, paranasal sinus and nasal cavity cancer, parathyroid cancer, penile cancer, pheochromocytoma, pineoblastoma, pituitary tumor, plasma cell neoplasm/multiple myeloma, pleuropulmonary blastoma, primary central nervous system lymphoma, prostate cancer, rectal cancer, renal cell (kidney) cancer, renal pelvis and ureter transitional cell cancer, retinoblastoma, rhabdomyosarcoma, salivary gland cancer, soft tissue sarcoma, uterine sarcoma, Sezary syndrome, non-melanoma skin cancer, merkel cell skin carcinoma, small intestine cancer, soft tissue sarcoma, squamous cell carcinoma, cutaneous t-cell lymphoma, testicular cancer, thymoma, thymic carcinoma, thyroid cancer, gestational trophoblastic tumor, carcinoma of unknown primary site, cancer of unknown primary site, urethral cancer, endometrial uterine cancer, uterine sarcoma, vaginal cancer, visual pathway and hypothalamic glioma, vulvar cancer, Waldenström's Macroglobulinemia, and Wilms' Tumor.

An oligopeptide or polypeptide is within the scope of the invention if it has an amino acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to least one of the CDR's of antibodies A1-A14; and/or to a CDR of a activin A binding agent that cross-blocks the binding of at least one of antibodies A1-A14 to activin A, and/or is cross-blocked from binding to activin A by at least one of antibodies A1-A14; and/or to a CDR of a activin A binding agent wherein the binding agent can block the binding of activin A to activin A receptor.

Activin A binding agent polypeptides and antibodies are within the scope of the invention if they have amino acid sequences that are at least 85%, 86%, 87%, 88%, 89%, 90%, 91%, 92%, 93%, 94%, 95%, 96%, 97%, 98% or 99% identical to a variable region of at least one of antibodies A1-A14, and cross-block the binding of at least one of antibodies A1-A14 to activin A, and/or are cross-blocked from binding to activin A by at least one of antibodies A1-A14; and/or can block the inhibitory effect of activin A on an activin A receptor.

Therapeutic antibodies may be used that specifically bind to intact activin A, in which sequences in the region of approximately C11-S33 (first loop) and approximately C81-

E111 (second loop) retain the conformation of native activin A. Such mapping and binding is described in Example 6, below.

Antibodies according to the invention may have a binding affinity for human activin A of less than or equal to $1\times10^{-7}$M, less than or equal to $1\times10^{-8}$M, less than or equal to $1\times10^{-9}$M, less than or equal to $1\times10^{-10}$M, less than or equal to $1\times10^{-11}$M, or less than or equal to $1\times10^{-12}$ M.

The affinity of an antibody or binding partner, as well as the extent to which an antibody inhibits binding, can be determined by one of ordinary skill in the art using conventional techniques, for example those described by Scatchard et al. (*Ann. N.Y. Acad. Sci.* 51:660-672 (1949)) or by surface plasmon resonance (SPR; BIAcore, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., *Cancer Res.* 53:2560-65 (1993)).

An antibody according to the present invention may belong to any immunoglobin class, for example IgG, IgE, IgM, IgD, or IgA. It may be obtained from or derived from an animal, for example, fowl (e.g., chicken) and mammals, which includes but is not limited to a mouse, rat, hamster, rabbit, or other rodent, cow, horse, sheep, goat, camel, human, or other primate. The antibody may be an internalizing antibody. Production of antibodies is disclosed generally in U.S. Patent Publication No. 2004/0146888 A1.

Characterization Assays

In the methods described above to generate antibodies according to the invention, including the manipulation of the specific A1-A14 CDRs into new frameworks and/or constant regions, appropriate assays are available to select the desired antibodies (i.e. assays for determining binding affinity to activin A; cross-blocking assays; Biacore-based competition binding assay;" in vivo assays).

Therapeutic Methods and Administration of Antigen Binding Proteins

Certain methods provided herein comprise administering an activin A binding antigen binding protein to a subject, thereby reducing an activin A-induced biological response that plays a role in a particular condition. In particular embodiments, methods of the invention involve contacting endogenous activin A with an activin A binding antigen binding protein, e.g., via administration to a subject or in an ex vivo procedure.

The term "treatment" encompasses alleviation or prevention of at least one symptom or other aspect of a disorder, or reduction of disease severity, and the like. In addition, "treatment" further relates to administering a therapeutic agent described herein for preventing or alleviating at least one symptom or other aspect of a disorder in a subject in need thereof. An antigen binding protein need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient an activin A antagonist in an amount and for a time sufficient to induce a sustained improvement over baseline of an indicator that reflects the severity of the particular disorder.

As is understood in the pertinent field, pharmaceutical compositions comprising the molecules of the invention are administered to a subject in need thereof in a manner appropriate to the indication. Pharmaceutical compositions may be administered by any suitable technique, including but not limited to parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g., at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of antigen binding proteins in ex vivo procedures also is contemplated. For example, a patient's blood or other bodily fluid may be contacted with an antigen binding protein that binds full-length activin A, one or more activin A isoform, or other partial length activin A ex vivo. The antigen binding protein may be bound to a suitable insoluble matrix or solid support material.

Advantageously, antigen binding proteins are administered in the form of a composition comprising one or more additional components such as a physiologically acceptable carrier, excipient or diluent. Optionally, the composition additionally comprises one or more physiologically active agents, for example, a second activin A receptor-inhibiting substance, an anti-angiogenic substance, a chemotherapeutic substance, an analgesic substance, etc., non-exclusive examples of which are provided herein. In various particular embodiments, the composition comprises one, two, three, four, five, or six physiologically active agents in addition to an activin A-binding antigen binding protein.

In one embodiment, the pharmaceutical composition comprise an antigen binding protein of the invention together with one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in Remington's Pharmaceutical Sciences, 16$^{th}$ Ed. (1980) and 20$^{th}$ Ed. (2000), Mack Publishing Company, Easton, Pa.

Kits for use by medical practitioners include an antigen binding protein of the invention and a label or other instructions for use in treating any of the conditions discussed herein. In one embodiment, the kit includes a sterile preparation of one or more antigen binding proteins, which may be in the form of a composition as disclosed above, and may be in one or more vials.

Dosages and the frequency of administration may vary according to such factors as the route of administration, the particular antigen binding proteins employed, the nature and severity of the disease to be treated, whether the condition is acute or chronic, and the size and general condition of the subject. Appropriate dosages can be determined by procedures known in the pertinent art, e.g., in clinical trials that may involve dose escalation studies.

An antigen binding protein of the invention may be administered, for example, once or more than once, e.g., at regular intervals over a period of time. In particular embodiments, an antigen binding protein is administered over a period of at least a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the antigen binding protein is administered until the patient manifests a medically relevant degree of improvement over baseline for the chosen indicator or indicators.

Particular embodiments of the present invention involve administering an antigen binding protein at a dosage of from about 1 ng of antigen binding protein per kg of subject's weight per day ("1 ng/kg/day") to about 10 mg/kg/day, more preferably from about 500 ng/kg/day to about 5 mg/kg/day, and most preferably from about 5 µg/kg/day to about 2 mg/kg/day, to a subject. In additional embodiments, an antigen binding protein is administered to adults one time per week, two times per week, or three or more times per week, to treat an activin A mediated disease, condition or disorder, e.g., a medical disorder disclosed herein. If injected, the effective amount of antigen binding protein per adult dose may range from 1-20 mg/m$^2$, and preferably is about 5-12 mg/m$^2$. Alternatively, a flat dose may be administered; the amount may range from 5-100 mg/dose. One range for a flat dose is about 20-30 mg per dose. In one embodiment of the invention, a flat dose of 25 mg/dose is repeatedly administered by injection. If a route of administration other than injection is used, the dose is appropriately adjusted in accordance with standard medical practices. One example of a therapeutic regimen involves injecting a dose of about 20-30 mg of antigen binding protein one to three times per week over a period of at least three weeks, though treatment for longer periods may be necessary to induce the desired degree of improvement. For pediatric subjects (age 4-17), one exemplary suitable regimen involves the subcutaneous injection of 0.4 mg/kg, up to a maximum dose of 25 mg of antigen binding protein administered two or three times per week.

Particular embodiments of the methods provided herein involve subcutaneous injection of from 0.5 mg to 10 mg, preferably from 3 to 5 mg, of an antigen binding protein, once or twice per week. Another embodiment is directed to pulmonary administration (e.g., by nebulizer) of 3 or more mg of antigen binding protein once a week.

Examples of therapeutic regimens provided herein comprise subcutaneous injection of an antigen binding protein once a week, at a dose of 1.5 to 3 mg, to treat a condition in which activin A signaling plays a role. Examples of such conditions are provided herein and include, for example, cachexia, cancer, rheumatoid arthritis, and all conditions in which loss of body weight, body mass, body fat, or inability to maintain body weight, body mass, body fat, play a role. Weekly administration of antigen binding protein is continued until a desired result is achieved, e.g., the subject's symptoms subside. Treatment may resume as needed, or, alternatively, maintenance doses may be administered.

Other examples of therapeutic regimens provided herein comprise subcutaneous or intravenous administration of a dose of 1, 3, 5, 6, 7, 8, 9, 10, 11, 12, 15, or 20 milligrams of an activin A inhibitor of the present invention per kilogram body mass of the subject (mg/kg). The dose can be administered once to the subject, or more than once at a certain interval, for example, once a day, three times a week, twice a week, once a week, three times a month, twice a month, once a month, once every two months, once every three months, once every six months, or once a year. The duration of the treatment, and any changes to the dose and/or frequency of treatment, can be altered or varied during the course of treatment in order to meet the particular needs of the subject.

In another embodiment, an antigen binding protein is administered to the subject in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. In one embodiment, an improvement is considered to be sustained if the subject exhibits the improvement on at least two occasions separated by two to four weeks. The degree of improvement generally is determined by a physician, who may make this determination based on signs, symptoms, biopsies, or other test results, and who may also employ questionnaires that are administered to the subject, such as quality-of-life questionnaires developed for a given disease.

A subject's levels of activin A may be monitored before, during and/or after treatment with an antigen binding protein, to detect changes, if any, in their levels. For some disorders, the incidence of elevated activin A levels may vary according to such factors as the stage of the disease or the particular form of the disease. Known techniques may be employed for measuring activin A levels, e.g., in a subject's serum. Activin A levels in blood samples may be measured using any suitable technique, for example, ELISA.

Particular embodiments of methods and compositions of the invention involve the use of an antigen binding protein and one or more additional activin A antagonists, for example, two or more antigen binding proteins of the invention, or an antigen binding protein of the invention and one or more other activin A antagonists. In further embodiments, antigen binding protein are administered alone or in combination with other agents useful for treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which an antigen binding protein is administered at least once during a course of treatment that involves administering at least one other therapeutic agent to the patient.

Examples of other agents that may be co-administered with an antigen binding protein are other antigen binding proteins or therapeutic polypeptides that are chosen according to the particular condition to be treated. Alternatively, non-proteinaceous drugs that are useful in treating one of the particular conditions discussed above may be co-administered with an activin A antagonist.

Combination Therapy

In another aspect, the present invention provides a method of treating a subject with an activin A inhibiting antigen binding protein and one or more other treatments. In one embodiment, such a combination therapy achieves synergy or an additive effect by, for example, attacking multiple sites or molecular targets in a tumor. Types of combination therapies that can be used in connection with the present invention include inhibiting or activating (as appropriate) multiple nodes in a single disease-related pathway, multiple pathways in a target cell, and multiple cell types within a target tissue (e.g., within a tumor). For example, an activin A inhibitor of the present invention can be combined with a treatment that promotes apoptosis or inhibits angiogenesis. In another embodiment, a targeted agent, that, when used by itself, fails to elicit a therapeutically desired effect, could be used to, for example, sensitize cancer cells or augment treatment effect of other agents. In another embodiment, an activin A inhibitor according to the invention is used in combination with a cytotoxic drug or other targeted agent that induces apoptosis. In another embodiment, an activin A inhibitor is used in combination with one or more agents that inhibit different targets that are involved in cell survival (e.g., PKB, mTOR), different receptor tyrosine kinases (e.g., ErbB1, ErbB2, c-Met, c-kit), or different cell types (e.g., KDR inhibitors, c-fms). In another embodiment, an activin A inhibitor of the invention is added to the existing standard of care for a particular condition. Examples of therapeutic agents include, but are not limited to, gemcitabine, taxol, taxotere, and CPT-11.

In another embodiment, the method comprises administering one or more of the activin A antagonists described herein and one or more other treatments (e.g., a therapeutic or palliative treatment), for example, anti-cancer treatments (such as surgery, ultrasound, radiotherapy, chemotherapy, or treatment with another anti-cancer agent). Where a method comprises administering more than one treatment to a subject, it is to be understood that the order, timing, number, concentration, and volume of the administrations is limited only by the medical requirements and limitations of the treatment, i.e., two treatments can be administered to the subject, e.g., simultaneously, consecutively, alternately, or according to any other regimen. Examples of agents that can be administered in combination with the activin A antagonists described herein include, but are not limited to, neutrophil-boosting agents, irinothecan, SN-38, gemcitabine, herstatin, or an activin A-binding herstatin derivative (as described, for example, in U.S. Pat. App. No. 05/0272637), AVASTIN® (Genentech, South San Francisco, Calif.), HERCEPTIN® (Genentech), RITUXAN® (Genentech), ARIMIDEX® (AstraZeneca, Wilmington, Del.), IRESSA® (AstraZeneca), BEXXAR® (Corixa, Seattle, Wash.), ZEVALIN® (Biogen Idec, Cambridge, Mass.), ERBITUX® (Imclone Systems Inc., New York, N.Y.), GEMZAR® (Eli Lilly and Co., Indianapolis, Ind.), CAMPTOSAR® (Pfizer, New York, N.Y.), GLEEVEC® (Novartis), SU-11248 (Pfizer), BMS-354825 (Bristol-Myers Squibb), panitumumab (Abgenix, Fremont, Calif./Amgen Inc., Thousand Oaks, Calif.), and denosumab (Amgen Inc., Thousand Oaks, Calif.).

The development of suitable dosing and treatment regimens for using the particular compositions described herein in a variety of treatment regimens, including e.g., subcutaneous, oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein subcutaneously, parenterally, intravenously, intramuscularly, or even intraperitoneally. Such approaches are well known to the skilled artisan, some of which are further described, for example, in U.S. Pat. Nos. 5,543,158; 5,641,515 and 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, *Remington's Pharmaceutical*

Sciences, 15th ed., pp. 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, *Trends Biotechnol.* 16(7):307-21, 1998; Takakura, *Nippon Rinsho* 56(3):691-95, 1998; Chandran et al., *Indian J. Exp. Biol.* 35(8):801-09, 1997; Margalit, *Crit. Rev. Ther. Drug Carrier Syst.* 12(2-3):233-61, 1995; U.S. Pat. Nos. 5,567,434; 5,552,157; 5,565,213; 5,738,868 and 5,795,587, each specifically incorporated herein by reference in its entirety). The use of liposomes does not appear to be associated with autoimmune responses or unacceptable toxicity after systemic delivery. In certain embodiments, liposomes are formed from phospholipids that are dispersed in an aqueous medium and spontaneously form multilamellar concentric bilayer vesicles (also termed multilamellar vesicles (MLVs)).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., *Drug Dev. Ind. Pharm.* 24(12):1113-28, 1998). To avoid side effects due to intracellular polymeric overloading, such ultrafine particles (sized around 0.1 µm) may be designed using polymers able to be degraded in vivo. Such particles can be made as described, for example, by Couvreur et al., *Crit. Rev. Ther. Drug Carrier Syst.* 5(1):1-20, 1988; zur Muhlen et al., *Eur. J. Pharm. Biopharm.* 45(2):149-55, 1998; Zambaux et al., *J. Controlled Release* 50(1-3):31-40, 1998; and U.S. Pat. No. 5,145,684.

In addition, pharmaceutical compositions of the present invention may be placed within containers, along with packaging material that provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) that may be necessary to reconstitute the pharmaceutical composition.

The dose administered may range from 0.01 mg/kg to 100 mg/kg of body weight. As will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

The invention also provides a diagnostic kit comprising at least one anti-activin A binding agent according to the present invention. The binding agent may be an antibody. In addition, such a kit may optionally comprise one or more of the following:

(1) instructions for using the one or more binding agent(s) for screening, diagnosis, prognosis, therapeutic monitoring or any combination of these applications;
(2) a labeled binding partner to the anti-activin A binding agent(s);
(3) a solid phase (such as a reagent strip) upon which the anti-activin A binding agent(s) is immobilized; and
(4) a label or insert indicating regulatory approval for screening, diagnostic, prognostic or therapeutic use or any combination thereof.

If no labeled binding partner to the binding agent(s) is provided, the binding agent(s) itself can be labeled with one or more of a detectable marker(s), e.g. a chemiluminescent, enzymatic, fluorescent, or radioactive moiety.

The following examples are offered by way of illustration, and not by way of limitation.

EXAMPLES

Example 1

Recombinant Expression of Activin A

Ultra Filtration and Diafiltration (UF/DF) of Conditioned Media.

R-HuActivinA was expressed in chinese hamster ovary (CHO) cells. A series of steps was developed to generate active, purified material. The purification process began by concentrating (dialfiltration) the conditioned media (C.M.) between 15 to 20 fold using an Amicon S10Y10 spiral cartridge. The media was then buffer exchanged (diafiltered) using 5 volumes of 10 mM tris buffer Ph 7.0, filtered and stored.

Cation Exchange Chromatography.

The r-HuActivin A was applied at 5 ml/minute at 4-80 C to a 2.6×7 cm (Pharmacia)S-Sepharose Fast Flow column equilibrated in 10 mM Tris buffer Ph 7.0. The column was washed with the equilibration buffer. The r-HuActivin A was eluted from the column with a gradient of increasing sodium chloride concentration to 0.4M over 20 column volumes buffered with 10 Mm Tris Ph 7.0. The appropriate fractions were pooled and stored 4-80 C.

Reverse Phase HPLC C4 Chromatography.

The S-Sepharose column pool pH was adjusted to 2.0 with trifluoroacetic acid (TFA). The pool was then applied to a 1×25 cm Vydac C4 column at room temperature equilibrated with 75% A buffer (0.1% TFA in water), and 25% B buffer (90% acetonitrile, 0.1% TFA, 9.9% water). The column was then washed with the equilibration buffer. R-HuActivin A was eluted with a gradient of 25% B buffer to 50% B buffer over 50 minutes at a flow rate of 5 ml/minute. The appropriate fractions were pooled, and lyophylized.

High Performance Cation Exchange Chromatography.

A 5 ml S Sepharose High Performance column was equilibrated with 8M urea, 10 mM sodium phosphate, Ph 7.0 (A buffer) at room temperature. The lyophilized C4 pool was resuspended in A buffer and applied at 5 ml/minute, and washed with A buffer. The r-HuActivin A was eluted from the column with a gradient of increasing sodium chloride concentration to 0.15M over 30 column volumes buffered with 8M urea, 10 mM sodium phosphate, pH 7.0. The appropriate fractions were pooled and stored 4-80° C.

Reverse Phase HPLC C4 Chromatography.

The S-Sepharose column pool pH was adjusted to 2.0 with Trifluroacetic Acid (TFA). The pool was then applied to a 1×25 cm Vydac C4 column at room temperature equilibrated with 75% A buffer (0.1% TFA in water), and 25% B buffer (90% acetonitrile, 0.1% TFA, 9.9% water). The column was then washed extensively to remove urea and salts with the equilibration buffer. R-HuActivin A was eluted with a gradient of 25% B buffer to 50% B buffer over 50 minutes at a flow rate of 5 ml/minute. The appropriate fractions were pooled, and the final purified r-HuActivin A was lyophilized and stored in aliquots –80° C. SEQ ID NO:225 provides the amino acid sequence for activin A.

Example 2

Generation of Anti-Activin A Hybridomas

Antibodies to activin A were raised in XenoMouse® mice (Abgenix, Fremont, Calif.), which are mice containing human immunoglobulin genes. The XenoMouse® strain XMG2 was used to produce fully human IgG2 Kappa antibodies. A second strain was used to produce fully human IgG4 Kappa antibodies. Mice were immunized with activin A.

The mice were injected with antigen (activin A) according to standard protocols (US 2005/0118643; WO 2005/694879) in the hind footpads (5 µg per footpad). Initial injections contained the adjuvant TiterMax® Gold (Sigma, Cat #T2684). In subsequent injections, each mouse was injected with a total of 5 µg of antigen in the adjuvant alum gel (aluminum phosphate gel adjuvant; Superfos Biosector a/s, distributed by E. M. Sargent Pulp and Chemical Co., Clifton N.J., cat #1452-250). The final injection contained a total of 10 µg of antigen per mouse and did not contain an adjuvant.

Each mouse was bled two days after the sixth injection. Blood samples from those bleeds were assayed by ELISA to determine the titer of antibodies to activin A. Four days after the final injection, the mice were sacrificed and their draining lymph nodes were harvested and the lymphocytes were recovered. Lymphocytes from the mice of each of the three groups were separately pooled. To enrich the lymphocyte samples for B-cells, T-cells were depleted by adding anti-CD90 magnetic beads (Miltenyi Biotech cat. #491-01) and then passing the lymphocytes through an LS$^+$ column (Miltenyi Biotech cat. #424-01).

Each of the samples of B-cell enriched lymphocytes was then fused with P3 myeloma cells using an electrocell fusion device (Genetronic, Inc., Model ECM 2001) to create hybridomas. The three groups of fused hybridoma lines were then plated in 96-well plates hybridoma media as described (WO 2005/094879) although other suitable media known in the art can be used. The hybridoma lines were cultured for 14 days at 37° C., in 15% $CO_2$.

After 14 days, culture supernatants were assayed by ELISA to detect the presence of human IgG antibodies to activin A. Culture supernatants that tested positive in that ELISA were tested for the presence of human kappa chain in a second ELISA. In that second ELISA, the conditions were identical to the first ELISA, except that the secondary antibody was a goat anti-human kappa chain antibody conjugated to horseradish peroxidase. Hybridomas that tested positive in both ELISA assays were further expanded to produce 5 ml of supernatant for subsequent testing.

A total of 160 anti-activin A hybridoma samples derived from the xeno mice were screened using a cell-based functional assay and BIAcore binding analysis as described in the Examples below. Twenty-three hybridomas were further characterized for their properties related to expression, purification, cell-based assay, binding analysis, sequence analysis, MS, and SEC. From these, three potent Mabs, A1, A2, and A3, were identified for further testing as described below. The amino acid sequences for these antibodies are as follows: A1: SEQ ID NO:9 (light chain variable); SEQ ID NO:84 (light chain constant); SEQ ID NO:10 (heavy chain variable); and SEQ ID NO:214 (heavy chain constant). A2: SEQ ID NO:25 (light chain variable); SEQ ID NO:100 (light chain constant); SEQ ID NO:26 (heavy chain variable); and SEQ ID NO:215 (heavy chain constant). A3: SEQ ID NO:41 (light chain variable); SEQ ID NO:108 (light chain constant); SEQ ID NO:42 (heavy chain variable); and SEQ ID NO:221 (heavy chain constant).

Example 3

Expression and Purification of Human Anti-HuActivin A Antibodies in Cho Cells

CS-9 cells used for transfection of the anti-huActivin A expression plasmids were a serum-free suspension CHO cell line. The CS-9 clone was selected as the host cell line for expression of recombinant proteins and banked in serum-free medium. The bank was tested for adventious agents and sterility and found to be free of viral, *mycoplasma* and microbial agents.

Anti-hu Activin A expressing cell lines were scaled up using a typical fed-batch process. Cells were inoculated into a Wave bioreactor upon expansion. Culture was fed three times on approximately day 3, day 5 and day 9 with bolus feeds and harvested on day 11. Cells were spun down and conditioned media was filtered through a ten inch 0.45/0.2 micron pre filter, followed by a filtration through a six inch 0.2 micron filter.

Purification of Mab's from Hybridoma Conditioned Media (C.M.):

To between 7 to 10 ml of C.M.'s was added 100 µl of a 1:2 slurry of Mab Select resin equilibrated in PBS. The tubes were placed on rotators at 4-8° C. overnight. The tubes were centrifuged at 1,000×g for 5 minutes and the non-bound fraction was decanted. The resin was washed with 5 ml of PBS, and centrifuged and decanted as above. The resin was then transferred to a SPIN-X, 0.45 um, 2 ml tube. The resin was washed an additional two times with 0.5 ml of PBS and centrifuged. The Mab's were eluted with 0.2 ml of 0.1M acetic acid by incubating at room temperature with occasional mixing for 10 minutes. The tubes were centrifuged, and 30 ul of 1M Tris buffer Ph 8.0 is added to the eluate. Purified Mab's were stored 4-8° C.

Example 4

C2C12 Cell Based Activin Activity Assay

This assay demonstrates the activin A neutralizing capability of the antibody being tested by measuring the extent that binding of activin A to its receptor is inhibited. An activin-responsive reporter cell line was generated by transfection of C2C12 myoblast cells (ATCC No: CRL-1772) with a pMARE-luc construct. The pMARE-luc construct was made by cloning twelve repeats of the CAGA sequence, representing the activin response elements (Dennler et al. EMBO 17: 3091-3100 (1998)) into a pLuc-MCS reporter vector (Stratagene cat #219087) upstream of the TATA box. The myoblast C2C12 cells naturally express activin IIB receptors (actRIIB) on the cell surface. When activin binds the cell receptors, the Smad pathway is activated, and phosphorylated Smad binds to the response element (Macias-Silva et al. Cell 87:1215 (1996)), resulting in the expression of the luciferase gene. Luciferase activity is then measured using a commercial luciferase reporter assay kit (cat #E4550, Promega, Madison, Wis.) according to manufacturer's protocol.

A stable line of C2C12 cells that had been transfected with pMARE-luc (C2C12/pMARE clone #44) was used to measure activin activity according to the following procedure.

Equal numbers of the reporter cells (C2C12/pMARE clone #44) were plated into 96 well cultures. A first round screening using two dilutions of condition medium which contains antibodies was performed with the activin A concentration fixed at 4 nM. Recombinant mature activin A was pre-incubated for 1 hour at room temperature with condition medium at 2× and 5× dilutions respectively. The reporter cell culture was treated with activin with or without antibodies for six hours. Activin A activity was measured by determining the luciferase activity in the treated cultures. This assay was used to initially identify antibodies that inhibited the activin A signaling activity in the reporter assay. Subsequently, a nine point titration curve was generated with the activin A concentration fixed at 4 nM. The activin A was preincubated with each of the following nine concentrations of purified antibodies: 0.004 nM, 0.04 nM, 0.4 nM, 4 nM, 20 nM, 40 nM, 200 nM, 400 nM and 2 µM for one hour before adding the mixture to the reporter cell culture. The $IC_{50}$ values were for a number of antibodies A1, A2 and A3 are provided in Table 3.

TABLE 3

| MAb | Cell $IC_{50}$ (nM) |
|---|---|
| A1 | <3 |
| A2 | <3 |
| A3 | <3 |

Example 5

Biacore® Assay

An affinity analysis of activin A antibodies A1, A2 and A3 was performed on a BIAcore®3000 (Biacore, Inc., Piscataway, N.J.), apparatus using sensor chip CM5, and 0.005 percent P20 surfactant (Biacore, Inc.) as running buffer. Recombinant mature activin A protein was immobilized to a research grade CM5 sensor chip (Biacore, Inc.) via primary amine groups using the Amine Coupling Kit (Biacore, Inc.) according to the manufacturer's suggested protocol.

Direct binding assays were used to screen antibodies in order of their ability to bind to immobilized activin A. Binding assays were carried by injection of two concentrations (40 and 400 nM) of each candidate antibody to the immobilized activin A surface at a flow rate of 50 µl/min for 3 minutes. After a dissociation time of 3 minutes, the surface was regenerated. Binding curves were compared qualitatively for binding signal intensity, as well as for dissociation rates. Antibody binding kinetic parameters including ka (association rate constant), kd (dissociation rate constant) and KD (dissociation equilibrium constant) were determined using the BIA evaluation 3.1 computer program (Biacore, Inc.). The lower the dissociation equilibrium constants (expressed in nM), the greater the affinity of the antibody for activin A.

Example 6

Activin A Binding Region Mapping for Monoclonal Antibodies

Antibody binding regions on activin A were determined using multiple biochemical methods, including western under reducing or non-reducing conditions, limited protease digestion using LysC, peptide analysis by MS, and peptide competition using BIAcore.

Cys-knots are key structural characteristics for TGF-β family members. Breaking S—S with reducing agent deteriorated activin A structure and decreased activin A binding to the neutralizing antibodies, including A-1. This data demonstrated that Cys-knots are important for activin A binding with these neutralizing antibodies that bind specifically to activin A compared to activin B. Cys-knots make two distant loops of sequences structurally adjacent to each other. These two regions are a sequence in the region of approximately C11-S33 (first loop) and approximately C81-E111 (second loop) activin A (FIG. 7). A limited LysC digestion revealed that these two regions were protected by antibody A-1, indicating they interact with the neutralizing antibodies directly. The neutralizing antibodies are sensitive to conformational changes of activin A, suggesting they bind to non-linear epitopes of the antigen. Further peptide analysis indicated that fragments G-1 to K7 and S57-F74 in activin A are not required for its binding with the neutralizing antibodies directly. A comparison of the sequence of activin A compared to activin B shows that some of the sequence differences occur in this region.

Example 7

Selectivity Assays

These assays were performed using BIAcore® technology, to determine the selectivity of binding of antibodies A1, A2 and A3 to various activins and other TGF-β family members, including activin A, activin B, activin AB, inhibin A, GDF-8, GDF-11, TGF-β-1, TGF-β-3, and BMP4 (all from R & D Systems). ActRIIB/Fc was covalently coupled to research grade sensor chips according to manufacturer's suggested protocol. Because BIAcore assays detect changes in the refractive index, the difference between the response detected with injection over the immobilized receptor surfaces compared with the response detected with injection over the control surface in the absence of any antibody represents the actual binding of the various ligands to the receptor. With pre-incubation of antibodies and activin and TGF-β molecules, a change (increase or decrease) in binding response indicates antibody binding to the TGFβ family of molecules. The antibodies all bound to activin A but not to activin B, GDF-8, GDF-11, TGF-β-1, TGF-β-3, and BMP4, thus indicating specificity for activin A.

Example 8

KinEx A™ Equilibrium Assays

Figure 8A:
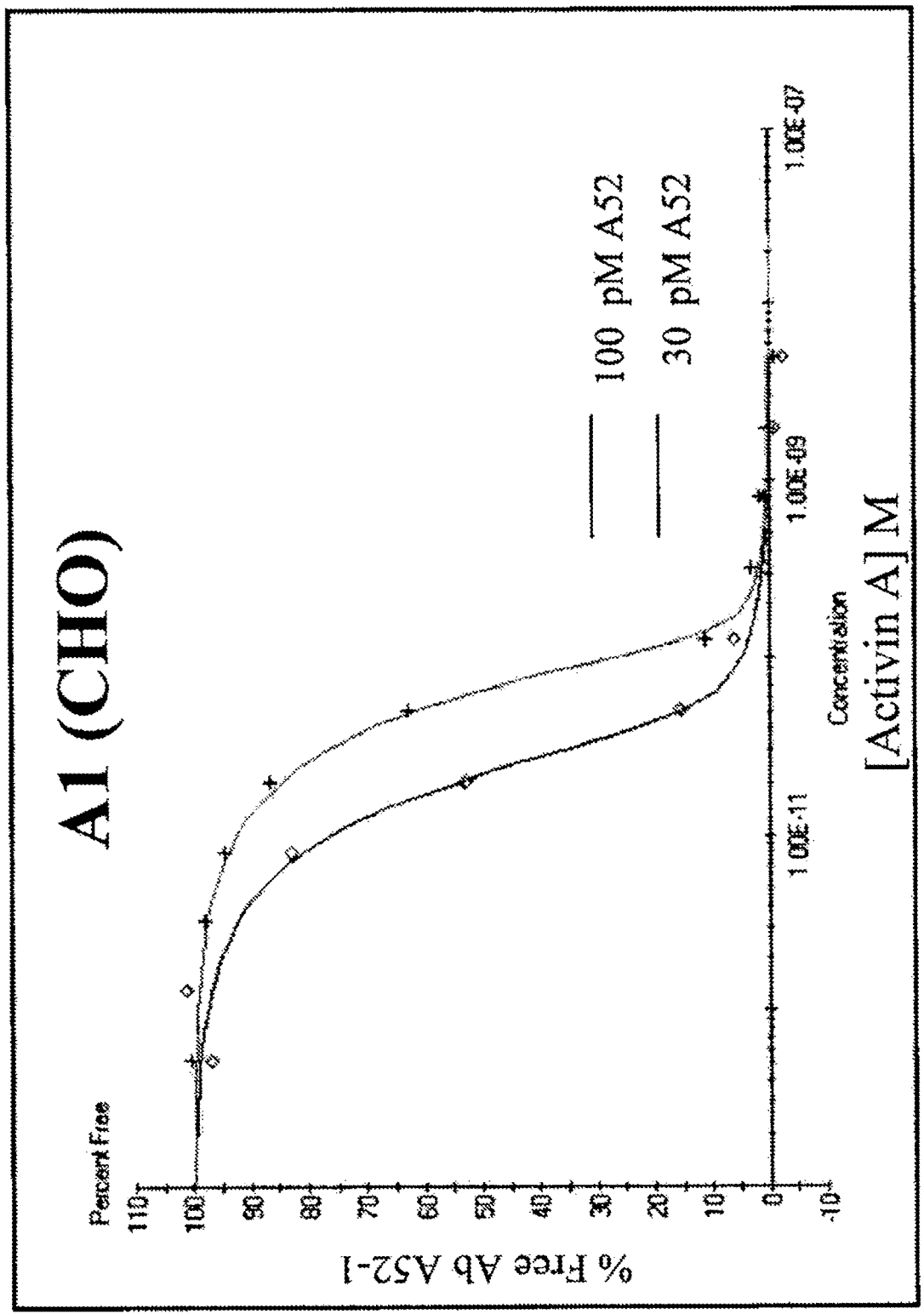
FIG. 8A is a graph showing the binding affinities of antibodies A1, as determined using KinExA. The dissociation equilibrium constant was obtained from non-linear regression of the competition curves using a dual-curve one-site homogeneous binding model using the KinExA software.
Figure 8B:
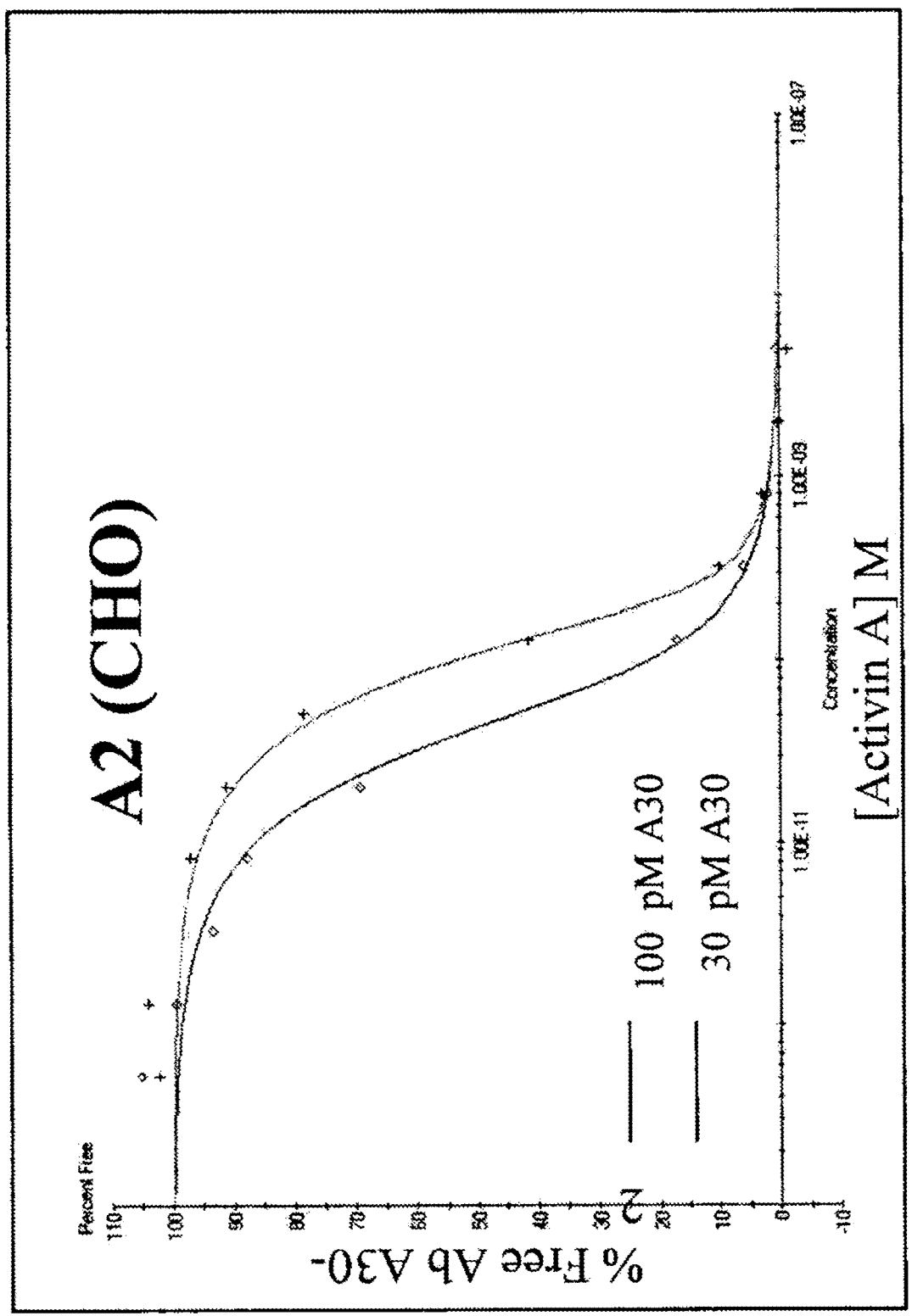
FIG. 8B is a graph showing the binding affinities of antibodies A2, as determined using KinExA.
Figure 8C:
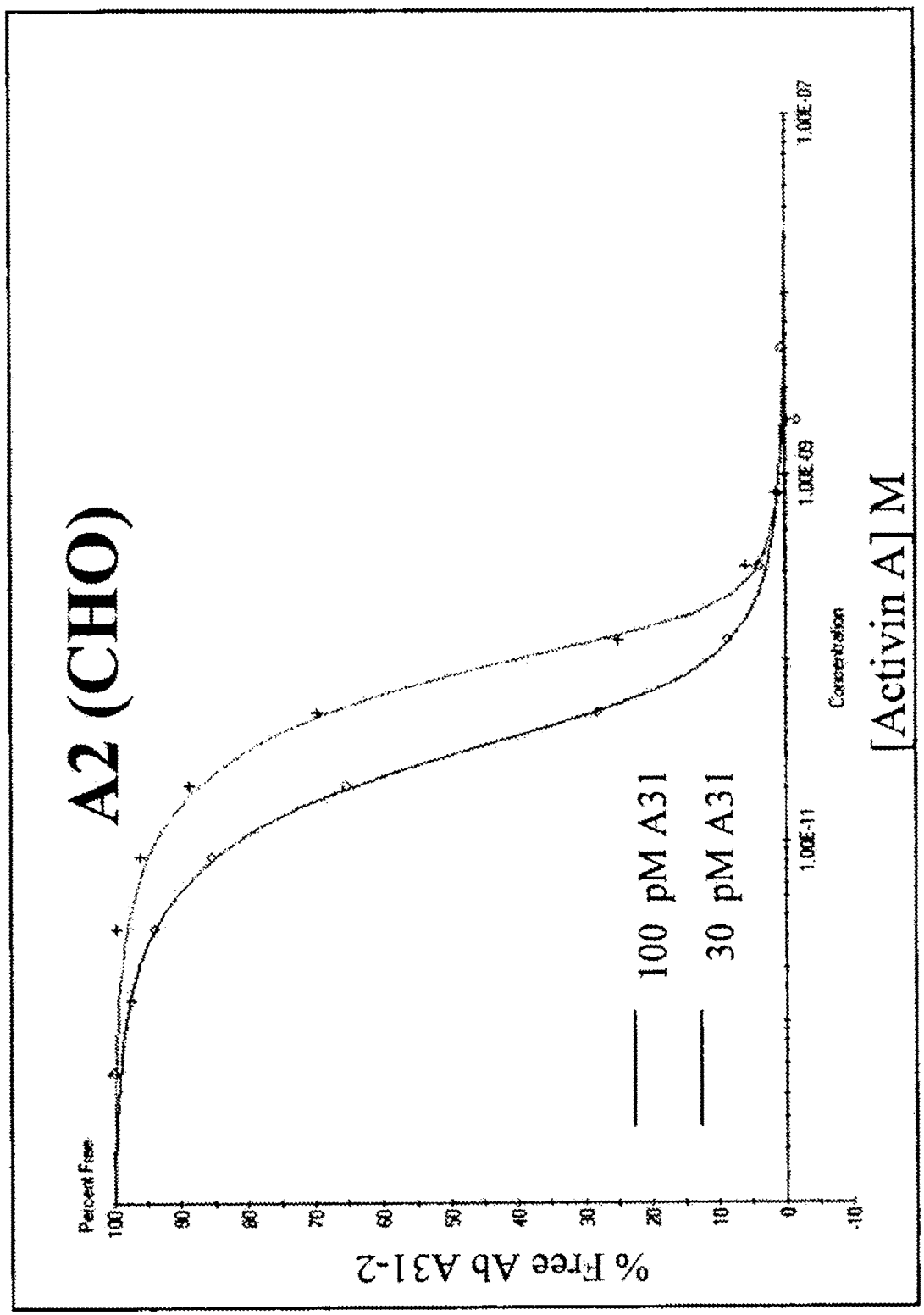
FIG. 8C is a graph showing the binding affinities of antibodies A2, as determined using KinExA.

Solution-based equilibrium-binding assays using KinExA™ technology (Sapidyne Instruments, Inc.) were used to determine the dissociation equilibrium (KD) of activin A binding to antibody molecules. This solution-based assay is considered to be more sensitive than the BIAcore assay in some instances. Reacti-Gel™ 6× was pre-coated with about 50 μg/ml activin A overnight, and then blocked with BSA. 30 pM and 100 pM of antibody samples were incubated with various concentrations (0.5 pM to 5 nM) of activin A in sample buffer at room temperature for 8 hours before being run through the activin A-coated beads. The amount of the bead-bound antibody was quantified by fluorescent (Cy5) labeled goat anti-human-Fc antibody at 1 mg/ml in superblock. The binding signal was proportional to the concentration of free antibody at equilibrium with a given activin A concentration. KD was obtained from the nonlinear regression of the competition curves using a dual-curve one-site homogeneous binding model provided in the KinEx A™ software (Sapidyne Instruments, Inc.). The results are shown in FIG. 8. A1 shows the strongest binding affinity for activin A ($K_D$~3 pM). A2 and A3 bound to activin A at ~15 pM and ~8 pM, respectively.

Example 9

Protective Effects of Anti-Activin on Body Weight and Muscle Mass Loss in Collagen-Induced Arthritis Model This example was designed to test if activin inhibitors can rescue muscle wasting condition observed in collagen-induced arthritis. Collagen-induced arthritis (CIA) is a widely used mouse model sharing several clinical and pathological features with rheumatoid arthritis (RA). The precise mechanisms for CIA is not known, however, there is considerable evidence to suggest that CIA is a Th-1 mediated inflammatory disease. Rheumatoid arthritis is a common autoimmune disease that leads to joint inflammation, and progressive cartilage/bone erosion. Even if the RA progression is under control, loss of BCM is not corrected without additional, direct intervention.

The collagen-induced arthritis model was prepared as follows. DBA/1J male mice (The Jackson Laboratory, Bar Harbor, Me.), 8 weeks of age (20-23 g), were used. Immunization was carried out on day 1 and day 21 by injecting 1000 g Bovine Collagen II (Chondrex, Redmond, Wash.) emulsified in 100 μl of CFA or ICFA, intradermally at the base of the tail. Three groups of ten mice each were used. Group 1 (control) received vehicle only. Group 2 (experimental, collagen injection) received vehicle only as treatment. Group 3 was injected with collagen and treated with anti-Activin A antibody A1.

The arthritic clinical index used was:
0=normal joint no signs of arthritis
1=swelling and/or redness of one digit
2=two joints involved
3=more than two joints
4=severe arthritis of the entire paw and digits The treatment consisted of activin antibody injection (s.c.) beginning on Day 8, 5 mg/kg, s.c. twice a week. The endpoints measured were body weight, muscle/fat mass, food intake and inflammatory cytokines.

Body weight. Untreated CIA animals lost twenty-five percent of their body weight and muscle mass compared to normal animals, which provided the evidence of rheumatoid cachexia. Anti-activin A (A-1) treatments significantly increased ($p<0.05$) body weight compared to that of CIA control but not to the normal control animals.

Muscle mass. Treatment with monoclonal antibody A1 significantly increased muscle mass ($p<0.05$) in CIA animals, compared to that of untreated CIA animals. In the CIA controls, the muscle mass at 95 days was 1.5 g; whereas in the antibody-treated CIA animals, the muscle mass at 95 days was 2.5 g. The results are shown in FIG. 1.

Figure 2:
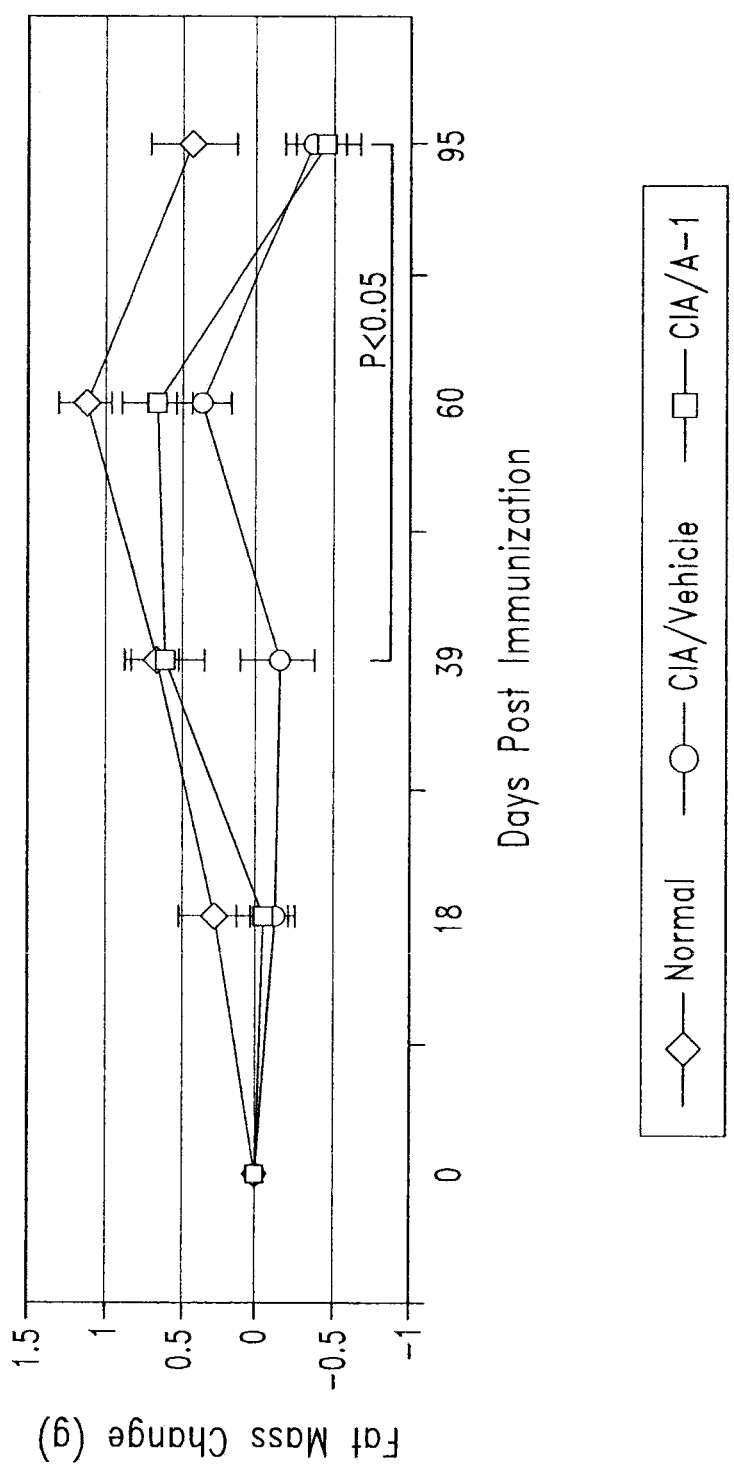
FIG. 2 provides the fat mass change for collagen induced arthritis mice treated with anti-activin A antibody A1.

Fat mass. Anti-activin A antibody did not reverse the fat loss in CIA animals. The results are shown in FIG. 2.

The preservation of body weight and muscle mass in the treated animals provides support for activin A antibodies as a therapeutic for improving quality of life and lowering mortality in rheumatoid arthritis sufferers.

Example 10

Intramuscular Cho/Activin Xenograft in Young Adult Nude Mice

CHO cells stably transfected with activin A (CHO/Activin) were implanted into young adult CD1 nu/nu mice via intramuscular injection at various doses, $1\times10^6$, $5\times10^6$, and $10\times10^6$. The same doses of non-transfected CHO cells were injected into separate groups of mice as controls. CHO/Activin implantation induced a rapid and drastic body weight loss compared to controls.

At day 12, the CHO/control group for $1\times10^6$ cells had a loss of 10% of body weight, whereas the CHO/anti-activin A group had a 10% gain in body weight. The $5\times10^6$ and $10\times10^6$ cell anti-activin A groups also showed body weight increases of about 10%, whereas the control $5\times10^6$ and $10\times10^6$ cell groups lost 25-30% of the body weight.

Serum activin A levels in mice were measured on day 12 post xenograft implantation. The levels of serum activin A in parental CHO implanted control mice were <2 ng/ml. In contrast, the mice bearing CHO/Activin xenograft showed dramatically elevated serum activin A. There was a significant correlation between the serum activin A level and the severity of body weight loss as indicated by the statistical analysis, indicating that activin A overexpression is responsible for the body weight loss seen in CHO/Activin xenograft mice.

Mice (n=14 per group) were implanted with CHO/Activin xenograft and subsequently injected with either vehicle or each of the three anti-activin A monoclonal antibody, A1, A2 and A3. Twelve out of fourteen of the mice in the vehicle group died by day 25 post CHO/Activin implantation, while only one of forty-two CHO/Activin implanted mice in the anti-activin A Mab treatment groups died at the time. By day 38, the majority of mice in the Mab treatment groups continued to survive well, with survival rates as follows: thirteen out of fourteen for A1 group and ten out of fourteen for either A2 or A3 group.

Figure 3:
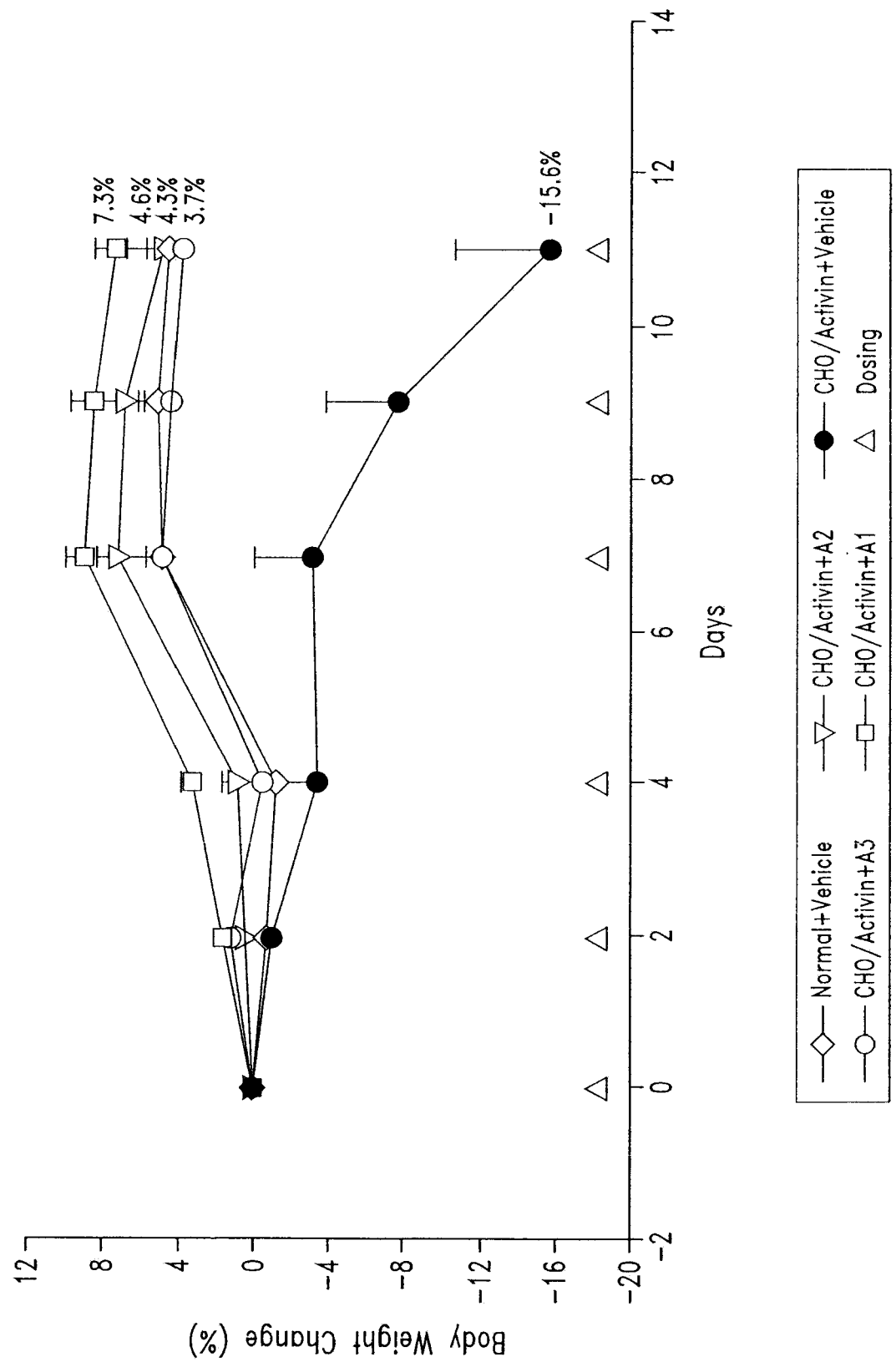
FIG. 3 provides data showing that anti-activin A treatment using antibodies A1, A2 and A3 prevents body weight loss in young adult nude mice with an intramuscular CHO/Activin xenograft.
Figure 4:
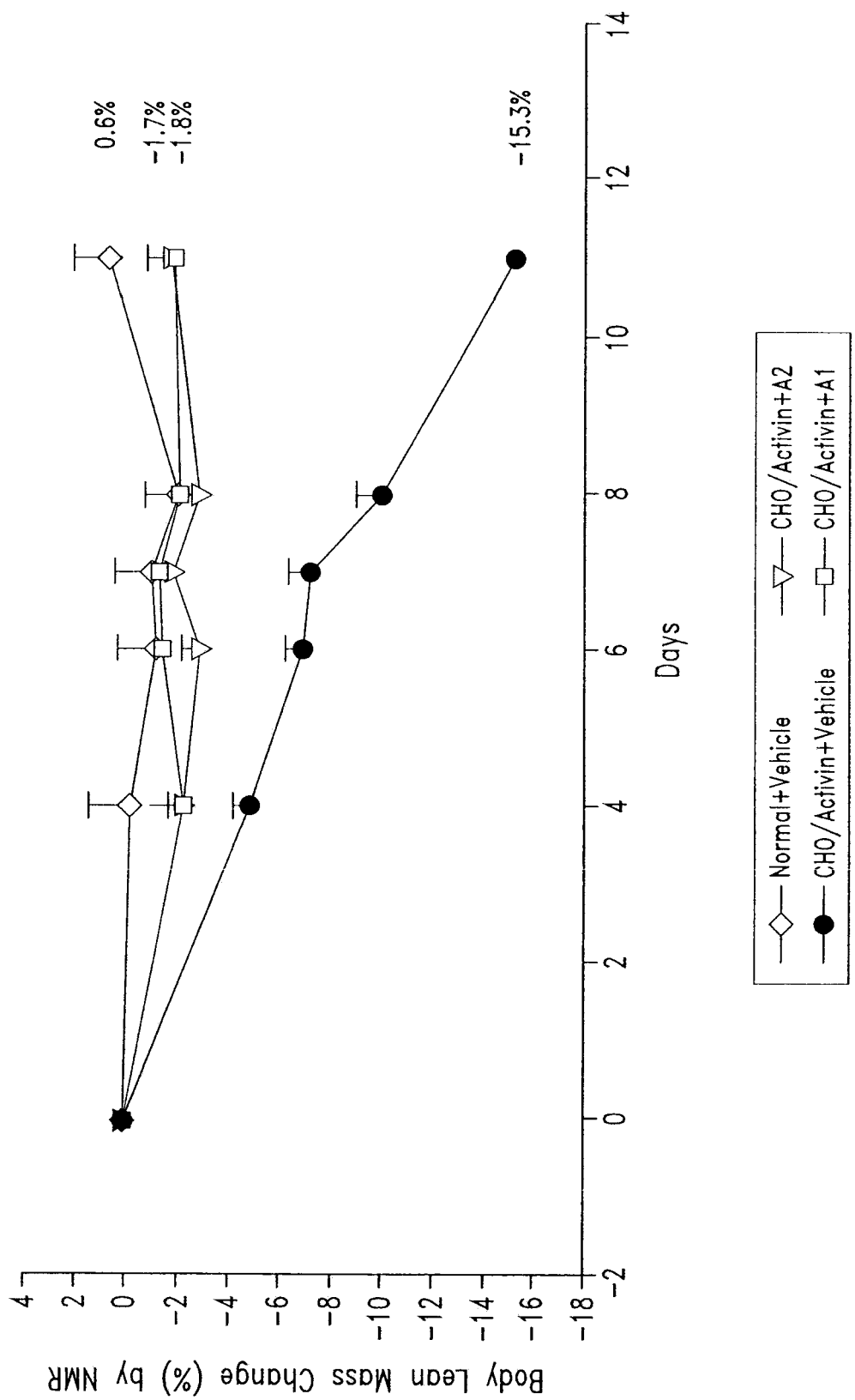
FIG. 4 provides NMR data showing that anti-activin A treatment prevents loss of lean body mass in young adult nude mice with an intramuscular CHO/Activin xenograft.

Body weight data show that treatment with anti-activin A Mab, A1 or A2, completely prevented the body weight loss in CHO/Activin xenograft-bearing mice, indicating that the anti-activin A Mabs were effective in neutralizing activin A activity in vivo. As shown in FIG. 3, NMR data revealed that treatment with anti-activin A Mab, A1 prevented the progressive loss of lean body mass seen in CHO/Activin-bearing mice. Treatment with this antibody also caused an increase in food intake.

Necropsy data indicate that treatment with anti-activin A Mab, A1 and A2, prevented the severe reduction in lean carcass weights seen in CHO/Activin-bearing mice (Table 5). Terminal necropsy data indicate that treatment with anti-activin A Mab, A1 and A2, prevented the severe reduction in fat mass seen in CHO/Activin-xenograft bearing mice (Table 5).

The percentage of animals bearing a visible tumor at the xenograft site was analyzed during terminal necropsy on day 12 post CHO/Activin implantation. As shown in Table 5, data revealed that 80% of the mice in the vehicle group developed visually identifiable xenograft tumors at the injection site. A significantly decreased rate of visible tumor formation in the anti-activin A Mab treatment groups was observed.

Upon necropsy, all the visually identifiable tumors at the CHO/Activin xenograft sites were dissected from the animals and weighed. A significant decrease in tumor mass was observed in the activin A Mab treatment group compared to vehicle group (Table 5).

TABLE 5

| Treatment | Lean carcass mass (g) on day 12 | Periuterine fat tissue (g) on day 12 | Tumor xenograft development, percent of animals, on day 12 | Tumor weight (g) on day 12 |
|---|---|---|---|---|
| Nude mice plus vehicle | 9 ± 0.25 | 0.18 ± 0.02 | Not applicable | Not applicable |
| CHO/Activin plus vehicle | 7.5 ± 0.25 | 0.10 ± 0.02 | 80% | 0.11 ± .01 |
| CHO/Activin plus A-1 antibody | 9.2 ± 0.25 | 0.17 ± 0.04 | 20% | 0.01 ± 0.005 |
| CHO/Activin plus A-2 antibody | 8.9 ± 0.25 | 0.16 ± 0.03 | 50% | 0.01 ± 0.005 |

The foregoing experiments on xenograft tumor development led to several conclusions regarding the use of anti-activin A antibodies to improve survival from cancer. Activin A played a causal role in the development of cachexia syndrome in nude mice bearing CHO/Activin xenograft. The loss of body weight correlated well with the increase in serum activin level in this model. Anti-activin A Mabs prevented the body weight loss and cachexia syndrome seen in CHO/Activin xenograft tumor-bearing mice. Anti-activin A Mabs suppressed xenograft growth, thereby significantly reducing the percentage of mice bearing visible xenograft tumors as well as decreasing the xenograft tumor sizes. Anti-activin A Mabs prevented the death resulting from CHO/Activin exograft, markedly promoting animal survival.

Example 11

Anti-Activin Monoclonal Antibody A1 in AAV-Activin Mice

Postnatal overexpression of activin A led to severe cachexia-like wasting syndrome in C57Bl/6 mice. The body weight decreased over day 1, 4, 9 and 11, going from 16 grams to 14, 12.5, and finally 10.5 grams at day 11. There was also a loss of fat weight, lean carcass weight, and gastrocnemeus muscle weight.

Figure 5:
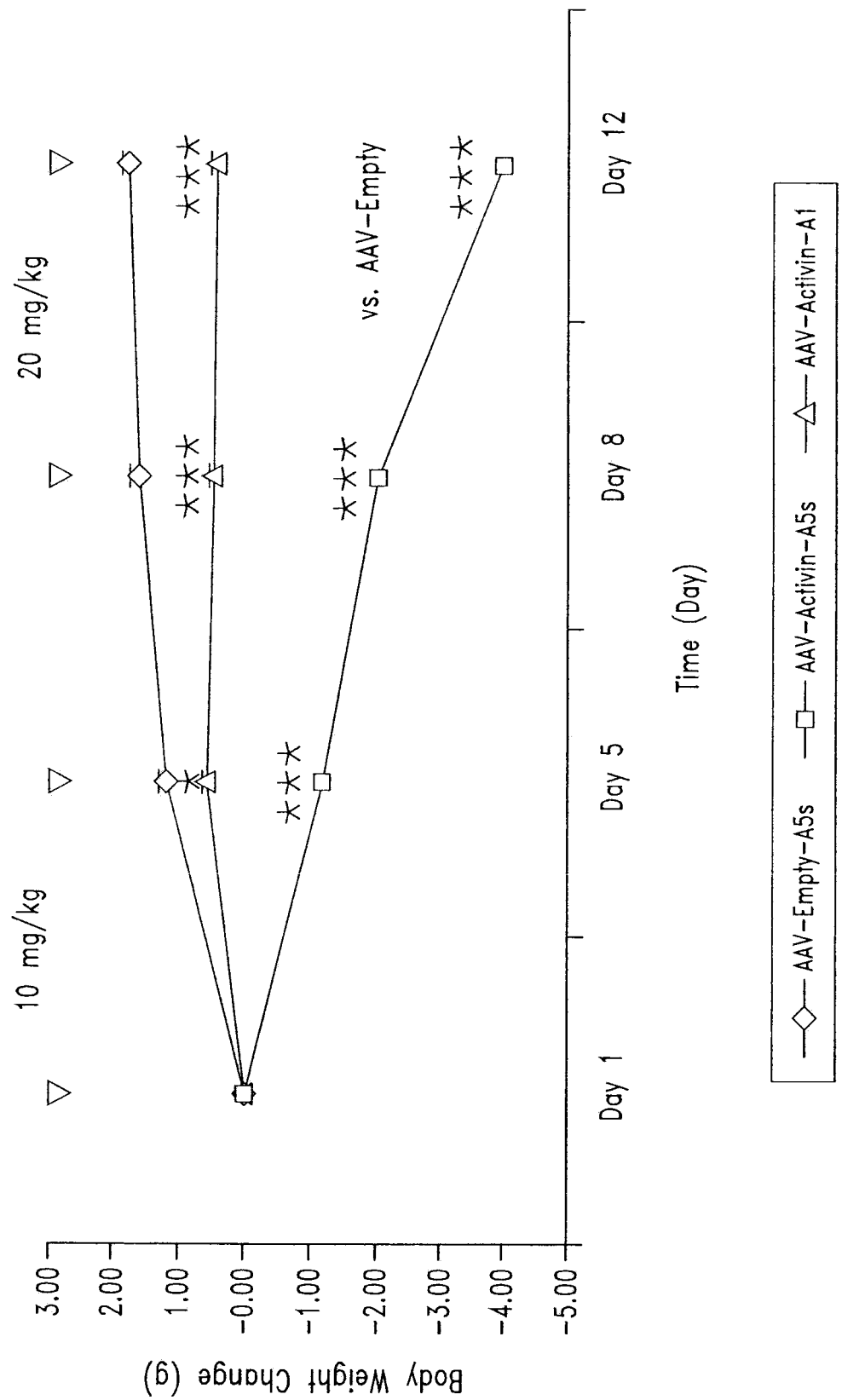
FIG. 5 provides the effect of anti-activin A antibody A1 on body weight changes in AAV-activin A transduced mice.
Figure 6:
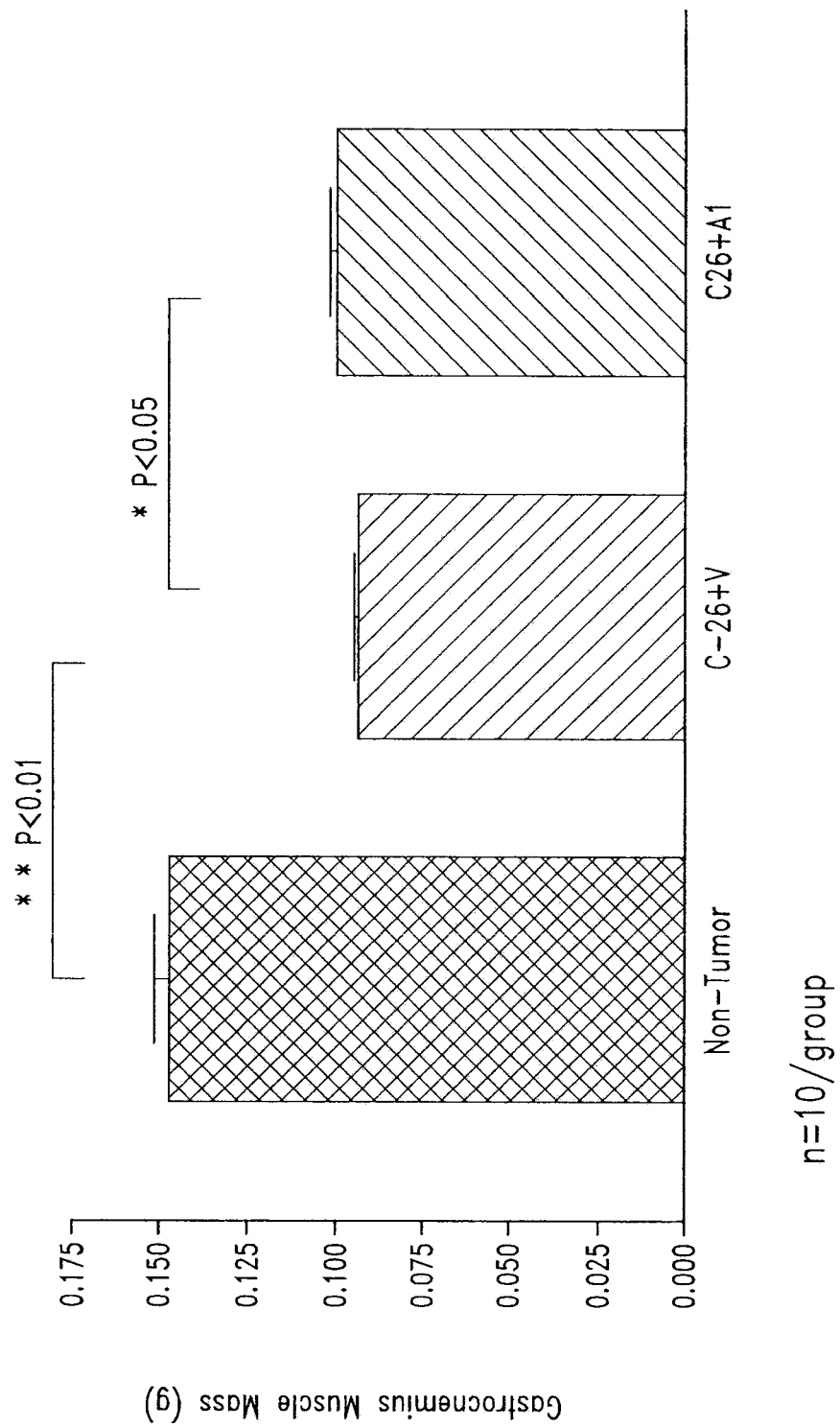
FIG. 6 provides the gastrocnemius muscle mass in a CDF1 mouse Colon-26 cancer cachexis model with and without treatment with anti-activin A antibody A1, eighteen days after tumor inoculation.
Figure 7:
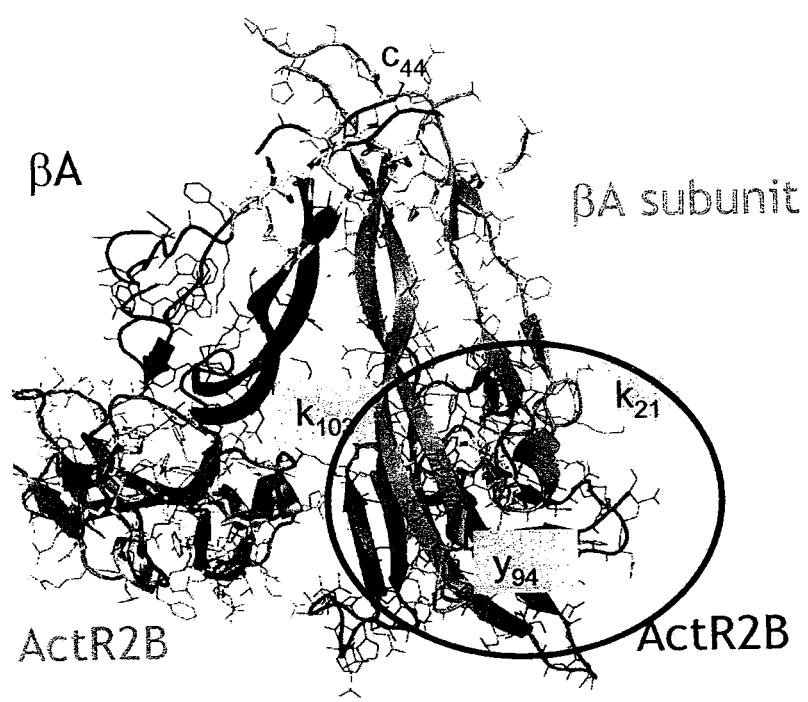
FIG. 7 shows a model of activin A, with the region of antibody binding circled. K21, K103 and X94 refer to lysine residues at position 21 and 103, and a tyrosine residue at position 94.

To determine whether antibody directed to activin A could alleviate or prevent the effects of activin A, the following experiments were performed. AAV-Activin or empty AAV vector (control) were injected at $1 \times 10^{13}$ pfu/mouse into 8 week old male C57Bl/6 mice (n=10-12) via the tail veins. FIG. 5 shows the effect of anti-Activin A monoclonal antibody A1 on body weight change in the transduced mice at days 1, 5, 8 and 12. The antibody prevented the body weight change observed in the control mice. Antibody treatment improved food intake in this animal model.

Example 12

Protective Effect of Anti-Activin-A Mab A1 Against Body Weight and Lean Mass Losses in Colon-26 Cancer Cachexia Model This example demonstrates the muscle preserving effect of the anti-Activin-A monoclonal antibody A-1 in a murine cancer cachexia model. The model of cancer cachexia was established by using the syngenic murine colon 26 adenocarcinoma cells inoculation in 8.5 weeks old male CDF1 mice ($0.5 \times 10^6$ cells/mouse) on day 0. The anti-Activin-A MAb A-1 treatment (10 mg/kg, sc) was initiated on day 4 and was given 3 times weekly for 18 days. Sodium acetate buffer (10 nm sodium acetate, 5% sucrose, pH 5.0) as vehicle was used in the tumor-bearing control group mice. One group of age and weight matched normal CDF1 mice without tumors was used as parallel baseline control. Body weight and food intake were monitored three times weekly. Tumor size was measured three times per week by digital calipers. Body composition was measured using NMR at the beginning and the end of the study to monitor changes in lean and fat mass. At the end of the experiment, the mice were euthanized in a $CO_2$ chamber. Terminal block samples were collected and serum Activin-A levels were analyzed by ELISA. The lean carcass were weighed and recorded, and the gastrocnemius muscles and tumors were weighed and properly saved.

All results were expressed as mean±standard error of the mean (SEM). Non-paired T-test was performed to determine statistical difference between groups by using the Graph Pad Prizm software. Statistical significance from vehicle was represented by p values less than 0.05.

The data show that A-1 treated mice had significantly higher body weight than vehicle treated mice (21.30±0.54 g vs. 19.21±0.38 g, P<0.05, Day 15 and 19.66±0.22 g vs. 18.11±0.19 g, P<0.05, day 18). There was a significant body weight loss in tumor-bearing mice treated with vehicle compared to age-matched non-tumor-bearing mice (25.48±0.35 g vs. 18.11±0.19 g, p<0.005). Thus, the activin A antibody treatment helped to maintain body weight.

Tumor growth was monitored with a digitized calipers measurement and tumor size was calculated with the equation of: Tumor dimension (mm$^3$=L (mm)*W (mm)*W (mm) *0.5. The tumor size was not different between the antibody A1 treated and vehicle treated two groups.

After C-26 tumor cell inoculation, the mice in vehicle treated group had a dramatic body weight loss compared to non tumor-bearing mice (25.48±0.35 g vs. 18.11±0.19 g, p<0.01). However, A-1 treatment attenuated the average weight loss (19.66±0.22 g vs. 18.11±0.19 g, P<0.05).

A-1 treatment resulted in a significant preservation of the skeletal muscle mass. A-1 treated mice had greater weight of the gastrocnemius muscle mass (0.099±0.002 g vs. 0.093±0.001, p<0.05) than that in the C26 vehicle treated group.

At the end of the experiment, the terminal tissue dissection was performed. The control C-26 tumor-bearing mice had significantly lower lean carcass weight (6.75±0.11 g) than that of the antibody A1 treated mice (7.20±0.16 g, p<0.05 vs. C-26+vehicle group).

The lean body mass was markedly lost in C-26 vehicle treated group (−1.85±0.24 g compared to their initial body lean mass). Treatment with A-1 in C-26 tumor-bearing mice significantly attenuated the loss of lean body mass (−0.60±0.26 g, p<0.05 vs. C26-vehicle group).

Anti-Activin A monoclonal antibody A1 treatment is effective in attenuation of cancer cachexia induced whole body weight lose. The protective effect of antibody A1 is associated with preserving skeletal muscle mass, lean carcass mass and total lean body mass in a well-established murine cancer cachexia animal model.

The present study provides preclinical evidence that neutralization of active A using monoclonal antibody A1 significantly attenuated body weight loss and preserved skeletal muscle and lean body mass.

Example 13

Activin A ELISA

Antibodies to activin A can be used to assay and quantitate activin A in samples, such as biological samples. Recombinant human activin A (100 ng/ml, cat #10-85106) and assay diluting buffer (0 mg/ml, cat #10-85101) were purchased from DSLabs (Webster, Tex.) and stored at 4° C. Standards were prepared fresh before the experiment by diluting into assay buffer.

Human sera were obtained from Bioreclamation Inc. (Hicksville, N.Y.). Sera for activin A measurement were aliquoted in 110 µl to minimize variation due to freeze-thaw. The samples were diluted ⅓ with assay buffer and measured in the ELISA.

Activin A ELISA (one-step ELISA) is performed using the following steps:

Corning Costar 3590 96-well plats were coated with 100 µl of 4 µg/mL anti-activin A Mab (A2) overnight at room temperature while gently shaking at 500-600 rpm. The wells (400 µl/well) were washed three times with PBS containing 0.02% (v/v) Tween 20. The wells were blocked in 300 µl of I-blocking buffer for two hours at room temperature, then blocking buffer was removed.

100 µl of standard activin A/or 100 µl of diluted samples were added, and 25 µl of 0.5 µg/mL anti-activin A mAb-HRP labelled (A1/HRP) was added in assay buffer. For free activin A measurements, sera were diluted in ⅓ with assay buffer. For total activin A measurements, sera were (1) acidified (pH 4-5) with 20% HCL (2 µl per 110 µl sera), (2) incubated for 15 minutes at room temperature, (3) neutralized by adding 2 µl of 5 N NaOH (2 µl per 110 µl sera), and (4) diluted in ⅓ with assay buffer.

Incubation was carried out for 2 hours at room temperature while shaking at 600-700 rpm. The wells (400 µl/well) were washed three times with PBS containing 0.02% (v/v) Tween-20. 100 µl of TMB (R&D System, Minneapolis, Minn.) was added, followed by an incubation for twenty minutes at room temperature. 50 µl of stop solution (R&D System, Minneapolis, Minn.) was added. OD measurement was performed using 450 nm in Molecular Device SpectraMax M5.

A standard curve was generated by plotting absorbance at 450 nm vs. the log of the rh-activin concentration, by using a log-log (or a five-parameter logistic) curve-fitting program of Molecular Device. Values for sample concentrations were obtained by interpolation of their absorbance from the standard.

The Capturing Antibody was A-3 anti-activin A mAb, 20.78 mg/ml. The Detection Antibody was A-1 anti-activin A mAb-HRP, 0.65 HRP/Ab, 12.05 mg/ml. The Blocking Buffer was I-blocking buffer. The wash buffer was PBS/ 0.1% Tween-20. The assay buffer (Reagent Diluent) was 0 mg/ml activin A buffer.

Example 14

Activin A Protease Protection Analysis

Protease protection assays were conducted in order to identify epitope binding of activin A antibodies. Recombinant human activin A degraded preparation was analyzed by three methods. The first method examined an activin A preparation that had been degraded during purification. The second method included proteolysis of the activin A preparation with Lysine C, chymotrypsin, pepsin and thermolysin. The third method included chemical degradation of the preparation using cyanogen bromide.

Thus, for the proteolysis of human activin and antibody complex, 5 micrograms of activin A and 90 micrograms of antibody were mixed in 100 microliters of 0.1 M ammonium bicarbonate (pH 7.8) and kept at room temperature for approximately 20 minutes before treatment with 2% by weight of the particular selected protease. Digestion of the protein was allowed to proceed at 37 degrees Celsius for 90 minutes. Control samples containing activin A alone or antibody alone were carried out in an identical fashion. The samples were acidified prior to RP-HPLC analysis.

For the cyanogen bromide digestion of activin A, CNBr fragments of activin A were generated by incubating 10 micrograms of the protein with CNBr in 100 mincroliters of 90% TFA overnight at room temperature. The sample was kept in the dark throughout the incubation and was dried in a vacuum prior to RP-HPLC analysis.

The RP-HPLC was utilized to analyze the fragments generated as described above. Briefly, the column was equilibrated with solvent, the sample was injected and the column was washed with solvent before a linear gradient was applied. Column effluent was monitored by absorbance at 215 nm. The eluted samples were manually collected and analyzed by Edman degradation and mass spectrometry.

The preparation that had been degraded during purification contained the following species:
1. Gly$^1$-His$^{59}$ (6,456.2 Da)
2. Ser$^{60}$-Tyr$^{94}$ (4,102.9 Da)
3. Asp$^{95}$-Ser$^{116}$ (2,452.8 Da)
4. Gly$^1$-Tyr$^{94}$ (10,541.1 Da)

The preparation that had been degraded by a chymotryptic-like activity had the following species cleaved at the locations indicated in SEQ ID NO: 225:

(SEQ ID NO: 262)
1. $_1$GLECDGKVNICCKKQFFVSFKDIGWNDWII$^{30}$ (SEQ ID NO: 263)
2. $_{31}$APSGYHANYCEGECPSHIAGTSGSSLSFH↓S$_{60}$ (SEQ ID NO: 264)
3. $_{61}$TVINHYRMRGHSPFANLKSCCVPTKLRPMS$_{90}$ (SEQ ID NO: 265)
4. $_{91}$MLYY↓DDGQNIIKKDIQNMIVEECGCS$_{116}$

The species set forth in FIG. 9 indicate the locations of cleavage sites when the activin A preparation was degraded by chymotrypsin, Lysine C (LysC), or Cyanogen Bromide (CNBr).

Example 15

Activin A Binding Assay

Monoclonal antibodies A1, A2, and A3 bind to activin A but not activin B, according to the binding affinities listed in Table 6. Thus, an affinity analysis of activin A antibodies A1, A2, and A3 was performed in order to determine the region or structure needed for neutralizing antibody binding. Several activin A binding proteins are known, including ActRII (A/B), ActRI (A/B)(Alt4), follistatin, and follistatin related gene (FLRG).

Figure 10:
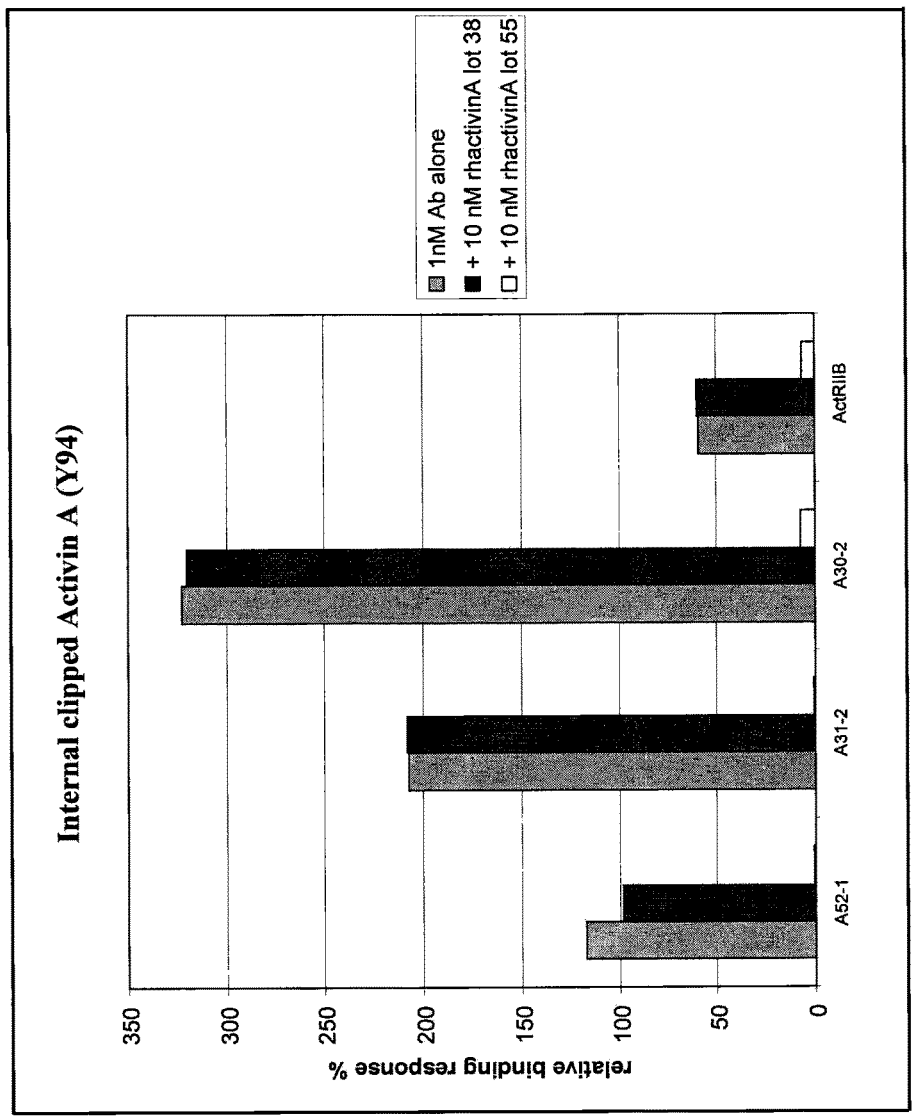
FIG. 10 is a graph showing binding affinities of antibodies A1, A2, and A3 for intact activin A (indicated by lot 55), as well as activin A that is cleaved at the tyrosine residue at amino acid position number 94 (indicated by lot 38).
Figure 11A:
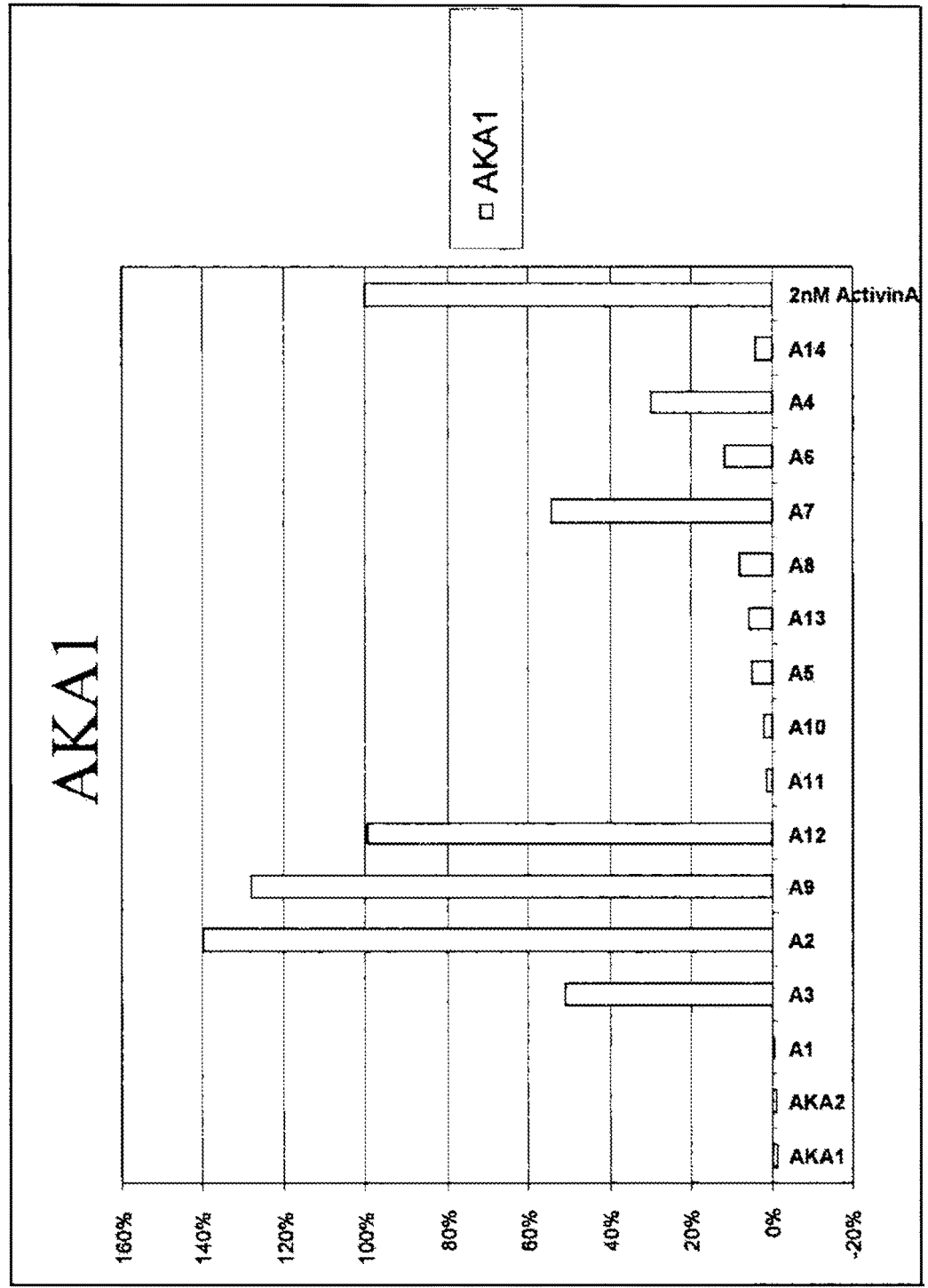
FIG. 11A is a graph showing binding affinities of a commercially available antibody (AKA1) for activin A or activin B on immobilized antibody surfaces.
Figure 11B:
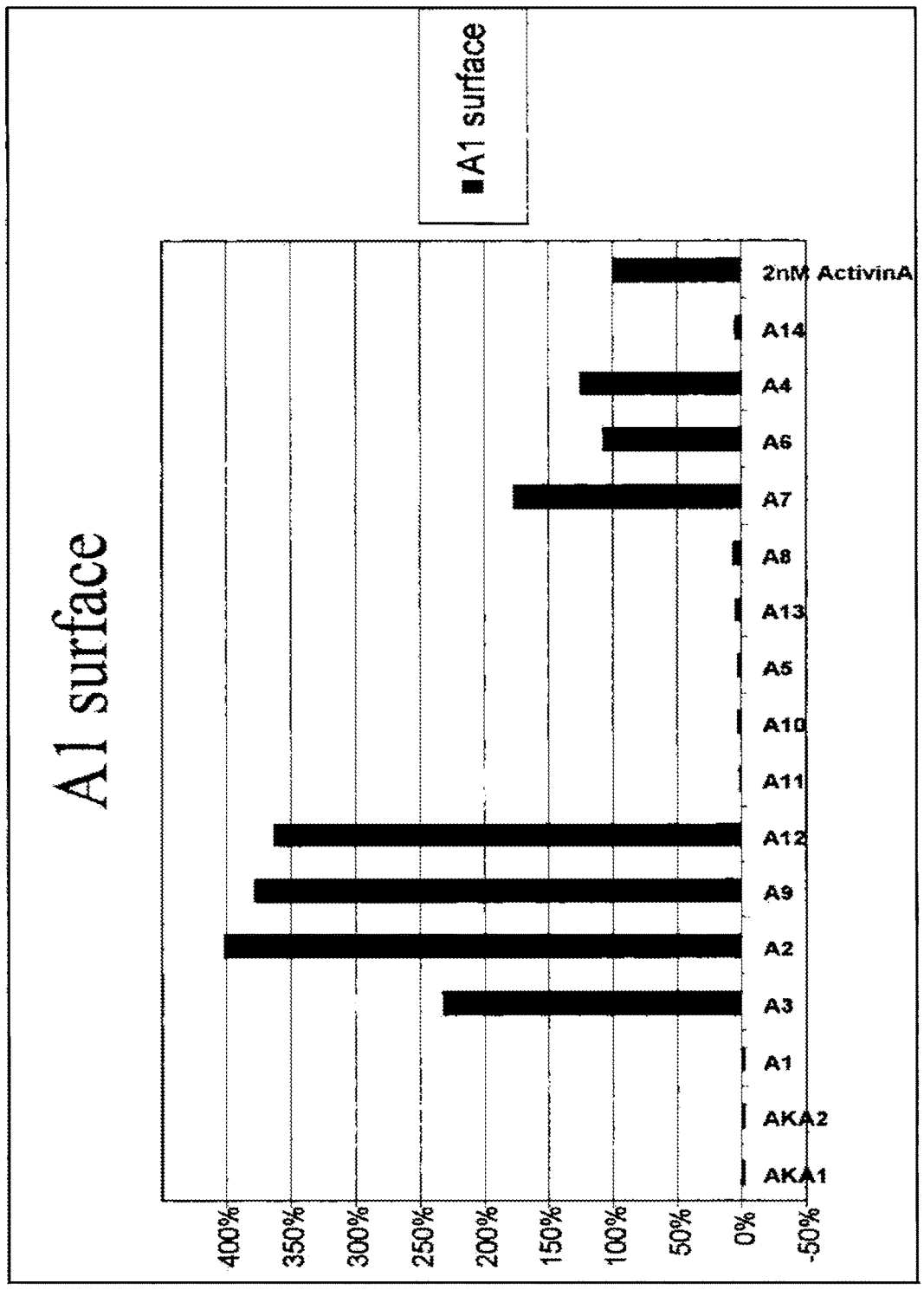
FIG. 11B is a graph showing binding affinities of antibody A1 for activin A or activin B on immobilized antibody surfaces.
Figure 11C:
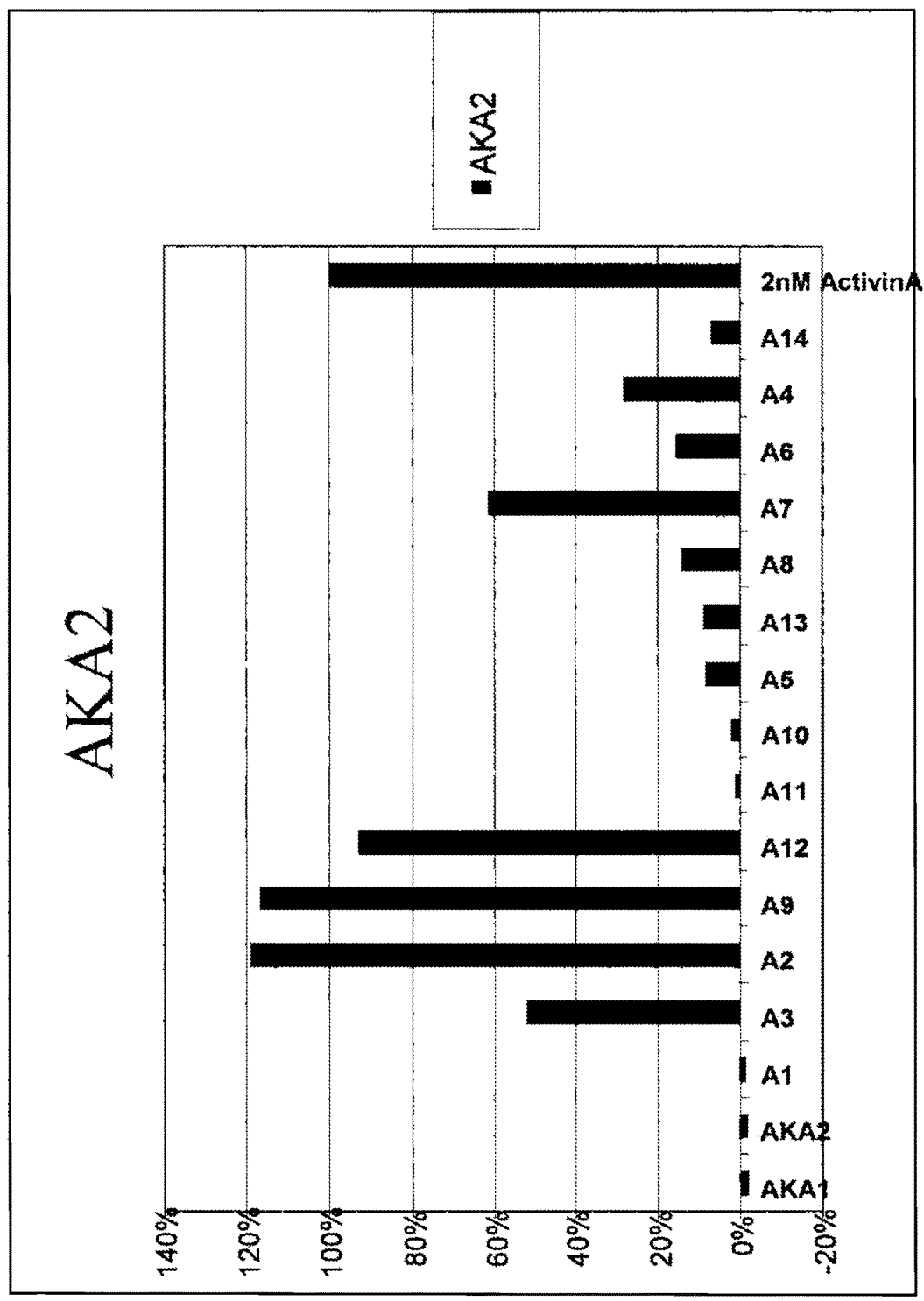
FIG. 11C is a graph showing binding affinities of a commercially available antibody (AKA2) for activin A or activin B on immobilized antibody surfaces.
Figure 11D:
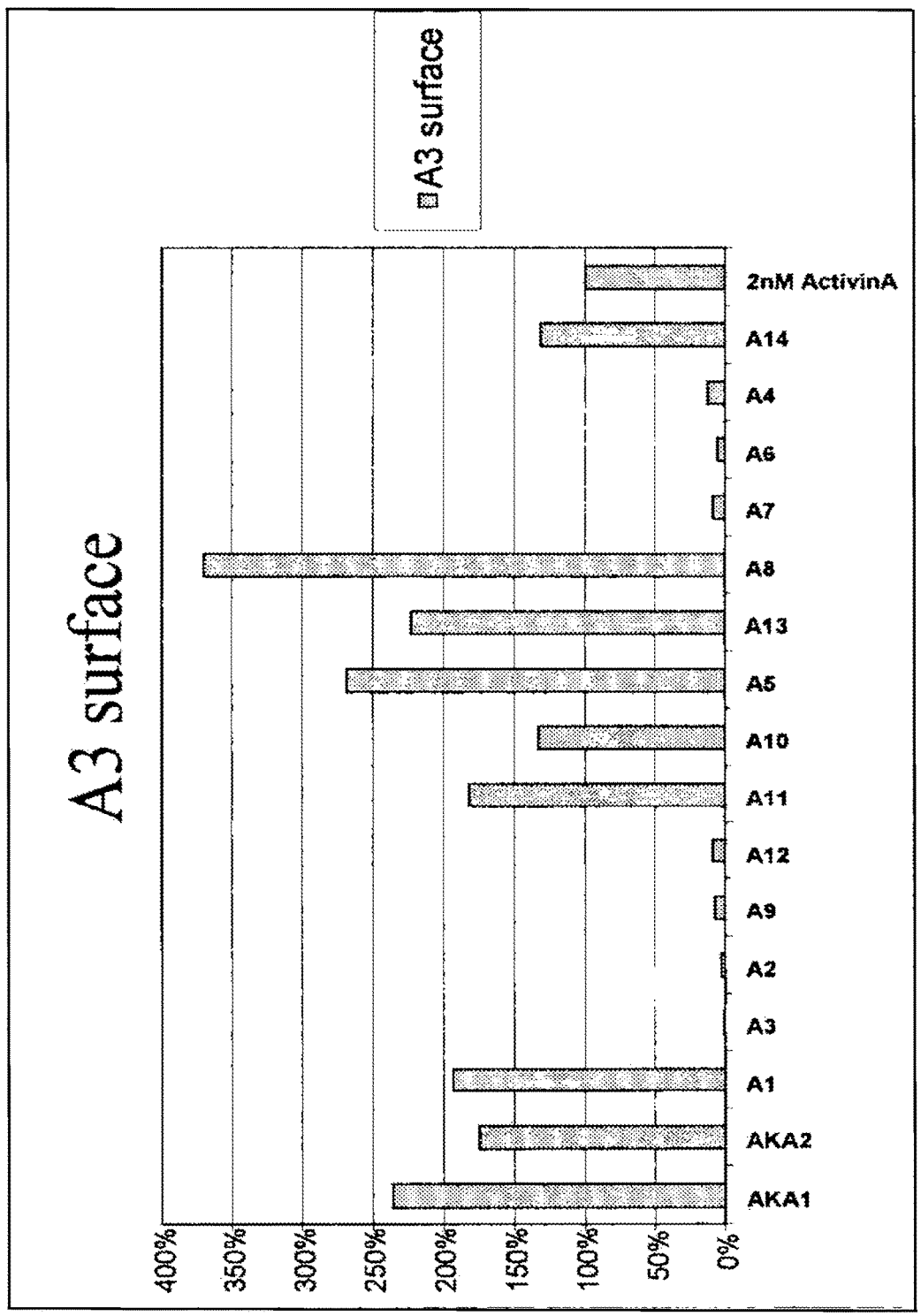
FIG. 11D is a graph showing binding affinities of a commercially available antibody (AKA3) for activin A or activin B on immobilized antibody surfaces.

Binding assays were conducted to screen antibodies in order to assess their ability to bind to immobilized antibody surfaces (activin A and/or activin B). Binding assays were performed utilizing 2 nM rhActivin A and 20 nM of each antibody immobilized on a surface. The following antibodies were immobilized on a surface and tested: AKA1 (commercially available), AKA2 (commercially available), A1, and A3. Results of the antibody assay are indicated in FIG. 10.

|  | Anti-Activin A Ab | | | | |
| --- | --- | --- | --- | --- | --- |
|  | A2 | A3 | A1 | AKA1 | AKA2 |
| Activin A | $K_D$~25 pM | $K_D$~11 pM | $K_D$~3 pM | $K_D$~4 pM | $K_D$~4 pM |
| Activin B | — | — | — | — | — |

Example 16

Activin A Binding Assay Region Mapping (Biacore)

Blocking assays were conducted on immobilized recombinant human activin RIB-Fc chimera surfaces, recombinant human activin RIIB-Fc chimera surfaces, and recombinant human RIIA-Fc chimera recombinant surfaces, as described in Example 5. Monoclonal antibodies A1, A2, AKA1, and AKA2 on each chimera surface were incubated with 1 nM activin A, and the relative binding response (%) was measured. An increased binding response in the presence of antibodies indicates that activin A is able to bind to the immobilized receptor surfaces and the antibodies in solution simultaneously, which is referred to as "carry on". Results are indicated in Table 7 and FIG. 11, where EC50 means the effective concentration that yields 50% binding.

TABLE 7

| EC50 (nM) | rhActivin RIB/Fc Chimera | rhActivin RIIB/Fc Chimera | rhActivin FIIA/Fc Chimera |
| --- | --- | --- | --- |
| AKA1 | Partially block | 0.30 | 0.35 |
| AKA2 | Partially block | 0.36 | 0.37 |
| A1 | 0.29 | 0.29 | 0.29 |
| A2 | 0.18 | Carry on | Carry on |

Example 17

Activin A/B Chimeras

Figure 12A:
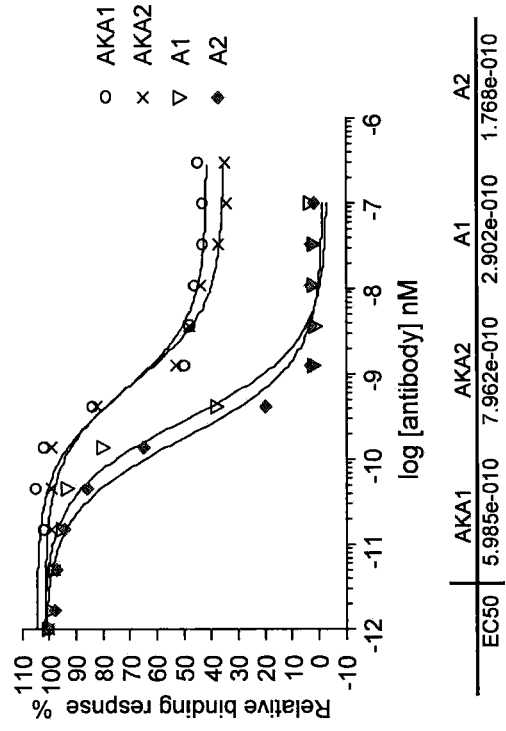
FIG. 12A shows antibody binding to activin A/activin B chimeras by antibody A1 and A2, as well as two commercially available activin A antibodies.
Figure 12B:
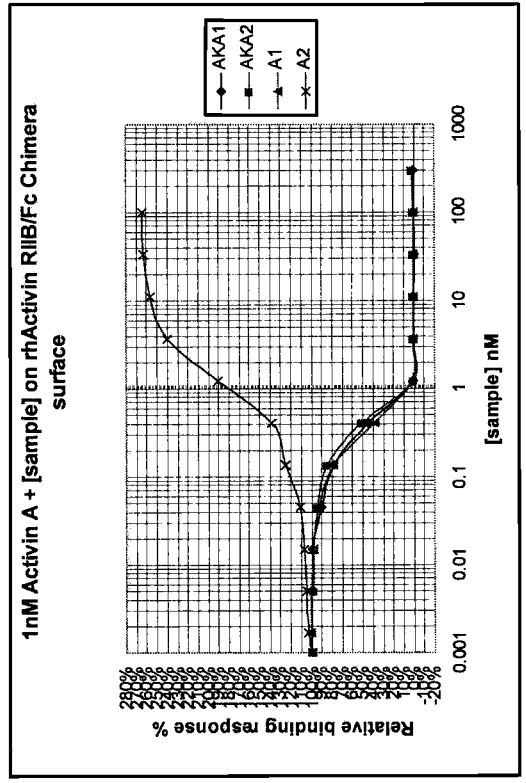
FIG. 12B shows antibody binding to activin A/activin B chimeras by antibody A1 and A2, as well as two commercially available activin A antibodies.

Activin A/B chimeras were generated in order to further assess the epitope binding abilities of monoclonal antibodies A1, A2, and A3, as described in Examples 5 and 16. As indicated in FIG. 12, two chimeras were tested: Activin A 13/39 B (containing amino acids 1-116 of activin A except that amino acids at positions 13-39 of activin A are substituted with the corresponding amino acids at positions 13-39 from activin B—SEQ ID NO: 243), and activin A 82/107 B (containing amino acids 1-116 of activin A except that amino acids at positions 82-107 of activin A are substituted with the corresponding amino acids at positions 82-107 from activin B—SEQ ID NO: 244).

Figure 14:
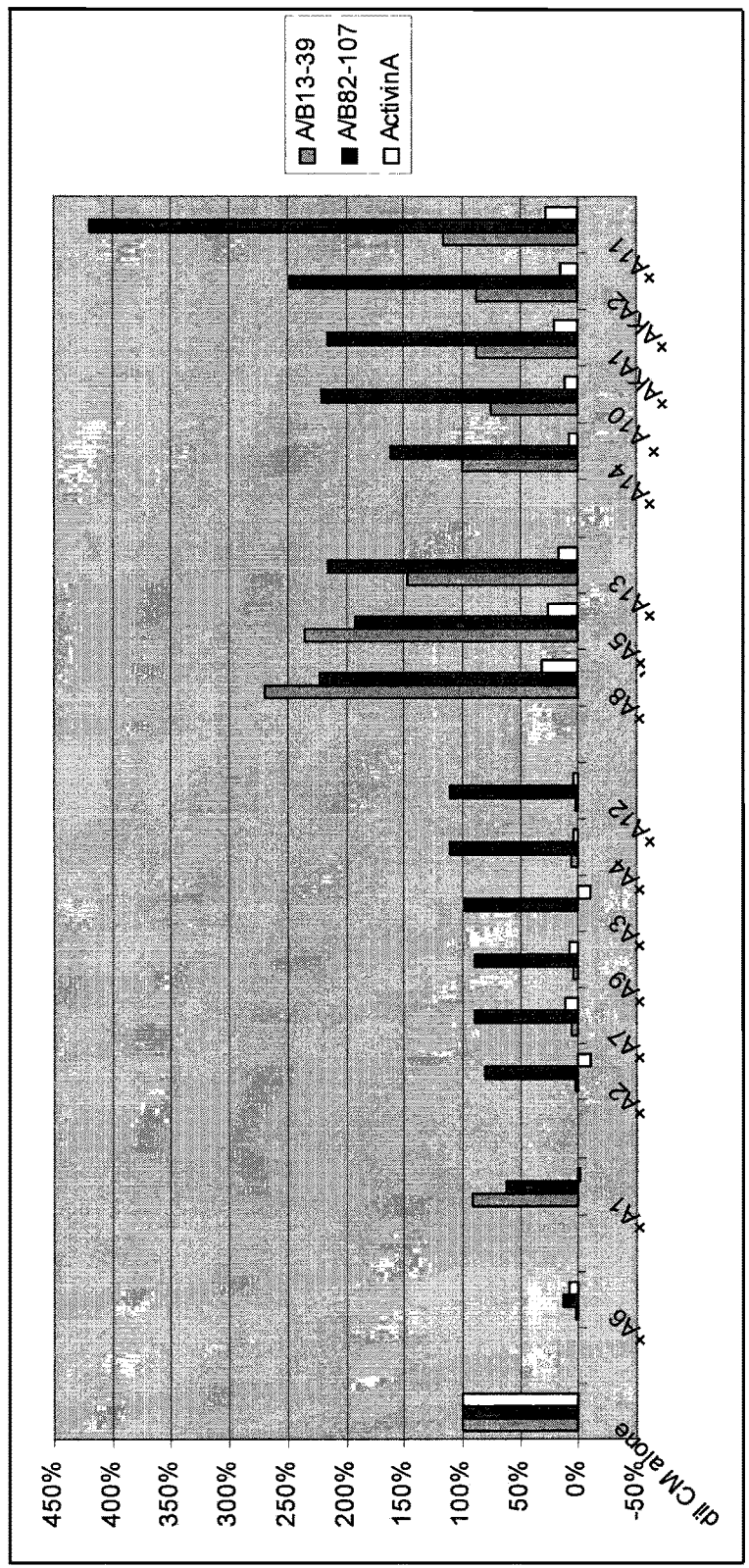
FIG. 14 shows binding of several antibodies, including A1, A2, and A3, to different epitopes of activin A; two commercially available activin A antibodies were also tested.

Briefly, a full length activin A clone was used as a template for amplification by PCR using Pfu ultra polymerase (Stratagene) and primers (SEQ ID NO: 245 and SEQ ID NO: 246) at the start of the mature protein sequence. The resulting PCR product was column purified (Qiagen), digested with SalI and XbaI restriction enzymes (Roche) and gel isolated (Qiagen). The synthetic gene cassettes containing the modified mature protein sequences were designed by utilizing the amino acid sequences from full length activin A and activin B and back translating into DNA sequences codon optimized for expression in a mammalian host cell by using the Gene Designer program (Version 1.0.4, DNA 2.0, Inc.) (BMC Bioinformatics, 7: 285 (2006)). The sequences were digested with XbaI and NotI and gel isolated. The activin A PCR product was ligated under standard reaction conditions using T4 DNA ligase (New England Biolabs, Inc.) with either the 13-39 synthetic gene fragment (SEQ ID NO: 247) or the 82-107 synthetic gene fragment (SEQ ID NO: 213) and a SalI/NotI digested expression vector (pDR-Salpha 24) to produce full length expression constructs. The synthetic gene construct of activin A with amino acids 13-39 replaced with activin B sequence (SEQ ID NO: 247) and the synthetic gene construct of acivin A with amino acids 82-107 replaced with activin B sequence (SEQ ID NO: 248) were then utilized in the epitope mapping experiments (results shown in FIG. 14).

From the foregoing, although specific embodiments of the invention have been described herein for purposes of illustration, various modifications may be made without deviating from the spirit and scope of the invention. Accordingly, the invention is not limited except as by the appended claims. All publications, published patent applications, and patent documents disclosed herein are hereby incorporated by reference.

The invention claimed is:

1. A method of attenuating cachexia in a subject, comprising administering an effective amount of a pharmaceutically acceptable composition comprising a pharmaceutically acceptable excipient and an isolated antibody or antigen binding fragment thereof, comprising:
   a. a light chain variable domain (VL) comprising:
      i. a light chain CDR1 sequence of SEQ ID NO:11;
      ii. a light chain CDR2 sequence of SEQ ID NO:12; and
      iii. a light chain CDR3 sequence of SEQ ID NO:13; and
   b. a heavy chain variable domain (VH) comprising:
      i. a heavy chain CDR1 sequence of SEQ ID NO:62;
      ii. a heavy chain CDR2 sequence of SEQ ID NO:63; and
      iii. a heavy chain CDR3 sequence of SEQ ID NO:64.

2. A method of ameliorating the loss of body weight in a subject, comprising administering an effective amount of a pharmaceutically acceptable composition comprising a pharmaceutically acceptable excipient and an isolated antibody or antigen binding fragment thereof, comprising:
   a. a light chain variable domain (VL) comprising:
      i. a light chain CDR1 sequence of SEQ ID NO:11;
      ii. a light chain CDR2 sequence of SEQ ID NO:12; and
      iii. a light chain CDR3 sequence of SEQ ID NO:13; and
   b. a heavy chain variable domain (VH) comprising:
      i. a heavy chain CDR1 sequence of SEQ ID NO:62;
      ii. a heavy chain CDR2 sequence of SEQ ID NO:63; and
      iii. a heavy chain CDR3 sequence of SEQ ID NO:64.

3. A method of ameliorating the loss of muscle mass in a subject, comprising administering an effective amount of a pharmaceutically acceptable composition comprising a pharmaceutically acceptable excipient and an isolated antibody or antigen binding fragment thereof, comprising:
   a. a light chain variable domain (VL) comprising:
      i. a light chain CDR1 sequence of SEQ ID NO:11;
      ii. a light chain CDR2 sequence of SEQ ID NO:12; and
      iii. a light chain CDR3 sequence of SEQ ID NO:13; and
   b. a heavy chain variable domain (VH) comprising:
      i. a heavy chain CDR1 sequence of SEQ ID NO:62;
      ii. a heavy chain CDR2 sequence of SEQ ID NO:63; and
      iii. a heavy chain CDR3 sequence of SEQ ID NO:64.

4. A method of ameliorating the loss of fat mass in a subject, comprising administering an effective amount of a pharmaceutically acceptable composition comprising a pharmaceutically acceptable excipient and an isolated antibody or antigen binding fragment thereof, comprising:
   a. a light chain variable domain (VL) comprising:
      i. a light chain CDR1 sequence of SEQ ID NO:11;
      ii. a light chain CDR2 sequence of SEQ ID NO:12; and
      iii. a light chain CDR3 sequence of SEQ ID NO:13; and
   b. a heavy chain variable domain (VH) comprising:
      i. a heavy chain CDR1 sequence of SEQ ID NO:62;
      ii. a heavy chain CDR2 sequence of SEQ ID NO:63; and
      iii. a heavy chain CDR3 sequence of SEQ ID NO:64.

* * * * *

SEQUENCE LISTING

<160> NUMBER OF SEQ ID NOS: 266

<210> SEQ ID NO 1
<211> LENGTH: 318
<212> TYPE: DNA
<213> ORGANISM: Homo sapiens

<400> SEQUENCE: 1

| tcctatgagg tgactcaggc accctcagtg tccgtgtccc aggacagac agccagcatc | 60 |
| acctgctctg gagataaatt gggggataaa tatgcttgtt ggtatcagca gaagccaggc | 120 |
| cagtcccctg tgctggtcat ctatcaagat agcaagcggc cctcagggat ccctgagcga | 180 |
| ttctctggct ccaactctgg aaacacagcc actctgacca tcagcgggac ccaggctatg | 240 |
| gatgaggctg actattactg tcaggcgtgg gacagcagca ctgcggtatt cggcggaggg | 300 |
| accaagctga ccgtccta | 318 |

<210> SEQ ID NO 2
<211> LENGTH: 366
<212> TYPE: DNA
<213> ORGANISM: Homo sapiens

<400> SEQUENCE: 2

| caggttcagc tggtgcagtc tggagctgag gtgaagaagc ctggggcctc agtgaaggtc | 60 |
| tcctgcaagg cttctggtta cacctttacc agttatggtc tcagctgggt gcgacaggcc | 120 |
| cctggacaag gcttgagtg gatgggatgg atcatccctt acaatggtaa cacaaactct | 180 |
| gcacagaaac tccagggcag agtcaccatg accacagaca catccacgag cacagcctac | 240 |
| atggagctga ggagcctgag atctgacgac acggccgtgt atttctgtgc gagagacagg | 300 |
| gactacggtg tcaattatga tgcttttgat atctggggcc aagggacaat ggtcaccgtc | 360 |
| tcttca | 366 |

<210> SEQ ID NO 3
<211> LENGTH: 33
<212> TYPE: DNA
<213> ORGANISM: Homo sapiens

<400> SEQUENCE: 3

| tctggagata aattggggga taaatatgct tgt | 33 |

<210> SEQ ID NO 4
<211> LENGTH: 21
<212> TYPE: DNA
<213> ORGANISM: Homo sapiens

<400> SEQUENCE: 4

| caagatagca agcggccctc a | 21 |

<210> SEQ ID NO 5
<211> LENGTH: 27
<212> TYPE: DNA
<213> ORGANISM: Homo sapiens

<400> SEQUENCE: 5

| caggcgtggg acagcagcac tgcggta | 27 |

<210> SEQ ID NO 6
<211> LENGTH: 30
<212> TYPE: DNA
<213> ORGANISM: Homo sapiens

<210> SEQ ID NO 7
<211> LENGTH: 51
<212> TYPE: DNA
<213> ORGANISM: Homo sapiens

<400> SEQUENCE: 7
tggatcatcc cttacaatgg taacacaaac tctgcacaga aactccaggg c          51

<210> SEQ ID NO 8
<211> LENGTH: 39
<212> TYPE: DNA
<213> ORGANISM: Homo sapiens

<400> SEQUENCE: 8
gacagggact acggtgtcaa ttatgatgct tttgatatc                        39

<210> SEQ ID NO 9
<211> LENGTH: 106
<212> TYPE: PRT
<213> ORGANISM: Homo sapiens

<400> SEQUENCE: 9

Ser Tyr Glu Val Thr Gln Ala Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu
            100                 105

<210> SEQ ID NO 10
<211> LENGTH: 122
<212> TYPE: PRT
<213> ORGANISM: Homo sapiens

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Pro Gly Gln Gly Leu Glu Trp Met
        35                  40                  45

Gly Trp Ile Ile Pro Tyr Asn Gly Asn Thr Asn Ser Ala Gln Lys Leu
    50                  55                  60

Gln Gly Arg Val Thr Met Thr Thr Asp Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Arg Asp Tyr Gly Val Asn Tyr Asp Ala Phe Asp Ile Trp
            100                 105                 110
Gly Gln Gly Thr Met Val Thr Val Ser Ser
        115                 120

<210> SEQ ID NO 11
<211> LENGTH: 11
<212> TYPE: PRT
<213> ORGANISM: Homo sapiens

<400> SEQUENCE: 11

Ser Gly Asp Lys Leu Gly Asp Lys Tyr Ala Cys
1               5                   10

<210> SEQ ID NO 12
<211> LENGTH: 7
<212> TYPE: PRT
<213> ORGANISM: Homo sapiens

<400> SEQUENCE: 12

Gln Asp Ser Lys Arg Pro Ser
1               5

<210> SEQ ID NO 13
<211> LENGTH: 9
<212> TYPE: PRT
<213> ORGANISM: Homo sapiens

<400> SEQUENCE: 13

Gln Ala Trp Asp Ser Ser Thr Ala Val
1               5

<210> SEQ ID NO 14
<211> LENGTH: 11
<212> TYPE: PRT
<213> ORGANISM: Homo sapiens

<400> SEQUENCE: 14

Arg Ala Ser Gln Gly Ile Arg Asn Asn Leu Gly
1               5                   10

<210> SEQ ID NO 15
<211> LENGTH: 7
<212> TYPE: PRT
<213> ORGANISM: Homo sapiens

<400> SEQUENCE: 15

Ala Ala Ser Ser Leu Gln Ser
1               5

<210> SEQ ID NO 16
<211> LENGTH: 9
<212> TYPE: PRT
<213> ORGANISM: Homo sapiens

<400> SEQUENCE: 16

Leu Gln His Asn Ser Tyr Pro Trp Thr
1               5

<210> SEQ ID NO 17
<211> LENGTH: 321
<212> TYPE: DNA
<213> ORGANISM: Homo sapiens

<400> SEQUENCE: 17

```
gacatccaga tgacccagtc tccatcctcc ctgtctgcat ctgtaggaga cagagtcacc        60
atcacttgcc gggcaagtca gggcattaga aataatttag gctggtatca gcagaaacca       120
gggaaagccc ctaagcgcct gatttatgct gcatccagtt tgcaaagtgg ggtcccatca       180
aggttcagcg gcagtggatc tgggacagaa ttcactctca caatcagcag tctgcagcct       240
gaagatttta caacttatta ctgtctacag cataatagtt acccgtggac gttcggccaa       300
gggaccaagg tggaaatcaa a                                                 321
```

<210> SEQ ID NO 18
<211> LENGTH: 373
<212> TYPE: DNA
<213> ORGANISM: Homo sapiens

<400> SEQUENCE: 18

```
caggtgcagc tggtggagtc tgggggaggc gtggtccagc ctgggaggtc cctgagactc        60
tcctgtgcag cgtctggatt caccttcagt agttacggca tgcactgggt ccgccaggct       120
ccaggcaagg ggctggagtg ggtggcagtt atatggtatg atggaagtaa taaataccat       180
gcagactccg tgaagggccg attccaccat tccagagaca attccaagaa cacgctgtat       240
ctgcaagtga acagcctgag agccgaggac acggctgtgt attactgtgt gagaagtcgg       300
aactggaact acgacaacta ctactacggt ctggacgtct ggggccaagg gaccacggtc       360
accgtctcct cag                                                          373
```

<210> SEQ ID NO 19
<211> LENGTH: 33
<212> TYPE: DNA
<213> ORGANISM: Homo sapiens

<400> SEQUENCE: 19

```
cgggcaagtc agggcattag aaataattta ggc                                     33
```

<210> SEQ ID NO 20
<211> LENGTH: 21
<212> TYPE: DNA
<213> ORGANISM: Homo sapiens

<400> SEQUENCE: 20

```
gctgcatcca gtttgcaaag t                                                  21
```

<210> SEQ ID NO 21
<211> LENGTH: 27
<212> TYPE: DNA
<213> ORGANISM: Homo sapiens

<400> SEQUENCE: 21

```
ctacagcata atagttaccc gtggacg                                            27
```

<210> SEQ ID NO 22
<211> LENGTH: 30
<212> TYPE: DNA
<213> ORGANISM: Homo sapiens

<400> SEQUENCE: 22

```
ggattcacct tcagtagtta cggcatgcac                                         30
```

<210> SEQ ID NO 23
<211> LENGTH: 51

<212> TYPE: DNA
<213> ORGANISM: Homo sapiens

<400> SEQUENCE: 23
gttatatggt atgatggaag taataaatac catgcagact ccgtgaaggg c    51

<210> SEQ ID NO 24
<211> LENGTH: 45
<212> TYPE: DNA
<213> ORGANISM: Homo sapiens

<400> SEQUENCE: 24
agtcggaact ggaactacga caactactac tacggtctgg acgtc    45

<210> SEQ ID NO 25
<211> LENGTH: 107
<212> TYPE: PRT
<213> ORGANISM: Homo sapiens

<400> SEQUENCE: 25

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asn
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Thr Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 26
<211> LENGTH: 124
<212> TYPE: PRT
<213> ORGANISM: Homo sapiens

<400> SEQUENCE: 26

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Val Arg Ser Arg Asn Trp Asn Tyr Asp Tyr Tyr Gly Leu Asp
            100                 105                 110

Val Trp Gly Gln Gly Thr Thr Val Thr Val Ser Ser
        115                 120

```
<210> SEQ ID NO 27
<211> LENGTH: 11
<212> TYPE: PRT
<213> ORGANISM: Homo sapiens

<400> SEQUENCE: 27

Arg Ala Ser Gln Gly Ile Arg Asn Asn Leu Gly
1               5                   10

<210> SEQ ID NO 28
<211> LENGTH: 7
<212> TYPE: PRT
<213> ORGANISM: Homo sapiens

<400> SEQUENCE: 28

Ala Ala Ser Ser Leu Gln Ser
1               5

<210> SEQ ID NO 29
<211> LENGTH: 9
<212> TYPE: PRT
<213> ORGANISM: Homo sapiens

<400> SEQUENCE: 29

Leu Gln His Asn Ser Tyr Pro Trp Thr
1               5

<210> SEQ ID NO 30
<211> LENGTH: 10
<212> TYPE: PRT
<213> ORGANISM: Homo sapiens

<400> SEQUENCE: 30

Gly Phe Thr Phe Ser Ser Tyr Gly Met His
1               5                   10

<210> SEQ ID NO 31
<211> LENGTH: 17
<212> TYPE: PRT
<213> ORGANISM: Homo sapiens

<400> SEQUENCE: 31

Val Ile Trp Tyr Asp Gly Ser Asn Lys Tyr His Ala Asp Ser Val Lys
1               5                   10                  15

Gly

<210> SEQ ID NO 32
<211> LENGTH: 15
<212> TYPE: PRT
<213> ORGANISM: Homo sapiens

<400> SEQUENCE: 32

Ser Arg Asn Trp Asn Tyr Asp Asn Tyr Tyr Tyr Gly Leu Asp Val
1               5                   10                  15

<210> SEQ ID NO 33
<211> LENGTH: 321
<212> TYPE: DNA
<213> ORGANISM: Homo sapiens

<400> SEQUENCE: 33
gacatccaga tgacccagtc tccatcctcc ctgtctgcat ctgtaggaga cagagtcacc      60
atcacttgcc gggcaagtca gggcattaga aatgatttag ctggtatca gcagaaacca    120
```

```
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtcgacag caaaatactt acccgctcac tttcggcgga    300
gggaccaagg tggagatcaa a                                              321

<210> SEQ ID NO 34
<211> LENGTH: 369
<212> TYPE: DNA
<213> ORGANISM: Homo sapiens

<400> SEQUENCE: 34
gaggtgcagt tggtggagtc tgggggaggc ttggtccagc ctggggggtc cctgagactc     60
tcctgtgcag cctctggatt cacctttagt agttattgga tgagctgggt ccgccaggct    120
ccagggaagg ggctggagtg cgtggccaac ataaagcaag atggaagtga ggaatactat    180
gtggactctg tgaagggccg attcaccatc tccagagaca cgccaagaa ttcactgtat    240 ctgcaaatga acagcctgag agccgaggac acggctgtgt attactgtgc gagaggtagc    300
agcagctggt actactacaa ctacggtatg gacgtctggg gccaagggac cacggtcacc    360
gtctcctca                                                            369

<210> SEQ ID NO 35
<211> LENGTH: 33
<212> TYPE: DNA
<213> ORGANISM: Homo sapiens

<400> SEQUENCE: 35
cgggcaagtc agggcattag aaatgattta ggc                                  33

<210> SEQ ID NO 36
<211> LENGTH: 21
<212> TYPE: DNA
<213> ORGANISM: Homo sapiens

<400> SEQUENCE: 36
gctgcatcca gtttgcaaag t                                               21

<210> SEQ ID NO 37
<211> LENGTH: 27
<212> TYPE: DNA
<213> ORGANISM: Homo sapiens

<400> SEQUENCE: 37
cgacagcaaa atacttaccc gctcact                                         27

<210> SEQ ID NO 38
<211> LENGTH: 30
<212> TYPE: DNA
<213> ORGANISM: Homo sapiens

<400> SEQUENCE: 38
ggattcacct ttagtagtta ttggatgagc                                      30

<210> SEQ ID NO 39
<211> LENGTH: 51
<212> TYPE: DNA
<213> ORGANISM: Homo sapiens

<400> SEQUENCE: 39
aacataaagc aagatggaag tgaggaatac tatgtggact ctgtgaaggg c              51
```

<210> SEQ ID NO 40
<211> LENGTH: 42
<212> TYPE: DNA
<213> ORGANISM: Homo sapiens

<400> SEQUENCE: 40
ggtagcagca gctggtacta ctacaactac ggtatggacg tc                42

<210> SEQ ID NO 41
<211> LENGTH: 107
<212> TYPE: PRT
<213> ORGANISM: Homo sapiens

<400> SEQUENCE: 41

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Arg Gln Gln Asn Thr Tyr Pro Leu
                85                  90                  95

Thr Phe Gly Gly Gly Thr Lys Val Glu Ile Lys
            100                 105
```

<210> SEQ ID NO 42
<211> LENGTH: 123
<212> TYPE: PRT
<213> ORGANISM: Homo sapiens

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Cys Val
        35                  40                  45

Ala Asn Ile Lys Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ser Ser Trp Tyr Tyr Tyr Asn Tyr Gly Met Asp Val
            100                 105                 110

Trp Gly Gln Gly Thr Thr Val Thr Val Ser Ser
        115                 120
```

<210> SEQ ID NO 43
<211> LENGTH: 11
<212> TYPE: PRT
<213> ORGANISM: Homo sapiens

<400> SEQUENCE: 43

Arg Ala Ser Gln Gly Ile Arg Asn Asp Leu Gly
1               5                   10

<210> SEQ ID NO 44
<211> LENGTH: 7
<212> TYPE: PRT
<213> ORGANISM: Homo sapiens

<400> SEQUENCE: 44

Ala Ala Ser Ser Leu Gln Ser
1               5

<210> SEQ ID NO 45
<211> LENGTH: 9
<212> TYPE: PRT
<213> ORGANISM: Homo sapiens

<400> SEQUENCE: 45

Arg Gln Gln Asn Thr Tyr Pro Leu Thr
1               5

<210> SEQ ID NO 46
<211> LENGTH: 10
<212> TYPE: PRT
<213> ORGANISM: Homo sapiens

<400> SEQUENCE: 46

Gly Phe Thr Phe Ser Ser Tyr Trp Met Ser
1               5                   10

<210> SEQ ID NO 47
<211> LENGTH: 17
<212> TYPE: PRT
<213> ORGANISM: Homo sapiens

<400> SEQUENCE: 47

Asn Ile Lys Gln Asp Gly Ser Glu Glu Tyr Tyr Val Asp Ser Val Lys
1               5                   10                  15

Gly

<210> SEQ ID NO 48
<211> LENGTH: 14
<212> TYPE: PRT
<213> ORGANISM: Homo sapiens

<400> SEQUENCE: 48

Gly Ser Ser Ser Trp Tyr Tyr Asn Tyr Gly Met Asp Val
1               5                   10

<210> SEQ ID NO 49
<211> LENGTH: 336
<212> TYPE: DNA
<213> ORGANISM: Homo sapiens

<400> SEQUENCE: 49
gatattgtga tgactcagtc tccactctcc ctgcccgtca cccctggaga gccggcctcc    60
atctcctgca ggtctagtca gagcctcctg catagtactg gatacaacta tttggattgg    120
tacctgcaga agccagggca gtctccacag ctcctgatct atttgggttc ttttcgggcc    180
tccggggtcc ctgacaggtt cagtggcagt gggtcaggca cagattttac actgaaaatc    240
agcagagtgg aggctgagga tgttggggtt tattactgca tgcaagctct ccaaactccg    300
tgcagttttg gccaggggac caagctggag atcaag 336

<210> SEQ ID NO 50
<211> LENGTH: 363
<212> TYPE: DNA
<213> ORGANISM: Homo sapiens

<400> SEQUENCE: 50
caggtgcagc tggtgcagtc tggggctgag gtgaagaagc ctggggcctc agtgaaggtc 60
tcctgcaagg cttctggata caccttcacc ggctactata tccactgggt gcgacaggcc 120
cctggacaag gcttgagtg gatgggatgg atcaaccta acagtggtgg cacaaactat 180
gcacagaagt ttcagggcag ggtcaccatg accagggaca cgtccatcag cacagcctac 240
atggagctga gcaggctgag atctgacgac acggccgtgt atttctgtgc gagagattcg 300
gggtatagca gcagctggca ctttgactac tggggccagg gaaccctggt caccgtctcc 360
tca 363

<210> SEQ ID NO 51
<211> LENGTH: 48
<212> TYPE: DNA
<213> ORGANISM: Homo sapiens

<400> SEQUENCE: 51
aggtctagtc agagcctcct gcatagtact ggatacaact atttggat 48

<210> SEQ ID NO 52
<211> LENGTH: 21
<212> TYPE: DNA
<213> ORGANISM: Homo sapiens

<400> SEQUENCE: 52
ttgggttctt ttcgggcctc c 21

<210> SEQ ID NO 53
<211> LENGTH: 26
<212> TYPE: DNA
<213> ORGANISM: Homo sapiens

<400> SEQUENCE: 53
atgcaagctc tccaaactcc gtgcag 26

<210> SEQ ID NO 54
<211> LENGTH: 30
<212> TYPE: DNA
<213> ORGANISM: Homo sapiens

<400> SEQUENCE: 54
ggatacacct tcaccggcta ctatatccac 30

<210> SEQ ID NO 55
<211> LENGTH: 51
<212> TYPE: DNA
<213> ORGANISM: Homo sapiens

<400> SEQUENCE: 55
tggatcaacc ctaacagtgg tggcacaaac tatgcacaga gtttcaggg c 51

<210> SEQ ID NO 56
<211> LENGTH: 36
<212> TYPE: DNA
<213> ORGANISM: Homo sapiens

```
<400> SEQUENCE: 56
gattcggggt atagcagcag ctggcactttt gactac                               36

<210> SEQ ID NO 57
<211> LENGTH: 112
<212> TYPE: PRT
<213> ORGANISM: Homo sapiens

<400> SEQUENCE: 57

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Gly Tyr Asn Tyr Leu Asp Trp Tyr Leu Gln Lys Pro Gly Gln Ser
        35                  40                  45

Pro Gln Leu Leu Ile Tyr Leu Gly Ser Phe Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Cys Ser Phe Gly Gln Gly Thr Lys Leu Glu Ile Lys
            100                 105                 110

<210> SEQ ID NO 58
<211> LENGTH: 121
<212> TYPE: PRT
<213> ORGANISM: Homo sapiens

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Asp Ser Gly Tyr Ser Ser Trp His Phe Asp Tyr Trp Gly
            100                 105                 110

Gln Gly Thr Leu Val Thr Val Ser Ser
        115                 120

<210> SEQ ID NO 59
<211> LENGTH: 11
<212> TYPE: PRT
<213> ORGANISM: Homo sapiens

<400> SEQUENCE: 59

Ser Gly Asp Lys Leu Gly Asp Lys Tyr Ala Cys
1               5                   10

<210> SEQ ID NO 60
```

```
<211> LENGTH: 7
<212> TYPE: PRT
<213> ORGANISM: Homo sapiens

<400> SEQUENCE: 60

Gln Asp Ser Lys Arg Pro Ser
1               5

<210> SEQ ID NO 61
<211> LENGTH: 9
<212> TYPE: PRT
<213> ORGANISM: Homo sapiens

<400> SEQUENCE: 61

Gln Ala Trp Asp Ser Ser Thr Ala Val
1               5

<210> SEQ ID NO 62
<211> LENGTH: 10
<212> TYPE: PRT
<213> ORGANISM: Homo sapiens

<400> SEQUENCE: 62

Gly Tyr Thr Phe Thr Ser Tyr Gly Leu Ser
1               5                   10

<210> SEQ ID NO 63
<211> LENGTH: 17
<212> TYPE: PRT
<213> ORGANISM: Homo sapiens

<400> SEQUENCE: 63

Trp Ile Ile Pro Tyr Asn Gly Asn Thr Asn Ser Ala Gln Lys Leu Gln
1               5                   10                  15

Gly

<210> SEQ ID NO 64
<211> LENGTH: 13
<212> TYPE: PRT
<213> ORGANISM: Homo sapiens

<400> SEQUENCE: 64

Asp Arg Asp Tyr Gly Val Asn Tyr Asp Ala Phe Asp Ile
1               5                   10

<210> SEQ ID NO 65
<211> LENGTH: 339
<212> TYPE: DNA
<213> ORGANISM: Homo sapiens

<400> SEQUENCE: 65
gacatcgtga tgacccagtc tccagactcc ctggctgtgt ctctgggcga gagggccacc      60
atcacctgca gtccagcca gagtatttta tacagttcca acaataagaa gtatctagtt     120
tggtaccagc agaaaccagg acagcctcct aagctgatca tttactggac atctatgcgg    180
gaatccgggg tccctgaccg attcagtggc agcgggtctg ggacagattt cactctcacc    240
atcaacagcc tgcaggctga agatgtggca gtttattact gtcagcaata ttatagtact    300
ccgtggacgt tcggccaagg gaccaaggtg gaaatcaaa                            339

<210> SEQ ID NO 66
<211> LENGTH: 488
<212> TYPE: DNA
```

<213> ORGANISM: Homo sapiens

<400> SEQUENCE: 66

```
caggtgcagc tgcaggagtc gggcccagga ctggtgaagc cttcggagac cctgtccctc    60
acctgcactg tctctggtgg ctccatcaat agtttctact ggagctggat ccggcagccc   120
ccagggaagg gactggagtg gattgggtat atctattaca gtgggagcac caactacaat   180
ccctccctca agagtcgagt caccatatca gtagacacgt ccaagaccca gttctccctg   240
aagctgagct ctgtgaccgc tgcggacacg gccgtgtatt actgtgcgag agacagtata   300
gcagccccct ttgactactg gggccaggga accctggtca ccgtctcctc agcttccacc   360
aagggcccat ccgtcttccc cctggcgccc tgctccagga gcacctccga gagcacagcc   420
gccctgggct gcctggtcaa ggactacttc cccgaaccgg tgacggtgtc gtggaactca   480
tgcgccct                                                            488
```

<210> SEQ ID NO 67
<211> LENGTH: 51
<212> TYPE: DNA
<213> ORGANISM: Homo sapiens

<400> SEQUENCE: 67

```
aagtccagcc agagtatttt atacagttcc aacaataaga agtatctagt t             51
```

<210> SEQ ID NO 68
<211> LENGTH: 21
<212> TYPE: DNA
<213> ORGANISM: Homo sapiens

<400> SEQUENCE: 68

```
tggacatcta tgcgggaatc c                                              21
```

<210> SEQ ID NO 69
<211> LENGTH: 27
<212> TYPE: DNA
<213> ORGANISM: Homo sapiens

<400> SEQUENCE: 69

```
cagcaatatt atagtactcc gtggacg                                        27
```

<210> SEQ ID NO 70
<211> LENGTH: 30
<212> TYPE: DNA
<213> ORGANISM: Homo sapiens

<400> SEQUENCE: 70

```
ggtggctcca tcaatagttt ctactggagc                                     30
```

<210> SEQ ID NO 71
<211> LENGTH: 48
<212> TYPE: DNA
<213> ORGANISM: Homo sapiens

<400> SEQUENCE: 71

```
tatatctatt acagtgggag caccaactac aatccctccc tcaagagt                 48
```

<210> SEQ ID NO 72
<211> LENGTH: 27
<212> TYPE: DNA
<213> ORGANISM: Homo sapiens

<400> SEQUENCE: 72

```
gacagtatag cagcccccctt tgactac                                    27
```

<210> SEQ ID NO 73
<211> LENGTH: 113
<212> TYPE: PRT
<213> ORGANISM: Homo sapiens
<400> SEQUENCE: 73

```
Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Ile Leu Tyr Ser
            20                  25                  30

Ser Asn Asn Lys Lys Tyr Leu Val Trp Tyr Gln Gln Lys Pro Gly Gln
        35                  40                  45

Pro Pro Lys Leu Ile Ile Tyr Trp Thr Ser Met Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys
```

<210> SEQ ID NO 74
<211> LENGTH: 117
<212> TYPE: PRT
<213> ORGANISM: Homo sapiens
<400> SEQUENCE: 74

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Phe
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Thr Gln Phe Ser Leu
65                  70                  75                  80

Lys Leu Ser Ser Val Thr Ala Ala Asp Thr Ala Val Tyr Tyr Cys Ala
                85                  90                  95

Arg Asp Ser Ile Ala Ala Pro Phe Asp Tyr Trp Gly Gln Gly Thr Leu
            100                 105                 110

Val Thr Val Ser Ser
            115
```

<210> SEQ ID NO 75
<211> LENGTH: 17
<212> TYPE: PRT
<213> ORGANISM: Homo sapiens
<400> SEQUENCE: 75

```
Lys Ser Ser Gln Ser Ile Leu Tyr Ser Ser Asn Asn Lys Lys Tyr Leu
1               5                   10                  15

Val
```

<210> SEQ ID NO 76
<211> LENGTH: 7
<212> TYPE: PRT
<213> ORGANISM: Homo sapiens

<400> SEQUENCE: 76

Trp Thr Ser Met Arg Glu Ser
1               5

<210> SEQ ID NO 77
<211> LENGTH: 9
<212> TYPE: PRT
<213> ORGANISM: Homo sapiens

<400> SEQUENCE: 77

Gln Gln Tyr Tyr Ser Thr Pro Trp Thr
1               5

<210> SEQ ID NO 78
<211> LENGTH: 10
<212> TYPE: PRT
<213> ORGANISM: Homo sapiens

<400> SEQUENCE: 78

Gly Gly Ser Ile Asn Ser Phe Tyr Trp Ser
1               5                   10

<210> SEQ ID NO 79
<211> LENGTH: 16
<212> TYPE: PRT
<213> ORGANISM: Homo sapiens

<400> SEQUENCE: 79

Tyr Ile Tyr Tyr Ser Gly Ser Thr Asn Tyr Asn Pro Ser Leu Lys Ser
1               5                   10                  15

<210> SEQ ID NO 80
<211> LENGTH: 9
<212> TYPE: PRT
<213> ORGANISM: Homo sapiens

<400> SEQUENCE: 80

Asp Ser Ile Ala Ala Pro Phe Asp Tyr
1               5

<210> SEQ ID NO 81
<211> LENGTH: 321
<212> TYPE: DNA
<213> ORGANISM: Homo sapiens

<400> SEQUENCE: 81
gacatccaga tgacccagtc tccatcctcc ctgtctgcat ctgtaggaga cagagtcacc    60
atcacttgcc gggcaagtca gagcattagc aactatttaa attggtatca gcagagacca   120
gggaaagccc ctaagctcct gatctatgct acatccagtt tgcaaagtgg ggtcccatca   180
aggttcagtg gcagtggatc tgggacagat tcactctcac ccatcagcag tctgcaacct   240
gaagattttg taagttacta ctgtcaacag agttacagta tttcgcccac tttcggcggc   300
gggaccaagg tggagaacaa a                                             321

<210> SEQ ID NO 82
<211> LENGTH: 357
<212> TYPE: DNA

<213> ORGANISM: Homo sapiens

<400> SEQUENCE: 82

```
caggtgcagc tacagcagtg gggcgcagga ctgttgaagc cttcggagac cctgtccctc      60
acctgcgctg tctatggtgg gtccttcagt gcttactact ggagctggat ccgccagccc     120
ccagggaagg gactggagtg gattggggaa atcaatcata gtggaggcac caactacaac     180
ccgtccctca agagtcgagt caccatatca gtagacacgt ccaagaacca gttctccctg     240
aagctgagct ctgtgaccgc cgcggacacg gctgtgtatt actgtgcgag agtacagtgg     300
ctcgaactgg cctactttga ctactggggc cagggaaccc tggtcaccgt ctcctca       357
```

<210> SEQ ID NO 83
<211> LENGTH: 33
<212> TYPE: DNA
<213> ORGANISM: Homo sapiens

<400> SEQUENCE: 83

```
cgggcaagtc agagcattag caactattta aat                                  33
```

<210> SEQ ID NO 84
<211> LENGTH: 106
<212> TYPE: PRT
<213> ORGANISM: Homo sapiens

<400> SEQUENCE: 84

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 85
<211> LENGTH: 27
<212> TYPE: DNA
<213> ORGANISM: Homo sapiens

<400> SEQUENCE: 85

```
caacagagtt acagtatttc gcccact                                         27
```

<210> SEQ ID NO 86
<211> LENGTH: 30
<212> TYPE: DNA
<213> ORGANISM: Homo sapiens

<400> SEQUENCE: 86

```
ggtgggtcct tcagtgctta ctactggagc                                      30
```

<210> SEQ ID NO 87
<211> LENGTH: 48
<212> TYPE: DNA

<213> ORGANISM: Homo sapiens

<400> SEQUENCE: 87
gaaatcaatc atagtggagg caccaactac aacccgtccc tcaagagt     48

<210> SEQ ID NO 88
<211> LENGTH: 33
<212> TYPE: DNA
<213> ORGANISM: Homo sapiens

<400> SEQUENCE: 88
gtacagtggc tcgaactggc ctactttgac tac     33

<210> SEQ ID NO 89
<211> LENGTH: 107
<212> TYPE: PRT
<213> ORGANISM: Homo sapiens

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Arg Pro Gly Lys Ala Pro Lys Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Val Ser Tyr Tyr Cys Gln Gln Ser Tyr Ser Ile Ser Pro
                85                  90                  95

Thr Phe Gly Gly Gly Thr Lys Val Glu Asn Lys
            100                 105

<210> SEQ ID NO 90
<211> LENGTH: 119
<212> TYPE: PRT
<213> ORGANISM: Homo sapiens

<400> SEQUENCE: 90

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Ala Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Gly Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Gln Trp Leu Glu Leu Ala Tyr Phe Asp Tyr Trp Gly Gln Gly
            100                 105                 110

Thr Leu Val Thr Val Ser Ser
        115

<210> SEQ ID NO 91

```
<210> SEQ ID NO 91
<211> LENGTH: 11
<212> TYPE: PRT
<213> ORGANISM: Homo sapiens

<400> SEQUENCE: 91

Arg Ala Ser Gln Ser Ile Ser Asn Tyr Leu Asn
1               5                   10

<210> SEQ ID NO 92
<211> LENGTH: 7
<212> TYPE: PRT
<213> ORGANISM: Homo sapiens

<400> SEQUENCE: 92

Ala Thr Ser Ser Leu Gln Ser
1               5

<210> SEQ ID NO 93
<211> LENGTH: 9
<212> TYPE: PRT
<213> ORGANISM: Homo sapiens

<400> SEQUENCE: 93

Gln Gln Ser Tyr Ser Ile Ser Pro Thr
1               5

<210> SEQ ID NO 94
<211> LENGTH: 10
<212> TYPE: PRT
<213> ORGANISM: Homo sapiens

<400> SEQUENCE: 94

Gly Gly Ser Phe Ser Ala Tyr Tyr Trp Ser
1               5                   10

<210> SEQ ID NO 95
<211> LENGTH: 16
<212> TYPE: PRT
<213> ORGANISM: Homo sapiens

<400> SEQUENCE: 95

Glu Ile Asn His Ser Gly Gly Thr Asn Tyr Asn Pro Ser Leu Lys Ser
1               5                   10                  15

<210> SEQ ID NO 96
<211> LENGTH: 11
<212> TYPE: PRT
<213> ORGANISM: Homo sapiens

<400> SEQUENCE: 96

Val Gln Trp Leu Glu Leu Ala Tyr Phe Asp Tyr
1               5                   10

<210> SEQ ID NO 97
<211> LENGTH: 321
<212> TYPE: DNA
<213> ORGANISM: Homo sapiens

<400> SEQUENCE: 97
gacatccaga tgacccagtc tccatcctcc ctgtctgcat ctgtaggaga cagagtcacc      60
atcacttgcc gggcaggtca gggcattaga aatgatttag tctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
```

```
gaagattttg caacttatta ctgtctacaa cataatactt acccattcac tttcggccct    300
gggaccaaag tggatatcaa a                                              321
```

<210> SEQ ID NO 98
<211> LENGTH: 363
<212> TYPE: DNA
<213> ORGANISM: Homo sapiens

<400> SEQUENCE: 98

```
caggtgcagc tggtggactc tgggggaggc gtggtccagc ctggaggtc  cctgagactc    60 tcctgtgcag cgtctggatt caccttcatt agctatggca tgcactgggt ccgccaggct   120
ccaggcaagg ggctggagtg ggtggcagtt atctggtatg atggaagtac tgaatactat   180
gcagactccg tgaagggccg attcaccatc tccagagaca attccaagaa cacgctgtat   240
ctgcaaatga acagcctgag agccgaggac acggctgtgt attactgtgc gagagagagg   300
cagtggctct accactacgg tatggacgtc tggggccaag ggaccacggt caccgtctcc   360
tca                                                                 363
```

<210> SEQ ID NO 99
<211> LENGTH: 33
<212> TYPE: DNA
<213> ORGANISM: Homo sapiens

<400> SEQUENCE: 99

```
cgggcaggtc agggcattag aaatgattta gtc                                 33
```

<210> SEQ ID NO 100
<211> LENGTH: 107
<212> TYPE: PRT
<213> ORGANISM: Homo sapiens

<400> SEQUENCE: 100

```
Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 101
<211> LENGTH: 27
<212> TYPE: DNA
<213> ORGANISM: Homo sapiens

<400> SEQUENCE: 101

```
ctacaacata atacttaccc attcact                                        27
```

<210> SEQ ID NO 102
<211> LENGTH: 30

```
<212> TYPE: DNA
<213> ORGANISM: Homo sapiens

<400> SEQUENCE: 102
ggattcacct tcattagcta tggcatgcac                                     30

<210> SEQ ID NO 103
<211> LENGTH: 51
<212> TYPE: DNA
<213> ORGANISM: Homo sapiens

<400> SEQUENCE: 103
gttatctggt atgatggaag tactgaatac tatgcagact ccgtgaaggg c             51

<210> SEQ ID NO 104
<211> LENGTH: 36
<212> TYPE: DNA
<213> ORGANISM: Homo sapiens

<400> SEQUENCE: 104
gagaggcagt ggctctacca ctacggtatg gacgtc                              36

<210> SEQ ID NO 105
<211> LENGTH: 107
<212> TYPE: PRT
<213> ORGANISM: Homo sapiens

<400> SEQUENCE: 105
```

Asp Ile Gln Met Thr Gln Ser Pro Ser Ser Leu Ser Ala Ser Val Gly
1               5                   10                  15

Asp Arg Val Thr Ile Thr Cys Arg Ala Gly Gln Gly Ile Arg Asn Asp
            20                  25                  30

Leu Val Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Phe
                85                  90                  95

Thr Phe Gly Pro Gly Thr Lys Val Asp Ile Lys
            100                 105

```
<210> SEQ ID NO 106
<211> LENGTH: 121
<212> TYPE: PRT
<213> ORGANISM: Homo sapiens

<400> SEQUENCE: 106
```

Gln Val Gln Leu Val Asp Ser Gly Gly Val Val Gln Pro Gly Arg
1               5                   10                  15

Ser Leu Arg Leu Ser Cys Ala Ala Ser Gly Phe Thr Phe Ile Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Thr Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                 85                  90                  95
Ala Arg Glu Arg Gln Trp Leu Tyr His Tyr Gly Met Asp Val Trp Gly
            100                 105                 110
Gln Gly Thr Thr Val Thr Val Ser Ser
        115                 120
```

<210> SEQ ID NO 107
<211> LENGTH: 11
<212> TYPE: PRT
<213> ORGANISM: Homo sapiens

<400> SEQUENCE: 107

```
Arg Ala Gly Gln Gly Ile Arg Asn Asp Leu Val
1               5                   10
```

<210> SEQ ID NO 108
<211> LENGTH: 107
<212> TYPE: PRT
<213> ORGANISM: Homo sapiens

<400> SEQUENCE: 108

```
Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

<210> SEQ ID NO 109
<211> LENGTH: 9
<212> TYPE: PRT
<213> ORGANISM: Homo sapiens

<400> SEQUENCE: 109

```
Leu Gln His Asn Thr Tyr Pro Phe Thr
1               5
```

<210> SEQ ID NO 110
<211> LENGTH: 10
<212> TYPE: PRT
<213> ORGANISM: Homo sapiens

<400> SEQUENCE: 110

```
Gly Phe Thr Phe Ile Ser Tyr Gly Met His
1               5                   10
```

<210> SEQ ID NO 111
<211> LENGTH: 17
<212> TYPE: PRT
<213> ORGANISM: Homo sapiens

<400> SEQUENCE: 111

```
Val Ile Trp Tyr Asp Gly Ser Thr Glu Tyr Tyr Ala Asp Ser Val Lys
1               5                   10                  15

Gly
```

<210> SEQ ID NO 112
<211> LENGTH: 12
<212> TYPE: PRT
<213> ORGANISM: Homo sapiens

<400> SEQUENCE: 112

```
Glu Arg Gln Trp Leu Tyr His Tyr Gly Met Asp Val
1               5                   10
```

<210> SEQ ID NO 113
<211> LENGTH: 339
<212> TYPE: DNA
<213> ORGANISM: Homo sapiens

<400> SEQUENCE: 113

```
gacatcgtga tgacccagtc tccagactcc ctggctgtgt ctctgggcga gagggccacc    60
atcacctgca gtccagcca gagtatttta tacagctcca acaataagaa gtatctagtt   120
tggtaccagc agaaaccagg acagcctcct aagttgatca tttactggac atctatgcgg   180
gaatccgggg tccctgaccg attcagtggc agcgggtctg ggacagattt cactctcacc   240
atcagcagcc tgcaggctga agatgtggca gtttattact gtcagcaata ttatagtact   300
ccgtggacgt tcggccaagg gaccaaggtg gaaatcaaa                          339
```

<210> SEQ ID NO 114
<211> LENGTH: 351
<212> TYPE: DNA
<213> ORGANISM: Homo sapiens

<400> SEQUENCE: 114

```
caggtgcagc tgcaggagtc gggcccagga ctggtgaagc cctcggagac cctgtccctc    60
acctgcactg tctctggtgg ctccatcaat agtttctact ggagctggat ccggcagccc   120
ccagggaagg gactggagtg gattgggtat atctattaca gtgggagcac caactacaat   180
ccctccctca gaggcgagt caccatatca gtagacacgt ccaagaccca gttctccctg   240
aagctgagct ctgtgaccgc tgcggacacg gccgtgtatt actgtgcgag agacagtata   300
gcagccccct tgactactg gggccaggga accctggtca ccgtctcctc a             351
```

<210> SEQ ID NO 115
<211> LENGTH: 17
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Arg OR Lys
<220> FEATURE:
<221> NAME/KEY: VARIANT
<222> LOCATION: 6
<223> OTHER INFORMATION: Xaa = Leu OR Ile
<220> FEATURE:
<221> NAME/KEY: VARIANT
<222> LOCATION: 8
<223> OTHER INFORMATION: Xaa = His OR Tyr
<220> FEATURE:
<221> NAME/KEY: VARIANT
<222> LOCATION: 10
<223> OTHER INFORMATION: Xaa = Thr OR Ser
<220> FEATURE:
<221> NAME/KEY: VARIANT

```
<222> LOCATION: 11
<223> OTHER INFORMATION: Xaa = Gly OR Asn
<220> FEATURE:
<221> NAME/KEY: VARIANT
<222> LOCATION: 12
<223> OTHER INFORMATION: Xaa = Tyr OR Asn
<220> FEATURE:
<221> NAME/KEY: VARIANT
<222> LOCATION: (13)...(13)
<223> OTHER INFORMATION: Xaa = Asn OR Lys
<220> FEATURE:
<221> NAME/KEY: VARIANT
<222> LOCATION: (14)...(14)
<223> OTHER INFORMATION: Xaa = Lys OR -Xaa (Xaa deleted)
<220> FEATURE:
<221> NAME/KEY: VARIANT
<222> LOCATION: (17)...(17)
<223> OTHER INFORMATION: Xaa = Asp OR Val

<400> SEQUENCE: 115

Xaa Ser Ser Gln Ser Xaa Leu Xaa Ser Xaa Xaa Xaa Xaa Xaa Tyr Leu
1               5                   10                  15

Xaa

<210> SEQ ID NO 116
<211> LENGTH: 11
<212> TYPE: PRT
<213> ORGANISM: Homo sapiens
<220> FEATURE:
<221> NAME/KEY: VARIANT
<222> LOCATION: 3
<223> OTHER INFORMATION: Xaa = Ser OR Gly
<220> FEATURE:
<221> NAME/KEY: VARIANT
<222> LOCATION: 5
<223> OTHER INFORMATION: Xaa = Ser OR Gly
<220> FEATURE:
<221> NAME/KEY: VARIANT
<222> LOCATION: 7
<223> OTHER INFORMATION: Xaa = Ser OR Arg
<220> FEATURE:
<221> NAME/KEY: VARIANT
<222> LOCATION: 9
<223> OTHER INFORMATION: Xaa = Tyr OR Asp OR Asn
<220> FEATURE:
<221> NAME/KEY: VARIANT
<222> LOCATION: 11
<223> OTHER INFORMATION: Xaa = Asp OR Val OR Gly
<220> FEATURE:
<221> NAME/KEY: VARIANT
<222> LOCATION: 3, 5, 7, 9, 11
<223> OTHER INFORMATION: Xaa = Any Amino Acid

<400> SEQUENCE: 116

Arg Ala Xaa Gln Xaa Ile Xaa Asn Xaa Leu Xaa
1               5                   10

<210> SEQ ID NO 117
<211> LENGTH: 27
<212> TYPE: DNA
<213> ORGANISM: Homo sapiens

<400> SEQUENCE: 117
cagcaatatt atagtactcc gtggacg                                   27

<210> SEQ ID NO 118
<211> LENGTH: 30
<212> TYPE: DNA
<213> ORGANISM: Homo sapiens

<400> SEQUENCE: 118
```

```
ggtggctcca tcaatagttt ctactggagc                                          30
```

<210> SEQ ID NO 119
<211> LENGTH: 48
<212> TYPE: DNA
<213> ORGANISM: Homo sapiens

<400> SEQUENCE: 119

```
tatatctatt acagtgggag caccaactac aatccctccc tcaagagg                      48
```

<210> SEQ ID NO 120
<211> LENGTH: 27
<212> TYPE: DNA
<213> ORGANISM: Homo sapiens

<400> SEQUENCE: 120

```
gacagtatag cagccccctt tgactac                                             27
```

<210> SEQ ID NO 121
<211> LENGTH: 113
<212> TYPE: PRT
<213> ORGANISM: Homo sapiens

<400> SEQUENCE: 121

Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Ile Leu Tyr Ser
            20                  25                  30

Ser Asn Asn Lys Lys Tyr Leu Val Trp Tyr Gln Gln Lys Pro Gly Gln
        35                  40                  45

Pro Pro Lys Leu Ile Ile Tyr Trp Thr Ser Met Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys

<210> SEQ ID NO 122
<211> LENGTH: 117
<212> TYPE: PRT
<213> ORGANISM: Homo sapiens

<400> SEQUENCE: 122

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Phe
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Arg Arg Val Thr Ile Ser Val Asp Thr Ser Lys Thr Gln Phe Ser Leu
65                  70                  75                  80

Lys Leu Ser Ser Val Thr Ala Ala Asp Thr Ala Val Tyr Tyr Cys Ala
                85                  90                  95

```
Arg Asp Ser Ile Ala Ala Pro Phe Asp Tyr Trp Gly Gln Gly Thr Leu
                100                 105                 110
Val Thr Val Ser Ser
        115

<210> SEQ ID NO 123
<211> LENGTH: 11
<212> TYPE: PRT
<213> ORGANISM: Homo sapiens
<220> FEATURE:
<221> NAME/KEY: VARIANT
<222> LOCATION: 3
<223> OTHER INFORMATION: Xaa = Glu OR Asp
<220> FEATURE:
<221> NAME/KEY: VARIANT
<222> LOCATION: 5
<223> OTHER INFORMATION: Xaa = Trp OR Leu
<220> FEATURE:
<221> NAME/KEY: VARIANT
<222> LOCATION: 7
<223> OTHER INFORMATION: Xaa = Glu OR Asp
<220> FEATURE:
<221> NAME/KEY: VARIANT
<222> LOCATION: 9
<223> OTHER INFORMATION: Xaa = Tyr OR Phe
<220> FEATURE:
<221> NAME/KEY: VARIANT
<222> LOCATION: 10
<223> OTHER INFORMATION: Xaa = Ala OR Val
<220> FEATURE:
<221> NAME/KEY: VARIANT
<222> LOCATION: 11
<223> OTHER INFORMATION: Xaa = Cys OR Phe

<400> SEQUENCE: 123

Ser Gly Xaa Lys Xaa Gly Xaa Lys Xaa Xaa Xaa
1               5                   10

<210> SEQ ID NO 124
<211> LENGTH: 7
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Ala OR Trp OR Leu
<220> FEATURE:
<221> NAME/KEY: VARIANT
<222> LOCATION: 2
<223> OTHER INFORMATION: Xaa = Thr OR Ala OR Gly
<220> FEATURE:
<221> NAME/KEY: VARIANT
<222> LOCATION: 4
<223> OTHER INFORMATION: Xaa = Ser OR Met OR Phe
<220> FEATURE:
<221> NAME/KEY: VARIANT
<222> LOCATION: 5
<223> OTHER INFORMATION: Xaa = Leu OR Arg
<220> FEATURE:
<221> NAME/KEY: VARIANT
<222> LOCATION: 6
<223> OTHER INFORMATION: Xaa = Gln OR Glu OR Ala
<220> FEATURE:
<221> NAME/KEY: VARIANT
<222> LOCATION: 1, 2, 4, 5, 6
<223> OTHER INFORMATION: Xaa = Any Amino Acid

<400> SEQUENCE: 124

Xaa Xaa Ser Xaa Xaa Xaa Ser
1               5

<210> SEQ ID NO 125
<211> LENGTH: 9
```

<210> SEQ ID NO 125
<211> LENGTH: 8
<212> TYPE: PRT
<213> ORGANISM: Homo sapiens

<400> SEQUENCE: 125

Gln Gln Tyr Tyr Ser Thr Pro Trp Thr
1               5

<210> SEQ ID NO 126
<211> LENGTH: 10
<212> TYPE: PRT
<213> ORGANISM: Homo sapiens

<400> SEQUENCE: 126

Gly Gly Ser Ile Asn Ser Phe Tyr Trp Ser
1               5                   10

<210> SEQ ID NO 127
<211> LENGTH: 16
<212> TYPE: PRT
<213> ORGANISM: Homo sapiens

<400> SEQUENCE: 127

Tyr Ile Tyr Tyr Ser Gly Ser Thr Asn Tyr Asn Pro Ser Leu Lys Arg
1               5                   10                  15

<210> SEQ ID NO 128
<211> LENGTH: 7
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Gln OR Leu OR His
<220> FEATURE:
<221> NAME/KEY: VARIANT
<222> LOCATION: 3
<223> OTHER INFORMATION: Xaa = Thr OR Asn OR Ser
<220> FEATURE:
<221> NAME/KEY: VARIANT
<222> LOCATION: 1, 3
<223> OTHER INFORMATION: Xaa = Any Amino Acid

<400> SEQUENCE: 128

Xaa Asp Xaa Lys Arg Pro Ser
1               5

<210> SEQ ID NO 129
<211> LENGTH: 321
<212> TYPE: DNA
<213> ORGANISM: Homo sapiens

<400> SEQUENCE: 129
gacatccaga tgacccagtc tccatcctcc ctgtctgcat ctgtaggaga cagagtcacc      60
atcacttgcc gggcaagtca gggcattaga aataatttag gctggtatca gcagaaacca    120
gggaaagccc ctaagcgcct gatttatgct gcatccagtt tgcaaagtgg ggtcccatca    180
aggttcagcg gcagtggatc tgggacagaa ttcactctca caatcagcag cctgcagcct    240
gaagatttta caacttatta ctgtctacag cataatagtt acccgtggac gttcggccaa    300
gggaccaagg tggaaatcaa a                                              321

<210> SEQ ID NO 130
<211> LENGTH: 372
<212> TYPE: DNA
<213> ORGANISM: Homo sapiens

```
<400> SEQUENCE: 130
caggtgcagc tggtggagtc tgggggaggc gtggtccagc ctggggaggtc cctgagactc    60 tcctgtgcag cgtctggatt caccttcagt agttacggca tgcactgggt ccgccaggct   120
ccaggcaagg ggctggagtg ggtggcagtt atatggtatg atggaagtaa taaataccat   180
gcagactccg tgaagggccg attcaccatc tccagagaca attccaagaa cacgctgtat   240
ctgcaagtga acagcctgag agccgaggac acggctgtgt attactgtgt gagaagtcgg   300
aactggaact acgacaacta ctactacggt ctggacgtct ggggccaagg gaccacggtc   360
accgtctcct ca                                                        372

<210> SEQ ID NO 131
<211> LENGTH: 9
<212> TYPE: PRT
<213> ORGANISM: Homo sapiens
<220> FEATURE:
<221> NAME/KEY: VARIANT
<222> LOCATION: 5
<223> OTHER INFORMATION: Xaa = Thr OR Ser
<220> FEATURE:
<221> NAME/KEY: VARIANT
<222> LOCATION: 7
<223> OTHER INFORMATION: Xaa = Pro OR Thr
<220> FEATURE:
<221> NAME/KEY: VARIANT
<222> LOCATION: 8
<223> OTHER INFORMATION: Xaa = Phe OR Trp
<220> FEATURE:
<221> NAME/KEY: VARIANT
<222> LOCATION: 5, 7, 8
<223> OTHER INFORMATION: Xaa = Any Amino Acid

<400> SEQUENCE: 131

Leu Gln His Asn Xaa Tyr Xaa Xaa Thr
1               5

<210> SEQ ID NO 132
<211> LENGTH: 9
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Met OR Gln OR Arg
<220> FEATURE:
<221> NAME/KEY: VARIANT
<222> LOCATION: 3
<223> OTHER INFORMATION: Xaa = Ala OR Tyr OR Gln OR Ser
<220> FEATURE:
<221> NAME/KEY: VARIANT
<222> LOCATION: 4
<223> OTHER INFORMATION: Xaa = Leu OR Tyr OR Asn
<220> FEATURE:
<221> NAME/KEY: VARIANT
<222> LOCATION: 5
<223> OTHER INFORMATION: Xaa = Gln OR Ser OR Thr
<220> FEATURE:
<221> NAME/KEY: VARIANT
<222> LOCATION: 6
<223> OTHER INFORMATION: Xaa = Thr OR Tyr OR Ile
<220> FEATURE:
<221> NAME/KEY: VARIANT
<222> LOCATION: 7
<223> OTHER INFORMATION: Xaa = Pro OR Ser
<220> FEATURE:
<221> NAME/KEY: VARIANT
<222> LOCATION: (8)...(8)
<223> OTHER INFORMATION: Xaa = Cys OR Trp OR Leu OR Pro
<220> FEATURE:
<221> NAME/KEY: VARIANT
<222> LOCATION: (9)...(9)
```

```
<223> OTHER INFORMATION: Xaa = Ser OR Thr

<400> SEQUENCE: 132

Xaa Gln Xaa Xaa Xaa Xaa Xaa Xaa Xaa
1               5

<210> SEQ ID NO 133
<211> LENGTH: 27
<212> TYPE: DNA
<213> ORGANISM: Homo sapiens

<400> SEQUENCE: 133
ctacagcata atagttaccc gtggacg                                          27

<210> SEQ ID NO 134
<211> LENGTH: 11
<212> TYPE: PRT
<213> ORGANISM: Homo sapiens
<220> FEATURE:
<221> NAME/KEY: VARIANT
<222> LOCATION: 4
<223> OTHER INFORMATION: Xaa = Ile OR Phe
<220> FEATURE:
<221> NAME/KEY: VARIANT
<222> LOCATION: 5
<223> OTHER INFORMATION: Xaa = Asn OR Ser
<220> FEATURE:
<221> NAME/KEY: VARIANT
<222> LOCATION: 6
<223> OTHER INFORMATION: Xaa = Ser OR Ala
<220> FEATURE:
<221> NAME/KEY: VARIANT
<222> LOCATION: 7
<223> OTHER INFORMATION: Xaa = Gly OR -Xaa (Xaa deleted)
<220> FEATURE:
<221> NAME/KEY: VARIANT
<222> LOCATION: 8
<223> OTHER INFORMATION: Xaa = Gly OR -Xaa (Xaa deleted)
<220> FEATURE:
<221> NAME/KEY: VARIANT
<222> LOCATION: 9
<223> OTHER INFORMATION: Xaa = Phe OR Tyr

<400> SEQUENCE: 134

Gly Gly Ser Xaa Xaa Xaa Xaa Xaa Xaa Tyr Trp
1               5                   10

<210> SEQ ID NO 135
<211> LENGTH: 51
<212> TYPE: DNA
<213> ORGANISM: Homo sapiens

<400> SEQUENCE: 135
gttatatggt atgatggaag taataaatac catgcagact ccgtgaaggg c               51

<210> SEQ ID NO 136
<211> LENGTH: 45
<212> TYPE: DNA
<213> ORGANISM: Homo sapiens

<400> SEQUENCE: 136
agtcggaact ggaactacga caactactac tacggtctgg acgtc                      45

<210> SEQ ID NO 137
<211> LENGTH: 107
<212> TYPE: PRT
<213> ORGANISM: Homo sapiens

<400> SEQUENCE: 137
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Gly Trp Tyr Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Thr Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 138
<211> LENGTH: 124
<212> TYPE: PRT
<213> ORGANISM: Homo sapiens

<400> SEQUENCE: 138

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Val Arg Ser Arg Asn Trp Asn Tyr Asp Asn Tyr Tyr Tyr Gly Leu Asp
            100                 105                 110

Val Trp Gly Gln Gly Thr Thr Val Thr Val Ser Ser
        115                 120

<210> SEQ ID NO 139
<211> LENGTH: 10
<212> TYPE: PRT
<213> ORGANISM: Homo sapiens
<220> FEATURE:
<221> NAME/KEY: VARIANT
<222> LOCATION: 2
<223> OTHER INFORMATION: Xaa = Tyr OR Phe
<220> FEATURE:
<221> NAME/KEY: VARIANT
<222> LOCATION: 3
<223> OTHER INFORMATION: Xaa = Tyr OR Ser
<220> FEATURE:
<221> NAME/KEY: VARIANT
<222> LOCATION: 5
<223> OTHER INFORMATION: Xaa = Thr OR Ser OR Ile
<220> FEATURE:
<221> NAME/KEY: VARIANT
<222> LOCATION: 6
<223> OTHER INFORMATION: Xaa = Gly OR Ser
<220> FEATURE:
<221> NAME/KEY: VARIANT
<222> LOCATION: 8
<223> OTHER INFORMATION: Xaa = Tyr OR Gly OR Trp

```
<220> FEATURE:
<221> NAME/KEY: VARIANT
<222> LOCATION: 9
<223> OTHER INFORMATION: Xaa = Ile OR Met
<220> FEATURE:
<221> NAME/KEY: VARIANT
<222> LOCATION: (10)...(10)
<223> OTHER INFORMATION: Xaa = His OR Gly

<400> SEQUENCE: 139

Gly Xaa Xaa Phe Xaa Xaa Tyr Xaa Xaa Xaa
1               5                   10

<210> SEQ ID NO 140
<211> LENGTH: 10
<212> TYPE: PRT
<213> ORGANISM: Homo sapiens
<220> FEATURE:
<221> NAME/KEY: VARIANT
<222> LOCATION: 2
<223> OTHER INFORMATION: Xaa = Tyr OR Phe
<220> FEATURE:
<221> NAME/KEY: VARIANT
<222> LOCATION: 5
<223> OTHER INFORMATION: Xaa = Thr OR Ser
<220> FEATURE:
<221> NAME/KEY: VARIANT
<222> LOCATION: 6
<223> OTHER INFORMATION: Xaa = Ser OR Ala
<220> FEATURE:
<221> NAME/KEY: VARIANT
<222> LOCATION: 8
<223> OTHER INFORMATION: Xaa = Gly OR Trp
<220> FEATURE:
<221> NAME/KEY: VARIANT
<222> LOCATION: 9
<223> OTHER INFORMATION: Xaa = Leu OR Met OR Ile
<220> FEATURE:
<221> NAME/KEY: VARIANT
<222> LOCATION: 10
<223> OTHER INFORMATION: Xaa = Ser OR His

<400> SEQUENCE: 140

Gly Xaa Thr Phe Xaa Xaa Tyr Xaa Xaa Xaa
1               5                   10

<210> SEQ ID NO 141
<211> LENGTH: 9
<212> TYPE: PRT
<213> ORGANISM: Homo sapiens

<400> SEQUENCE: 141

Leu Gln His Asn Ser Tyr Pro Trp Thr
1               5

<210> SEQ ID NO 142
<211> LENGTH: 16
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Tyr OR Glu
<220> FEATURE:
<221> NAME/KEY: VARIANT
<222> LOCATION: 3
<223> OTHER INFORMATION: Xaa = Ser OR Tyr OR Asn
<220> FEATURE:
<221> NAME/KEY: VARIANT
<222> LOCATION: 4
<223> OTHER INFORMATION: Xaa = Tyr OR His
<220> FEATURE:
<221> NAME/KEY: VARIANT
```

```
<222> LOCATION: 7
<223> OTHER INFORMATION: Xaa = Ser OR Gly
<220> FEATURE:
<221> NAME/KEY: VARIANT
<222> LOCATION: 9
<223> OTHER INFORMATION: Xaa = Tyr OR Asn
<220> FEATURE:
<221> NAME/KEY: VARIANT
<222> LOCATION: 16
<223> OTHER INFORMATION: Xaa = Ser OR Arg

<400> SEQUENCE: 142

Xaa Ile Xaa Xaa Ser Gly Xaa Thr Xaa Tyr Asn Pro Ser Leu Lys Xaa
1               5                   10                  15

<210> SEQ ID NO 143
<211> LENGTH: 17
<212> TYPE: PRT
<213> ORGANISM: Homo sapiens

<400> SEQUENCE: 143

Val Ile Trp Tyr Asp Gly Ser Asn Lys Tyr His Ala Asp Ser Val Lys
1               5                   10                  15

Gly

<210> SEQ ID NO 144
<211> LENGTH: 15
<212> TYPE: PRT
<213> ORGANISM: Homo sapiens

<400> SEQUENCE: 144

Ser Arg Asn Trp Asn Tyr Asp Asn Tyr Tyr Tyr Gly Leu Asp Val
1               5                   10                  15

<210> SEQ ID NO 145
<211> LENGTH: 315
<212> TYPE: DNA
<213> ORGANISM: Homo sapiens

<400> SEQUENCE: 145
tcctatgagc tgactcagcc accctcagtg tccgtgtccc caggacagac agccagcatc      60
acctgctctg gagaaaaatg gggagagaaa tatgcttgtt ggtatcagca gaagccaggc     120
cagtcccctg tgctggtcat ctatcaagat accaagcggc cctccgggat ccctgagcga     180
ttctctggct ccatttctgg gaacacagcc actctgacca tcagcgggac ccaggctatg     240
gatgaggctg actattattg tcaggcgtgg gacaggagca ctgtattcgg cggagggacc     300
aagctgaccg tccta                                                     315

<210> SEQ ID NO 146
<211> LENGTH: 348
<212> TYPE: DNA
<213> ORGANISM: Homo sapiens

<400> SEQUENCE: 146
gaggtgcagc tggtgcagtc tggagcagag gtgaaaaagc ccggggagtc tctgaagatc      60
tcctgtcagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcag caccgcctac     240 ctgcagtgga gcagcctgaa ggcctcggac accgccatgt attactgtgc gagacaagga     300
ctggggtttg actactgggg ccagggaacc ctggtcaccg tctcctca                 348
```

```
<210> SEQ ID NO 147
<211> LENGTH: 33
<212> TYPE: DNA
<213> ORGANISM: Homo sapiens

<400> SEQUENCE: 147
tctggagaaa aatggggaga gaaatatgct tgt                                    33

<210> SEQ ID NO 148
<211> LENGTH: 21
<212> TYPE: DNA
<213> ORGANISM: Homo sapiens

<400> SEQUENCE: 148
caagatacca agcggccctc c                                                 21

<210> SEQ ID NO 149
<211> LENGTH: 24
<212> TYPE: DNA
<213> ORGANISM: Homo sapiens

<400> SEQUENCE: 149
caggcgtggg acaggagcac tgta                                              24

<210> SEQ ID NO 150
<211> LENGTH: 30
<212> TYPE: DNA
<213> ORGANISM: Homo sapiens

<400> SEQUENCE: 150
ggatacagct ttaccagcta ctggatcggc                                        30

<210> SEQ ID NO 151
<211> LENGTH: 51
<212> TYPE: DNA
<213> ORGANISM: Homo sapiens

<400> SEQUENCE: 151
atcatctatc tggtgactc tgataccaga tacagcccgt ccttccaagg c                 51

<210> SEQ ID NO 152
<211> LENGTH: 21
<212> TYPE: DNA
<213> ORGANISM: Homo sapiens

<400> SEQUENCE: 152
caaggactgg ggtttgacta c                                                 21

<210> SEQ ID NO 153
<211> LENGTH: 105
<212> TYPE: PRT
<213> ORGANISM: Homo sapiens

<400> SEQUENCE: 153
```

Ser Tyr Glu Leu Thr Gln Pro Pro Ser Val Ser Val Ser Pro Gly Gln
1               5                   10                  15

Thr Ala Ser Ile Thr Cys Ser Gly Glu Lys Trp Gly Glu Lys Tyr Ala
            20                  25                  30

Cys Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser

```
                50              55              60
Ile Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Arg Ser Thr Val Phe
                 85                  90                  95

Gly Gly Gly Thr Lys Leu Thr Val Leu
                100                 105

<210> SEQ ID NO 154
<211> LENGTH: 116
<212> TYPE: PRT
<213> ORGANISM: Homo sapiens

<400> SEQUENCE: 154

Glu Val Gln Leu Val Gln Ser Gly Ala Glu Val Lys Lys Pro Gly Glu
  1               5                  10                  15

Ser Leu Lys Ile Ser Cys Gln Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gln Gly Leu Gly Phe Asp Tyr Trp Gly Gln Gly Thr Leu Val
                100                 105                 110

Thr Val Ser Ser
            115

<210> SEQ ID NO 155
<211> LENGTH: 11
<212> TYPE: PRT
<213> ORGANISM: Homo sapiens

<400> SEQUENCE: 155

Ser Gly Glu Lys Trp Gly Glu Lys Tyr Ala Cys
  1               5                  10

<210> SEQ ID NO 156
<211> LENGTH: 7
<212> TYPE: PRT
<213> ORGANISM: Homo sapiens

<400> SEQUENCE: 156

Gln Asp Thr Lys Arg Pro Ser
  1               5

<210> SEQ ID NO 157
<211> LENGTH: 8
<212> TYPE: PRT
<213> ORGANISM: Homo sapiens

<400> SEQUENCE: 157

Gln Ala Trp Asp Arg Ser Thr Val
  1               5

<210> SEQ ID NO 158
<211> LENGTH: 10
```

-continued

<212> TYPE: PRT
<213> ORGANISM: Homo sapiens

<400> SEQUENCE: 158

Gly Tyr Ser Phe Thr Ser Tyr Trp Ile Gly
1               5                   10

<210> SEQ ID NO 159
<211> LENGTH: 17
<212> TYPE: PRT
<213> ORGANISM: Homo sapiens

<400> SEQUENCE: 159

Ile Ile Tyr Pro Gly Asp Ser Asp Thr Arg Tyr Ser Pro Ser Phe Gln
1               5                   10                  15
Gly

<210> SEQ ID NO 160
<211> LENGTH: 7
<212> TYPE: PRT
<213> ORGANISM: Homo sapiens

<400> SEQUENCE: 160

Gln Gly Leu Gly Phe Asp Tyr
1               5

<210> SEQ ID NO 161
<211> LENGTH: 318
<212> TYPE: DNA
<213> ORGANISM: Homo sapiens

<400> SEQUENCE: 161
tcctatgagc tgactcagcc accctcagtg tccgtgtccc caggacagac agccagcatc    60
acctgctctg gagataaaatt gggggataaa tttgctttct ggtatcagct gaagccaggc   120
cagtcccctg tgctggtcat ctatcaagat aacaagcggc cctcagggat ccctgagcga   180
ttctctggct ccaactctgg gaacacagcc actctgacca tcagcgggac ccaggctatg   240
gatgcggctg acttttactg tcaggcgtgg gacagcagca ctgtggtatt cggcggaggg   300
accaagctga ccgtccta                                                 318

<210> SEQ ID NO 162
<211> LENGTH: 363
<212> TYPE: DNA
<213> ORGANISM: Homo sapiens

<400> SEQUENCE: 162
caggtgcagc tgcaggagtc gggcccagga ctggtgaagc cttcacagac cctgtccctc    60
acctgcactg tctctggtgg ctccatcagc agtggtggtt actactggag ctggatccgc   120
cagcacccag ggaagggcct ggagtggatt gggtacatct cttacagtgg gagcacctac   180
tacaacccgt ccctcaagag tcgagttacc atatcagttg acacgtctaa gaaccagttc   240
tccctgaagc tgaactctgt gactgccgcg gacacggccg tgtattactg tgcgcgcgct   300
tacggtgact atcgcggctg gttcgacccc tggggccagg aaccctggt caccgtctcc     360 tca                                                                 363

<210> SEQ ID NO 163
<211> LENGTH: 33
<212> TYPE: DNA
<213> ORGANISM: Homo sapiens

<210> SEQ ID NO 163

<400> SEQUENCE: 163
tctggagata aattgggga taaatttgct ttc 33

<210> SEQ ID NO 164
<211> LENGTH: 21
<212> TYPE: DNA
<213> ORGANISM: Homo sapiens

<400> SEQUENCE: 164
caagataaca agcggccctc a 21

<210> SEQ ID NO 165
<211> LENGTH: 27
<212> TYPE: DNA
<213> ORGANISM: Homo sapiens

<400> SEQUENCE: 165
caggcgtggg acagcagcac tgtggta 27

<210> SEQ ID NO 166
<211> LENGTH: 36
<212> TYPE: DNA
<213> ORGANISM: Homo sapiens

<400> SEQUENCE: 166
ggtggctcca tcagcagtgg tggttactac tggagc 36

<210> SEQ ID NO 167
<211> LENGTH: 48
<212> TYPE: DNA
<213> ORGANISM: Homo sapiens

<400> SEQUENCE: 167
tacatctctt acagtgggag cacctactac aacccgtccc tcaagagt 48

<210> SEQ ID NO 168
<211> LENGTH: 33
<212> TYPE: DNA
<213> ORGANISM: Homo sapiens

<400> SEQUENCE: 168
gcttacggtg actatcgcgg ctggttcgac ccc 33

<210> SEQ ID NO 169
<211> LENGTH: 106
<212> TYPE: PRT
<213> ORGANISM: Homo sapiens

<400> SEQUENCE: 169

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Phe Ala
            20                  25                  30

Phe Trp Tyr Gln Leu Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Ala Ala Asp Phe Tyr Cys Gln Ala Trp Asp Ser Ser Thr Val Val

```
                    85                  90                  95

Phe Gly Gly Gly Thr Lys Leu Thr Val Leu
            100                 105

<210> SEQ ID NO 170
<211> LENGTH: 121
<212> TYPE: PRT
<213> ORGANISM: Homo sapiens

<400> SEQUENCE: 170

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Ser Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Arg Ala Tyr Gly Asp Tyr Arg Gly Trp Phe Asp Pro Trp Gly
            100                 105                 110

Gln Gly Thr Leu Val Thr Val Ser Ser
        115                 120

<210> SEQ ID NO 171
<211> LENGTH: 11
<212> TYPE: PRT
<213> ORGANISM: Homo sapiens

<400> SEQUENCE: 171

Ser Gly Asp Lys Leu Gly Asp Lys Phe Ala Phe
1               5                   10

<210> SEQ ID NO 172
<211> LENGTH: 7
<212> TYPE: PRT
<213> ORGANISM: Homo sapiens

<400> SEQUENCE: 172

Gln Asp Asn Lys Arg Pro Ser
1               5

<210> SEQ ID NO 173
<211> LENGTH: 9
<212> TYPE: PRT
<213> ORGANISM: Homo sapiens

<400> SEQUENCE: 173

Gln Ala Trp Asp Ser Ser Thr Val Val
1               5

<210> SEQ ID NO 174
<211> LENGTH: 12
<212> TYPE: PRT
<213> ORGANISM: Homo sapiens

<400> SEQUENCE: 174

Gly Gly Ser Ile Ser Ser Gly Gly Tyr Tyr Trp Ser
```

```
1               5                   10
```

<210> SEQ ID NO 175
<211> LENGTH: 16
<212> TYPE: PRT
<213> ORGANISM: Homo sapiens

<400> SEQUENCE: 175

```
Tyr Ile Ser Tyr Ser Gly Ser Thr Tyr Tyr Asn Pro Ser Leu Lys Ser
1               5                   10                  15
```

<210> SEQ ID NO 176
<211> LENGTH: 11
<212> TYPE: PRT
<213> ORGANISM: Homo sapiens

<400> SEQUENCE: 176

```
Ala Tyr Gly Asp Tyr Arg Gly Trp Phe Asp Pro
1               5                   10
```

<210> SEQ ID NO 177
<211> LENGTH: 321
<212> TYPE: DNA
<213> ORGANISM: Homo sapiens

<400> SEQUENCE: 177

| | | | |
|---|---|---|---|
| gacatccaga tgacccagtc tccatcctcc ctgtctgcat ctgtaggaga cagagtcacc | | | 60 |
| atcacttgcc gggcaagtca gggcattaga aatgatttag gctggtatca gcagaaacca | | | 120 |
| gggaaagccc ctaagcgcct gatctatgct gcatccagtt tgcaaagtgg ggtcccatca | | | 180 |
| aggttcagcg gcagtggatc tgggacagaa ttcactctca caatcagcag cctgcagcct | | | 240 |
| gaagattgtg caacttatta ttgtctacag cataatagtt atacgtggac gttcggccaa | | | 300 |
| gggaccaagg tggaaatcaa a | | | 321 |

<210> SEQ ID NO 178
<211> LENGTH: 372
<212> TYPE: DNA
<213> ORGANISM: Homo sapiens

<400> SEQUENCE: 178

| | | | |
|---|---|---|---|
| caggtgcagc tggtggagtc tggggggaggc gtggtccagc ctgggaggtc cctgagactc | | | 60 |
| tcctgtgtag cgtctggatt caccttcagt gcctatggca tgcactgggt ccgccaggct | | | 120 |
| ccaggcaagg gctggagtg gtggcagtt atatggtatg atggaagtaa taaatactat | | | 180 |
| gcagactccg tgaagggccg attcatcatc tccagagaca attccaagaa cacgctgtat | | | 240 |
| ctgcaaatga acagcctgag agccgaggac acggctgtgt attactgtgc gagaagtcgg | | | 300 |
| aactggaact acgactccta ccaatacggt ttggacgtct ggggccaagg gaccacggtc | | | 360 |
| accgtctcct ca | | | 372 |

<210> SEQ ID NO 179
<211> LENGTH: 17
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Asn OR Val
<220> FEATURE:
<221> NAME/KEY: VARIANT
<222> LOCATION: 3
<223> OTHER INFORMATION: Xaa = Trp OR Lys

```
<220> FEATURE:
<221> NAME/KEY: VARIANT
<222> LOCATION: 4
<223> OTHER INFORMATION: Xaa = Tyr OR Gln
<220> FEATURE:
<221> NAME/KEY: VARIANT
<222> LOCATION: 8
<223> OTHER INFORMATION: Xaa = Asn OR Glu OR Ser
<220> FEATURE:
<221> NAME/KEY: VARIANT
<222> LOCATION: 9
<223> OTHER INFORMATION: Xaa = Lys OR Glu
<220> FEATURE:
<221> NAME/KEY: VARIANT
<222> LOCATION: 11
<223> OTHER INFORMATION: Xaa = His OR Tyr
<220> FEATURE:
<221> NAME/KEY: VARIANT
<222> LOCATION: (12)...(12)
<223> OTHER INFORMATION: Xaa = Ala OR Val

<400> SEQUENCE: 179

Xaa Ile Xaa Xaa Asp Gly Ser Xaa Xaa Tyr Xaa Xaa Asp Ser Val Lys
1               5                   10                  15

Gly

<210> SEQ ID NO 180
<211> LENGTH: 17
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Trp OR Ile
<220> FEATURE:
<221> NAME/KEY: VARIANT
<222> LOCATION: 3
<223> OTHER INFORMATION: Xaa = Asn OR Ile OR Ser OR Tyr
<220> FEATURE:
<221> NAME/KEY: VARIANT
<222> LOCATION: 4
<223> OTHER INFORMATION: Xaa = Pro OR Ala
<220> FEATURE:
<221> NAME/KEY: VARIANT
<222> LOCATION: 5
<223> OTHER INFORMATION: Xaa = Asn OR Tyr OR Gly
<220> FEATURE:
<221> NAME/KEY: VARIANT
<222> LOCATION: 6
<223> OTHER INFORMATION: Xaa = Ser OR Asn OR Asp
<220> FEATURE:
<221> NAME/KEY: VARIANT
<222> LOCATION: 7
<223> OTHER INFORMATION: Xaa = Gly OR Ser
<220> FEATURE:
<221> NAME/KEY: VARIANT
<222> LOCATION: (8)...(8)
<223> OTHER INFORMATION: Xaa = Gly OR Asn OR Asp
<220> FEATURE:
<221> NAME/KEY: VARIANT
<222> LOCATION: (10)...(10)
<223> OTHER INFORMATION: Xaa = Asn OR Arg
<220> FEATURE:
<221> NAME/KEY: VARIANT
<222> LOCATION: (11)...(11)
<223> OTHER INFORMATION: Xaa = Tyr OR Ser
<220> FEATURE:
<221> NAME/KEY: VARIANT
<222> LOCATION: (12)...(12)
<223> OTHER INFORMATION: Xaa = Ala OR Ser
<220> FEATURE:
<221> NAME/KEY: VARIANT
<222> LOCATION: (13)...(13)
<223> OTHER INFORMATION: Xaa = Gln OR Pro
<220> FEATURE:
<221> NAME/KEY: VARIANT
```

```
<222> LOCATION: (14)...(14)
<223> OTHER INFORMATION: Xaa = Lys OR Ser
<220> FEATURE:
<221> NAME/KEY: VARIANT
<222> LOCATION: (15)...(15)
<223> OTHER INFORMATION: Xaa = Phe OR Leu

<400> SEQUENCE: 180

Xaa Ile Xaa Xaa Xaa Xaa Xaa Xaa Thr Xaa Xaa Xaa Xaa Xaa Gln
1               5                   10                  15

Gly

<210> SEQ ID NO 181
<211> LENGTH: 27
<212> TYPE: DNA
<213> ORGANISM: Homo sapiens

<400> SEQUENCE: 181
ctacagcata atagttatac gtggacg                                     27

<210> SEQ ID NO 182
<211> LENGTH: 30
<212> TYPE: DNA
<213> ORGANISM: Homo sapiens

<400> SEQUENCE: 182
ggattcacct tcagtgccta tggcatgcac                                  30

<210> SEQ ID NO 183
<211> LENGTH: 51
<212> TYPE: DNA
<213> ORGANISM: Homo sapiens

<400> SEQUENCE: 183
gttatatggt atgatggaag taataaatac tatgcagact ccgtgaaggg c          51

<210> SEQ ID NO 184
<211> LENGTH: 45
<212> TYPE: DNA
<213> ORGANISM: Homo sapiens

<400> SEQUENCE: 184
agtcggaact ggaactacga ctcctaccaa tacggtttgg acgtc                 45

<210> SEQ ID NO 185
<211> LENGTH: 107
<212> TYPE: PRT
<213> ORGANISM: Homo sapiens

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Cys Ala Thr Tyr Tyr Cys Leu Gln His Asn Ser Tyr Thr Trp
                85                  90                  95
```

```
Thr Phe Gly Gln Gly Thr Lys Val Glu Ile Lys
            100                 105
```

<210> SEQ ID NO 186
<211> LENGTH: 124
<212> TYPE: PRT
<213> ORGANISM: Homo sapiens

<400> SEQUENCE: 186

```
Gln Val Gln Leu Val Glu Ser Gly Gly Val Val Gln Pro Gly Arg
1               5                   10                  15

Ser Leu Arg Leu Ser Cys Val Ala Ser Gly Phe Thr Phe Ser Ala Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Ile Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Asn Trp Asn Tyr Asp Ser Tyr Gln Tyr Gly Leu Asp
            100                 105                 110

Val Trp Gly Gln Gly Thr Thr Val Thr Val Ser Ser
            115                 120
```

<210> SEQ ID NO 187
<211> LENGTH: 11
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Val OR -Xaa (Xaa deleted)
<220> FEATURE:
<221> NAME/KEY: VARIANT
<222> LOCATION: 2
<223> OTHER INFORMATION: Xaa = Gln OR -Xaa (Xaa deleted)
<220> FEATURE:
<221> NAME/KEY: VARIANT
<222> LOCATION: 3
<223> OTHER INFORMATION: Xaa = Asp OR Trp OR -Xaa (Xaa deleted)
<220> FEATURE:
<221> NAME/KEY: VARIANT
<222> LOCATION: 4
<223> OTHER INFORMATION: Xaa = Ser OR Leu OR -Xaa (Xaa deleted)
<220> FEATURE:
<221> NAME/KEY: VARIANT
<222> LOCATION: 5
<223> OTHER INFORMATION: Xaa = Ile OR Glu OR Gln
<220> FEATURE:
<221> NAME/KEY: VARIANT
<222> LOCATION: 6
<223> OTHER INFORMATION: Xaa = Ala OR Leu OR Gly
<220> FEATURE:
<221> NAME/KEY: VARIANT
<222> LOCATION: (7)...(7)
<223> OTHER INFORMATION: Xaa = Ala OR Leu
<220> FEATURE:
<221> NAME/KEY: VARIANT
<222> LOCATION: (8)...(8)
<223> OTHER INFORMATION: Xaa = Pro OR Tyr OR Gly

<400> SEQUENCE: 187

```
Xaa Xaa Xaa Xaa Xaa Xaa Xaa Xaa Phe Asp Tyr
1               5                   10
```

```
<210> SEQ ID NO 188
<211> LENGTH: 13
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Asp OR -Xaa (Xaa deleted)
<220> FEATURE:
<221> NAME/KEY: VARIANT
<222> LOCATION: 2
<223> OTHER INFORMATION: Xaa = Gln OR -Xaa (Xaa deleted)
<220> FEATURE:
<221> NAME/KEY: VARIANT
<222> LOCATION: 3
<223> OTHER INFORMATION: Xaa = Asp OR Ala
<220> FEATURE:
<221> NAME/KEY: VARIANT
<222> LOCATION: 5
<223> OTHER INFORMATION: Xaa = Tyr OR Gly
<220> FEATURE:
<221> NAME/KEY: VARIANT
<222> LOCATION: 7
<223> OTHER INFORMATION: Xaa = Ser OR Tyr
<220> FEATURE:
<221> NAME/KEY: VARIANT
<222> LOCATION: 8
<223> OTHER INFORMATION: Xaa = Ser OR Arg
<220> FEATURE:
<221> NAME/KEY: VARIANT
<222> LOCATION: (11)...(11)
<223> OTHER INFORMATION: Xaa = Phe OR -Xaa (Xaa deleted)
<220> FEATURE:
<221> NAME/KEY: VARIANT
<222> LOCATION: (12)...(12)
<223> OTHER INFORMATION: Xaa = Gly OR Asp
<220> FEATURE:
<221> NAME/KEY: VARIANT
<222> LOCATION: (13)...(13)
<223> OTHER INFORMATION: Xaa = His OR Pro

<400> SEQUENCE: 188

Xaa Xaa Xaa Tyr Xaa Asp Xaa Xaa Gly Trp Xaa Xaa Xaa
1               5                   10

<210> SEQ ID NO 189
<211> LENGTH: 9
<212> TYPE: PRT
<213> ORGANISM: Homo sapiens

<400> SEQUENCE: 189

Leu Gln His Asn Ser Tyr Thr Trp Thr
1               5

<210> SEQ ID NO 190
<211> LENGTH: 10
<212> TYPE: PRT
<213> ORGANISM: Homo sapiens

<400> SEQUENCE: 190

Gly Phe Thr Phe Ser Ala Tyr Gly Met His
1               5                   10

<210> SEQ ID NO 191
<211> LENGTH: 17
<212> TYPE: PRT
<213> ORGANISM: Homo sapiens

<400> SEQUENCE: 191

Val Ile Trp Tyr Asp Gly Ser Asn Lys Tyr Tyr Ala Asp Ser Val Lys
1               5                   10                  15
```

Gly

<210> SEQ ID NO 192
<211> LENGTH: 15
<212> TYPE: PRT
<213> ORGANISM: Homo sapiens

<400> SEQUENCE: 192

Ser Arg Asn Trp Asn Tyr Asp Ser Tyr Gln Tyr Gly Leu Asp Val
1               5                   10                  15

<210> SEQ ID NO 193
<211> LENGTH: 315
<212> TYPE: DNA
<213> ORGANISM: Homo sapiens

<400> SEQUENCE: 193

```
tcctatgagc tgactcagcc accctcagtg tccgtgtccc caggacagac agccagcatc      60
acctgctctg gagataaaatt ggggataaa tatgtttgtt ggtatcagca gaagccaggc     120
cagtcccctg aactggtcat ctatctagat aacaagcggc cctcagggat ccctgagcga    180
ttctctggct ccaactctgg gaacacagcc actctgacca tcagcgggac ccaggctatg    240
gatgaggctg actattactg tcaggcgtgg gacagcagca cggtattcgg cggagggacc    300
aaactgaccg tcctg                                                     315
```

<210> SEQ ID NO 194
<211> LENGTH: 363
<212> TYPE: DNA
<213> ORGANISM: Homo sapiens

<400> SEQUENCE: 194

```
caggttcagc tggtgcagtc tggagctgag gtgaagaagc ctggggcctc agtgaaggtc      60
tcctgcaagg cttctggtta cacctttacc agctatggta tcagctgggt gcgacaggcc    120
cctggacaag gcttgagag gatgggatgg atcagcgctt acaatggtaa cacaaactat     180
gcacagaagt tccagggcag agtcaccatg accacagaca catcaacgac cacagcctac    240
atggagctga ggagcctgag atctgacgac acggccgtgt attactgtgc gagagatcaa    300
gattactatg atagtagtgg ttggggccac tggggccagg gaaccctggt caccgtctcc    360
tca                                                                   363
```

<210> SEQ ID NO 195
<211> LENGTH: 33
<212> TYPE: DNA
<213> ORGANISM: Homo sapiens

<400> SEQUENCE: 195

```
tctggagata aattggggga taaatatgtt tgt                                   33
```

<210> SEQ ID NO 196
<211> LENGTH: 21
<212> TYPE: DNA
<213> ORGANISM: Homo sapiens

<400> SEQUENCE: 196

```
ctagataaca agcggccctc a                                               21
```

<210> SEQ ID NO 197
<211> LENGTH: 24

```
<212> TYPE: DNA
<213> ORGANISM: Homo sapiens

<400> SEQUENCE: 197
caggcgtggg acagcagcac ggta                                      24

<210> SEQ ID NO 198
<211> LENGTH: 30
<212> TYPE: DNA
<213> ORGANISM: Homo sapiens

<400> SEQUENCE: 198
ggttacacct ttaccagcta tggtatcagc                                30

<210> SEQ ID NO 199
<211> LENGTH: 51
<212> TYPE: DNA
<213> ORGANISM: Homo sapiens

<400> SEQUENCE: 199
tggatcagcg cttacaatgg taacacaaac tatgcacaga agttccaggg c        51

<210> SEQ ID NO 200
<211> LENGTH: 36
<212> TYPE: DNA
<213> ORGANISM: Homo sapiens

<400> SEQUENCE: 200
gatcaagatt actatgatag tagtggttgg ggccac                         36

<210> SEQ ID NO 201
<211> LENGTH: 105
<212> TYPE: PRT
<213> ORGANISM: Homo sapiens

<400> SEQUENCE: 201
```

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Cys Trp Tyr Gln Gln Lys Pro Gly Gln Ser Pro Glu Leu Val Ile Tyr
        35                  40                  45

Leu Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Phe
                85                  90                  95

Gly Gly Gly Thr Lys Leu Thr Val Leu
            100                 105

```
<210> SEQ ID NO 202
<211> LENGTH: 121
<212> TYPE: PRT
<213> ORGANISM: Homo sapiens

<400> SEQUENCE: 202
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Arg Met
            35                  40                  45

Gly Trp Ile Ser Ala Tyr Asn Gly Asn Thr Asn Tyr Ala Gln Lys Phe
        50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Thr Ala Val Tyr Tyr Cys
                85                  90                  95

Ala Arg Asp Gln Asp Tyr Tyr Asp Ser Ser Gly Trp Gly His Trp Gly
                100                 105                 110

Gln Gly Thr Leu Val Thr Val Ser Ser
        115                 120

<210> SEQ ID NO 203
<211> LENGTH: 11
<212> TYPE: PRT
<213> ORGANISM: Homo sapiens

<400> SEQUENCE: 203

Ser Gly Asp Lys Leu Gly Asp Lys Tyr Val Cys
1               5                   10

<210> SEQ ID NO 204
<211> LENGTH: 7
<212> TYPE: PRT
<213> ORGANISM: Homo sapiens

<400> SEQUENCE: 204

Leu Asp Asn Lys Arg Pro Ser
1               5

<210> SEQ ID NO 205
<211> LENGTH: 8
<212> TYPE: PRT
<213> ORGANISM: Homo sapiens

<400> SEQUENCE: 205

Gln Ala Trp Asp Ser Ser Thr Val
1               5

<210> SEQ ID NO 206
<211> LENGTH: 10
<212> TYPE: PRT
<213> ORGANISM: Homo sapiens

<400> SEQUENCE: 206

Gly Tyr Thr Phe Thr Ser Tyr Gly Ile Ser
1               5                   10

<210> SEQ ID NO 207
<211> LENGTH: 17
<212> TYPE: PRT
<213> ORGANISM: Homo sapiens

<400> SEQUENCE: 207

Trp Ile Ser Ala Tyr Asn Gly Asn Thr Asn Tyr Ala Gln Lys Phe Gln
1               5                   10                  15

Gly

<210> SEQ ID NO 208
<211> LENGTH: 12

<212> TYPE: PRT
<213> ORGANISM: Homo sapiens

<400> SEQUENCE: 208

Asp Gln Asp Tyr Tyr Asp Ser Ser Gly Trp Gly His
1               5                   10

<210> SEQ ID NO 209
<211> LENGTH: 316
<212> TYPE: DNA
<213> ORGANISM: Homo sapiens

<400> SEQUENCE: 209

```
tcctatgagc tgactcagcc accctcagtg tccgtgtccc caggacagac agcctccatc      60
acctgctctg gagataaatt gggggataaa tatgctttct ggtatcagca gaagccaggc     120
cagtcccctg tgctggtctt ctatcatgat accaagcggc cctcagggat ccctgagcga     180
ttctctggct ccaactctgg gaacacagcc actctgacca tcagcgggac ccaggctatg     240
gatgaggctg actatcactg tcaggcgtgg acagcagca cggtcttcgg cggagggacc      300
aagctgaccg tcctac                                                     316
```

<210> SEQ ID NO 210
<211> LENGTH: 363
<212> TYPE: DNA
<213> ORGANISM: Homo sapiens

<400> SEQUENCE: 210

```
caggttcagc tggtgcaatc tggagctgag gtgaagaagc ctggggcctc agtgaaggtc      60
tcctgcaaga cttctggtta cacctttacc agctatggta tcagctgggt gcgacaggcc     120
cctggacaag gcttgagtg gatgggatgg atcagccctt acaatggtaa cacaaactat      180
gcacagaagt tccagggcag agtcaccatg accacagaca atccacgag cacagcctac      240
atggagctga ggagcctgcg atctgacgac acggccgtgt attactgtgc gagagatcaa     300
gattactatg atagtagtgg ttgggacccc tggggccagg gaaccctggt caccgtctcc     360
tcg                                                                   363
```

<210> SEQ ID NO 211
<211> LENGTH: 33
<212> TYPE: DNA
<213> ORGANISM: Homo sapiens

<400> SEQUENCE: 211

```
tctggagata aattggggga taaatatgct ttc                                   33
```

<210> SEQ ID NO 212
<211> LENGTH: 21
<212> TYPE: DNA
<213> ORGANISM: Homo sapiens

<400> SEQUENCE: 212

```
catgatacca agcggccctc a                                                21
```

<210> SEQ ID NO 213
<211> LENGTH: 360
<212> TYPE: DNA
<213> ORGANISM: Artificial Sequence
<220> FEATURE:
<223> OTHER INFORMATION: Activin A/B Chimera

<400> SEQUENCE: 213

```
ggtctagagt gtgatggcaa ggtcaacatc tgctgtaaga aacagttctt tgtcagtttc      60
aaggacatcg gctggaatga ctggatcatt gctccctctg gctatcatgc caactactgc     120
gagggtgagt gcccgagcca tatagcaggc acgtccgggt caagcttgtc cttccactca     180
acagtcatca accactaccg catgcgggc catagcccct ttgccaacct caaatcatgc     240
tgtattccca ccaagctgag caccatgtcc atgttgtact ttgatgatga gtacaacatc     300
gtcaaaaggg acgttccgaa catgatcgtg gaggagtgtg ggtgctcatg agcggccgct     360
```

<210> SEQ ID NO 214
<211> LENGTH: 326
<212> TYPE: PRT
<213> ORGANISM: Homo sapiens

<400> SEQUENCE: 214

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
```

Ser Leu Ser Pro Gly Lys
325

<210> SEQ ID NO 215
<211> LENGTH: 326
<212> TYPE: PRT
<213> ORGANISM: Homo sapiens

<400> SEQUENCE: 215

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 216
<211> LENGTH: 36

```
<212> TYPE: DNA
<213> ORGANISM: Homo sapiens

<400> SEQUENCE: 216
gatcaagatt actatgatag tagtggttgg gacccc                                    36

<210> SEQ ID NO 217
<211> LENGTH: 105
<212> TYPE: PRT
<213> ORGANISM: Homo sapiens

<400> SEQUENCE: 217
```

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Phe Trp Tyr Gln Gln Lys Pro Gly Gln Ser Pro Val Leu Val Phe Tyr
        35                  40                  45

His Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr His Cys Gln Ala Trp Asp Ser Ser Thr Val Phe
                85                  90                  95

Gly Gly Gly Thr Lys Leu Thr Val Leu
            100                 105

```
<210> SEQ ID NO 218
<211> LENGTH: 121
<212> TYPE: PRT
<213> ORGANISM: Homo sapiens

<400> SEQUENCE: 218
```

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Pro Tyr Asn Gly Asn Thr Asn Tyr Ala Gln Lys Phe
    50                  55                  60

Gln Gly Arg Val Thr Met Thr Thr Asp Lys Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Gln Asp Tyr Tyr Asp Ser Ser Gly Trp Asp Pro Trp Gly
            100                 105                 110

Gln Gly Thr Leu Val Thr Val Ser Ser
        115                 120

```
<210> SEQ ID NO 219
<211> LENGTH: 11
<212> TYPE: PRT
<213> ORGANISM: Homo sapiens

<400> SEQUENCE: 219
```

Ser Gly Asp Lys Leu Gly Asp Lys Tyr Ala Phe
1               5                   10

```
<210> SEQ ID NO 220
<211> LENGTH: 7
<212> TYPE: PRT
<213> ORGANISM: Homo sapiens

<400> SEQUENCE: 220

His Asp Thr Lys Arg Pro Ser
1               5

<210> SEQ ID NO 221
<211> LENGTH: 326
<212> TYPE: PRT
<213> ORGANISM: Homo sapiens

<400> SEQUENCE: 221

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320
```

Ser Leu Ser Pro Gly Lys
           325

<210> SEQ ID NO 222
<211> LENGTH: 318
<212> TYPE: DNA
<213> ORGANISM: Homo sapiens

<400> SEQUENCE: 222
ggtcagccca aggctgcccc ctcggtcact ctgttcccgc cctcctctga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac accctccaaa   180
caaagcaaca acaagtacgc ggccagcagc tatctgagcc tgacgcctga gcagtggaag   240
tcccacagaa gctacagctg ccaggtcacg catgaaggga gcaccgtgga agagacagtg   300
gcccctacag aatgttca                                                 318

<210> SEQ ID NO 223
<211> LENGTH: 321
<212> TYPE: DNA
<213> ORGANISM: Homo sapiens

<400> SEQUENCE: 223
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                             321

<210> SEQ ID NO 224
<211> LENGTH: 12
<212> TYPE: PRT
<213> ORGANISM: Homo sapiens

<400> SEQUENCE: 224

Asp Gln Asp Tyr Tyr Asp Ser Ser Gly Trp Asp Pro
1               5                   10

<210> SEQ ID NO 225
<211> LENGTH: 116
<212> TYPE: PRT
<213> ORGANISM: Homo sapiens

<400> SEQUENCE: 225

Gly Leu Glu Cys Asp Gly Lys Val Asn Ile Cys Cys Lys Lys Gln Phe
1               5                   10                  15

Phe Val Ser Phe Lys Asp Ile Gly Trp Asn Asp Trp Ile Ile Ala Pro
            20                  25                  30

Ser Gly Tyr His Ala Asn Tyr Cys Glu Gly Glu Cys Pro Ser His Ile
        35                  40                  45

Ala Gly Thr Ser Gly Ser Ser Leu Ser Phe His Ser Thr Val Ile Asn
    50                  55                  60

His Tyr Arg Met Arg Gly His Ser Pro Phe Ala Asn Leu Lys Ser Cys
65                  70                  75                  80

Cys Val Pro Thr Lys Leu Arg Pro Met Ser Met Leu Tyr Tyr Asp Asp
                85                  90                  95

Gly Gln Asn Ile Ile Lys Lys Asp Ile Gln Asn Met Ile Val Glu Glu
            100                 105                 110

Cys Gly Cys Ser
        115

<210> SEQ ID NO 226
<211> LENGTH: 8
<212> TYPE: PRT
<213> ORGANISM: Homo sapiens

<400> SEQUENCE: 226

Asp Tyr Lys Asp Asp Asp Asp Lys
1               5

<210> SEQ ID NO 227
<211> LENGTH: 636
<212> TYPE: DNA
<213> ORGANISM: Homo sapiens

<400> SEQUENCE: 227
tcctatgagg tgactcaggc accctcagtg tccgtgtccc caggacagac agccagcatc      60
acctgctctg gagataaaat tggggataaa tatgcttgtt ggtatcagca gaagccaggc     120
cagtcccctg tgctggtcat ctatcaagat agcaagcggc cctcagggat ccctgagcga     180
ttctctggct ccaactctgg aaacacagcc actctgacca tcagcgggac ccaggctatg     240
gatgaggctg actattactg tcaggcgtgg gacagcagca ctgcggtatt cggcggaggg     300
accaagctga ccgtcctagg tcagcccaag gctgccccct cggtcactct gttcccgccc     360
tcctctgagg agcttcaagc caacaaggcc acactggtgt gtctcataag tgacttctac     420
ccgggagccg tgacagtggc ctggaaggca gatagcagcc ccgtcaaggc gggagtggag     480
accaccacac cctccaaaca aagcaacaac aagtacgcgg ccagcagcta tctgagcctg     540
acgcctgagc agtggaagtc cacagaagc tacagctgcc aggtcacgca tgaagggagc      600
accgtggaga agacagtggc ccctacagaa tgttca                              636

<210> SEQ ID NO 228
<211> LENGTH: 1344
<212> TYPE: DNA
<213> ORGANISM: Homo sapiens

<400> SEQUENCE: 228
caggttcagc tggtgcagtc tggagctgag gtgaagaagc ctggggcctc agtgaaggtc      60
tcctgcaagg cttctggtta cacctttacc agttatggtc tcagctgggt gcgacaggcc     120
cctggacaag gcttgagtg gatgggatgg atcatcccct acaatggtaa cacaaactct      180
gcacagaaac tccagggcag agtcaccatg accacagaca tccacgag cacagcctac       240 atggagctga ggagcctgag atctgacgac acggccgtgt atttctgtgc gagagacagg     300
gactacggtg tcaattatga tgcttttgat atctggggcc aagggacaat ggtcaccgtc     360
tcttcagcct ccaccaaggg cccatcggtc ttcccctgg cgccctgctc caggagcacc      420
tccgagagca gcggccct gggctgcctg gtcaaggact acttcccga accggtgacg        480 gtgtcgtgga actcaggcgc tctgaccagc ggcgtgcaca ccttcccagc tgtcctacag     540
tcctcaggac tctactccct cagcagcgtg gtgaccgtgc ctccagcaa cttcggcacc     600 cagacctaca cctgcaacgt agatcacaag cccagcaaca ccaaggtgga caagacagtt     660
gagcgcaaat gttgtgtcga gtgcccaccg tgcccagcac cacctgtggc aggaccgtca     720

```
gtcttcctct tccccccaaa acccaaggac accctcatga tctcccggac ccctgaggtc    780
acgtgcgtgg tggtggacgt gagccacgaa gaccccgagg tccagttcaa ctggtacgtg    840
gacggcgtgg aggtgcataa tgccaagaca aagccacggg aggagcagtt caacagcacg    900
ttccgtgtgg tcagcgtcct caccgttgtg caccaggact ggctgaacgg caaggagtac    960
aagtgcaagg tctccaacaa aggcctccca gcccccatcg agaaaaccat ctccaaaacc   1020
aaagggcagc cccgagaacc acaggtgtac accctgcccc catcccggga ggagatgacc   1080
aagaaccagg tcagcctgac ctgcctggtc aaaggcttct accccagcga catcgccgtg   1140 gagtggggaga gcaatgggca gccggagaac aactacaaga ccacacctcc catgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaa                                          1344

<210> SEQ ID NO 229
<211> LENGTH: 642
<212> TYPE: DNA
<213> ORGANISM: Homo sapiens

<400> SEQUENCE: 229
gacatccaga tgacccagtc tccatcctcc ctgtctgcat ctgtaggaga cagagtcacc     60
atcacttgcc gggcaagtca gggcattaga aataatttag gctggtatca gcagaaacca    120
gggaaagccc ctaagcgcct gatttatgct gcatccagtt tgcaaagtgg ggtcccatca    180
aggttcagcg gcagtggatc tgggacagaa ttcactctca caatcagcag tctgcagcct    240
gaagatttta caacttatta ctgtctacag cataatagtt acccgtggac gttcggccaa    300
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga gaaacacaaa gtctacgcct gcgaagtcac ccatcagggc    600
ctgagctcgc ccgtcacaaa gagcttcaac aggggagagt gt                      642

<210> SEQ ID NO 230
<211> LENGTH: 1350
<212> TYPE: DNA
<213> ORGANISM: Homo sapiens

<400> SEQUENCE: 230
caggtgcagc tggtggagtc tgggggaggc gtggtccagc ctgggaggtc cctgagactc     60
tcctgtgcag cgtctggatt caccttcagt agttacggca tgcactgggt ccgccaggct    120
ccaggcaagg gctggagtg gtggcagtt atatggtatg atggaagtaa taataccat    180 gcagactccg tgaagggccg attcaccatc tccagagaca attccaagaa cacgctgtat    240
ctgcaagtga acagcctgag agccgaggac acggctgtgt attactgtgt gagaagtcgg    300
aactggaact acgacaacta ctactacggt ctggacgtct ggggccaagg gaccacggtc    360
accgtctcct cagcctccac caagggccca tcggtcttcc cctggcgccc tgctccagg    420 agcacctccg agagcacagc ggccctgggc tgcctggtca aggactactt ccccgaaccg    480
gtgacggtgt cgtggaactc aggcgctctg accagcggcg tgcacacctt cccagctgtc    540
```

```
ctacagtcct caggactcta ctccctcagc agcgtggtga ccgtgccctc cagcaacttc     600
ggcacccaga cctacacctg caacgtagat cacaagccca gcaacaccaa ggtggacaag     660
acagttgagc gcaaatgttg tgtcgagtgc ccaccgtgcc cagcaccacc tgtggcagga     720
ccgtcagtct tcctcttccc cccaaaaccc aaggacaccc tcatgatctc ccggacccct     780
gaggtcacgt gcgtggtggt ggacgtgagc cacgaagacc ccgaggtcca gttcaactgg     840
tacgtggacg gcgtggaggt gcataatgcc aagacaaagc cacgggagga gcagttcaac     900
agcacgttcc gtgtggtcag cgtcctcacc gttgtgcacc aggactggct gaacggcaag     960
gagtacaagt gcaaggtctc caacaaaggc ctcccagccc ccatcgagaa aaccatctcc    1020
aaaaccaaag ggcagccccg agaaccacag gtgtacaccc tgcccccatc ccgggaggag    1080
atgaccaaga accaggtcag cctgacctgc ctggtcaaag gcttctaccc cagcgacatc    1140
gccgtggagt gggagagcaa tgggcagccg gagaacaact acaagaccac acctcccatg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                    1350

<210> SEQ ID NO 231
<211> LENGTH: 642
<212> TYPE: DNA
<213> ORGANISM: Homo sapiens

<400> SEQUENCE: 231
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtcgacag caaaatactt acccgctcac tttcggcgga     300
gggaccaagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg    540
ctgagcaaag cagactacga gaaacacaaa gtctacgcct gcgaagtcac ccatcagggc     600
ctgagctcgc ccgtcacaaa gagcttcaac aggggagagt gt                       642

<210> SEQ ID NO 232
<211> LENGTH: 1347
<212> TYPE: DNA
<213> ORGANISM: Homo sapiens

<400> SEQUENCE: 232
gaggtgcagt tggtggagtc tgggggaggc ttggtccagc ctggggggtc cctgagactc      60
tcctgtgcag cctctggatt cacctttagt agttattgga tgagctgggt ccgccaggct     120
ccagggaagg ggctggagtg cgtggccaac ataaagcaag atggaagtga ggaatactat     180
gtggactctg tgaagggccg attcaccatc tccagagaca acgccaagaa ttcactgtat     240
ctgcaaatga acagcctgag agccgaggac acggctgtgt attactgtgc gagaggtagc     300
agcagctggt actactacaa ctacggtatg gacgtctggg gccaagggac cacggtcacc     360
gtctcctcag cctccaccaa gggcccatcg gtcttccccc tggcgccctg ctccaggagc     420
```

-continued

```
acctccgaga gcacagcggc cctgggctgc ctggtcaagg actacttccc cgaaccggtg    480
acggtgtcgt ggaactcagg cgctctgacc agcggcgtgc acaccttccc agctgtccta    540
cagtcctcag gactctactc cctcagcagc gtggtgaccg tgccctccag caacttcggc    600
acccagacct acacctgcaa cgtagatcac aagcccagca acaccaaggt ggacaagaca    660
gttgagcgca aatgttgtgt cgagtgccca ccgtgcccag caccacctgt ggcaggaccg    720
tcagtcttcc tcttcccccc aaaacccaag gacacccctca tgatctcccg gacccctgag    780
gtcacgtgcg tggtggtgga cgtgagccac gaagacccgc aggtccagtt caactggtac    840
gtggacggcg tggaggtgca taatgccaag acaaagccac gggaggagca gttcaacagc    900
acgttccgtg tggtcagcgt cctcaccgtt gtgcaccagg actggctgaa cggcaaggag    960
tacaagtgca aggtctccaa caaaggcctc ccagccccca tcgagaaaac catctccaaa   1020
accaaagggc agccccgaga accacaggtg tacaccctgc ccccatcccg ggaggagatg   1080
accaagaacc aggtcagcct gacctgcctg gtcaaaggct tctacccag cgacatcgcc    1140 gtggagtggg agagcaatgg gcagccggag aacaactaca agaccacacc tcccatgctg   1200
gactccgacg gctccttctt cctctacagc aagctcaccg tggacaagag caggtggcag   1260 cagggggaacg tcttctcatg ctccgtgatg catgaggctc tgcacaacca ctacacgcag   1320
aagagcctct ccctgtctcc gggtaaa                                       1347
```

<210> SEQ ID NO 233
<211> LENGTH: 212
<212> TYPE: PRT
<213> ORGANISM: Homo sapiens

<400> SEQUENCE: 233

```
Ser Tyr Glu Val Thr Gln Ala Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205
```

Thr Glu Cys Ser
    210

<210> SEQ ID NO 234
<211> LENGTH: 448
<212> TYPE: PRT
<213> ORGANISM: Homo sapiens

<400> SEQUENCE: 234

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Pro Gly Gln Gly Leu Glu Trp Met
        35                  40                  45

Gly Trp Ile Ile Pro Tyr Asn Gly Asn Thr Asn Ser Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Arg Asp Tyr Gly Val Asn Tyr Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys

```
                355                 360                 365
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
                435                 440                 445

<210> SEQ ID NO 235
<211> LENGTH: 214
<212> TYPE: PRT
<213> ORGANISM: Homo sapiens

<400> SEQUENCE: 235

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Thr Thr Tyr Tyr Cys Leu Gln His Asn Ser Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 236
<211> LENGTH: 450
<212> TYPE: PRT
<213> ORGANISM: Homo sapiens

<400> SEQUENCE: 236

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

```
            20                  25                  30
Gly Met His Trp Val Arg Gln Ala Pro Gly Lys Gly Leu Glu Trp Val
            35                  40                  45
Ala Val Ile Trp Tyr Asp Gly Ser Asn Lys Tyr His Ala Asp Ser Val
50                  55                  60
Lys Gly Arg Phe Thr Ile Ser Arg Asp Asn Ser Lys Asn Thr Leu Tyr
65                  70                  75                  80
Leu Gln Val Asn Ser Leu Arg Ala Glu Asp Thr Ala Val Tyr Tyr Cys
                85                  90                  95
Val Arg Ser Arg Asn Trp Asn Tyr Asp Asn Tyr Tyr Gly Leu Asp
            100                 105                 110
Val Trp Gly Gln Gly Thr Thr Val Thr Val Ser Ser Ala Ser Thr Lys
            115                 120                 125
Gly Pro Ser Val Phe Pro Leu Ala Pro Cys Ser Arg Ser Thr Ser Glu
            130                 135                 140
Ser Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
                180                 185                 190
Val Thr Val Pro Ser Ser Asn Phe Gly Thr Gln Thr Tyr Thr Cys Asn
            195                 200                 205
Val Asp His Lys Pro Ser Asn Thr Lys Val Asp Lys Thr Val Glu Arg
            210                 215                 220
Lys Cys Cys Val Glu Cys Pro Pro Cys Pro Ala Pro Pro Val Ala Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Gln Phe Asn Trp Tyr Val Asp Gly Val Glu Val His
            275                 280                 285
Asn Ala Lys Thr Lys Pro Arg Glu Glu Gln Phe Asn Ser Thr Phe Arg
            290                 295                 300
Val Val Ser Val Leu Thr Val Val His Gln Asp Trp Leu Asn Gly Lys
305                 310                 315                 320
Glu Tyr Lys Cys Lys Val Ser Asn Lys Gly Leu Pro Ala Pro Ile Glu
                325                 330                 335
Lys Thr Ile Ser Lys Thr Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Met
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
```

Gly Lys
    450

<210> SEQ ID NO 237
<211> LENGTH: 214
<212> TYPE: PRT
<213> ORGANISM: Homo sapiens

<400> SEQUENCE: 237

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Arg Gln Gln Asn Thr Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 238
<211> LENGTH: 449
<212> TYPE: PRT
<213> ORGANISM: Homo sapiens

<400> SEQUENCE: 238

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Cys Val
        35                  40                  45

Ala Asn Ile Lys Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ser Trp Tyr Tyr Tyr Asn Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
210                 215                 220

Cys Cys Val Glu Cys Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 239
<211> LENGTH: 321
<212> TYPE: DNA
<213> ORGANISM: Homo sapiens

<400> SEQUENCE: 239
cgaactgtgg ctgcaccatc tgtcttcatc ttcccgccat ctgatgagca gttgaaatct    60

| | |
|---|---|
| ggaactgcct ctgttgtgtg cctgctgaat aacttctatc ccagagaggc caaagtacag | 120 |
| tggaaggtgg ataacgccct ccaatcgggt aactcccagg agagtgtcac agagcaggac | 180 |
| agcaaggaca gcacctacag cctcagcagc accctgacgc tgagcaaagc agactacgag | 240 |
| aaacacaaag tctacgcctg cgaagtcacc catcagggcc tgagctcgcc cgtcacaaag | 300 |
| agcttcaaca ggggagagtg t | 321 |

<210> SEQ ID NO 240
<211> LENGTH: 978
<212> TYPE: DNA
<213> ORGANISM: Homo sapiens

<400> SEQUENCE: 240

| | |
|---|---|
| gcctccacca agggcccatc ggtcttcccc ctggcgccct gctccaggag cacctccgag | 60 |
| agcacagcgg ccctgggctg cctggtcaag gactacttcc ccgaaccggt gacggtgtcg | 120 |
| tggaactcag gcgctctgac cagcggcgtg cacaccttcc cagctgtcct acagtcctca | 180 |
| ggactctact ccctcagcag cgtggtgacc gtgccctcca gcaacttcgg cacccagacc | 240 |
| tacacctgca acgtagatca caagcccagc aacaccaagg tggacaagac agttgagcgc | 300 |
| aaatgttgtg tcgagtgccc accgtgccca gcaccacctg tggcaggacc gtcagtcttc | 360 |
| ctcttccccc caaaacccaa ggacaccctc atgatctccc ggacccctga ggtcacgtgc | 420 |
| gtggtggtgg acgtgagcca cgaagacccc gaggtccagt tcaactggta cgtggacggc | 480 |
| gtggaggtgc ataatgccaa gacaaagcca cgggaggagc agttcaacag cacgttccgt | 540 |
| gtggtcagcg tcctcaccgt tgtgcaccag gactggctga acggcaagga gtacaagtgc | 600 |
| aaggtctcca acaaaggcct cccagccccc atcgagaaaa ccatctccaa aaccaaaggg | 660 |
| cagccccgag aaccacaggt gtacaccctg cccccatccc gggaggagat gaccaagaac | 720 |
| caggtcagcc tgacctgcct ggtcaaaggc ttctacccca gcgacatcgc cgtggagtgg | 780 |
| gagagcaatg ggcagccgga gaacaactac aagaccacac ctcccatgct ggactccgac | 840 |
| ggctccttct tcctctacag caagctcacc gtggacaaga gcaggtggca gcagggaac | 900 |
| gtcttctcat gctccgtgat gcatgaggct ctgcacaacc actacacgca gaagagcctc | 960 |
| tccctgtctc cgggtaaa | 978 |

<210> SEQ ID NO 241
<211> LENGTH: 978
<212> TYPE: DNA
<213> ORGANISM: Homo sapiens

<400> SEQUENCE: 241

| | |
|---|---|
| gcctccacca agggcccatc ggtcttcccc ctggcgccct gctccaggag cacctccgag | 60 |
| agcacagcgg ccctgggctg cctggtcaag gactacttcc ccgaaccggt gacggtgtcg | 120 |
| tggaactcag gcgctctgac cagcggcgtg cacaccttcc cagctgtcct acagtcctca | 180 |
| ggactctact ccctcagcag cgtggtgacc gtgccctcca gcaacttcgg cacccagacc | 240 |
| tacacctgca acgtagatca caagcccagc aacaccaagg tggacaagac agttgagcgc | 300 |
| aaatgttgtg tcgagtgccc accgtgccca gcaccacctg tggcaggacc gtcagtcttc | 360 |
| ctcttccccc caaaacccaa ggacaccctc atgatctccc ggacccctga ggtcacgtgc | 420 |
| gtggtggtgg acgtgagcca cgaagacccc gaggtccagt tcaactggta cgtggacggc | 480 |
| gtggaggtgc ataatgccaa gacaaagcca cgggaggagc agttcaacag cacgttccgt | 540 |
| gtggtcagcg tcctcaccgt tgtgcaccag gactggctga acggcaagga gtacaagtgc | 600 |

```
aaggtctcca acaaaggcct cccagccccc atcgagaaaa ccatctccaa aaccaaaggg      660
cagccccgag aaccacaggt gtacaccctg cccccatccc gggaggagat gaccaagaac      720
caggtcagcc tgacctgcct ggtcaaaggc ttctacccca gcgacatcgc cgtggagtgg      780
gagagcaatg ggcagccgga gaacaactac aagaccacac ctcccatgct ggactccgac      840
ggctccttct tcctctacag caagctcacc gtggacaaga gcaggtggca gcagggaaac      900
gtcttctcat gctccgtgat gcatgaggct ctgcacaacc actacacgca gaagagcctc      960
tccctgtctc cgggtaaa                                                    978

<210> SEQ ID NO 242
<211> LENGTH: 824
<212> TYPE: DNA
<213> ORGANISM: Homo sapiens

<400> SEQUENCE: 242
gcctccacca agggcccatc ggtcttcccc ctggcgccct gctccaggag cacctccgag       60
agcacagcgg ccctgggctg cctggtcaag gactacttcc ccgaaccggt gacggtgtcg      120
tggaactcag gcgctctgac cagcggcgtg cacaccttcc cagctgtcct acagtcctca      180
ggactctact ccctcagcag cgtggtgacc gtgccctcca gcaacttcgg cacccagacc      240
tacacctgca acgtagatca caagcccagc aacaccaagg tggacaagac agttgagcgc      300
aaatgttgtg tcgagtgccc accgtgccca gcaccacctg tggcaggacc gtcagtcttc      360
ctcttccccc caaaacccaa ggacaccctc atgatctccc ggacccctga ggtcacgtgc      420
gtggtggtgg acgtgagcca cgaagacccc gaggtccagt tcaactggta cgtggacggc      480
gtggaggtgc ataatgccaa gacaaagcca cgggaggagc agttcaacag cacgttccgt      540
gtggtcagcg tcctcaccgt tgtgcaccag gactggctga acggcaagga gtacaagtgc      600
aaggtctcca acaaaggcct cccagccccc atcgagaaaa ccatctccaa aaccaaaggg      660
cagccccgag aaccacaggt gtacaccctg cccccatccc gggaggagat gaccaagaac      720
caggtcagcc tgacctgcct ggtcaaaggc ttctacccca gcgacatcgc cgtggagtgg      780
gagagcaatg ggcagccgga gaacaactac aagaccacac tcc                        824

<210> SEQ ID NO 243
<211> LENGTH: 116
<212> TYPE: PRT
<213> ORGANISM: Artificial Sequence
<220> FEATURE:
<223> OTHER INFORMATION: Activin A/B Chimera

<400> SEQUENCE: 243

Gly Leu Glu Cys Asp Gly Lys Val Asn Ile Cys Cys Arg Gln Gln Phe
1               5                   10                  15

Phe Ile Asp Phe Arg Leu Ile Gly Trp Asn Asp Trp Ile Ile Ala Pro
            20                  25                  30

Thr Gly Tyr Tyr Gly Asn Tyr Cys Glu Gly Glu Cys Pro Ser His Ile
        35                  40                  45

Ala Gly Thr Ser Gly Ser Ser Leu Ser Phe His Ser Thr Val Ile Asn
    50                  55                  60

His Tyr Arg Met Arg Gly His Ser Pro Phe Ala Asn Leu Lys Ser Cys
65                  70                  75                  80

Cys Val Pro Thr Lys Leu Arg Pro Met Ser Met Leu Tyr Tyr Asp Asp
                85                  90                  95
```

Gly Gln Asn Ile Ile Lys Lys Asp Ile Gln Asn Met Ile Val Glu Glu
                100                 105                 110
Cys Gly Cys Ser
        115

<210> SEQ ID NO 244
<211> LENGTH: 116
<212> TYPE: PRT
<213> ORGANISM: Artificial Sequence
<220> FEATURE:
<223> OTHER INFORMATION: Activin A/B Chimera

<400> SEQUENCE: 244

Gly Leu Glu Cys Asp Gly Lys Val Asn Ile Cys Cys Lys Lys Gln Phe
1               5                   10                  15

Phe Val Ser Phe Lys Asp Ile Gly Trp Asn Asp Trp Ile Ile Ala Pro
            20                  25                  30

Ser Gly Tyr His Ala Asn Tyr Cys Glu Gly Glu Cys Pro Ser His Ile
        35                  40                  45

Ala Gly Thr Ser Gly Ser Ser Leu Ser Phe His Ser Thr Val Ile Asn
    50                  55                  60

His Tyr Arg Met Arg Gly His Ser Pro Phe Ala Asn Leu Lys Ser Cys
65                  70                  75                  80

Cys Ile Pro Thr Lys Leu Ser Thr Met Ser Met Leu Tyr Phe Asp Asp
                85                  90                  95

Glu Tyr Asn Ile Val Lys Arg Asp Val Pro Asn Met Ile Val Glu Glu
                100                 105                 110

Cys Gly Cys Ser
        115

<210> SEQ ID NO 245
<211> LENGTH: 31
<212> TYPE: DNA
<213> ORGANISM: Artificial Sequence
<220> FEATURE:
<223> OTHER INFORMATION: Oligonucleotide

<400> SEQUENCE: 245
ctcgaggtcg actagaccac catgcccttg c                                    31

<210> SEQ ID NO 246
<211> LENGTH: 28
<212> TYPE: DNA
<213> ORGANISM: Artificial Sequence
<220> FEATURE:
<223> OTHER INFORMATION: Oligonucleotide

<400> SEQUENCE: 246
ccatcacact ctagaccccg ccgacgcc                                        28

<210> SEQ ID NO 247
<211> LENGTH: 360
<212> TYPE: DNA
<213> ORGANISM: Artificial Sequence
<220> FEATURE:
<223> OTHER INFORMATION: Activin A/B Chimera

<400> SEQUENCE: 247
ggtctagagt gtgatggcaa ggtcaacatc tgctgtaggc aacagttctt tatcgatttc     60
aggctcatcg gctggaatga ctggatcatt gctcccactg ctattatggg caactactgc    120
gagggtgagt gcccgagcca tatagcaggc acgtccgggt caagcttgtc cttccactca    180

```
acagtcatca accactaccg catgcggggc catagcccct ttgccaacct caaatcatgc      240
tgtgtgccca ccaagctgag acccatgtcc atgttgtact atgatgatgg tcaaaacatc      300
atcaaaaagg acattcagaa catgatcgtg gaggagtgtg ggtgctcatg agcggccgct      360
```

<210> SEQ ID NO 248
<211> LENGTH: 9
<212> TYPE: PRT
<213> ORGANISM: Artificial Sequence
<220> FEATURE:
<223> OTHER INFORMATION: Anti Activin A Antibody Peptide
<220> FEATURE:
<221> NAME/KEY: VARIANT
<222> LOCATION: 5
<223> OTHER INFORMATION: Xaa = Arg OR Ser
<220> FEATURE:
<221> NAME/KEY: VARIANT
<222> LOCATION: 8
<223> OTHER INFORMATION: Xaa = Val OR Ala
<220> FEATURE:
<221> NAME/KEY: VARIANT
<222> LOCATION: 9
<223> OTHER INFORMATION: Xaa = Val OR -Xaa (Xaa deleted)

<400> SEQUENCE: 248

Gln Ala Trp Asp Xaa Ser Thr Xaa Xaa
1               5

<210> SEQ ID NO 249
<211> LENGTH: 16
<212> TYPE: PRT
<213> ORGANISM: Artificial Sequence
<220> FEATURE:
<223> OTHER INFORMATION: Anti Activin A Antibody Peptide
<220> FEATURE:
<221> NAME/KEY: VARIANT
<222> LOCATION: 1
<223> OTHER INFORMATION: Xaa = Gly OR -Xaa (Xaa deleted)
<220> FEATURE:
<221> NAME/KEY: VARIANT
<222> LOCATION: 2
<223> OTHER INFORMATION: Xaa = Ser OR Glu OR -Xaa (Xaa deleted)
<220> FEATURE:
<221> NAME/KEY: VARIANT
<222> LOCATION: 3
<223> OTHER INFORMATION: Xaa = Arg OR Ser OR -Xaa (Xaa deleted)
<220> FEATURE:
<221> NAME/KEY: VARIANT
<222> LOCATION: 4
<223> OTHER INFORMATION: Xaa = Asp OR Asn OR Ser OR Gln
<220> FEATURE:
<221> NAME/KEY: VARIANT
<222> LOCATION: 5
<223> OTHER INFORMATION: Xaa = Ser OR Arg OR Trp
<220> FEATURE:
<221> NAME/KEY: VARIANT
<222> LOCATION: (6)...(6)
<223> OTHER INFORMATION: Xaa = Gly OR Asp OR Asn OR Tyr OR Leu
<220> FEATURE:
<221> NAME/KEY: VARIANT
<222> LOCATION: (8)...(8)
<223> OTHER INFORMATION: Xaa = Ser OR Gly OR Asp OR or -Xaa (Xaa
      deleted)
<220> FEATURE:
<221> NAME/KEY: VARIANT
<222> LOCATION: (9)...(9)
<223> OTHER INFORMATION: Xaa = Ser OR Val OR Asn OR Tyr
<220> FEATURE:
<221> NAME/KEY: VARIANT
<222> LOCATION: (10)...(10)
<223> OTHER INFORMATION: Xaa = Ser OR Asn OR Tyr OR His
<220> FEATURE:
<221> NAME/KEY: VARIANT
<222> LOCATION: (11)...(11)

```
<223> OTHER INFORMATION: Xaa = Trp OR Tyr OR Gln
<220> FEATURE:
<221> NAME/KEY: VARIANT
<222> LOCATION: (12)...(12)
<223> OTHER INFORMATION: Xaa = His OR Asp OR Tyr OR -Xaa (Xaa deleted)
<220> FEATURE:
<221> NAME/KEY: VARIANT
<222> LOCATION: (13)...(13)
<223> OTHER INFORMATION: Xaa = Phe OR Ala OR Gly
<220> FEATURE:
<221> NAME/KEY: VARIANT
<222> LOCATION: (14)...(14)
<223> OTHER INFORMATION: Xaa = Asp OR Phe OR Leu OR Met
<220> FEATURE:
<221> NAME/KEY: VARIANT
<222> LOCATION: (15)...(15)
<223> OTHER INFORMATION: Xaa = Tyr OR Asp
<220> FEATURE:
<221> NAME/KEY: VARIANT
<222> LOCATION: (16)...(16)
<223> OTHER INFORMATION: Xaa = Ile OR Val OR -Xaa (Xaa deleted)

<400> SEQUENCE: 249

Xaa Xaa Xaa Xaa Xaa Xaa Tyr Xaa Xaa Xaa Xaa Xaa Xaa Xaa Xaa
1               5                   10                  15

<210> SEQ ID NO 250
<211> LENGTH: 11
<212> TYPE: PRT
<213> ORGANISM: Artificial Sequence
<220> FEATURE:
<223> OTHER INFORMATION: Anti Activin A Antibody Peptide
<220> FEATURE:
<221> NAME/KEY: VARIANT
<222> LOCATION: 3
<223> OTHER INFORMATION: Xaa = Ser OR Gly
<220> FEATURE:
<221> NAME/KEY: VARIANT
<222> LOCATION: 7
<223> OTHER INFORMATION: Xaa = Ser OR Arg
<220> FEATURE:
<221> NAME/KEY: VARIANT
<222> LOCATION: 9
<223> OTHER INFORMATION: Xaa = Asp OR Asn
<220> FEATURE:
<221> NAME/KEY: VARIANT
<222> LOCATION: 11
<223> OTHER INFORMATION: Xaa = Val OR Gly

<400> SEQUENCE: 250

Arg Ala Xaa Gln Gly Ile Xaa Asn Xaa Leu Xaa
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Anti Activin A Antibody Peptide

<400> SEQUENCE: 251

Arg Ala Ser Gln Ser Ile Ser Asn Tyr Leu Asn Thr
1               5                   10

<210> SEQ ID NO 252
<211> LENGTH: 12
<212> TYPE: PRT
<213> ORGANISM: Artificial Sequence
<220> FEATURE:
<223> OTHER INFORMATION: Anti Activin A Antibody Peptide
<220> FEATURE:
<221> NAME/KEY: VARIANT
<222> LOCATION: 4
```

```
<223> OTHER INFORMATION: Xaa = Ile OR Phe
<220> FEATURE:
<221> NAME/KEY: VARIANT
<222> LOCATION: 5
<223> OTHER INFORMATION: Xaa = Asn OR Ser
<220> FEATURE:
<221> NAME/KEY: VARIANT
<222> LOCATION: 6
<223> OTHER INFORMATION: Xaa = Ser OR Ala
<220> FEATURE:
<221> NAME/KEY: VARIANT
<222> LOCATION: 7
<223> OTHER INFORMATION: Xaa = -Xaa (Xaa deleted) OR Gly
<220> FEATURE:
<221> NAME/KEY: VARIANT
<222> LOCATION: 8
<223> OTHER INFORMATION: Xaa = -Xaa (Xaa deleted) OR Gly
<220> FEATURE:
<221> NAME/KEY: VARIANT
<222> LOCATION: (9)...(9)
<223> OTHER INFORMATION: Xaa = Phe OR Tyr

<400> SEQUENCE: 252

Gly Gly Ser Xaa Xaa Xaa Xaa Xaa Xaa Tyr Trp Ser
1               5                   10

<210> SEQ ID NO 253
<211> LENGTH: 16
<212> TYPE: PRT
<213> ORGANISM: Artificial Sequence
<220> FEATURE:
<223> OTHER INFORMATION: Anti Activin A Antibody Peptide

<400> SEQUENCE: 253

Arg Ser Ser Gln Ser Leu Leu His Ser Thr Gly Tyr Asn Tyr Leu Asp
1               5                   10                  15

<210> SEQ ID NO 254
<211> LENGTH: 7
<212> TYPE: PRT
<213> ORGANISM: Artificial Sequence
<220> FEATURE:
<223> OTHER INFORMATION: Anti Activin A Antibody Peptide

<400> SEQUENCE: 254

Leu Gly Ser Phe Arg Ala Ser
1               5

<210> SEQ ID NO 255
<211> LENGTH: 9
<212> TYPE: PRT
<213> ORGANISM: Artificial Sequence
<220> FEATURE:
<223> OTHER INFORMATION: Anti Activin A Antibody Peptide

<400> SEQUENCE: 255

Met Gln Ala Leu Gln Thr Pro Cys Ser
1               5

<210> SEQ ID NO 256
<211> LENGTH: 10
<212> TYPE: PRT
<213> ORGANISM: Artificial Sequence
<220> FEATURE:
<223> OTHER INFORMATION: Anti Activin A Antibody Peptide

<400> SEQUENCE: 256

Gly Tyr Thr Phe Thr Gly Tyr Tyr Ile His
1               5                   10
```

```
<210> SEQ ID NO 257
<211> LENGTH: 10
<212> TYPE: PRT
<213> ORGANISM: Artificial Sequence
<220> FEATURE:
<223> OTHER INFORMATION: Anti Activin A Antibody Peptide
<220> FEATURE:
<221> NAME/KEY: VARIANT
<222> LOCATION: 2
<223> OTHER INFORMATION: Xaa = Tyr OR Phe
<220> FEATURE:
<221> NAME/KEY: VARIANT
<222> LOCATION: 3
<223> OTHER INFORMATION: Xaa = Thr OR Ser
<220> FEATURE:
<221> NAME/KEY: VARIANT
<222> LOCATION: 5
<223> OTHER INFORMATION: Xaa = Thr OR Ser OR Ile
<220> FEATURE:
<221> NAME/KEY: VARIANT
<222> LOCATION: 6
<223> OTHER INFORMATION: Xaa = Gly OR Ser
<220> FEATURE:
<221> NAME/KEY: VARIANT
<222> LOCATION: 8
<223> OTHER INFORMATION: Xaa = Tyr OR Gly OR Trp
<220> FEATURE:
<221> NAME/KEY: VARIANT
<222> LOCATION: (9)...(9)
<223> OTHER INFORMATION: Xaa = Ile OR Met
<220> FEATURE:
<221> NAME/KEY: VARIANT
<222> LOCATION: (10)...(10)
<223> OTHER INFORMATION: Xaa = His OR Gly

<400> SEQUENCE: 257

Gly Xaa Xaa Phe Xaa Xaa Tyr Xaa Xaa Xaa
1               5                   10

<210> SEQ ID NO 258
<211> LENGTH: 17
<212> TYPE: PRT
<213> ORGANISM: Artificial Sequence
<220> FEATURE:
<223> OTHER INFORMATION: Anti Activin A Antibody Peptide

<400> SEQUENCE: 258

Trp Ile Asn Pro Asn Ser Gly Gly Thr Asn Tyr Ala Gln Lys Phe Gln
1               5                   10                  15

Gly

<210> SEQ ID NO 259
<211> LENGTH: 17
<212> TYPE: PRT
<213> ORGANISM: Artificial Sequence
<220> FEATURE:
<223> OTHER INFORMATION: Anti Activin A Antibody Peptide

<400> SEQUENCE: 259

Trp Ile Ser Pro Tyr Asn Gly Asn Thr Asn Tyr Ala Gln Lys Phe Gln
1               5                   10                  15

Gly

<210> SEQ ID NO 260
<211> LENGTH: 12
<212> TYPE: PRT
<213> ORGANISM: Artificial Sequence
<220> FEATURE:
<223> OTHER INFORMATION: Anti Activin A Antibody Peptide
```

```
<400> SEQUENCE: 260

Asp Ser Gly Tyr Ser Ser Ser Trp His Phe Asp Tyr
1               5                   10

<210> SEQ ID NO 261
<211> LENGTH: 13
<212> TYPE: PRT
<213> ORGANISM: Artificial Sequence
<220> FEATURE:
<223> OTHER INFORMATION: Anti Activin A Antibody Peptide

<400> SEQUENCE: 261

Gly Ser Ser Ser Trp Tyr Tyr Tyr Asn Gly Met Asp Val
1               5                   10

<210> SEQ ID NO 262
<211> LENGTH: 30
<212> TYPE: PRT
<213> ORGANISM: Artificial Sequence
<220> FEATURE:
<223> OTHER INFORMATION: Amino acid residues 1-30 of Activin A

<400> SEQUENCE: 262

Gly Leu Glu Cys Asp Gly Lys Val Asn Ile Cys Cys Lys Lys Gln Phe
1               5                   10                  15

Phe Val Ser Phe Lys Asp Ile Gly Trp Asn Asp Trp Ile Ile
            20                  25                  30

<210> SEQ ID NO 263
<211> LENGTH: 30
<212> TYPE: PRT
<213> ORGANISM: Artificial Sequence
<220> FEATURE:
<223> OTHER INFORMATION: Amino acid residues 31-60 of Activin A

<400> SEQUENCE: 263

Ala Pro Ser Gly Tyr His Ala Asn Tyr Cys Glu Gly Glu Cys Pro Ser
1               5                   10                  15

His Ile Ala Gly Thr Ser Gly Ser Ser Leu Ser Phe His Ser
            20                  25                  30

<210> SEQ ID NO 264
<211> LENGTH: 30
<212> TYPE: PRT
<213> ORGANISM: Artificial Sequence
<220> FEATURE:
<223> OTHER INFORMATION: Amino acid residues 61-90 of Activin A

<400> SEQUENCE: 264

Thr Val Ile Asn His Tyr Arg Met Arg Gly His Ser Pro Phe Ala Asn
1               5                   10                  15

Leu Lys Ser Cys Cys Val Pro Thr Lys Leu Arg Pro Met Ser
            20                  25                  30

<210> SEQ ID NO 265
<211> LENGTH: 26
<212> TYPE: PRT
<213> ORGANISM: Artificial Sequence
<220> FEATURE:
<223> OTHER INFORMATION: Amino acid residues 91-116 of Activin A

<400> SEQUENCE: 265

Met Leu Tyr Tyr Asp Asp Gly Gln Asn Ile Ile Lys Lys Asp Ile Gln
1               5                   10                  15
```

```
Asn Met Ile Val Glu Glu Cys Gly Cys Ser
            20                  25

<210> SEQ ID NO 266
<211> LENGTH: 116
<212> TYPE: PRT
<213> ORGANISM: Artificial Sequence
<220> FEATURE:
<223> OTHER INFORMATION: Activin A 13/39 B

<400> SEQUENCE: 266

Gly Leu Glu Cys Asp Gly Lys Val Asn Ile Cys Cys Arg Gln Gln Phe
1               5                   10                  15

Phe Ile Asp Phe Arg Leu Ile Gly Trp Asn Asp Trp Ile Ile Ala Pro
            20                  25                  30

Thr Gly Tyr Tyr Gly Asn Tyr Cys Glu Gly Glu Cys Pro Ser His Ile
        35                  40                  45

Ala Gly Thr Ser Gly Ser Ser Leu Ser Phe His Ser Thr Val Ile Asn
    50                  55                  60

His Tyr Arg Met Arg Gly His Ser Pro Phe Ala Asn Leu Lys Ser Cys
65                  70                  75                  80

Cys Val Pro Thr Lys Leu Arg Pro Met Ser Met Leu Tyr Tyr Asp Asp
                85                  90                  95

Gly Gln Asn Ile Ile Lys Lys Asp Ile Gln Asn Met Ile Val Glu Glu
            100                 105                 110

Cys Gly Cys Ser
            115
```